United States Patent
Flohr et al.

(10) Patent No.: US 10,398,702 B2
(45) Date of Patent: Sep. 3, 2019

(54) DIMERIC COMPOUNDS

(71) Applicant: Hoffmann-La Roche Inc., Little Falls, NJ (US)

(72) Inventors: Alexander Flohr, Basel (CH); Guido Galley, Basel (CH); Roger Norcross, Basel (CH); Nicolas Zorn, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 16/095,262

(22) PCT Filed: May 5, 2017

(86) PCT No.: PCT/EP2017/060732
§ 371 (c)(1),
(2) Date: Oct. 19, 2018

(87) PCT Pub. No.: WO2017/194390
PCT Pub. Date: Nov. 16, 2017

(65) Prior Publication Data
US 2019/0134050 A1    May 9, 2019

(30) Foreign Application Priority Data
May 9, 2016 (EP) .................... 16168792

(51) Int. Cl.
*A61K 31/5355* (2006.01)
*C07D 413/14* (2006.01)
*A61P 35/00* (2006.01)
*C07K 16/18* (2006.01)

(52) U.S. Cl.
CPC .......... *A61K 31/5355* (2013.01); *A61P 35/00* (2018.01); *C07D 413/14* (2013.01); *C07K 16/18* (2013.01)

(58) Field of Classification Search
None
See application file for complete search history.

(56) References Cited

FOREIGN PATENT DOCUMENTS

| WO | 2014060767 | * | 4/2014 |
| WO | 2014060770 | * | 4/2014 |

* cited by examiner

*Primary Examiner* — Karl J Puttlitz

(57) ABSTRACT

The present invention provides a compound of formula I which act as inhibitors of SMAC protein binding to Inhibitor of Apoptosis Proteins (IAPs), and/or inhibitors of activated caspase protein binding to IAPs (I) their manufacture, pharmaceutical compositions containing them and their use as therapeutically active substances, alone or in combination with DR5/FAP agonist antibodies. The active compound of the present invention is useful in the amelioration, treatment or control of cancer, especially solid tumors.

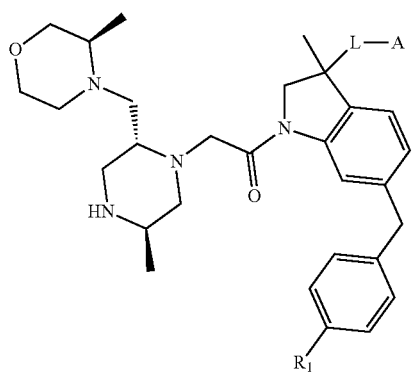

12 Claims, 2 Drawing Sheets
Specification includes a Sequence Listing.

SEQUENCE LISTING

```
<160> NUMBER OF SEQ ID NOS: 23

<210> SEQ ID NO 1
<211> LENGTH: 5
<212> TYPE: PRT
<213> ORGANISM: Artificial Sequence
<220> FEATURE:
<223> OTHER INFORMATION: DR5 (5E11)_CDRH1

<400> SEQUENCE: 1

Ser Tyr Ala Met Ser
1               5

<210> SEQ ID NO 2
<211> LENGTH: 17
<212> TYPE: PRT
<213> ORGANISM: Artificial Sequence
<220> FEATURE:
<223> OTHER INFORMATION: DR5 (5E11)_CDRH2

<400> SEQUENCE: 2

Ala Ile Ser Gly Ser Gly Gly Ser Thr Tyr Tyr Ala Asp Ser Val Lys
1               5                   10                  15

Gly

<210> SEQ ID NO 3
<211> LENGTH: 8
<212> TYPE: PRT
<213> ORGANISM: Artificial Sequence
<220> FEATURE:
<223> OTHER INFORMATION: DR5 (5E11)_CDRH3

<400> SEQUENCE: 3
```

```
Gly Val Arg Val Ser Phe Asp Tyr
1               5

<210> SEQ ID NO 4
<211> LENGTH: 12
<212> TYPE: PRT
<213> ORGANISM: Artificial Sequence
<220> FEATURE:
<223> OTHER INFORMATION: DR5 (5E11)_CDRHL1

<400> SEQUENCE: 4

Arg Ala Ser Gln Ser Val Ser Ser Ser Tyr Leu Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: DR5 (5E11)_CDRL2

<400> SEQUENCE: 5

Gly Ala Ser Ser Arg Ala Thr
1               5

<210> SEQ ID NO 6
<211> LENGTH: 9
<212> TYPE: PRT
<213> ORGANISM: Artificial Sequence
<220> FEATURE:
<223> OTHER INFORMATION: DR5 (5E11)_CDRL3

<400> SEQUENCE: 6

Gln Gln Gly Thr Thr His Pro Ile Thr
1               5

<210> SEQ ID NO 7
<211> LENGTH: 117
<212> TYPE: PRT
<213> ORGANISM: Artificial Sequence
<220> FEATURE:
<223> OTHER INFORMATION: DR5 (5E11)_VH

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Val Arg Val Ser Phe Asp Tyr Trp Gly Gln Gly Thr Leu
            100                 105                 110

Val Thr Val Ser Ser
        115

<210> SEQ ID NO 8
<211> LENGTH: 108
```

```
<212> TYPE: PRT
<213> ORGANISM: Artificial Sequence
<220> FEATURE:
<223> OTHER INFORMATION: DR5 (5E11)_VL

<400> SEQUENCE: 8

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Thr Thr His Pro
                85                  90                  95

Ile Thr Phe Gly Gln Gly Thr Lys Val Glu Ile Lys
            100                 105

<210> SEQ ID NO 9
<211> LENGTH: 5
<212> TYPE: PRT
<213> ORGANISM: Artificial Sequence
<220> FEATURE:
<223> OTHER INFORMATION: FAP (28H1)_CDRH1

<400> SEQUENCE: 9

Ser His Ala Met Ser
1               5

<210> SEQ ID NO 10
<211> LENGTH: 16
<212> TYPE: PRT
<213> ORGANISM: Artificial Sequence
<220> FEATURE:
<223> OTHER INFORMATION: FAP (28H1)_CDRH2

<400> SEQUENCE: 10

Ala Ile Trp Ala Ser Gly Glu Gln Tyr Tyr Ala Asp Ser Val Lys Gly
1               5                   10                  15

<210> SEQ ID NO 11
<211> LENGTH: 8
<212> TYPE: PRT
<213> ORGANISM: Artificial Sequence
<220> FEATURE:
<223> OTHER INFORMATION: FAP (28H1)_CDRH3

<400> SEQUENCE: 11

Gly Trp Leu Gly Asn Phe Asp Tyr
1               5

<210> SEQ ID NO 12
<211> LENGTH: 12
<212> TYPE: PRT
<213> ORGANISM: Artificial Sequence
<220> FEATURE:
<223> OTHER INFORMATION: FAP (28H1)_CDRL1

<400> SEQUENCE: 12

Arg Ala Ser Gln Ser Val Ser Arg Ser Tyr Leu Ala
1               5                   10
```

<210> SEQ ID NO 13
<211> LENGTH: 7
<212> TYPE: PRT
<213> ORGANISM: Artificial Sequence
<220> FEATURE:
<223> OTHER INFORMATION: FAP (28H1)_CDRL2

<400> SEQUENCE: 13

Gly Ala Ser Thr Arg Ala Thr
1               5

<210> SEQ ID NO 14
<211> LENGTH: 9
<212> TYPE: PRT
<213> ORGANISM: Artificial Sequence
<220> FEATURE:
<223> OTHER INFORMATION: FAP (28H1)_CDRL3

<400> SEQUENCE: 14

Gln Gln Gly Gln Val Ile Pro Pro Thr
1               5

<210> SEQ ID NO 15
<211> LENGTH: 116
<212> TYPE: PRT
<213> ORGANISM: Artificial Sequence
<220> FEATURE:
<223> OTHER INFORMATION: FAP (28H1)_VH

<400> SEQUENCE: 15

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Ala Met Ser Trp Val Arg Gln Ala Pro Gly Lys Gly Leu Glu Trp Val
        35                  40                  45

Ser Ala Ile Trp Ala Ser Gly Glu Gln Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Gly Trp Leu Gly Asn Phe Asp Tyr Trp Gly Gln Gly Thr Leu Val
            100                 105                 110

Thr Val Ser Ser
        115

<210> SEQ ID NO 16
<211> LENGTH: 108
<212> TYPE: PRT
<213> ORGANISM: Artificial Sequence
<220> FEATURE:
<223> OTHER INFORMATION: FAP (28H1)_VL

<400> SEQUENCE: 16

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Arg Ser
            20                  25                  30

Tyr Leu Ala Trp Tyr Gln Gln Lys Pro Gly Gln Ala Pro Arg Leu Leu
        35                  40                  45

```
Ile Ile Gly Ala Ser Thr Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Gly Gln Val Ile Pro
                 85                  90                  95

Pro Thr Phe Gly Gln Gly Thr Lys Val Glu Ile Lys
            100                 105

<210> SEQ ID NO 17
<211> LENGTH: 691
<212> TYPE: PRT
<213> ORGANISM: Artificial Sequence
<220> FEATURE:
<223> OTHER INFORMATION: DR5(5E11)-FAP(28H1) VHCL

<400> SEQUENCE: 17

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Lys Gly Val Arg Val Ser Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
290                 295                 300
```

```
Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys Ser
        435                 440                 445

Gly Gly Gly Gly Ser Gly Gly Gly Ser Gly Gly Gly Gly Ser Gly
450                 455                 460

Gly Gly Gly Ser Glu Val Gln Leu Leu Glu Ser Gly Gly Gly Leu Val
465                 470                 475                 480

Gln Pro Gly Gly Ser Leu Arg Leu Ser Cys Ala Ala Ser Gly Phe Thr
                485                 490                 495

Phe Ser Ser His Ala Met Ser Trp Val Arg Gln Ala Pro Gly Lys Gly
            500                 505                 510

Leu Glu Trp Val Ser Ala Ile Trp Ala Ser Gly Glu Gln Tyr Tyr Ala
        515                 520                 525

Asp Ser Val Lys Gly Arg Phe Thr Ile Ser Arg Asp Asn Ser Lys Asn
530                 535                 540

Thr Leu Tyr Leu Gln Met Asn Ser Leu Arg Ala Glu Asp Thr Ala Val
545                 550                 555                 560

Tyr Tyr Cys Ala Lys Gly Trp Leu Gly Asn Phe Asp Tyr Trp Gly Gln
                565                 570                 575

Gly Thr Leu Val Thr Val Ser Ser Ala Ser Val Ala Ala Pro Ser Val
            580                 585                 590

Phe Ile Phe Pro Pro Ser Asp Glu Gln Leu Lys Ser Gly Thr Ala Ser
        595                 600                 605

Val Val Cys Leu Leu Asn Asn Phe Tyr Pro Arg Glu Ala Lys Val Gln
610                 615                 620

Trp Lys Val Asp Asn Ala Leu Gln Ser Gly Asn Ser Gln Glu Ser Val
625                 630                 635                 640

Thr Glu Gln Asp Ser Lys Asp Ser Thr Tyr Ser Leu Ser Ser Thr Leu
                645                 650                 655

Thr Leu Ser Lys Ala Asp Tyr Glu Lys His Lys Val Tyr Ala Cys Glu
            660                 665                 670

Val Thr His Gln Gly Leu Ser Ser Pro Val Thr Lys Ser Phe Asn Arg
        675                 680                 685

Gly Glu Cys
    690

<210> SEQ ID NO 18
<211> LENGTH: 689
```

```
<212> TYPE: PRT
<213> ORGANISM: Artificial Sequence
<220> FEATURE:
<223> OTHER INFORMATION: DR5(5E11)-FAP (28H1) VHCL Removal of C-term.
      Lysine in Fc P329G/LALA mut.

<400> SEQUENCE: 18
```

| | | | | | | | | | | | | | | | |
|---|---|---|---|---|---|---|---|---|---|---|---|---|---|---|---|
| Glu | Val | Gln | Leu | Leu | Glu | Ser | Gly | Gly | Gly | Leu | Val | Gln | Pro | Gly | Gly |
| 1 | | | | 5 | | | | | 10 | | | | | 15 | |
| Ser | Leu | Arg | Leu | Ser | Cys | Ala | Ala | Ser | Gly | Phe | Thr | Phe | Ser | Ser | Tyr |
| | | | 20 | | | | | 25 | | | | | 30 | | |
| Ala | Met | Ser | Trp | Val | Arg | Gln | Ala | Pro | Gly | Lys | Gly | Leu | Glu | Trp | Val |
| | | 35 | | | | | 40 | | | | | 45 | | | |
| Ser | Ala | Ile | Ser | Gly | Ser | Gly | Gly | Ser | Thr | Tyr | Tyr | Ala | Asp | Ser | Val |
| | 50 | | | | | 55 | | | | | 60 | | | | |
| Lys | Gly | Arg | Phe | Thr | Ile | Ser | Arg | Asp | Asn | Ser | Lys | Asn | Thr | Leu | Tyr |
| 65 | | | | | 70 | | | | | 75 | | | | | 80 |
| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |
| Ala | Lys | Gly | Val | Arg | Val | Ser | Phe | Asp | Tyr | Trp | Gly | Gln | Gly | Thr | Leu |
| | | | 100 | | | | | 105 | | | | | 110 | | |
| Val | Thr | Val | Ser | Ser | Ala | Ser | Thr | Lys | Gly | Pro | Ser | Val | Phe | Pro | Leu |
| | | 115 | | | | | 120 | | | | | 125 | | | |
| Ala | Pro | Ser | Ser | Lys | Ser | Thr | Ser | Gly | Gly | Thr | Ala | Ala | Leu | Gly | Cys |
| | 130 | | | | | 135 | | | | | 140 | | | | |
| Leu | Val | Lys | Asp | Tyr | Phe | Pro | Glu | Pro | Val | Thr | Val | Ser | Trp | Asn | Ser |
| 145 | | | | | 150 | | | | | 155 | | | | | 160 |
| Gly | Ala | Leu | Thr | Ser | Gly | Val | His | Thr | Phe | Pro | Ala | Val | Leu | Gln | Ser |
| | | | | 165 | | | | | 170 | | | | | 175 | |
| Ser | Gly | Leu | Tyr | Ser | Leu | Ser | Ser | Val | Val | Thr | Val | Pro | Ser | Ser | Ser |
| | | | 180 | | | | | 185 | | | | | 190 | | |
| Leu | Gly | Thr | Gln | Thr | Tyr | Ile | Cys | Asn | Val | Asn | His | Lys | Pro | Ser | Asn |
| | | 195 | | | | | 200 | | | | | 205 | | | |
| Thr | Lys | Val | Asp | Lys | Lys | Val | Glu | Pro | Lys | Ser | Cys | Asp | Lys | Thr | His |
| | 210 | | | | | 215 | | | | | 220 | | | | |
| Thr | Cys | Pro | Pro | Cys | Pro | Ala | Pro | Glu | Ala | Ala | Gly | Gly | Pro | Ser | Val |
| 225 | | | | | 230 | | | | | 235 | | | | | 240 |
| Phe | Leu | Phe | Pro | Pro | Lys | Pro | Lys | Asp | Thr | Leu | Met | Ile | Ser | Arg | Thr |
| | | | | 245 | | | | | 250 | | | | | 255 | |
| Pro | Glu | Val | Thr | Cys | Val | Val | Val | Asp | Val | Ser | His | Glu | Asp | Pro | Glu |
| | | | 260 | | | | | 265 | | | | | 270 | | |
| Val | Lys | Phe | Asn | Trp | Tyr | Val | Asp | Gly | Val | Glu | Val | His | Asn | Ala | Lys |
| | | 275 | | | | | 280 | | | | | 285 | | | |
| Thr | Lys | Pro | Arg | Glu | Glu | Gln | Tyr | Asn | Ser | Thr | Tyr | Arg | Val | Val | Ser |
| | 290 | | | | | 295 | | | | | 300 | | | | |
| Val | Leu | Thr | Val | Leu | His | Gln | Asp | Trp | Leu | Asn | Gly | Lys | Glu | Tyr | Lys |
| 305 | | | | | 310 | | | | | 315 | | | | | 320 |
| Cys | Lys | Val | Ser | Asn | Lys | Ala | Leu | Gly | Ala | Pro | Ile | Glu | Lys | Thr | Ile |
| | | | | 325 | | | | | 330 | | | | | 335 | |
| Ser | Lys | Ala | Lys | Gly | Gln | Pro | Arg | Glu | Pro | Gln | Val | Tyr | Thr | Leu | Pro |
| | | | 340 | | | | | 345 | | | | | 350 | | |
| Pro | Ser | Arg | Asp | Glu | Leu | Thr | Lys | Asn | Gln | Val | Ser | Leu | Thr | Cys | Leu |
| | | 355 | | | | | 360 | | | | | 365 | | | |
| Val | Lys | Gly | Phe | Tyr | Pro | Ser | Asp | Ile | Ala | Val | Glu | Trp | Glu | Ser | Asn |
| | 370 | | | | | 375 | | | | | 380 | | | | |

-continued

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
        420                 425                 430

His Asn His Tyr Thr Gln Lys Ser Leu Ser Leu Ser Pro Gly Gly Gly
            435                 440                 445

Gly Gly Ser Gly Gly Gly Ser Gly Gly Gly Ser Gly Gly Gly
    450                 455                 460

Gly Ser Glu Val Gln Leu Leu Glu Ser Gly Gly Gly Leu Val Gln Pro
465                 470                 475                 480

Gly Gly Ser Leu Arg Leu Ser Cys Ala Ala Ser Gly Phe Thr Phe Ser
            485                 490                 495

Ser His Ala Met Ser Trp Val Arg Gln Ala Pro Gly Lys Gly Leu Glu
        500                 505                 510

Trp Val Ser Ala Ile Trp Ala Ser Gly Glu Gln Tyr Tyr Ala Asp Ser
        515                 520                 525

Val Lys Gly Arg Phe Thr Ile Ser Arg Asp Asn Ser Lys Asn Thr Leu
        530                 535                 540

Tyr Leu Gln Met Asn Ser Leu Arg Ala Glu Asp Thr Ala Val Tyr Tyr
545                 550                 555                 560

Cys Ala Lys Gly Trp Leu Gly Asn Phe Asp Tyr Trp Gly Gln Gly Thr
            565                 570                 575

Leu Val Thr Val Ser Ser Ala Ser Val Ala Ala Pro Ser Val Phe Ile
        580                 585                 590

Phe Pro Pro Ser Asp Glu Gln Leu Lys Ser Gly Thr Ala Ser Val Val
        595                 600                 605

Cys Leu Leu Asn Asn Phe Tyr Pro Arg Glu Ala Lys Val Gln Trp Lys
    610                 615                 620

Val Asp Asn Ala Leu Gln Ser Gly Asn Ser Gln Glu Ser Val Thr Glu
625                 630                 635                 640

Gln Asp Ser Lys Asp Ser Thr Tyr Ser Leu Ser Ser Thr Leu Thr Leu
            645                 650                 655

Ser Lys Ala Asp Tyr Glu Lys His Lys Val Tyr Ala Cys Glu Val Thr
        660                 665                 670

His Gln Gly Leu Ser Ser Pro Val Thr Lys Ser Phe Asn Arg Gly Glu
        675                 680                 685

Cys

<210> SEQ ID NO 19
<211> LENGTH: 215
<212> TYPE: PRT
<213> ORGANISM: Artificial Sequence
<220> FEATURE:
<223> OTHER INFORMATION: DR5 (5E11) LC

<400> SEQUENCE: 19

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

```
Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
 65              70                  75                      80

Pro Glu Asp Phe Ala Val Tyr Tyr Cys Gln Gln Gly Thr Thr His Pro
                 85                  90                  95

Ile Thr Phe Gly Gln Gly Thr Lys Val Glu Ile Lys Arg Thr Val Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
210                 215

<210> SEQ ID NO 20
<211> LENGTH: 214
<212> TYPE: PRT
<213> ORGANISM: Artificial Sequence
<220> FEATURE:
<223> OTHER INFORMATION: FAP (28H1) _VLCH1

<400> SEQUENCE: 20

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Arg Ser
             20                  25                  30

Tyr Leu Ala Trp Tyr Gln Lys Pro Gly Gln Ala Pro Arg Leu Leu
         35                  40                  45

Ile Ile Gly Ala Ser Thr Arg Ala Thr Gly Ile Pro Asp Arg Phe Ser
    50                  55                  60

Gly Ser Gly Ser Gly Thr Asp Phe Thr Leu Thr Ile Ser Arg Leu Glu
 65              70                  75                      80

Pro Glu Asp Phe Ala Val Tyr Tyr Cys Gln Gln Gly Gln Val Ile Pro
                 85                  90                  95

Pro Thr Phe Gly Gln Gly Thr Lys Val Glu Ile Lys Ser Ser Ala Ser
                100                 105                 110

Thr Lys Gly Pro Ser Val Phe Pro Leu Ala Pro Ser Ser Lys Ser Thr
            115                 120                 125

Ser Gly Gly Thr Ala Ala Leu Gly Cys Leu Val Lys Asp Tyr Phe Pro
130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Gln Thr Tyr Ile
            180                 185                 190
```

```
Cys Asn Val Asn His Lys Pro Ser Asn Thr Lys Val Asp Lys Lys Val
            195                 200                 205

Glu Pro Lys Ser Cys Asp
    210

<210> SEQ ID NO 21
<211> LENGTH: 10
<212> TYPE: PRT
<213> ORGANISM: Artificial Sequence
<220> FEATURE:
<223> OTHER INFORMATION: modified peptide

<400> SEQUENCE: 21

Ala Val Pro Ile Ala Gln Lys Ser Glu Lys
1               5                   10

<210> SEQ ID NO 22
<211> LENGTH: 125
<212> TYPE: PRT
<213> ORGANISM: Artificial Sequence
<220> FEATURE:
<223> OTHER INFORMATION: BIR2 domain used for the TR-FRET assay

<400> SEQUENCE: 22

Met Arg His His His His His His Arg Asp His Phe Ala Leu Asp Arg
1               5                   10                  15

Pro Ser Glu Thr His Ala Asp Tyr Leu Leu Arg Thr Gly Gln Val Val
            20                  25                  30

Asp Ile Ser Asp Thr Ile Tyr Pro Arg Asn Pro Ala Met Tyr Ser Glu
        35                  40                  45

Glu Ala Arg Leu Lys Ser Phe Gln Asn Trp Pro Asp Tyr Ala His Leu
    50                  55                  60

Thr Pro Arg Glu Leu Ala Ser Ala Gly Leu Tyr Tyr Thr Gly Ile Gly
65                  70                  75                  80

Asp Gln Val Gln Cys Phe Ala Cys Gly Gly Lys Leu Lys Asn Trp Glu
                85                  90                  95

Pro Gly Asp Arg Ala Trp Ser Glu His Arg Arg His Phe Pro Asn Cys
            100                 105                 110

Phe Phe Val Leu Gly Arg Asn Leu Asn Ile Arg Ser Glu
        115                 120                 125

<210> SEQ ID NO 23
<211> LENGTH: 125
<212> TYPE: PRT
<213> ORGANISM: Artificial Sequence
<220> FEATURE:
<223> OTHER INFORMATION: BIR3 domain used for the TR-FRET assay

<400> SEQUENCE: 23

Met Arg His His His His His His Arg Ser Asp Ala Val Ser Ser Asp
1               5                   10                  15

Arg Asn Phe Pro Asn Ser Thr Asn Leu Pro Arg Asn Pro Ser Met Ala
            20                  25                  30

Asp Tyr Glu Ala Arg Ile Phe Thr Phe Gly Thr Trp Ile Tyr Ser Val
        35                  40                  45

Asn Lys Glu Gln Leu Ala Arg Ala Gly Phe Tyr Ala Leu Gly Glu Gly
    50                  55                  60

Asp Lys Val Lys Cys Phe His Cys Gly Gly Gly Leu Thr Asp Trp Lys
65                  70                  75                  80

Pro Ser Glu Asp Pro Trp Glu Gln His Ala Lys Trp Tyr Pro Gly Cys
```

|  |  | 85 |  |  | 90 |  |  | 95 |  |  |
|--|--|--|--|--|--|--|--|--|--|--|
Lys Tyr Leu Leu Glu Gln Lys Gly Gln Glu Tyr Ile Asn Asn Ile His
|  | 100 |  |  | 105 |  |  | 110 |  |
Leu Thr His Ser Leu Glu Glu Cys Leu Val Arg Thr Thr
|  | 115 |  |  | 120 |  |  | 125 |  |

DIMERIC COMPOUNDS

CROSS-REFERENCE TO RELATED APPLICATIONS

This application is a National Stage Application of PCT/EP2017/060732 filed May 5, 2017, which claims priority from European Patent Application No. 16168792.6, filed on May 9, 2016. The priority of both said PCT and European Patent Application are claimed. Each of prior mentioned applications is hereby incorporated by reference herein in its entirety.

SEQUENCE LISTING

The instant application contains a Sequence Listing which has been filed electronically in ASCII format and is hereby incorporated by reference in its entirety, Said ASCII copy, created on May 31, 2019, is named 036844-99194 (P33389)_LSL.txt and is 29,358 bytes in size.

FIELD OF THE INVENTION

The present invention relates to dimeric compounds which act as inhibitors of SMAC protein binding to Inhibitor of Apoptosis Proteins (IAPs), and/or inhibitors of activated caspase protein binding to IAPs. These molecules are useful in the amelioration, treatment or control of cancer, especially solid tumors. They can be combined with other agents such as DR5/FAP agonist antibodies.

These compounds bind to the BIR2 or BIR2 and BIR3 regions of IAP proteins, including XIAP and cIAP, resulting in activation or reactivation of the caspase cascade and, as such, are useful for the treatment of proliferative diseases, including cancer.

BACKGROUND OF THE INVENTION

Cancer is a disease of uncontrolled cell growth causing local expansion of a tumor and, potentially, distant metastases. One mechanism by which cancer cells grow is by avoidance of apoptosis, or programmed cell death. Alterations in apoptotic pathways have been linked to cancer cells being resistant to standard treatments, e.g., chemotherapeutics or radiation, and to the incidence and progression of cancer. See, e.g., E. Dean et al., "X-linked inhibitor of apoptosis protein as a therapeutic target," Expert Opin. Ther. Targets (2007) 11(11):1459-1471.

The two basic pathways for apoptotic cell death are the intrinsic pathway and the extrinsic pathway. The intrinsic apoptotic pathway can be initiated by various mechanisms including cellular stress and drug-induced DNA damage. The extrinsic pathway can be initiated by activation of the death receptors by a chemokine. Initiation of either pathway results in the activation of a family of proteases called caspases. Once activated, the caspases can act to cleave a variety of substrates creating a cascade of events that lead to the activation of the effector caspases 3 and 7 and eventual cell death. The IAP family of proteins can bind to and inhibit the activity of caspases thus inhibiting apoptosis. See, e.g., Dean, supra at 1460.

The IAPs can contain up to three copies of homologous structural domains called baculoviral IAP repeat (BIR) domains, BIR1, BIR2 and BIR3. The BIR3 domain of the prototypical IAPs, cIAP and XIAP, can bind to and inhibit activated caspase 9. The BIR2 domain, in contrast, binds to and inhibits caspases 3 and 7. The proapoptotic protein Smac (also known as DIABLO) can block the BIR2 and BIR3 domains of IAPs competing with activated caspases resulting in release of the activated caspases from the IAPs and completion of the apoptotic program. See, e.g., S. Wang, "Design of Small-Molecule Smac Mimetics as IAP Antagonists," Current Topics in Microbiology and Immunology 348, DOI 10.1007/82_2010_111, pp. 89-113.

Peptides and small molecules have been reported to bind to the BIR3 region of XIAP and cIAP, mimicking the action of Smac protein and releasing activated caspases. See, e.g., Dean, supra; and M. Gyrd-Hanse et al., "IAPs: From caspase inhibitors to modulators of NF-κB, inflammation and cancer," Nature Review/Cancer, August 2010, Vol 10:561-574.

XIAP inhibitors may potently sensitize previously resistant human cancer cell lines to DR5-induced apoptosis.

WO 2014060770 relates to new bicyclic heterocycles that might be antagonists of the IAP family of proteins (IAP). WO2014161845 relates to bispecific antibodies comprising at least one antigen binding site specific for DR5 and at least one antigen binding site specific for FAP, antibodies specific for DR5, methods for their production, pharmaceutical compositions containing said antibodies, and uses thereof.

It remains a problem in the art to find ways of effective therapies for targeting cancer using a XIAP inhibitor alone or in combination with DR5/FAP agonist antibodies.

SUMMARY OF THE INVENTION

One aspect of the present invention is a compound of Formula I

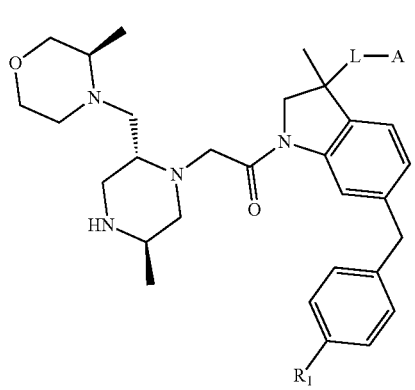

or pharmaceutically acceptable salts thereof, wherein L, A and $R_1$ are as described herein.

The present invention also relates to pharmaceutical compositions comprising one or more compounds of the invention, or a pharmaceutically acceptable salt thereof, and a pharmaceutically acceptable carrier or excipient.

The present invention further relates to a method of ameliorating, controlling or treating cancer, including specifically solid tumors, for example lung, pancreatic, colon, breast, bone and prostate cancers in a mammal, specifically a human, comprising administering to said mammal a therapeutically effective amount of a compound according to the invention or a pharmaceutically acceptable salt thereof.

DETAILED DESCRIPTION OF THE INVENTION

Definitions

Unless otherwise defined, all technical and scientific terms used herein have the same meaning as commonly understood by one of ordinary skill in the art to which this invention belongs.

As used herein, the following terms shall have the following definitions.

The term "$C_{1-6}$-alkyl", alone or in combination with other groups, means a monovalent linear or branched saturated hydrocarbon of 1 to 6 carbon atoms and is used alone or in combination with other terms. Examples include methyl (Me), ethyl (Et), propyl, isopropyl, butyl (also known as n-butyl), iso-butyl, sec-butyl, tert-butyl, pentyl, hexyl, and the like.

The term "$C_{1-6}$-alkoxy", alone or in combination with other groups, stands for an —O—$C_{1-6}$-alkyl radical which may be linear or branched, with single or multiple branching, wherein the alkyl group in general comprises 1 to 6 carbon atoms, for example, methoxy (OMe, MeO), ethoxy (OEt), propoxy, isopropoxy (i-propoxy), n-butoxy, i-butoxy (iso-butoxy), 2-butoxy (sec-butoxy), t-butoxy (tert-butoxy), isopentyloxy (i-pentyloxy) and the like. Particular "$C_{1-6}$-alkoxy" are groups with 1 to 4 carbon atoms, in particular 2-methoxypropanyl.

The term "$C_{1-6}$-alkoxy-$C_{1-6}$-alkyl", alone or in combination with other groups, means a "$C_{1-6}$-alkyl" as described herein that is substituted by a "$C_{1-6}$-alkoxy" as described herein. Examples include —C(H,Me)-OMe and the like.

The term "halogen" means at atom selected from F, Cl, Br or I. In particular embodiments halogen means F.

The term "$C_{3-6}$-heterocycloalkyl" alone or in combination with other groups, refers to a 3 to 6 membered carbon ring, having at least one heteroatom like O, N or S, in particular one O. A specific example is tetrahydropyranyl.

The term "half maximal inhibitory concentration" ($IC_{50}$) denotes the concentration of a particular compound required for obtaining 50% inhibition of a biological process in vitro. $IC_{50}$ values can be converted logarithmically to $pIC_{50}$ values (−log $IC_{50}$), in which higher values indicate exponentially greater potency. The $IC_{50}$ value is not an absolute value but depends on experimental conditions e.g. concentrations employed. The $IC_{50}$ value can be converted to an absolute inhibition constant (Ki) using the Cheng-Prusoff equation (Biochem. Pharmacol. (1973) 22:3099). The term "inhibition constant" (Ki) denotes the absolute binding affinity of a particular inhibitor to a receptor. It is measured using competition binding assays and is equal to the concentration where the particular inhibitor would occupy 50% of the receptors if no competing ligand (e.g. a radioligand) was present. Ki values can be converted logarithmically to pKi values (−log Ki), in which higher values indicate exponentially greater potency.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

"Pharmaceutically acceptable" such as pharmaceutically acceptable carrier, excipient, etc., means pharmacologically acceptable and substantially non-toxic to the subject to which the particular compound is administered.

"Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, trifluoroacetic acid and the like. Sample base-addition salts include those derived from ammonium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds. See e.g. Ansel et al., Pharmaceutical Dosage Forms and Drug Delivery Systems (1995) at pgs. 456-457.

As used in this application, if a formula or group appears to be missing a substituent, that is it appears the valence is not complete, it is presumed the missing substituent is an H.

Whenever a chiral carbon is present in a chemical structure, it is intended that all stereoisomers associated with that chiral carbon are encompassed by the structure as pure stereoisomers as well as mixtures thereof.

The invention also provides pharmaceutical compositions, methods of using, and methods of preparing the aforementioned compounds.

The term "A bispecific antibody that specifically binds death receptor 5 (DR5) and Fibroblast Activation Protein (FAP)" refers to a bispecific antibody that is capable of binding DR5 and FAP with sufficient affinity such that the antibody is useful as a diagnostic and/or therapeutic agent in targeting cells expressing DR5 and FAP). Specifically "A bispecific antibody that specifically binds death receptor 5 (DR5) and Fibroblast Activation Protein (FAP)" refers to a bispecific antibody targeting DR5 on a tumor cell and FAP in the stroma surrounding said tumor. In one embodiment, the extent of binding of a bispecific antibody that specifically binds death receptor 5 (DR5) and Fibroblast Activation Protein (FAP) to an unrelated, non-FAP or non-DR5 protein is less than about 10% of the binding of the antibody to DR5 or FAP as measured, e.g., by an Enzyme-linked immunosorbent assay (ELISA), surface plasmon resonance (SPR) based assays (e.g. Biacore) or flow cytometry (FACS). In certain embodiments, a bispecific antibody that specifically binds death receptor 5 (DR5) and Fibroblast Activation Protein (FAP) has a dissociation constant (Kd) of ≤1 µM, ≤100 nM, ≤10 nM, ≤1 nM, ≤0.1 nM, ≤0.01 nM, or ≤0.001 nM (e.g. $10^{-8}$M or less, e.g. from $10^{-8}$M to $10^{-13}$ M, e.g., from $10^{-9}$ M to $10^{-13}$ M). In certain embodiments, a bispecific antibody that specifically binds death receptor 5 (DR5) and Fibroblast Activation Protein (FAP) binds to an epitope of DR5 or FAP that is conserved among DR5 or FAP from different species. Preferably said bispecific antibody binds to human and cynomolgus monkey DR5 and to human, cynomolgus monkey and mouse FAP.

The terms "An antibody that specifically binds death receptor 5 (DR5)" refers to an antibody that is capable of binding DR5 with sufficient affinity such that the antibody is useful as a diagnostic and/or therapeutic agent in targeting cells expressing DR5. In one embodiment, the extent of binding of an antibody that specifically binds death receptor 5 (DR5) to an unrelated non-DR5 protein is less than about 10% of the binding of the antibody to DR5 as measured, e.g., by a radioimmunoassay (RIA) or flow cytometry (FACS). In certain embodiments, an antibody that specifically binds death receptor 5 (DR5) has a dissociation constant (Kd) of ≤1 μM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M). In certain embodiments, an antibody that specifically binds death receptor 5 (DR5) binds to an epitope of DR5 that is conserved among DR5 from different species. In particular said antibody binds to human and cynomolgus monkey DR5. The term "An antibody that specifically binds death receptor 5 (DR5)" also encompasses bispecific antibodies that are capable of binding DR5 and a second antigen.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

The term "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies, cross-Fab fragments; linear antibodies; single-chain antibody molecules (e.g. scFv); and multispecific antibodies formed from antibody fragments. scFv antibodies are, e.g. described in Houston, J. S., Methods in Enzymol. 203 (1991) 46-96). In addition, antibody fragments comprise single chain polypeptides having the characteristics of a VH domain, namely being able to assemble together with a VL domain, or of a VL domain, namely being able to assemble together with a VH domain to a functional antigen binding site and thereby providing the antigen binding property of full length antibodies.

The term "Fab fragment" refers to an antibody fragment comprising a light chain fragment comprising a VL domain and a constant domain of a light chain (CL), and a VH domain and a first constant domain (CH1) of a heavy chain. In one embodiment the bispecific antibodies of the invention comprise at least one Fab fragment, wherein either the variable regions or the constant regions of the heavy and light chain are exchanged. Due to the exchange of either the variable regions or the constant regions, said Fab fragment is also referred to as "cross-Fab fragment" or "xFab fragment" or "crossover Fab fragment". Two different chain compositions of a crossover Fab molecule are possible and comprised in the bispecific antibodies of the invention: On the one hand, the variable regions of the Fab heavy and light chain are exchanged, i.e. the crossover Fab molecule comprises a peptide chain composed of the light chain variable region (VL) and the heavy chain constant region (CH1), and a peptide chain composed of the heavy chain variable region (VH) and the light chain constant region (CL). This crossover Fab molecule is also referred to as CrossFab $_{(VLVH)}$. On the other hand, when the constant regions of the Fab heavy and light chain are exchanged, the crossover Fab molecule comprises a peptide chain composed of the heavy chain variable region (VH) and the light chain constant region (CL), and a peptide chain composed of the light chain variable region (VL) and the heavy chain constant region (CH1). This crossover Fab molecule is also referred to as CrossFab $_{(CLCH1)}$. Bispecific antibody formats comprising crossover Fab fragments have been described, for example, in WO 2009/080252, WO 2009/080253, WO 2009/080251, WO 2009/080254, WO 2010/136172, WO 2010/145792 and WO 2013/026831.

The terms "single chain Fab fragment" or "scFab" is a polypeptide consisting of an antibody heavy chain variable domain (VH), an antibody constant domain 1 (CH1), an antibody light chain variable domain (VL), an antibody light chain constant domain (CL) and a linker, wherein said antibody domains and said linker have one of the following orders in N-terminal to C-terminal direction:
a) VH-CH1-linker-VL-CL, b) VL-CL-linker-VH-CH1, c) VH-CL-linker-VL-CH1 or d) VL-CH1-linker-VH-CL; and wherein said linker is a polypeptide of at least 30 amino acids, preferably between 32 and 50 amino acids. Said single chain Fab fragments a) VH-CH1-linker-VL-CL, b) VL-CL-linker-VH-CH1, c) VH-CL-linker-VL-CH1 and d) VL-CH1-linker-VH-CL, are stabilized via the natural disulfide bond between the CL domain and the CH1 domain. In addition, these single chain Fab molecules might be further stabilized by generation of interchain disulfide bonds via insertion of cysteine residues (e.g. position 44 in the variable heavy chain and position 100 in the variable light chain according to Kabat numbering).

The term "N-terminus denotes the last amino acid of the N-terminus. The term "C-terminus denotes the last amino acid of the C-terminus.

The phrase "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "antigen binding domain" refers to the part of an antigen binding molecule that comprises the area which specifically binds to and is complementary to part or all of an antigen. Where an antigen is large, an antigen binding molecule may only bind to a particular part of the antigen, which part is termed an epitope. An antigen binding domain may be provided by, for example, one or more antibody variable domains (also called antibody variable regions). Preferably, an antigen binding domain comprises an antibody light chain variable region (VL) and an antibody heavy chain variable region (VH).

The term "chimeric" antibody refers to an antibody in which a portion of the heavy and/or light chain is derived from a particular source or species, while the remainder of the heavy and/or light chain is derived from a different source or species, usually prepared by recombinant DNA techniques. Chimeric antibodies comprising a rabbit variable region and a human constant region are preferred. Other preferred forms of "chimeric antibodies" encompassed by the present invention are those in which the constant region has been modified or changed from that of the original antibody to generate the properties according to the invention, especially in regard to C1q binding and/or Fc receptor (FcR) binding. Such chimeric antibodies are also referred to as "class-switched antibodies". Chimeric antibodies are the product of expressed immunoglobulin genes comprising DNA segments encoding immunoglobulin variable regions and DNA segments encoding immunoglobulin constant regions. Methods for producing chimeric antibodies involve conventional recombinant DNA and gene transfection techniques are well known in the art. See e.g. Morrison, S. L., et al., Proc. Natl. Acad. Sci. USA 81 (1984) 6851-6855; U.S. Pat. Nos. 5,202,238 and 5,204,244.

The term "Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); antibody-dependent cellular phagocytosis (ADCP), cytokine secretion, immune complex-mediated antigen uptake by antigen presenting cells; down regulation of cell surface receptors (e.g. B cell receptor); and B cell activation.

The terms "engineer, engineered, engineering", are considered to include any manipulation of the peptide backbone or the post-translational modifications of a naturally occurring or recombinant polypeptide or fragment thereof. Engineering includes modifications of the amino acid sequence, of the glycosylation pattern, or of the side chain group of individual amino acids, as well as combinations of these approaches.

The term "amino acid mutation" as used herein is meant to encompass amino acid substitutions, deletions, insertions, and modifications. Any combination of substitution, deletion, insertion, and modification can be made to arrive at the final construct, provided that the final construct possesses the desired characteristics, e.g., reduced binding to an Fc receptor, or increased association with another peptide. Amino acid sequence deletions and insertions include amino- and/or carboxy-terminal deletions and insertions of amino acids. Particular amino acid mutations are amino acid substitutions. For the purpose of altering e.g. the binding characteristics of an Fc region, non-conservative amino acid substitutions, i.e. replacing one amino acid with another amino acid having different structural and/or chemical properties, are particularly preferred. Amino acid substitutions include replacement by non-naturally occurring amino acids or by naturally occurring amino acid derivatives of the twenty standard amino acids (e.g. 4-hydroxyproline, 3-methylhistidine, ornithine, homoserine, 5-hydroxylysine). Amino acid mutations can be generated using genetic or chemical methods well known in the art. Genetic methods may include site-directed mutagenesis, PCR, gene synthesis and the like. It is contemplated that methods of altering the side chain group of an amino acid by methods other than genetic engineering, such as chemical modification, may also be useful. Various designations may be used herein to indicate the same amino acid mutation. For example, a substitution from proline at position 329 of the Fc domain to glycine can be indicated as 329G, G329, $G_{329}$, P329G, or Pro329Gly.

The term "Fc domain" or "Fc region" herein is used to define a C-terminal region of an immunoglobulin heavy chain that contains at least a portion of the constant region. The term includes native sequence Fc regions and variant Fc regions. Although the boundaries of the Fc region of an IgG heavy chain might vary slightly, the human IgG heavy chain Fc region is usually defined to extend from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991. A "subunit" of an Fc domain as used herein refers to one of the two polypeptides forming the dimeric Fc domain, i.e. a polypeptide comprising C-terminal constant regions of an immunoglobulin heavy chain, capable of stable self-association. For example, a subunit of an IgG Fc domain comprises an IgG CH2 and an IgG CH3 constant domain.

The phrase "modification promoting the association of the first and the second subunit of the Fc domain" means a manipulation of the peptide backbone or the post-translational modifications of an Fc domain subunit that reduces or prevents the association of a polypeptide comprising the Fc domain subunit with an identical polypeptide to form a homodimer. A modification promoting association as used herein particularly includes separate modifications made to each of the two Fc domain subunits desired to associate (i.e. the first and the second subunit of the Fc domain), wherein the modifications are complementary to each other so as to promote association of the two Fc domain subunits. For example, a modification promoting association may alter the structure or charge of one or both of the Fc domain subunits so as to make their association sterically or electrostatically favorable, respectively. Thus, (hetero)dimerization occurs between a polypeptide comprising the first Fc domain subunit and a polypeptide comprising the second Fc domain subunit, which might be non-identical in the sense that further components fused to each of the subunits (e.g. antigen binding moieties) are not the same. In some embodiments the modification promoting association comprises an amino acid mutation in the Fc domain, specifically an amino acid substitution. In a particular embodiment, the modification promoting association comprises a separate amino acid mutation, specifically an amino acid substitution, in each of the two subunits of the Fc domain.

The terms "full length antibody," "intact antibody," and "whole antibody" are used herein interchangeably to refer to an antibody having a structure substantially similar to a native antibody structure or having heavy chains that contain an Fc region as defined herein.

The term "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues. As also mentioned for chimeric and humanized antibodies according to the invention the term "human antibody" as used herein also comprises such antibodies which are modified in the constant region to generate the properties according to the invention, especially in regard to C1q binding and/or FcR binding, e.g. by "class switching" i.e. change or mutation of Fc parts (e.g. from IgG1 to IgG4 and/or IgG1/IgG4 mutation.)

The term "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization. Other forms of "humanized antibodies" encompassed by the present invention are those in which the constant region has been additionally modified or changed from that of the original antibody to generate the properties according to the invention, especially in regard to C1q binding and/or Fc receptor (FcR) binding.

The term "hypervariable region" or "HVR," as used herein refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, J. Mol. Biol. 196:901-917 (1987).) Exemplary CDRs (CDR-L1, CDR-L2, CDR-L3, CDR-H1, CDR-H2, and CDR-H3) occur at amino acid residues 24-34 of L, 50-56 of L2, 89-97 of L3, 31-35B of H1, 50-65 of H2, and 95-102 of H3. (Kabat et al., Sequences of Proteins of Immunological Interest, 5th Ed. Public Health Service, National Institutes of Health, Bethesda, Md. (1991).) Hypervariable regions (HVRs) are also referred to as complementarity determining regions (CDRs), and these terms are used herein interchangeably in reference to portions of the variable region that form the antigen binding regions. This particular region has been described by Kabat et al., U.S. Dept. of Health and Human Services, "Sequences of Proteins of Immunological Interest" (1983) and by Chothia et al., J. Mol. Biol. 196:901-917 (1987), where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table A as a comparison. The exact residue numbers which encompass a particular CDR will vary depending on the sequence and size of the CDR. Those skilled in the art can routinely determine which residues comprise a particular CDR given the variable region amino acid sequence of the antibody.

TABLE A

CDR Definitions[1]

| CDR | Kabat | Chothia | AbM[2] |
|---|---|---|---|
| $V_H$ CDR1 | 31-35 | 26-32 | 26-35 |
| $V_H$ CDR2 | 50-65 | 52-58 | 50-58 |
| $V_H$ CDR3 | 95-102 | 95-102 | 95-102 |
| $V_L$ CDR1 | 24-34 | 26-32 | 24-34 |
| $V_L$ CDR2 | 50-56 | 50-52 | 50-56 |
| $V_L$ CDR3 | 89-97 | 91-96 | 89-97 |

[1]Numbering of all CDR definitions in Table A is according to the numbering conventions set forth by Kabat et al. (see below).
[2]"AbM" with a lowercase "b" as used in Table A refers to the CDRs as defined by Oxford Molecular's "AbM" antibody modeling software.

Kabat et al. also defined a numbering system for variable region sequences that is applicable to any antibody. One of ordinary skill in the art can unambiguously assign this system of "Kabat numbering" to any variable region sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an antibody variable region are according to the Kabat numbering system.

With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, Front. Biosci. 13:1619-1633 (2008).) Unless otherwise indicated, HVR residues and other residues in the variable domain (e.g., FR residues) are numbered herein according to Kabat et al., supra.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., J. Chromatogr. B 848:79-87 (2007).

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term "naked antibody" refers to an antibody that is not conjugated to a heterologous moiety (e.g., a cytotoxic moiety) or radiolabel. The naked antibody may be present in a pharmaceutical formulation.

The terms "Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

The phrase "No substantial cross-reactivity" means that a molecule (e.g., an antibody) does not recognize or specifically bind an antigen different from the actual target antigen of the molecule (e.g. an antigen closely related to the target antigen), particularly when compared to that target antigen. For example, an antibody may bind less than about 10% to less than about 5% to an antigen different from the actual target antigen, or may bind said antigen different from the actual target antigen at an amount consisting of less than about 10%, 9%, 8% 7%, 6%, 5%, 4%, 3%, 2%, 1%, 0.5%, 0.2%, or 0.1%, preferably less than about 2%, 1%, or 0.5%, and most preferably less than about 0.2% or 0.1% antigen different from the actual target antigen.

The phrase "Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y, where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "death receptor 5 (DR5)", as used herein, refers to any native DR5 from any vertebrate source, including mammals such as primates (e.g. humans) and rodents (e.g., mice and rats), unless otherwise indicated. The term encompasses "full-length," unprocessed DR5 as well as any form of DR5 that results from processing in the cell. The term also encompasses naturally occurring variants of DR5, e.g., splice variants or allelic variants. The amino acid sequence of an exemplary human DR5 is disclosed in WO 2011/039126.

The term "Fibroblast activation protein (FAP)", as used herein, refers to any native FAP from any vertebrate source, including mammals such as primates (e.g. humans) and rodents (e.g., mice and rats), unless otherwise indicated. The term encompasses "full-length," unprocessed FAP as well as any form of FAP that results from processing in the cell. The term also encompasses naturally occurring variants of FAP, e.g., splice variants or allelic variants. Preferably, an anti-FAP antibody of the invention binds to the extracellular domain of FAP. The amino acid sequence of exemplary FAP polypeptide sequences, including the sequence of human FAP, are disclosed in WO 2012/020006.

The term cancer as used herein refers to proliferative diseases, such as the cancer is colorectal cancer, sarcoma, head and neck cancer, squamous cell carcinoma, breast cancer, pancreatic cancer, gastric cancer, non-small-cell lung carcinoma, small-cell lung cancer and mesothelioma, including refractory versions of any of the above cancers, or a combination of one or more of the above cancers. In one embodiment, the cancer is colorectal cancer and optionally the chemotherapeutic agent is Irinotecan. "Sarcoma" as used herein refers to a cancer type that grows in connective tissue. Sarcomas include Gastro-intestinal stromal tumours (a type of soft tissue sarcoma found in the stomach and intestines commonly known as GIST), soft tissue sarcomas (e.g. Leiomyosarcoma, Fibroblastic sarcoma, Liposarcoma, Kaposi's sarcoma (KS), Angiosarcoma, Malignant peripheral nerve sheath tumour (MPNST), Synovial sarcoma, Rhabdomyosarcoma) and bone sarcomas (e.g. Chondrosarcoma, Osteosarcoma, Ewing's sarcoma, Chordoma)

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. Kuby Immunology, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., J. Immunol. 150:880-887 (1993); Clarkson et al., Nature 352:624-628 (1991).

The term "antigen-binding site of an antibody" when used herein refer to the amino acid residues of an antibody which are responsible for antigen-binding. The antigen-binding portion of an antibody comprises amino acid residues from the "complementary determining regions" or "CDRs". "Framework" or "FR" regions are those variable domain regions other than the hypervariable region residues as herein defined. Therefore, the light and heavy chain variable domains of an antibody comprise from N- to C-terminus the domains FR1, CDR1, FR2, CDR2, FR3, CDR3, and FR4. Especially, CDR3 of the heavy chain is the region which contributes most to antigen binding and defines the antibody's properties. CDR and FR regions are determined according to the standard definition of Kabat et al., Sequences of Proteins of Immunological Interest, 5th ed., Public Health Service, National Institutes of Health, Bethesda, Md. (1991) and/or those residues from a "hypervariable loop".

Antibody specificity refers to selective recognition of the antibody for a particular epitope of an antigen. Natural antibodies, for example, are monospecific. "Bispecific antibodies" according to the invention are antibodies which have two different antigen-binding specificities. Antibodies of the present invention are specific for two different antigens, i.e. DR5 as first antigen and FAP as second antigen.

The term "monospecific" antibody as used herein denotes an antibody that has one or more binding sites each of which bind to the same epitope of the same antigen.

The term "bispecific" antibody as used herein denotes an antibody that has at least two binding sites each of which bind to different epitopes of the same antigen or a different antigen.

The antibody provided herein is a multispecific antibody, e.g. a bispecific antibody. Multispecific antibodies are monoclonal antibodies that have binding specificities for at least two different sites. Provided herein is a bispecific antibody, with binding specificities for FAP and DR5. In certain embodiments, bispecific antibodies may bind to two different epitopes of DR5. Bispecific antibodies may also be used to localize cytotoxic agents to cells which express DR5. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, Nature 305: 537 (1983)), WO 93/08829, and Traunecker et al., EMBO J. 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004); cross-linking two or more antibodies or fragments (see, e.g., U.S. Pat. No. 4,676,980, and Brennan et al., Science, 229: 81 (1985)); using leucine zippers to produce bi-specific antibodies (see, e.g., Kostelny et al., J. Immunol., 148(5):1547-1553 (1992)); using "diabody" technology for making bispecific antibody fragments (see, e.g., Hollinger et al., Proc. Natl. Acad. Sci. USA, 90:6444-6448 (1993)); and using single-chain Fv (sFv) dimers (see, e.g. Gruber et al., J. Immunol., 152:5368 (1994)); and preparing trispecific antibodies as described, e.g., in Tutt et al. J. Immunol. 147: 60 (1991).

Engineered antibodies with three or more functional antigen binding sites, including "Octopus antibodies," are also included herein (see, e.g. US 2006/0025576 A1).

The antibody or fragment herein also includes a "Dual Acting FAb" or "DAF" comprising at least one antigen binding site that binds to FAP or DR5 as well as another, different antigen (see, US 2008/0069820, for example).

The term "valent" as used within the current application denotes the presence of a specified number of binding sites in an antibody molecule. As such, the terms "bivalent", "tetravalent", and "hexavalent" denote the presence of two binding sites, four binding sites, and six binding sites, respectively, in an antibody molecule. The bispecific antibodies according to the invention are at least "bivalent" and may be "trivalent" or "multivalent" (e.g. "tetravalent" or "hexavalent").

Antibodies of the present invention have two or more binding sites and are bispecific. That is, the antibodies may be bispecific even in cases where there are more than two binding sites (i.e. that the antibody is trivalent or multivalent). Bispecific antibodies of the invention include, for example, multivalent single chain antibodies, diabodies and triabodies, as well as antibodies having the constant domain structure of full length antibodies to which further antigen-binding sites (e.g., single chain Fv, a VH domain and/or a VL domain, Fab, or (Fab)2) are linked via one or more peptide-linkers. The antibodies can be full length from a single species, or be chimerized or humanized.

The term "amino acid" as used within this application denotes the group of naturally occurring carboxy α-amino acids comprising alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

As used herein, the expressions "cell", "cell line", and "cell culture" are used interchangeably and all such designations include progeny. Thus, the words "transfectants" and "transfected cells" include the primary subject cell and cultures derived there from without regard for the number of transfers. It is also understood that all progeny may not be precisely identical in DNA content, due to deliberate or inadvertent mutations. Variant progeny that have the same function or biological activity as screened for in the originally transformed cell are included.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

As used herein, the term "binding" or "specifically binding" refers to the binding of the antibody to an epitope of the antigen in an in-vitro assay, preferably in a surface plasmon resonance assay (SPR, BIAcore, GE-Healthcare Uppsala, Sweden). The affinity of the binding is defined by the terms ka (rate constant for the association of the antibody from the antibody/antigen complex), kD (dissociation constant), and KD (kD/ka). Binding or specifically binding means a binding affinity (KD) of $10^{-8}$ mol/l or less, preferably $10^{-9}$ M to $10^{-13}$ mol/l.

Binding of the antibody to the death receptor can be investigated by a BIAcore assay (GE-Healthcare Uppsala, Sweden). The affinity of the binding is defined by the terms ka (rate constant for the association of the antibody from the antibody/antigen complex), kD (dissociation constant), and KD (kD/ka).

The term "epitope" includes any polypeptide determinant capable of specific binding to an antibody. In certain embodiments, epitope determinant include chemically active surface groupings of molecules such as amino acids, sugar side chains, phosphoryl, or sulfonyl, and, in certain embodiments, may have specific three dimensional structural characteristics, and or specific charge characteristics. An epitope is a region of an antigen that is bound by an antibody.

As used herein, the terms "engineer, engineered, engineering," particularly with the prefix "glyco-," as well as the term "glycosylation engineering" are considered to include any manipulation of the glycosylation pattern of a naturally occurring or recombinant polypeptide or fragment thereof. Glycosylation engineering includes metabolic engineering of the glycosylation machinery of a cell, including genetic manipulations of the oligosaccharide synthesis pathways to achieve altered glycosylation of glycoproteins expressed in cells. Furthermore, glycosylation engineering includes the effects of mutations and cell environment on glycosylation. In one embodiment, the glycosylation engineering is an alteration in glycosyltransferase activity. In a particular embodiment, the engineering results in altered glucosaminyltransferase activity and/or fucosyltransferase activity.

All separate embodiments may be combined.

In one embodiment, the present invention relates to compounds of Formula I

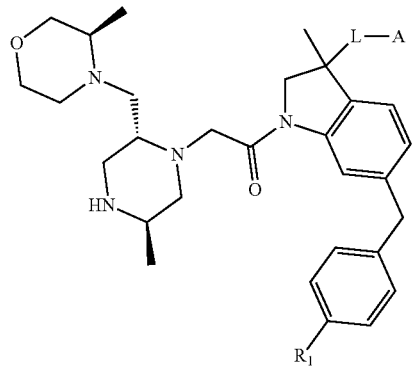

I wherein
A is selected from the group consisting of

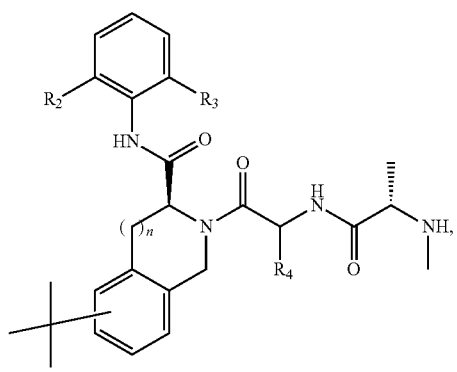

A-1

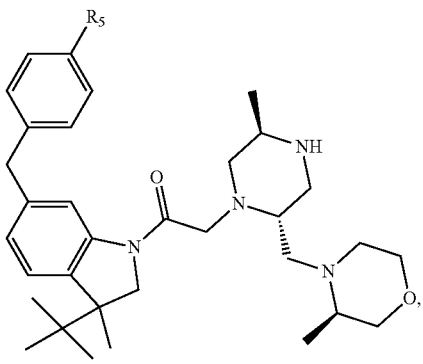

A-2

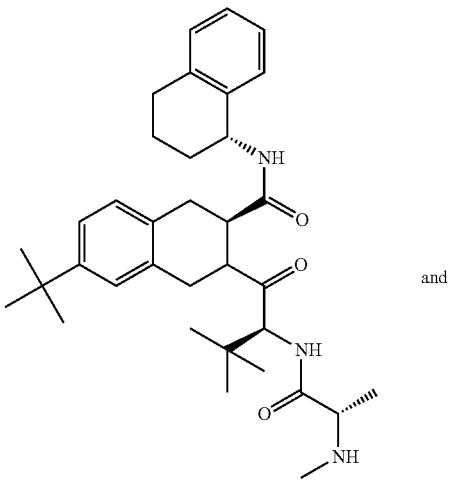

A-3 and

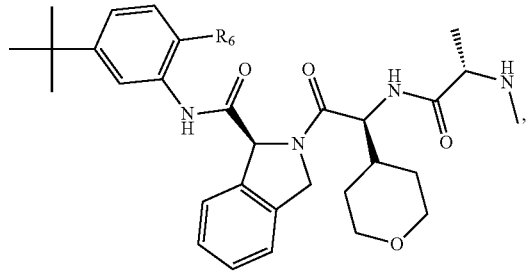

A-4 n = 0 or 1, $R_1$ is selected from the group consisting of H, halogen or $C_{1-6}$-alkyl, $R_2$ is selected from the group consisting of H, halogen or $C_{1-6}$-alkyl, $R_3$ is selected from the group consisting of H, halogen or $C_{1-6}$-alkyl, $R_4$ is selected from the group consisting of $C_{1-6}$-alkyl, $C_{1-6}$-alkoxy-$C_{1-6}$-alkyl or $C_{3-6}$-heterocycloalkyl, $R_5$ is selected from the group consisting of H, halogen or $C_{1-6}$-alkyl, $R_6$ is selected from the group consisting of H, halogen or $C_{1-6}$-alkyl, L is selected from the group consisting of

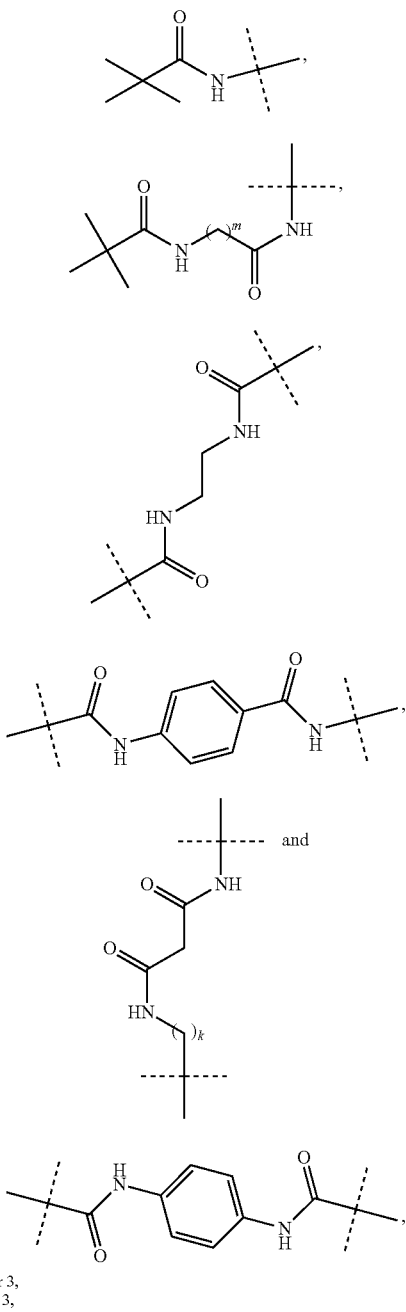

m = 1, 2 or 3,
k = 1, 2 or 3, or a pharmaceutically acceptable salt thereof.

One embodiment of the invention relates to a compound of Formula I as described herein, wherein the group L-A is selected from the group consisting of

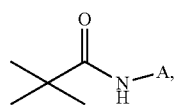

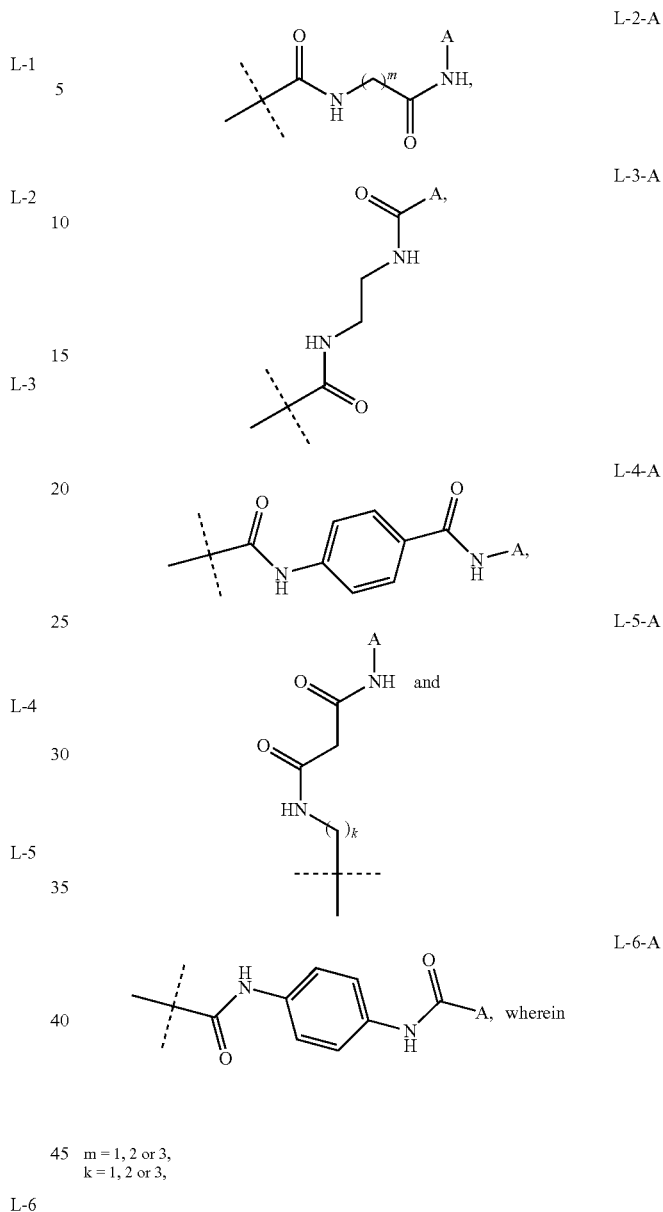

m = 1, 2 or 3,
k = 1, 2 or 3,

One embodiment of the invention relates to a compound of Formula I as described herein, wherein $R_1$ is F.

One embodiment of the invention relates to a compound of Formula I as described herein, wherein A is A-1.

One embodiment of the invention relates to a compound of Formula I as described herein, wherein A is A-1 and n is 0.

One embodiment of the invention relates to a compound of Formula I as described herein, wherein A is A-1 and n is 1.

One embodiment of the invention relates to a compound of Formula I as described herein, wherein A is A-1 and $R_2$ and $R_3$ are F.

One embodiment of the invention relates to a compound of Formula I as described herein, wherein A is A-1, n is 0 and $R_2$ and $R_3$ are F and $R_4$ is selected from the group consisting of

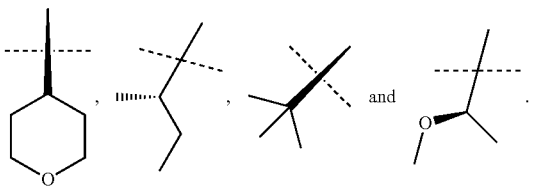

One embodiment of the invention relates to a compound of Formula I as described herein, wherein A is A-1, n is 1 and $R_2$ and $R_3$ are F and $R_4$ is selected from the group consisting of

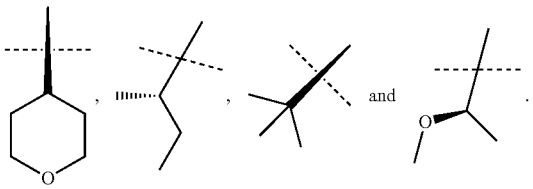

One embodiment of the invention relates to a compound of Formula I as described herein, wherein A is A-2.

One embodiment of the invention relates to a compound of Formula I as described herein, wherein A is A-2 and $R_5$ is F or wherein A is A-4 and $R_6$ is F.

One embodiment of the invention relates to a compound of Formula I as described herein, wherein A is A-2 and $R_5$ is F.

One embodiment of the invention relates to a compound of Formula I as described herein, wherein A is A-3.

One embodiment of the invention relates to a compound of Formula I as described herein, wherein A is A-4 and $R_6$ is F.

One embodiment of the invention relates to a compound of Formula I as described herein, wherein L is L-1, L-2, or L-3.

One embodiment of the invention relates to a compound of Formula I as described herein, wherein L is L-1.

One embodiment of the invention relates to a compound of Formula I as described herein, wherein L is L-2.

One embodiment of the invention relates to a compound of Formula I as described herein, wherein L is L-2 and m is 1.

One embodiment of the invention relates to a compound of Formula I as described herein, wherein L is L-2 and m is 2.

One embodiment of the invention relates to a compound of Formula I as described herein, wherein L is L-2 and m is 3.

One embodiment of the invention relates to a compound of Formula I as described herein, wherein L is L-3.

One embodiment of the invention relates to a compound of Formula I as described herein, wherein L is L-4 or L-6.

One embodiment of the invention relates to a compound of Formula I as described herein, wherein L is L-4.

One embodiment of the invention relates to a compound of Formula I as described herein, wherein L is L-5.

One embodiment of the invention relates to a compound of Formula I as described herein, wherein L is L-5 and k is 3.

One embodiment of the invention relates to a compound of Formula I as described herein, wherein L is L-6.

One embodiment of the invention relates to the compound as described herein, selected from the group consisting of N—((S)-3-((2,6-difluorophenyl)carbamoyl)-2-((S)-2-((S)-2-(methylamino)propanamido)-2-(tetrahydro-2H-pyran-4-yl)acetyl)isoindolin-5-yl)-6-(4-fluorobenzyl)-3-methyl-1-(2-((2R,5R)-5-methyl-2-(((R)-3-methylmorpholino)methyl)piperazin-1-yl)acetyl)indoline-3-carboxamide trihydrochloride, (3R)—N-[2-[[(3S)-3-[(2,6-difluorophenyl)carbamoyl]-2-[(2S)-2-[[(2S)-2-(methylamino)propanoyl]amino]-2-(oxan-4-yl)acetyl]-1,3-dihydroisoindol-5-yl]amino]-2-oxoethyl]-6-[(4-fluorophenyl)methyl]-3-methyl-1-[2-[(2R,5R)-5-methyl-2-[[(3R)-3-methylmorpholin-4-yl]methyl]piperazin-1-yl]acetyl]-2H-indole-3-carboxamide trihydrochloride, (3S)—N-[2-[[(3S)-3-[(2,6-difluorophenyl)carbamoyl]-2-[(2S)-2-[[(2S)-2-(methylamino)propanoyl]amino]-2-(oxan-4-yl)acetyl]-1,3-dihydroisoindol-5-yl]amino]-2-oxoethyl]-6-[(4-fluorophenyl)methyl]-3-methyl-1-[2-[(2R,5R)-5-methyl-2-[[(3R)-3-methylmorpholin-4-yl]methyl]piperazin-1-yl]acetyl]-2H-indole-3-carboxamide trihydrochloride, (3S)-2-[(2S)-3,3-dimethyl-2-[[(2S)-2-(methylamino)propanoyl]amino]butanoyl]-7-[[2-[[(3S)-6-[(4-fluorophenyl)methyl]-3-methyl-1-[2-[(2R,5R)-5-methyl-2-[[(3R)-3-methylmorpholin-4-yl]methyl]piperazin-1-yl]acetyl]-2H-indole-3-carbonyl]amino]acetyl]amino]-N-[(1R)-1,2,3,4-tetrahydronaphthalen-1-yl]-3,4-dihydro-1H-isoquinoline-3-carboxamide trihydrochloride, (3S)-2-[(2S)-3,3-dimethyl-2-[[(2S)-2-(methylamino)propanoyl]amino]butanoyl]-7-[[2-[[(3R)-6-[(4-fluorophenyl)methyl]-3-methyl-1-[2-[(2R,5R)-5-methyl-2-[[(3R)-3-methylmorpholin-4-yl]methyl]piperazin-1-yl]acetyl]-2H-indole-3-carbonyl]amino]acetyl]amino]-N-[(1R)-1,2,3,4-tetrahydronaphthalen-1-yl]-3,4-dihydro-1H-isoquinoline-3-carboxamide trihydrochloride, (3S)-2-((S)-3,3-dimethyl-2-((S)-2-(methylamino)propanamido)butanoyl)-7-(6-(4-fluorobenzyl)-3-methyl-1-(2-((2R,5R)-5-methyl-2-(((R)-3-methylmorpholino)methyl)piperazin-1-yl)acetyl)indoline-3-carboxamido)-N—((R)-1,2,3,4-tetrahydronaphthalen-1-yl)-1,2,3,4-tetrahydroisoquinoline-3-carboxamide trihydrochloride, (3S)-2-((S)-3,3-dimethyl-2-((S)-2-(methylamino)propanamido)butanoyl)-7-(2-(6-(4-fluorobenzyl)-3-methyl-1-(2-((2R,5R)-5-methyl-2-(((R)-3-methylmorpholino)methyl)piperazin-1-yl)acetyl)indoline-3-carboxamido)acetamido)-N—((R)-1,2,3,4-tetrahydronaphthalen-1-yl)-1,2,3,4-tetrahydroisoquinoline-3-carboxamide trihydrochloride, (3S)—N-(2,6-difluorophenyl)-7-(2-(6-(4-fluorobenzyl)-3-methyl-1-(2-((2R,5R)-5-methyl-2-(((R)-3-methylmorpholino)methyl)piperazin-1-yl)acetyl)indoline-3-carboxamido)acetamido)-2-((S)-2-((S)-2-(methylamino)propanamido)-2-(tetrahydro-2H-pyran-4-yl)acetyl)-1,2,3,4-tetrahydroisoquinoline-3-carboxamide trihydrochloride, (R)—N—((S)-3-((2,6-difluorophenyl)carbamoyl)-2-((S)-2-((S)-2-(methylamino)propanamido)-2-(tetrahydro-2H-pyran-4-yl)acetyl)isoindolin-5-yl)-6-(4-fluorobenzyl)-3-methyl-1-(2-((2R,5R)-5-methyl-2-(((R)-3-methylmorpholino)methyl)piperazin-1-yl)acetyl)indoline-3-carboxamide trihydrochloride, (R,R,R)—N,N'-(ethane-1,2-diyl)bis(6-(4-fluorobenzyl)-3-methyl-1-(2-((2R,5R)-5-methyl-2-(((R)-3-methylmorpholino)methyl)piperazin-1-yl)acetyl)indoline-3-carboxamide) trihydrochloride, (S)—N—((S)-3-((2,6-difluorophenyl)carbamoyl)-2-((S)-2-((S)-2-(methylamino)propanamido)-2-(tetrahydro-2H-pyran-4-yl)acetyl)isoindolin-5-yl)-6-(4-fluorobenzyl)-3-methyl-1-(2-((2R,5R)-5-methyl-2-(((R)-3-methylmorpholino)methyl)piperazin-1-yl)acetyl)indoline-3-carboxamide, (S)—N-(2-(((S)-1-((2,6-difluorophenyl)carbamoyl)-2-((S)-2-((S)-2-(methylamino)propanamido)-2-(tetrahydro-2H-pyran-4-yl)acetyl)isoindolin-5-yl)amino)-2-oxoethyl)-6-(4-fluorobenzyl)-3-methyl-1-(2-((2R,5R)-5-methyl-2-(((R)-3-methylmorpholino)methyl)piperazin-1-yl)acetyl)indoline-3-carboxamide trihydrochloride, (S)—N-(2-(((S)-3-((2,6-difluorophenyl)carbamoyl)-2-((2S,3R)-3-methoxy-2-((S)-2-(methylamino)propanamido)butanoyl)isoindolin-5-yl)amino)-2-oxoethyl)-6-(4-fluorobenzyl)-3-methyl-1-(2-((2R,5R)-5-methyl-2-(((R)-3-methylmorpholino)methyl)piperazin-1-yl)acetyl)indoline-3-carboxamide trihydrochloride, (S)—N-(2-(((S)-3-((2,6-difluorophenyl)carbamoyl)-2-((2S,3S)-3-methyl-2-((S)-2-(methylamino)propanamido)pentanoyl)isoindolin-5-yl)amino)-2-oxoethyl)-6-(4-fluorobenzyl)-3-methyl-1-(2-((2R,5R)-5-methyl-2-(((R)-3-methylmorpholino)methyl)piperazin-1-yl)acetyl)indoline-3-carboxamide trihydrochloride, (S)—N-(2-(((S)-3-((2,6-difluorophenyl)carbamoyl)-2-((S)-3,3-dimethyl-2-((S)-2-(methylamino)propanamido)butanoyl)isoindolin-5-yl)amino)-2-oxoethyl)-6-(4-fluorobenzyl)-3-methyl-1-(2-((2R,5R)-5-methyl-2-(((R)-3-methylmorpholino)methyl)piperazin-1-yl)acetyl)indoline-3-carboxamide trihydrochloride, (S)—N-(3-(((S)-3-((2,6-difluorophenyl)carbamoyl)-2-((S)-2-((S)-2-(methylamino)propanamido)-2-(tetrahydro-2H-pyran-4-yl)acetyl)isoindolin-5-yl)amino)-3-oxopropyl)-6-(4-fluorobenzyl)-3-methyl-1-(2-((2R,5R)-5-methyl-2-(((R)-3-methylmorpholino)methyl)piperazin-1-yl)acetyl)indoline-3-carboxamide trihydrochloride, (S)—N-(4-(((S)-3-((2,6-difluorophenyl)carbamoyl)-2-((S)-2-((S)-2-(methylamino)propanamido)-2-(tetrahydro-2H-pyran-4-yl)acetyl)isoindolin-5-yl)amino)-4-oxobutyl)-6-(4-fluorobenzyl)-3-methyl-1-(2-((2R,5R)-5-methyl-2-(((R)-3-methylmorpholino)methyl)piperazin-1-yl)acetyl)indoline-3-carboxamide trihydrochloride, N-(2-(((S)-3-((2,6-difluorophenyl)carbamoyl)-2-((S)-2-((S)-2-(methylamino)propanamido)-2-(tetrahydro-2H-pyran-4-yl)acetyl)isoindolin-5-yl)amino)-2-oxoethyl)-6-(4-fluorobenzyl)-3-methyl-1-(2-((2R,5R)-5-methyl-2-(((R)-3-methylmorpholino)methyl)piperazin-1-yl)acetyl)indoline-3-carboxamide trihydrochloride, N-(2-(4-fluoro-3-((S)-2-((S)-2-((S)-2-(methylamino)propanamido)-2-(tetrahydro-2H-pyran-4-yl)acetyl)isoindoline-1-carboxamido)benzamido)ethyl)-6-(4-fluorobenzyl)-3-methyl-1-(2-((2R,5R)-5-methyl-2-(((R)-3-methylmorpholino)methyl)piperazin-1-yl)acetyl)indoline-3-carboxamide dihydrochloride, N-(4-(((S)-3-((2,6-difluorophenyl)carbamoyl)-2-((S)-2-((S)-2-(methylamino)propanamido)-2-(tetrahydro-2H-pyran-4-yl)acetyl)isoindolin-5-yl)carbamoyl)phenyl)-6-(4-fluorobenzyl)-3-methyl-1-(2-((2R,5R)-5-methyl-2-(((R)-3-methylmorpholino)methyl)piperazin-1-yl)acetyl)indoline-3-carboxamide trihydrochloride, N-(4-(4-fluoro-3-((S)-2-((S)-2-((S)-2-(methylamino)propanamido)-2-(tetrahydro-2H-pyran-4-yl)acetyl)isoindoline-1-carboxamido)benzamido)phenyl)-6-(4-fluorobenzyl)-3-methyl-1-(2-((2R,5R)-5-methyl-2-(((R)-3-methylmorpholino)methyl)piperazin-1-yl)acetyl)indoline-3-carboxamide trihydrochloride, and N1-((S)-3-((2,6-difluorophenyl)carbamoyl)-2-((S)-2-((S)-2-(methylamino)propanamido)-2-(tetrahydro-2H-pyran-4-yl)acetyl)isoindolin-5-yl)-N3-(3-(6-(4-fluorobenzyl)-3-methyl-1-(2-((2R,5R)-5-methyl-2-(((R)-3-methylmorpholino)methyl)piperazin-1-yl)acetyl)indolin-3-yl)propyl)malonamide trihydrochloride.

One embodiment of the invention relates to compounds as described herein for use as a therapeutically active substance.

One embodiment of the invention relates to compounds as described herein for use in the therapeutic and/or prophylactic treatment of cancer.

One embodiment of the invention relates to monomers of Formula I-a of dimeric compounds of Formula I

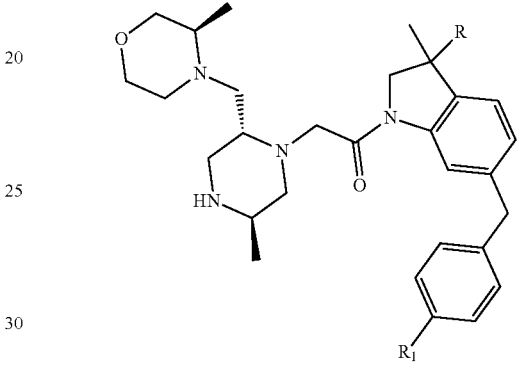

I-a wherein
$R_1$ is selected from the group consisting of H, halogen or $C_{1-6}$-alkyl, and
R is selected from the group consisting of

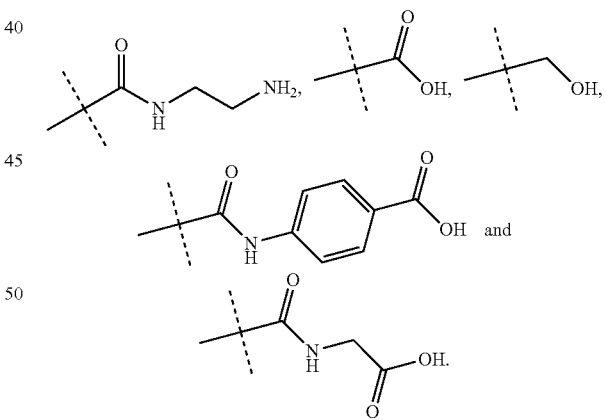

One embodiment of the invention relates to a pharmaceutical composition comprising any of the compounds as described herein, or a pharmaceutically acceptable salt thereof, as an active ingredient together with a pharmaceutically acceptable carrier or excipient.

One embodiment of the invention relates to compounds of Formula I as described herein for use as a therapeutically active substance.

One embodiment of the invention relates to compounds of Formula I as described herein for use in the therapeutic and/or prophylactic treatment of cancer.

One embodiment of the invention relates to a compound which act as inhibitors of SMAC protein binding to Inhibitor of Apoptosis Proteins (IAPs), and/or inhibitors of activated caspase protein binding to IAPs for use as a combination therapy with a bispecific antibody in a method of amelioration, treatment or control of cancer, especially solid tumors, wherein the bispecific antibody binds to Death Receptor 5 (DR5) and Fibroblast Activation Protein (FAP) and is comprising at least one antigen binding site specific for DR5 and at least one antigen binding site specific for FAP.

One embodiment of the invention relates to a compound of Formula I according to any one of claims 1-8 which act as inhibitors of SMAC protein binding to Inhibitor of Apoptosis Proteins (IAPs), and/or inhibitors of activated caspase protein binding to IAPs in combination with a bispecific antibody that binds to Death Receptor 5 (DR5) and Fibroblast Activation Protein (FAP) as described herein.

One embodiment of the invention relates to a compound which act as inhibitors of SMAC protein binding to Inhibitor of Apoptosis Proteins (IAPs), and/or inhibitors of activated caspase protein binding to IAPs for use as a combination therapy with a bispecific antibody as described herein, wherein the bispecific antibody comprises at least one antigen binding site specific for DR5 comprising a variable heavy chain comprising an amino acid sequence of SEQ ID NO.:7 and a variable light chain comprising an amino acid sequence of SEQ ID NO.:8; and at least one antigen binding site specific for FAP comprising a heavy chain variable region comprising an amino acid sequence of SEQ ID NO.:15 and a light chain variable region comprising an amino acid sequence of SEQ ID NO.:16.

One embodiment of the invention relates to a compound of Formula I as described herein which act as inhibitors of SMAC protein binding to Inhibitor of Apoptosis Proteins (IAPs), and/or inhibitors of activated caspase protein binding to IAPs in combination with a bispecific antibody that binds to Death Receptor 5 (DR5) and Fibroblast Activation Protein (FAP) as described herein, wherein the bispecific antibody comprises at least one antigen binding site specific for DR5 comprising a variable heavy chain comprising an amino acid sequence of SEQ ID NO.:7 and a variable light chain comprising an amino acid sequence of SEQ ID NO.:8; and at least one antigen binding site specific for FAP comprising a heavy chain variable region comprising an amino acid sequence of SEQ ID NO.:15 and a light chain variable region comprising an amino acid sequence of SEQ ID NO.:16.

One embodiment of the invention relates to a compound which act as inhibitors of SMAC protein binding to Inhibitor of Apoptosis Proteins (IAPs), and/or inhibitors of activated caspase protein binding to IAPs for use as a combination therapy with a bispecific antibody in a method of amelioration, treatment or control of cancer, especially solid tumors, wherein the bispecific antibody binds to Death Receptor 5 (DR5) and Fibroblast Activation Protein (FAP) as described herein, wherein the cancer is colorectal cancer, sarcoma, head and neck cancer, squamous cell carcinoma, breast cancer, pancreatic cancer, gastric cancer, non-small-cell lung carcinoma, small-cell lung cancer and mesothelioma.

One embodiment of the invention relates to a compound which act as inhibitors of SMAC protein binding to Inhibitor of Apoptosis Proteins (IAPs), and/or inhibitors of activated caspase protein binding to IAPs for use as a combination therapy with a bispecific antibody in a method of amelioration, treatment or control of cancer, especially solid tumors, wherein the bispecific antibody binds to Death Receptor 5 (DR5) and Fibroblast Activation Protein (FAP) as described herein, wherein the inhibitor of SMAC protein binding to Inhibitor of Apoptosis Proteins (IAPs) and the bispecific antibody are administered by alternation.

One embodiment of the invention relates to a compound of Formula I as described herein which act as inhibitors of SMAC protein binding to Inhibitor of Apoptosis Proteins (IAPs), and/or inhibitors of activated caspase protein binding to IAPs in combination with a bispecific antibody that binds to Death Receptor 5 (DR5) and Fibroblast Activation Protein (FAP) as described herein, wherein the bispecific antibody comprises amino acid sequences SEQ ID NO: 18, 19 and 20 or the bispecific antibody comprises amino acid sequences SEQ ID NO: 17, 19 and 20.

One embodiment of the invention relates to a compound of Formula I as described herein, which act as inhibitors of SMAC protein binding to Inhibitor of Apoptosis Proteins (IAPs), and/or inhibitors of activated caspase protein binding to IAPs in combination with a bispecific antibody that binds to Death Receptor 5 (DR5) and Fibroblast Activation Protein (FAP) as described herein, wherein the bispecific antibody comprises amino acid sequences SEQ ID NO: 18, 19 and 20 or the bispecific antibody comprises amino acid sequences SEQ ID NO: 17, 19 and 20.

One embodiment of the invention relates to a compound which act as inhibitors of SMAC protein binding to Inhibitor of Apoptosis Proteins (IAPs), and/or inhibitors of activated caspase protein binding to IAPs for use as a combination therapy with a bispecific antibody in a method of amelioration, treatment or control of cancer, especially solid tumors, wherein the bispecific antibody binds to Death Receptor 5 (DR5) and Fibroblast Activation Protein (FAP) as described herein, wherein antibody is human.

One embodiment of the invention relates to a compound which act as inhibitors of SMAC protein binding to Inhibitor of Apoptosis Proteins (IAPs), and/or inhibitors of activated caspase protein binding to IAPs for use as a combination therapy with a bispecific antibody in a method of amelioration, treatment or control of cancer, especially solid tumors, wherein the bispecific antibody binds to Death Receptor 5 (DR5) and Fibroblast Activation Protein (FAP) as described herein, wherein antibody is humanized.

One embodiment of the invention relates to a pharmaceutical composition comprising a compound which act as inhibitors of SMAC protein binding to Inhibitor of Apoptosis Proteins (IAPs), and/or inhibitors of activated caspase protein binding to IAPs for use as a combination therapy with a bispecific antibody in a method of amelioration, treatment or control of cancer, especially solid tumors, wherein the bispecific antibody binds to Death Receptor 5 (DR5) and Fibroblast Activation Protein (FAP) as described herein.

One embodiment of the invention relates to a kit comprising a first container comprising compound which act as inhibitors of SMAC protein binding to Inhibitor of Apoptosis Proteins (IAPs), and/or inhibitors of activated caspase protein binding to IAPs for use as a combination therapy and a second container comprising a bispecific antibody in a method of amelioration, treatment or control of cancer, especially solid tumors, wherein the bispecific antibody binds to Death Receptor 5 (DR5) and Fibroblast Activation Protein (FAP) as described herein.

One embodiment of the invention relates to the use of a compound which act as inhibitors of SMAC protein binding to Inhibitor of Apoptosis Proteins (IAPs), and/or inhibitors of activated caspase protein binding to IAPs and a bispecific antibody in a method of amelioration, treatment or control of cancer, especially solid tumors, wherein the bispecific antibody binds to Death Receptor 5 (DR5) and Fibroblast Activation Protein (FAP) as described herein.

One embodiment of the invention relates to compounds the use of a compound as described herein, or a pharmaceutically acceptable salt thereof, for the manufacture of a medicament for the therapeutic and/or prophylactic treatment of cancer.

One embodiment of the invention relates to bispecific antibody that binds to DR5 and FAP specifically crosslinks the death receptors and apoptosis of the target cell is induced. The advantage of these bispecific death receptor agonistic antibodies over conventional death receptor targeting antibodies is the specificity of induction of apoptosis only at the site where FAP is expressed. As outlined above the inventors of the present invention developed DR5 binding moieties with superior properties compared to known DR5 binders that can be incorporated into novel and advantageous DR5-FAP bispecific antibodies.

One embodiment of the invention relates to therapeutic combinations that comprise a bispecific antibody that binds to DR5 and FAP comprising
at least one antigen binding site specific for DR5, comprising
  (a) a heavy chain CDR1 of SEQ ID NO.:1;
  (b) a heavy chain CDR2 of SEQ ID NO.:2;
  (c) a heavy chain CDR3 of SEQ ID NO.:3;
  (d) a light chain CDR1 of SEQ ID NO.:4;
  (e) a light chain CDR2 of SEQ ID NO.:5;
  (f) a light chain CDR3 of SEQ ID NO.:6 and at least one antigen binding site specific for FAP, comprising
  (a) a heavy chain CDR1 of SEQ ID NO.:9;
  (b) a heavy chain CDR2 of SEQ ID NO.:10;
  (c) a heavy chain CDR3 of SEQ ID NO.:11;
  (d) a light chain CDR1 of SEQ ID NO.:12;
  (e) a light chain CDR2 of SEQ ID NO.:13;
  (f) a light chain CDR3 of SEQ ID NO.:14.

One embodiment of the invention relates to a bispecific antibody comprising at least one antigen binding site specific for DR5, comprising a variable heavy chain comprising an amino acid sequence of SEQ ID NO.:7 and a variable light chain comprising an amino acid sequence of SEQ ID NO.:8; and at least one antigen binding site specific for FAP, comprising a heavy chain variable region comprising an amino acid sequence of SEQ ID NO.:15 and a light chain variable region comprising an amino acid sequence of SEQ ID NO.:16.

One embodiment of the invention relates to a bispecific antibody comprising SEQ ID NO.:18, SEQ ID NO.:19 and SEQ ID NO.:20.

One embodiment of the invention relates to a bispecific antibody comprising SEQ ID NO.:17, SEQ ID NO.:19 and SEQ ID NO.:20.

One embodiment of the invention relates to a bispecific antibody that binds to DR5 and FAP comprises at least one antigen binding site specific for DR5 comprising a heavy chain variable domain (VH) sequence having at least 90%, 91%, 92%, 93%, 94%, 95%, 96%, 97%, 98%, 99%, or 100% sequence identity to the amino acid sequence of SEQ ID NO.:7, and at least one antigen binding site specific for FAP comprising a variable heavy chain of SEQ ID NO.:15 and a variable light chain of SEQ ID NO.:16.

One embodiment of the invention relates to a VH sequence having at least 90%, 91%, 92%, 93%, 94%, 95%, 96%, 97%, 98%, or 99% identity contains substitutions (e.g., conservative substitutions), insertions, or deletions relative to the reference sequence, but a bispecific antibody that binds to DR5 and FAP comprising that sequence retains the ability to bind to FAP and DR5. In certain embodiments, a total of 1 to 10 amino acids have been substituted, inserted and/or deleted in SEQ ID NO.:7. In certain embodiments, substitutions, insertions, or deletions occur in regions outside the HVRs (i.e., in the FRs). Optionally, the bispecific antibody that binds to DR5 and FAP comprises the VH sequence in SEQ ID NO.:7, including post-translational modifications of that sequence.

One embodiment of the invention relates to a bispecific antibody that binds to DR5 and FAP comprises at least one antigen binding site specific for DR5 comprising a light chain variable domain (VL) sequence having at least 90%, 91%, 92%, 93%, 94%, 95%, 96%, 97%, 98%, 99%, or 100% sequence identity to the amino acid sequence of SEQ ID NO.:8, and at least one antigen binding site specific for FAP comprising a variable heavy chain of SEQ ID NO.:15 and a variable light chain of SEQ ID NO.:16.

One embodiment of the invention relates to a VL sequence having at least 90%, 91%, 92%, 93%, 94%, 95%, 96%, 97%, 98%, or 99% identity contains substitutions (e.g., conservative substitutions), insertions, or deletions relative to the reference sequence, but a bispecific antibody that binds to DR5 and FAP comprising that sequence retains the ability to bind to DR5 and FAP. In certain embodiments, a total of 1 to 10 amino acids have been substituted, inserted and/or deleted in SEQ ID NO.:8. In certain embodiments, the substitutions, insertions, or deletions occur in regions outside the HVRs (i.e., in the FRs). Optionally, the bispecific antibody that binds to DR5 and FAP comprises the VL sequence in SEQ ID NO:8, including post-translational modifications of that sequence.

One embodiment of the invention relates to a bispecific antibody that binds to DR5 and FAP is provided, comprising at least one antigen binding site specific for DR5 comprising a variable light chain of SEQ ID NO.:8 and a variable heavy chain of SEQ ID NO.:7; and at least one antigen binding site specific for FAP, comprising a heavy chain variable domain (VH) sequence having at least 90%, 91%, 92%, 93%, 94%, 95%, 96%, 97%, 98%, 99%, or 100% sequence identity to the amino acid sequence of SEQ ID NO.:15. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but a bispecific antibody that binds to DR5 and FAP comprising that sequence retains the ability to bind to FAP and DR5. In certain embodiments, a total of 1 to 10 amino acids have been substituted, inserted and/or deleted in SEQ ID NO.:15. In certain embodiments, substitutions, insertions, or deletions occur in regions outside the HVRs (i.e., in the FRs). Optionally, the bispecific antibody that binds to DR5 and FAP comprises the VH sequence in SEQ ID NO.:15, including post-translational modifications of that sequence.

One embodiment of the invention relates to a bispecific antibody that binds to DR5 and FAP is provided, comprising at least one antigen binding site specific for DR5, comprising a variable light chain of SEQ ID NO.:8 and a variable heavy chain of SEQ ID NO.:7, and at least one antigen binding site specific for FAP, comprising a light chain variable domain (VL) having at least 90%, 91%, 92%, 93%, 94%, 95%, 96%, 97%, 98%, 99%, or 100% sequence identity to the amino acid sequence of SEQ ID NO.:16. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but a bispecific antibody that binds to DR5 and FAP comprising that sequence retains the ability to bind to DR5 and FAP. In certain embodiments, a total of 1 to 10 amino acids have been substituted, inserted and/or deleted in SEQ ID NO.:16. In certain embodiments, the substitutions, insertions, or deletions occur in regions outside the HVRs (i.e., in the FRs). Optionally, the bispecific antibody that binds to DR5 and FAP comprises the VL sequence in SEQ ID NO:16, including post-translational modifications of that sequence.

One embodiment of the invention relates to a bispecific antibody that binds to DR5 and FAP, wherein the antibody comprises a VH as in any of the embodiments provided above, and a VL as in any of the embodiments provided above. In one embodiment, the antibody comprises the VH and VL sequences in SEQ ID NO:7 and SEQ ID NO:8, and SEQ ID NO:15 and SEQ ID NO: 16, respectively, including post-translational modifications of those sequences.

One embodiment of the invention relates to a bispecific antibody that binds to DR5 and FAP according to any of the above embodiments is a monoclonal antibody, including a chimeric, humanized or human antibody. In one embodiment, said bispecific antibody that binds to DR5 and FAP according to any of the above embodiments is a human antibody.

The compounds of Formula I as well as their salts have at least one asymmetric carbon atom and therefore may be present as mixtures of different stereoisomers. The various isomers can be isolated by known separation methods, e.g., chromatography.

Compounds disclosed herein and covered by Formula I above may exhibit tautomerism or structural isomerism. It is intended that the invention encompasses any tautomeric or structural isomeric form of these compounds, or mixtures of such forms, and is not limited to any one tautomeric or structural isomeric form depicted in the formulas above.

Sequences

1. Amino Acid Sequences of Phage Display Derived DR5 Binders

| Description | Amino acid sequence | SEQ ID NO. |
|---|---|---|
| DR5 (5E11)_VH | EVQLLESGGGLVQPGGSLRLSCAAS GFTFSSYAMSWVRQAPGKGLEWVSA ISGSGGSTYYADSVKGRFTISRDNS KNTLYLQMNSLRAEDTAVYYCAKGV RVSFDYWGQGTLVTVSS | 7 |
| DR5 (5E11)_CDRH1 | SYAMS | 1 |
| DR5 (5E11)_CDRH2 | AISGSGGSTYYADSVKG | 2 |
| DR5 (5E11)_CDRH3 | DR5 | 3 |
| DR5 (5E11)_VL | EIVLTQSPGTLSLSPGERATLSCRA SQSVSSSYLAWYQQKPGQAPRLLIY GASSRATGIPDRFSGSGSGTDFTLT ISRLEPEDFAVYYCQQGTTHPITFG QGTKVEIK | 8 |
| DR5 (5E11)_CDRL1 | RASQSVSSSYLA | 4 |
| DR5 (5E11)_CDRL2 | GAS SRAT | 5 |
| DR5 (5E11)_CDRL3 | QQGTTHPIT | 6 |

2. Amino Acid Sequences of FAP Binders

| Name | Amino acid sequence | SEQ ID NO |
|---|---|---|
| FAP(28H1)_VH | EVQLLESGGGLVQPGGSLRLSCAAS GFTFSSHAMSWVRQAPGKGLEWVSA IWASGEQYYADSVKGRFTISRDNSK NTLYLQMNSLRAEDTAVYYCAKGWL GNFDYWGQGTLVTVSS | 15 |
| FAP(28H1)_VL | EIVLTQSPGTLSLSPGERATLSCRA SQSVSRSYLAWYQQKPGQAPRLLII GASTRATGIPDRFSGSGSGTDFTLT ISRLEPEDFAVYYCQQGQVIPPTFG QGTKVEIK | 16 |
| FAP (28H1)_CDRH1 | SHAMS | 9 |
| FAP (28H1)_CDRH2 | AIWASGEQYYADSVKG | 10 |
| FAP (28H1)_CDRH3 | GWLGNFDY | 11 |
| FAP (28H1)_CDRL1 | RASQSVSRSYLA | 12 |
| FAP (28H1)_CDRL2 | GASTRAT | 13 |
| FAP (28H1)_CDRL3 | QQGQVIPPT | 14 |

3. Amino Acid Sequences of Bispecific Molecules Comprising Phage Display Derived DR5 Binders

| Name | Amino acid sequence | SEQ ID NO: |
|---|---|---|
| DR5(5E11)-FAP (28H1) VHCL LVTVS pETR10334 2 + 2 | EVQLLESGGGLVQPGGSLRLSCAASGFTFSSYAMSWV RQAPGKGLEWVSAISGSGGSTYYADSVKGRFTISRDNS KNTLYLQMNSLRAEDTAVYYCAKGVRVSFDYWGQGT LVTVSSASTKGPSVFPLAPSSKSTSGGTAALGCLVKDYF PEPVTVSWNSGALTSGVHTFPAVLQSSGLYSLSSVVTV PSSSLGTQTYICNVNHKPSNTKVDKKVEPKSCDKTHTC PPCPAPELLGGPSVFLFPPKPKDTLMISRTPEVTCVVVD VSHEDPEVKFNWYVDGVEVHNAKTKPREEQYNSTYR VVSVLTVLHQDWLNGKEYKCKVSNKALPAPIEKTISK AKGQPREPQVYTLPPSRDELTKNQVSLTCLVKGFYPSD IAVEWESNGQPENNYKTTPPVLDSDGSFFLYSKLTVDK SRWQQGNVFSCSVMHEALHNHYTQKSLSLSPGKSGGG GSGGGGSGGGGSGGGGSEVQLLESGGGLVQPGGSLRL SCAASGFTFSSHAMSWVRQAPGKGLEWVSAIWASGEQ YYADSVKGRFTISRDNSKNTLYLQMNSLRAEDTAVYY CAKGWLGNFDYWGQGTLVTVSSASVAAPSVFIFPPSDE QLKSGTASVVCLLNNFYPREAKVQWKVDNALQSGNS QESVTEQDSKDSTYSLSSTLTLSKADYEKHKVYACEVT HQGLSSPVTKSFNRGEC | 17 |
| DR5(5E11)-FAP (28H1) VHCL 2 + 2 Removal of C-term. Lysine in Fc P329G/LALA mut. pETR11025 | EVQLLESGGGLVQPGGSLRLSCAASGFTFSSYAMSWV RQAPGKGLEWVSAISGSGGSTYYADSVKGRFTISRDNS KNTLYLQMNSLRAEDTAVYYCAKGVRVSFDYWGQGT LVTVSSASTKGPSVFPLAPSSKSTSGGTAALGCLVKDYF PEPVTVSWNSGALTSGVHTFPAVLQSSGLYSLSSVVTV PSSSLGTQTYICNVNHKPSNTKVDKKVEPKSCDKTHTC PPCPAPEAAGGPSVFLFPPKPKDTLMISRTPEVTCVVVD VSHEDPEVKFNWYVDGVEVHNAKTKPREEQYNSTYR VVSVLTVLHQDWLNGKEYKCKVSNKALGAPIEKTISK AKGQPREPQVYTLPPSRDELTKNQVSLTCLVKGFYPSD IAVEWESNGQPENNYKTTPPVLDSDGSFFLYSKLTVDK SRWQQGNVFSCSVMHEALHNHYTQKSLSLSPGGGGGS GGGGSGGGGSGGGGSEVQLLESGGGLVQPGGSLRLSC AASGFTFSSHAMSWVRQAPGKGLEWVSAIWASGEQY YADSVKGRFTISRDNSKNTLYLQMNSLRAEDTAVYYC AKGWLGNFDYWGQGTLVTVSSASVAAPSVFIFPPSDE QLKSGTASVVCLLNNFYPREAKVQWKVDNALQSGNS QESVTEQDSKDSTYSLSSTLTLSKADYEKHKVYACEVT HQGLSSPVTKSFNRGEC | 18 |
| DR5(5E11)LC pETR9044 | EIVLTQSPGTLSLSPGERATLSCRASQSVSSSYLAWYQQ KPGQAPRLLIYGASSRATGIPDRFSGSGSGTDFTLTISRL EPEDFAVYYCQQGTTHPITFGQGTKVEIKRTVAAPSVFI FPPSDEQLKSGTASVVCLLNNFYPREAKVQWKVDNAL QSGNSQESVTEQDSKDSTYSLSSTLTLSKADYEKHKVY ACEVTHQGLSSPVTKSFNRGEC | 19 |
| FAP(28H1)_VLCH1 pETR9537 | EIVLTQSPGTLSLSPGERATLSCRASQSVSRSYLAWYQQ KPGQAPRLLIIGASTRATGIPDRFSGSGSGTD-FTLTISRLE PEDFAVYYCQQGQVIPPTFGQGTKVEIKSSASTKGPSVF PLAPSSKSTSGGTAALGCLVKDYFPEPVTVSWNSGALT SGVHTFPAVLQSSGLYSLSSVVTVPSSSLGTQTYICNVN HKPSNTKVDKKVEPKSCD | 20 |

Dosages

The compounds of the invention preferably bind to BIR domains of an IAP preventing the IAP from binding to other proteins. Examples of Bir binding proteins include, but are not limited to, caspase 3, caspase 7, caspase 9, Smac and the like. Examples of IAPs include, but are not limited to, XIAP, cIAP1, cIAP2 or NAIP. In one aspect, the compound of the invention bind to the BIR2 and/or BIR3 domains of XIAP, cIAP1 and/or cIAP2. In another aspect, the compounds of the invention bind to the BIR2 domain of XIAP, cIAP1and/or cIAP2.

Compounds of the invention are useful for inducing apoptosis in cells or sensitizing cells to apoptotic signals, in particular cancer cells. Apoptotic signals can be induced in cancer cells by, e.g., radiation therapy or antineoplastic chemotherapy. Alternatively, apoptotic signals can be induced in cancer cells by activation of the death receptors by death receptor agonists. Death receptor agonists can be naturally occurring, e.g., tumor necrosis factor α, (TNF-α) or non-naturally occurring, e.g., a synthetic antibody such as a DR4 or DR5 antibody.

The compounds of the present invention are thus useful in the amelioration, control or treatment of cell proliferative disorders such as, in particular, oncological disorders. These compounds and formulations containing said compounds are anticipated to be useful in the treatment or control of blood cancers, such as, for example, acute myeloid leukemia, or solid tumors, such as, for example, breast, colon, lung and prostate tumors.

A "therapeutically effective amount" or "effective amount" of a compound in accordance with this invention means an amount of compound that is effective to prevent, alleviate or ameliorate symptoms of disease or prolong the survival of the subject being treated.

Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as one or more bolus injections or as a continuous infusion.

Pharmaceutical preparations useful in the practice of the invention, i.e., comprising the compounds of the invention can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions). Moreover, administration can be effected topically (e.g. in the form of ointments, creams or oils).

Compositions/Formulations

In an alternative embodiment, the present invention includes pharmaceutical compositions comprising at least one compound of Formula I, or a pharmaceutically acceptable salt thereof, and a pharmaceutically acceptable excipient and/or carrier.

These pharmaceutical compositions can be suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, as well as the particular mode of administration. The amount of active ingredient which can be combined with a carrier material to produce a single dosage form will generally be that amount of a Formula I compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

The compounds of Formula I and their pharmaceutically acceptable salts and esters can be processed with pharmaceutically inert, inorganic or organic adjuvants for the production of tablets, coated tablets, dragées and hard gelatin capsules. Lactose, polyvinylpyrrolidone, hydroxypropylmethylcellulose, hydroxypropylcellulose, microcrystalline cellulose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc. Suitable adjuvants for the production of solutions and syrups are, for example, $H_2O$, polyols, saccharose, invert sugar, glucose, etc. Suitable adjuvants for injection solutions are, for example, $H_2O$, alcohols, polyols, glycerol, vegetable oils, etc. Suitable adjuvants for suppositories are, for example, natural or hardened oils, waxes, fats, semi-solid or liquid polyols, etc. Suitable adjuvants for topical preparations are glycerides, semi-synthetic and synthetic glycerides, hydrogenated oils, liquid waxes, liquid paraffins, liquid fatty alcohols, sterols, polyethylene glycols and cellulose derivatives.

Moreover, the pharmaceutical preparations can contain preservatives, solubilizers, viscosity-increasing substances, stabilizers, wetting agents, emulsifiers, sweeteners, colorants, flavors, salts for varying the osmotic pressure, buffers, masking agents or antioxidants. They can also contain other therapeutic substances.

The compounds in the present invention (compounds of general Formula I) can be prepared using the general reaction scheme set out in the schemes below.

Scheme 1

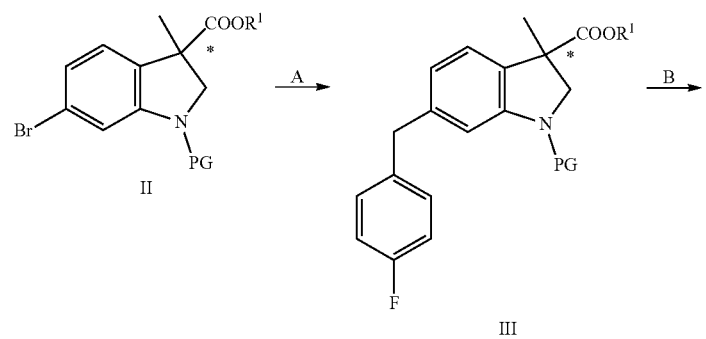

-continued
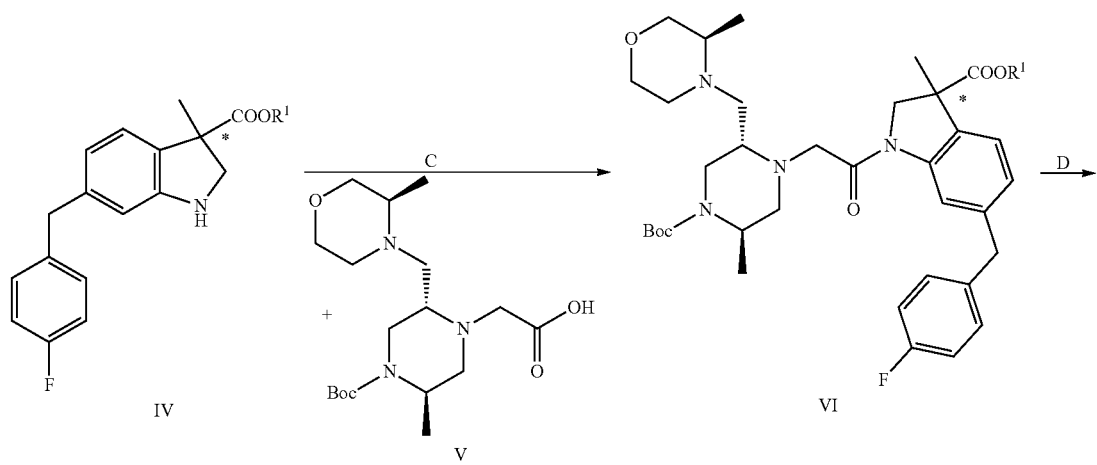
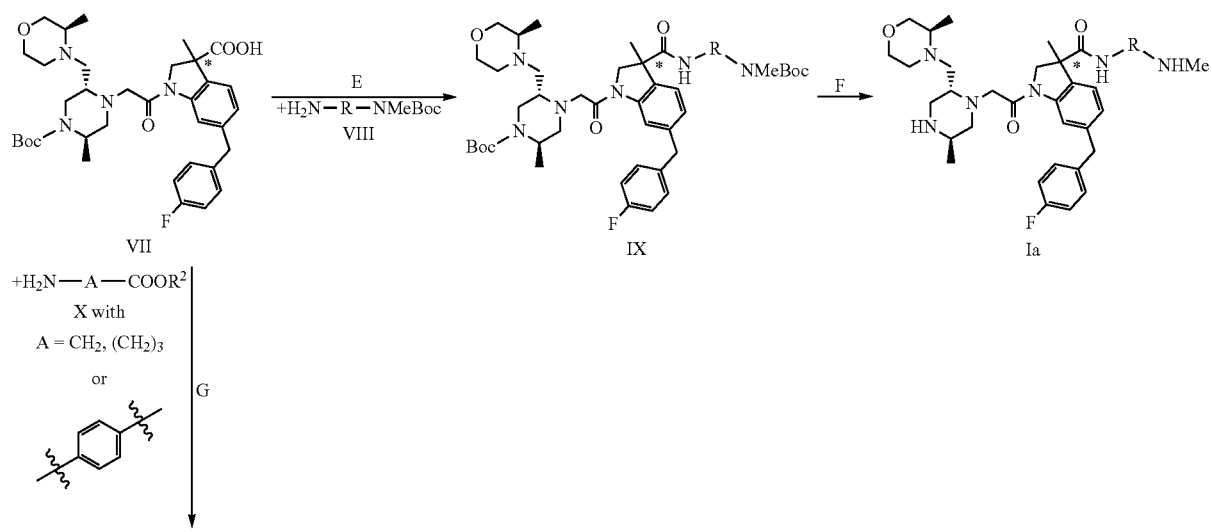
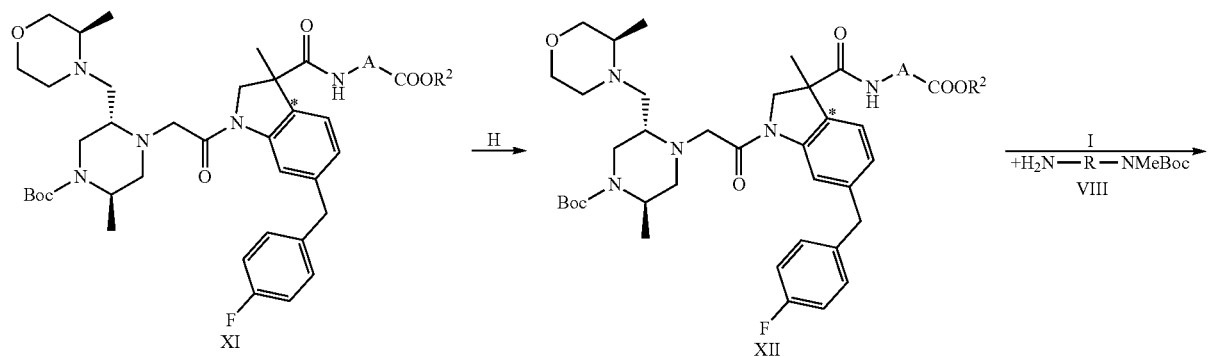

-continued
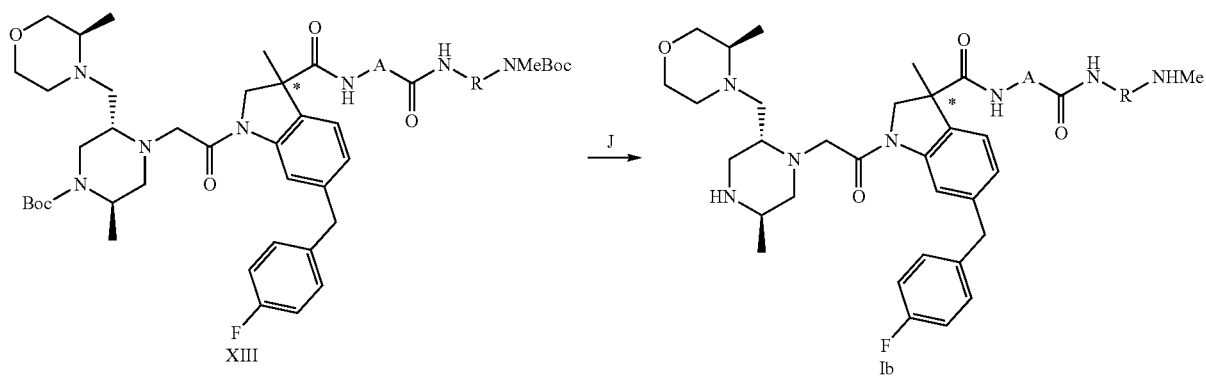
* racemic form or single enantiomers
A = CH$_2$, (CH$_2$)$_3$ or
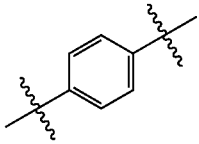
R$^1$, R$^2$ = Me or Et
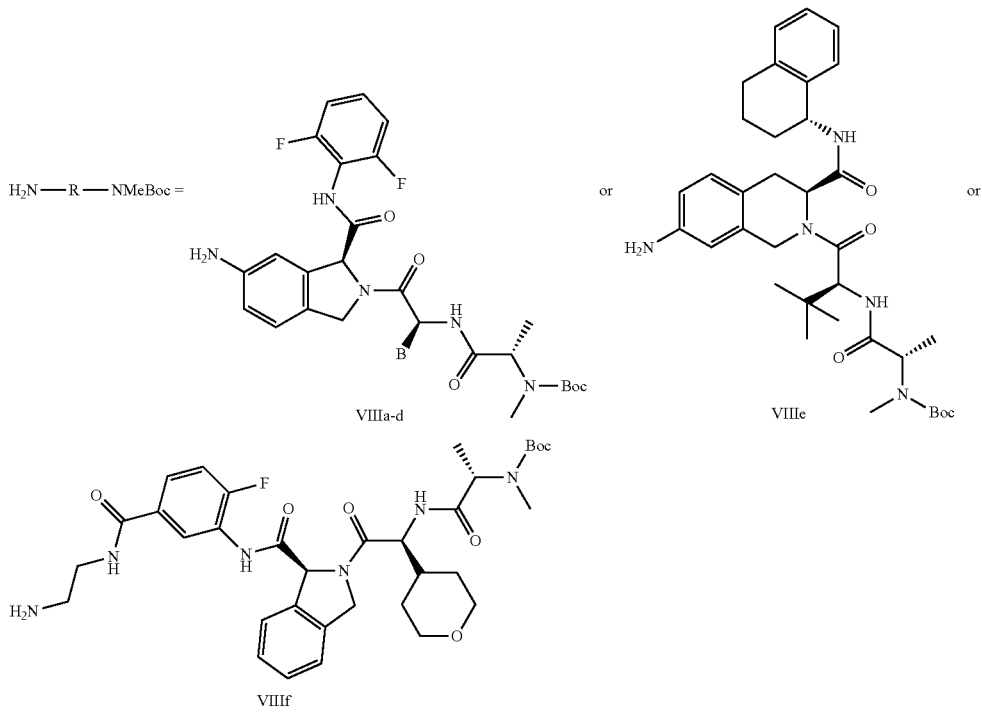
with
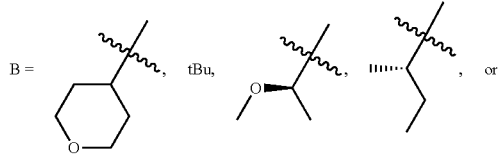
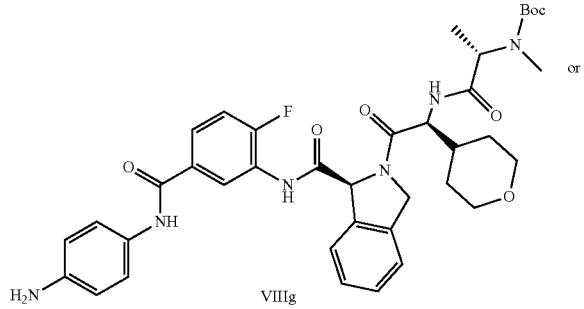

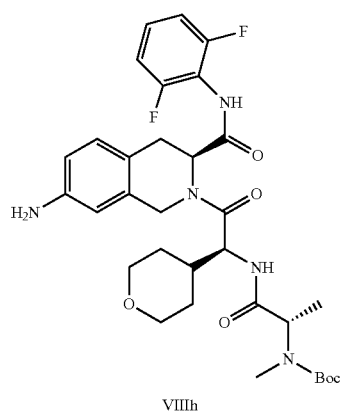

VIIIh or

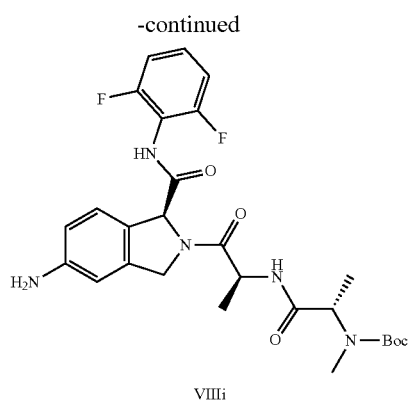

VIIIi

Step A: Coupling of the bromoderivative II with a suitable organometallic reagent such as (4-fluorobenzyl)zinc(II) chloride to form derivative III can be accomplished by using a palladium catalyst such as [1,1-bis(diphenylphosphino)ferrocene]dichloropalladium(II) or [1,1-bis(diphenylphosphino)ferrocene]dichloropalladium(II) dichloromethane complex in a suitable solvent such as dioxane, tetrahydrofurane, dimethoxyethane or diglyme at 60° C. to 120° C. for 1 h to 24 hrs. Particular conditions are the use of [1,1-bis(diphenylphosphino)ferrocene]dichloropalladium(II) dichloromethane complex in tetrahydrofurane at 90° C. in a sealed tube for 18 hrs.

Step B: Cleavage of the amino protecting group from derivative III can be effected with a variety of methods known in the art. The tert-butoxycarbonyl group can be cleaved using a mineral acid such as trifluoroacetic acid, dichloroacetic acid, acetic acid or p-toluenesulfonic acid in solvents such as dichloromethane, chloroform, tetrahydrofurane, methanol, ethanol or water at 0 to 60° C. A particular protecting group PG is the tert-butoxycarbonyl group. Preferred conditions are the use of HCl in dioxane for 5 hrs at 50° C.

Step C: Amide coupling can be achieved by reaction of amine IV with acid V in presence of an amide coupling reagent such as 1-ethyl-3-(3-dimethylaminopropyl)carbodiimide (EDC), dicyclohexylcabodiimde (DCC), O-(benzotriazol-1-yl)-N,N,N',N'-tetramethyluronium-hexafluorophosphate (HBTU), (1-[Bis(dimethylamino)methylene]-1H-1,2,3-triazolo[4,5-b]pyridinium 3-oxid hexafluorophosphate) (HATU), O-(benzotriazol-1-yl)-N,N,N',N'-tetramethyluronium-tetrafluoroborate (TBTU), propylphosphonic anhydride (T3P) or the like and a base such as triethylamine, diisopropylethylamine, N-methylmorpholine or pyridine in a solvent such as methylenechloride, 1,2-dichloroethane, tetrahydrofurane, dimethylformamide or ethyl acetate. Particular conditions are the use of propylphosphonic anhydride and N-methylmorpholine in ethyl acetate at room temperature for 18 hrs.

Step D: Saponification of the ester VI can be achieved by treatment with a base such as lithium hydroxide, potassium hydroxide or sodium hydroxide in water or a mixture of water and an organic solvent such as tetrahydrofuran, ethanol or methanol. Particular conditions are the use of lithium hydroxide in a mixture of ethanol and water at 60° C. for 3 hrs.

Step E: Amide coupling can be achieved by reaction of acid VII amine VIII in presence of an amide coupling reagent such as 1-ethyl-3-(3-dimethylaminopropyl)carbodiimide (EDC), dicyclohexylcabodiimde (DCC), O-(benzotriazol-1-yl)-N,N,N',N'-tetramethyluronium-hexafluorophosphate (HBTU), (1-[bis(dimethylamino)methylene]-1H-1,2,3-triazolo[4,5-b]pyridinium 3-oxid hexafluorophosphate) (HATU), O-(benzotriazol-1-yl)-N,N,N',N'-tetramethyluronium-tetrafluoroborate (TBTU), propylphosphonic anhydride (T3P) or the like and a base such as triethylamine, diisopropylethylamine, N-methylmorpholine or pyridine in a solvent such as methylenechloride, 1,2-dichloroethane, tetrahydrofurane, dimethylformamide or ethyl acetate. Particular conditions are the use of propylphosphonic anhydride and N-methylmorpholine in ethyl acetate at room temperature for 18 hrs.

Step F: Removal of the Boc N-protecting groups can be effected with mineral acids such as hydrochloric acid, sulfuric acid or phosphoric acid or organic acids such as trifluoroacetic acid, dichloroacetic acid, acetic acid or p-toluenesulfonic acid in solvents such as dichloromethane, chloroform, tetrahydrofurane, methanol, ethanol or water at 0° C. to 80° C. Particular conditions are HCl in a mixture of dioxane and ethylacetate at room temperature for 18 hours.

Step G: Amide coupling can be achieved by reaction of acid VII aminoester X in presence of an amide coupling reagent such as 1-ethyl-3-(3-dimethylaminopropyl)carbodiimide (EDC), dicyclohexylcabodiimde (DCC), O-(benzotriazol-1-yl)-N,N,N',N'-tetramethyluronium-hexafluorophosphate (HBTU), (1-[bis(dimethylamino)methylene]-1H-1,2,3-triazolo[4,5-b]pyridinium 3-oxid hexafluorophosphate) (HATU), O-(benzotriazol-1-yl)-N,N,N',N'-tetramethyluronium-tetrafluoroborate (TBTU), propylphosphonic anhydride (T3P) or the like and a base such as triethylamine, diisopropylethylamine, N-methylmorpholine or pyridine in a solvent such as methylenechloride, 1,2-dichloroethane, tetrahydrofurane, dimethylformamide or ethyl acetate. Particular conditions are the use of HATU and N-methylmorpholine in ethyl acetate at room temperature for 18 hrs.

Step H: Saponification of the ester XI can be achieved by treatment with a base such as lithium hydroxide, potassium hydroxide or sodium hydroxide in water or a mixture of water and an organic solvent such as tetrahydrofuran, ethanol or methanol. Particular conditions are the use of lithium hydroxide in a mixture of ethanol and water at 60° C. for 3 hrs.

Step I: Amide coupling can be achieved by reaction of acid XII amine VIII in presence of an amide coupling reagent such as 1-ethyl-3-(3-dimethylaminopropyl)carbodiimide (EDC), dicyclohexylcabodiimde (DCC), O-(benzotriazol-1-yl)-N,N,N',N'-tetramethyluronium-hexafluorophosphate (HBTU), O-(benzotriazol-1-yl)-N,N,N',N'-tetramethyluronium-tetrafluoroborate (TBTU), propylphosphonic anhydride (T3P) or the like and a base such as triethylamine, diisopropylethylamine, N-methylmorpholine or pyridine in a solvent such as methylenechloride, 1,2-dichloroethane, tetrahydrofurane or ethyl acetate. Particular conditions are the use of propylphosphonic anhydride and N-methylmorpholine in ethyl acetate at room temperature for 18 hrs.

Step J: Removal of the Boc N-protecting groups can be effected with mineral acids such as hydrochloric acid, sulfuric acid or phosphoric acid or organic acids such as trifluoroacetic acid, dichloroacetic acid, acetic acid or p-toluenesulfonic acid in solvents such as dichloromethane, chloroform, tetrahydrofurane, methanol, ethanol or water at 0° C. to 80° C. Particular conditions are HCl in a mixture of dioxane and ethylacetate at room temperature for 18 hours.

Scheme 2

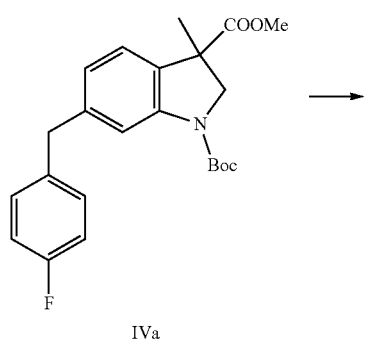

IVa

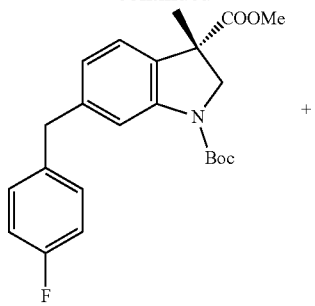

IVa-1

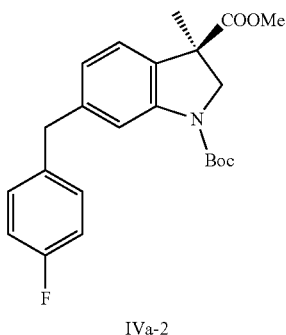

IVa-2

Ester IVa can be separated into its enantiomeric forms IVa-1 and IVa-2 by chiral separation. A preferred chiral separation is the chiral chromatography using a chiral stationary phase such as Chiralpak AD and a suitable solvent such as a mixture of isopropanol and heptane.

Scheme 3

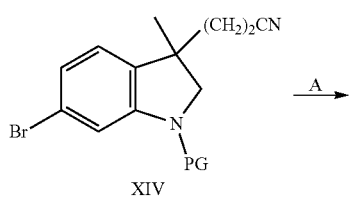

XIV

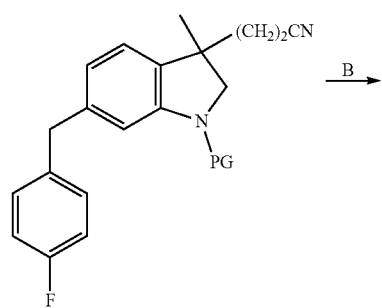

XV

-continued
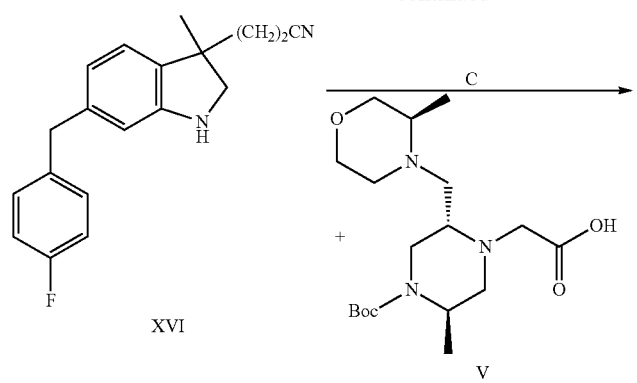
XVI
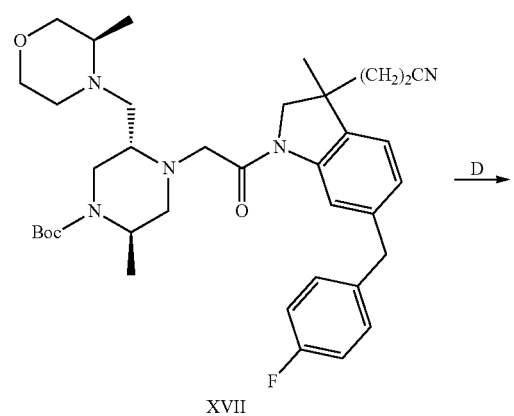
XVII
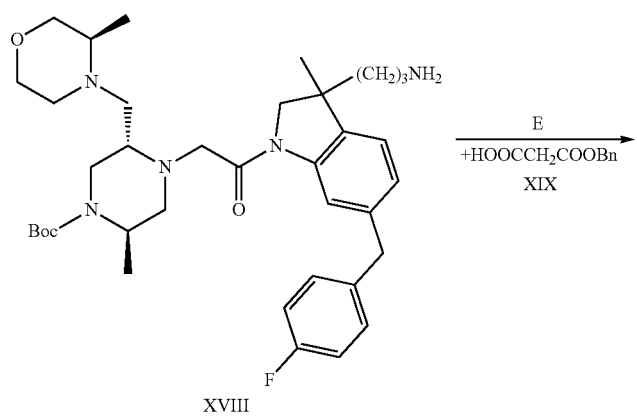
XVIII
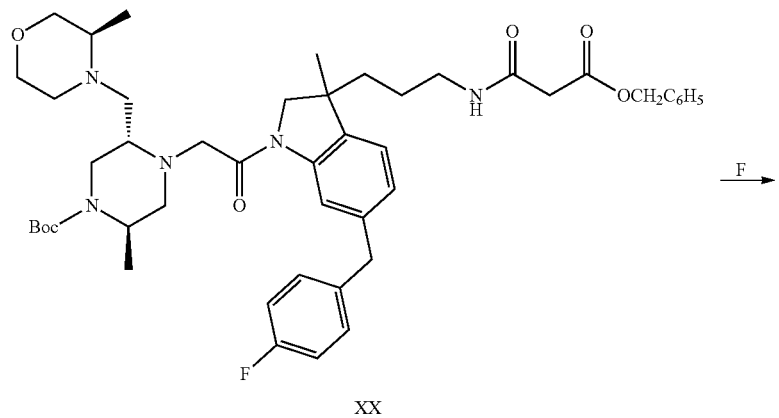
XX

-continued
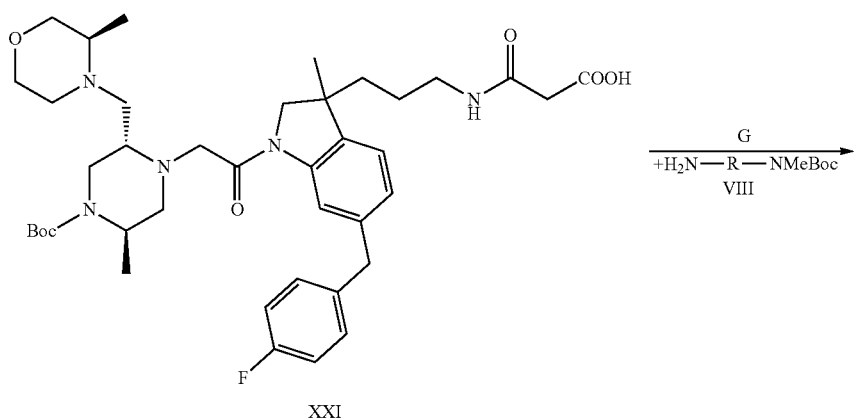
XXI
$$\xrightarrow[\text{VIII}]{\text{G} \atop +H_2N-R-NMeBoc}$$
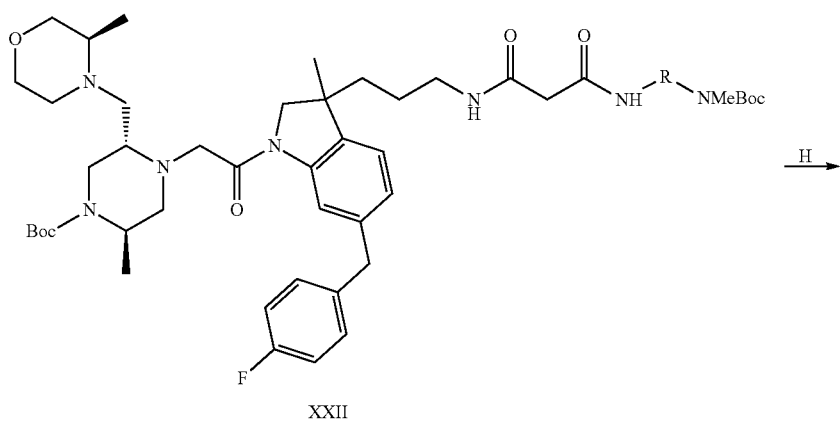
XXII
$$\xrightarrow{H}$$
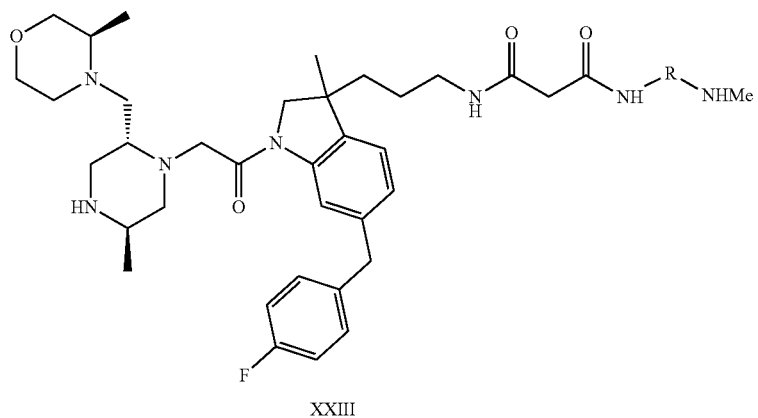
XXIII H₂N—R—NMeBoc =

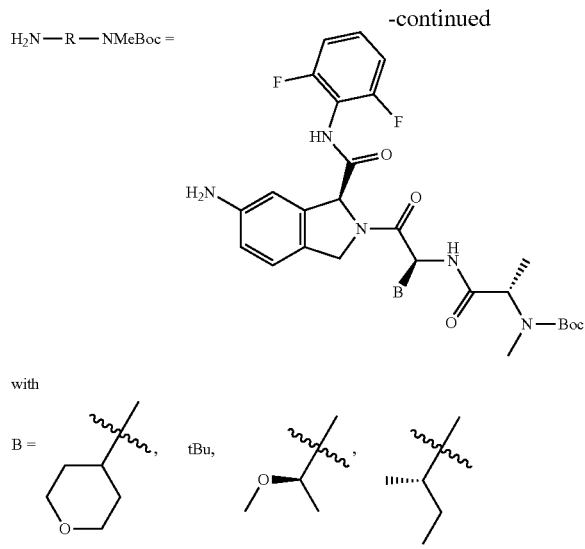

with

B = [tetrahydropyran-4-yl], tBu, [methoxy-isopropyl], [sec-butyl]

Step A: Coupling of the bromoderivative XIV with a suitable organometallic reagent such as (4-fluorobenzyl)zinc (II) chloride to form derivative XV can be accomplished by using a palladium catalyst such as [1,1-bis(diphenylphosphino)ferrocene]dichloropalladium(II) or [1,1-bis(diphenylphosphino)ferrocene]dichloropalladium(II) dichloromethane complex in a suitable solvent such as dioxane, tetrahydrofurane, dimethoxyethane or diglyme at 60° C. to 120° C. for 1 h to 24 hrs. Particular conditions are the use of [1,1-bis(diphenylphosphino)ferrocene]dichloropalladium (II) dichloromethane complex in tetrahydrofurane at 90° C. in a sealed tube for 2 hrs.

Step B: Cleavage of the amino protecting group from derivative XV can be effected with a variety of methods known in the art. The tert-butoxycarbonyl group can be cleaved using a mineral acid such as trifluoroacetic acid, dichloroacetic acid, acetic acid or p-toluenesulfonic acid in solvents such as dichloromethane, chloroform, tetrahydrofurane, methanol, ethanol or water at 0 to 60° C. A particular protecting group PG is the tert-butoxycarbonyl group. Preferred conditions are the use of HCl in methanol for 2 hrs at room temperature.

Step C: Amide coupling can be achieved by reaction of amine XVI with acid V in presence of an amide coupling reagent such as 1-ethyl-3-(3-dimethylaminopropyl)carbodiimide (EDC), dicyclohexylcabodiimde (DCC), O-(benzotriazol-1-yl)-N,N,N',N'-tetramethyluronium-hexafluorophosphate (HBTU), (1-[bis(dimethylamino)methylene]-1H-1,2,3-triazolo[4,5-b]pyridinium 3-oxid hexafluorophosphate) (HATU), O-(benzotriazol-1-yl)-N,N,N',N'-tetramethyluronium-tetrafluoroborate (TBTU), propylphosphonic anhydride (T3P) or the like and a base such as triethylamine, diisopropylethylamine, N-methylmorpholine or pyridine in a solvent such as methylenechloride, 1,2-dichloroethane, tetrahydrofurane, dimethylformamide or ethyl acetate. Particular conditions are the use of HATU and diisopropylethylamine in dimethylformamide at room temperature for 18 hrs.

Step D: Reduction of the nitrile can be achieved by reaction with boron hydride reagents in presence of nickel salts or by using a suitable catalyst such as Raney nickel in solvents like methanol or ethanol with or without adding ammonia at room temperature or elevated temperatures. Particular conditions are the use of hydrogen at atmospheric pressure, Raney nickel as catalyst and 7N ammonia solution in methanol as solvent at 60° C. for 18 hrs.

Step E: Amide coupling of amine XVIII with monobenzylmaloate XIX can be achieved in presence of an amide coupling reagent such as dicyclohexylcabodiimde (DCC), 1-ethyl-3-(3-dimethylaminopropyl)carbodiimide (EDC), O-(benzotriazol-1-yl)-N,N,N',N'-tetramethyluronium-hexafluorophosphate (HBTU), (1-[bis(dimethylamino)methylene]-1H-1,2,3-triazolo[4,5-b]pyridinium 3-oxid hexafluorophosphate) (HATU), O-(benzotriazol-1-yl)-N,N,N',N'-tetramethyluronium-tetrafluoroborate (TBTU), propylphosphonic anhydride (T3P) or the like and a base such as triethylamine, diisopropylethylamine, N-methylmorpholine or pyridine in a solvent such as methylenechloride, 1,2-dichloroethane, tetrahydrofurane, dimethylformamide or ethyl acetate. Particular conditions are the use of HATU and diisopropylethylamine in dimethylformamide at room temperature for 18 hrs.

Step F: Saponification of the ester XX can be achieved by treatment with a base such as lithium hydroxide, potassium hydroxide or sodium hydroxide in water or a mixture of water and an organic solvent such as tetrahydrofuran, ethanol or methanol, or by hydrogenation under normal or elevated pressure with a catalyst such as Pd—C in solvents such as methanol or ethanol. Particular conditions are the use of hydrogen at atmospheric pressure and palladium on charcoal as catalyst with the compound dissolved in methanol at room temperature for 6 hrs.

Step G: Amide coupling can be achieved by reaction of acid XXI amine VIII in presence of an amide coupling reagent such as 1-ethyl-3-(3-dimethylaminopropyl)carbodiimide (EDC), dicyclohexylcabodiimde (DCC), O-(benzotriazol-1-yl)-N,N,N',N'-tetramethyluronium-hexafluorophosphate (HBTU), O-(benzotriazol-1-yl)-N,N,N',N'-tetramethyluronium-tetrafluoroborate (TBTU), propylphosphonic anhydride (T3P) or the like and a base such as triethylamine, diisopropylethylamine, N-methylmorpholine or pyridine in a solvent such as methylenechloride, 1,2-dichloroethane, tetrahydrofurane or ethyl acetate. Particular conditions are the use of propylphosphonic anhydride and N-methylmorpholine in ethyl acetate at room temperature for 18 hrs.

Step H: Removal of the Boc N-protecting groups can be effected with mineral acids such as hydrochloric acid, sulfuric acid or phosphoric acid or organic acids such as trifluoroacetic acid, dichloroacetic acid, acetic acid or p-toluenesulfonic acid in solvents such as dichloromethane, chloroform, tetrahydrofurane, methanol, ethanol or water at 0° C. to 80° C. Particular conditions are HCl in a mixture of dioxane and ethylacetate at room temperature for 18 hours.
Scheme 4
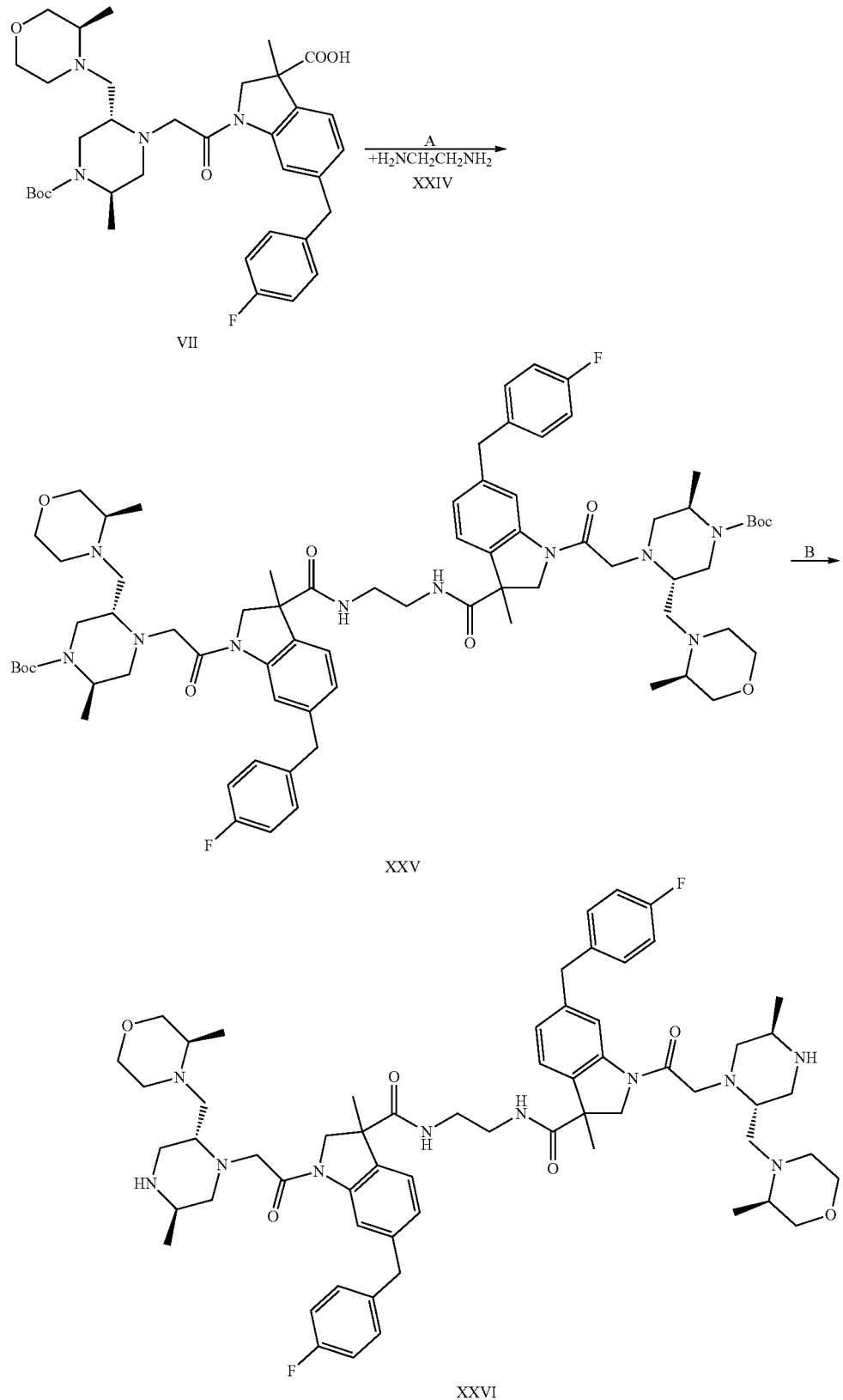

Step A: Amide coupling of amine VII with ethylene diamine XXIV can be achieved in presence of an amide coupling reagent such as dicyclohexylcabodiimde (DCC), 1-ethyl-3-(3-dimethylaminopropyl)carbodiimide (EDC), O-(benzotriazol-1-yl)-N,N,N',N'-tetramethyluronium-hexafluorophosphate (HBTU), (1-[bis(dimethylamino)methylene]-1H-1,2,3-triazolo[4,5-b]pyridinium 3-oxid hexafluorophosphate) (HATU), O-(benzotriazol-1-yl)-N,N,N',N'-tetramethyluronium-tetrafluoroborate (TBTU), propylphosphonic anhydride (T3P) or the like and a base such as triethylamine, diisopropylethylamine, N-methylmorpholine or pyridine in a solvent such as methylenechloride, 1,2-dichloroethane, tetrahydrofurane, dimethylformamide or ethyl acetate. Particular conditions are the use of HATU and diisopropylethylamine in dimethylformamide at room temperature for 18 hrs.

Step B: Removal of the Boc N-protecting groups can be effected with mineral acids such as hydrochloric acid, sulfuric acid or phosphoric acid or organic acids such as trifluoroacetic acid, dichloroacetic acid, acetic acid or p-toluenesulfonic acid in solvents such as dichloromethane, chloroform, tetrahydrofurane, methanol, ethanol or water at 0° C. to 80° C. Particular conditions are HCl in a mixture of dioxane and ethylacetate at room temperature for 18 hours.

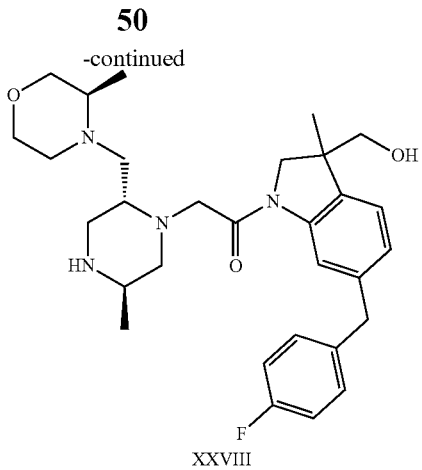

XXVIII

Step A: The ester VI can be transformed into the alcohol XXVII by reaction with an reducing agent such as lithium borohydride, sodium borohydride or Red-Al in a suitable solvent such as 1,2-dimethoxyethane, tetrahydrofurane, toluene, methanol or ethanol at −78° C. to reflux for 1-24 hrs. Particular conditions are used in the reaction with sodium borohydride in methanol at 0° C. for 5 h and allow the mixture to warm to room temperature overnight.

Step B: Removal of the Boc N-protecting group can be effected with mineral acids such as hydrochloric acid, sulfuric acid or phosphoric acid or organic acids such as trifluoroacetic acid, dichloroacetic acid, acetic acid or p-toluenesulfonic acid in solvents such as dichloromethane, chloroform, tetrahydrofurane, methanol, ethanol or water at 0° C. to 80° C. Particular conditions are HCl in a mixture of dioxane and ethylacetate at room temperature for 18 hours.

Scheme 5

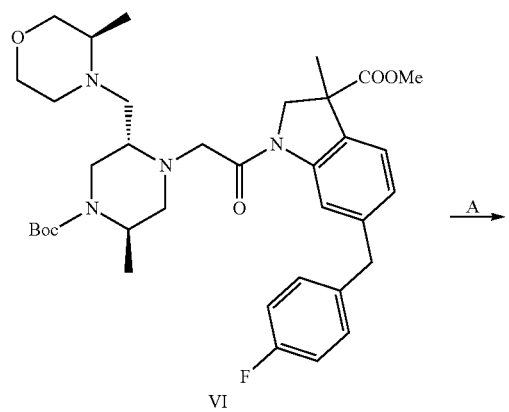

Scheme 6

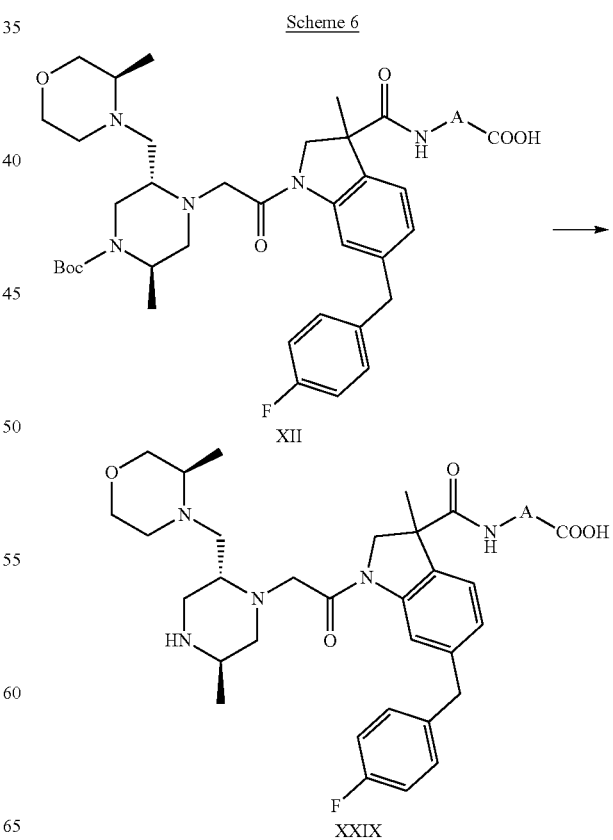

Removal of the Boc N-protecting group can be effected with mineral acids such as hydrochloric acid, sulfuric acid or phosphoric acid or organic acids such as trifluoroacetic acid, dichloroacetic acid, acetic acid or p-toluenesulfonic acid in solvents such as dichloromethane, chloroform, tetrahydrofurane, methanol, ethanol or water at 0° C. to 80° C. Particular conditions are HCl in a mixture of dioxane and ethylacetate at room temperature for 18 hours.

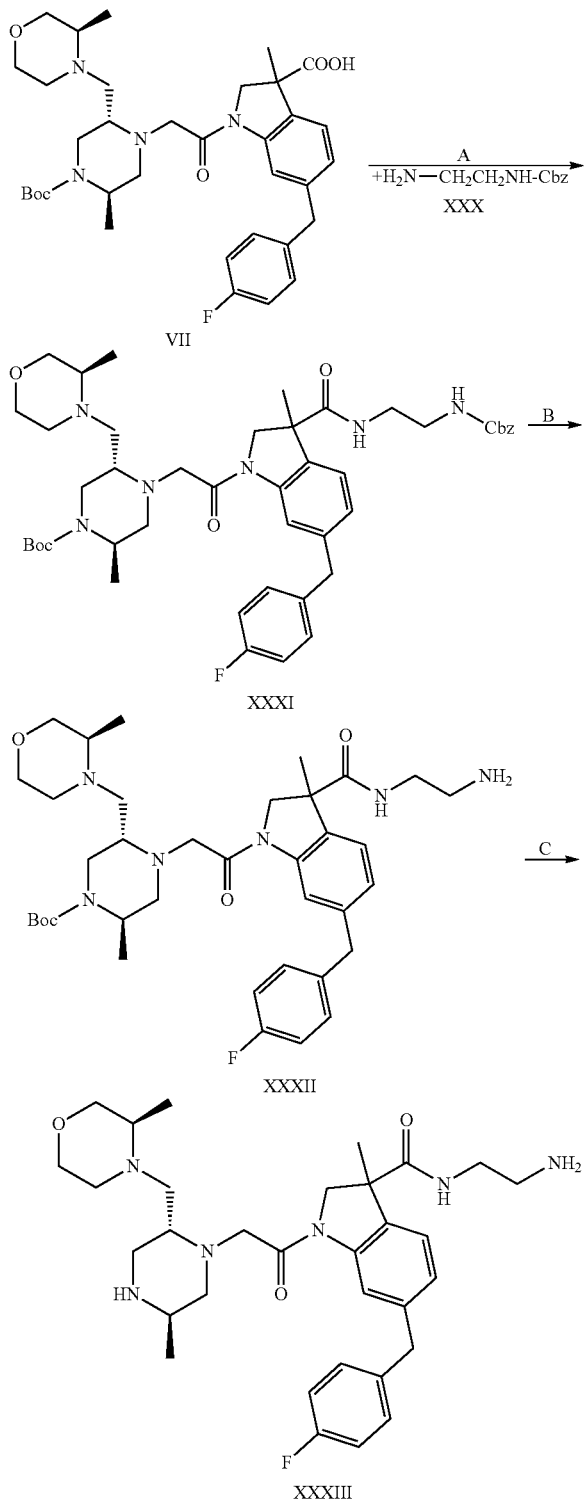

Step A: Amide coupling of amine VII with amine XXX can be achieved in presence of an amide coupling reagent such as dicyclohexylcabodiimde (DCC), 1-ethyl-3-(3-dimethylaminopropyl)carbodiimide (EDC), O-(benzotriazol-1-yl)-N,N,N',N'-tetramethyluronium-hexafluorophosphate (HBTU), (1-[bis(dimethylamino)methylene]-1H-1,2,3-triazolo[4,5-b]pyridinium 3-oxid hexafluorophosphate) (HATU), O-(benzotriazol-1-yl)-N,N,N',N'-tetramethyluronium-tetrafluoroborate (TBTU), propylphosphonic anhydride (T3P) or the like and a base such as triethylamine, diisopropylethylamine, N-methylmorpholine or pyridine in a solvent such as methylenechloride, 1,2-dichloroethane, tetrahydrofurane, dimethylformamide or ethyl acetate. Particular conditions are the use of HATU and diisopropylethylamine in dimethylformamide at room temperature for 18 hrs.

Step B: Removal of the Cbz group can be achieved by hydrogenation under normal or elevated pressure with a catalyst such as Pd—C in solvents such as methanol or ethanol. Particular conditions are the use of hydrogen at atmospheric pressure and palladium on charcoal as catalyst with the compound dissolved in methanol at room temperature for 6 hrs.

Step C: Removal of the Boc N-protecting group can be effected with mineral acids such as hydrochloric acid, sulfuric acid or phosphoric acid or organic acids such as trifluoroacetic acid, dichloroacetic acid, acetic acid or p-toluenesulfonic acid in solvents such as dichloromethane, chloroform, tetrahydrofurane, methanol, ethanol or water at 0° C. to 80° C. Particular conditions are HCl in a mixture of dioxane and ethylacetate at room temperature for 18 hours.

Methods to perform the above described reactions and processes would be apparent to those of ordinary skill in the art based on the present disclosure, or can be deduced in analogy from the examples. Starting materials are commercially available or can be made by methods analogous to those described in the Examples below.

Crystal Forms

When the compounds of the invention are solids, it is understood by those skilled in the art that these compounds, and their salts, may exist in different crystal or polymorphic forms, all of which are intended to be within the scope of the present invention and specified formulas.

Assays

TR-FRET Assays for XIAP BIR2 and BIR3

The ability of a test compound to inhibit the binding of BIR2 and/or BIR3 domains of the XIAP protein to Peptide A (a SMAC-derived peptide described below) evidences that the test compound acts as a SMAC-mimetic resulting in reactivation of a cell's apoptotic pathway.

The peptide AVPIAQKSEK (SEQ ID NO.:21) was identified as optimal for using in this assay as previously described (WO 2014/090709 A1). The peptide sequence was derivatized with biotin to provide AVPIAQKSEK-(ε-biotin)-OH (SEQ ID NO: 24) 1:2 TFA as the substrate for the TR-FRET assay.

The XIAP protein sequence was obtained from the SWISS-PROT protein sequence database and the BIR2 and BIR3 domains were derived from that. The sequence of the BIR2 domain used for the TR-FRET assay is (SEQ ID NO.: 22)
MRHHHHHHRDHFALDRPSETHADYLLRTGQVVDISDTIYPRNPAMYSEEAR

LKSFQNWPDYAHLTPRELASAGLYYTGIGDQVQCFACGGKLKNWEPGDRAW

SEHRRHFPNCFFVLGRNLNIRSE.

The sequence of the BIR3 domain used for the TR-FRET assay is (SEQ ID NO.: 23)
MRHHHHHHRSDAVSSDRNFPNSTNLPRNPSMADYEARIFTFGTWIYSVNKE

QLARAGFYALGEGDKVKCFHCGGGLTDWKPSEDPWEQHAKWYPGCKYLLEQ

KGQEYINNIHLTHSLEECLVRTT.

For the Bir2 assay, 3.5 nanomolar of 6× Histidine-tagged BIR2 domain ("6× Histidine" disclosed as SEQ ID NO: 25), corresponding to amino acids 124-240 of XIAP, was mixed with 3.6 nM of the peptide AVPIAQKSEK-(ε-biotin)-OH (SEQ ID NO: 24) 1:2 TFA, in the presence of 50 mM Tris-Cl, pH 7.5, 100 mM NaCl, 1 mM dithiothreitol (DTT) and 0.1 mg/mL bovine serum albumin (BSA). Following a 45 min. incubation at 37° C., Europium-Streptavidin (Eu-8044 streptavidin, PerkinElmer) and Allophycocyanin conjugated anti-Histidine antibody (Columbia Biosciences) were added to a final concentration of 0.6 nM and 1 nM, respectively. Time-resolved fluorescence resonance energy transfer (TR-FRET) signals were measured 1 hour later at room temperature. Test compound potency was assessed at 10 serially diluted concentrations. Percentage of inhibition at each concentration was determined to generate an $IC_{50}$ value for each test compound.

For the Bir3 assay, 13.3 nanomolar BIR3 domain, corresponding to amino acids 241-356 of XIAP, was mixed with 25.2 nM of the peptide AVPIAQKSEK-(ε-biotin)-OH (SEQ ID NO: 24) 1:2 TFA, in the presence of 50 mM Tris-Cl, pH 7.5, 100 mM NaCl, 1 mM dithiothreitol (DTT) and 0.1 mg/mL bovine serum albumin (BSA). Following a 45 min. incubation at 37° C., Europium-Streptavidin and Alliophycocyanin conjugated anti-Histidine antibody were added to a final concentration of 0.6 nM and 2.5 nM, respectively. Time-resolved fluorescence resonance energy transfer (TR-FRET) signals were measured 0.5 hour later at room temperature. Test compound potency was assessed at 10 serially diluted concentrations. Percentage of inhibition at each concentration was determined to generate an $IC_{50}$ value for each test compound.

TR-FRET Assays for cIAP BIR2 and BIR3

The peptide AVPIAQKSEK (SEQ ID NO: 21) was derivatized with biotin to provide AVPIAQKSEK-(ε-biotin)-OH (SEQ ID NO: 24) 1:2 TFA as the substrate for the TR-FRET assay.

The cIAP protein sequence was obtained from the SWISS-PROT protein sequence database and the BIR2 and BIR3 domains were derived from that. The sequence of the BIR2 domain used for the TR-FRET assay is

MGSSHHHHHHSSGLVPRGSHMASENLYFQGTNPYSYAMSTEEARFLTYHMW

PLTFLSPSELARAGFYYIGPGDRVACFAC GGKLSNWEPK DDAMSEHRRH

FPNCPFLENS LET

The sequence of the BIR3 domain used for the TR-FRET assay is

MAHHHHHHENLYFQGSSISNLSMQTHAARMRTFMYWPSSVPVQPEQLASAG

FYYVGRNDDVKCFCCDGGLRCWESGDDPWVEHAKWFPRCEFLIRMKGQEFV

DEIQGRY

For the Bir2 assay, 12 nanomolar of 6× Histidine-tagged $BIR_2$ domain ("6× Histidine38 disclosed as SEQ ID NO: 25), corresponding to amino acids 174-256 of cIAP, was mixed with 19.3 nM of the peptide AVPIAQKSEK-(ε-biotin)-OH (SEQ ID NO: 24) 1:2 TFA, in the presence of 50 mM Tris-Cl, pH 7.5, 100 mM NaCl, 1 mM dithiothreitol (DTT) and 0.1 mg/mL bovine serum albumin (BSA). Following a 45 min. incubation at 37° C., Europium-Streptavidin and Allophycocyanin conjugated anti-Histidine antibody were added to a final concentration of 0.6 nM and 4 nM, respectively and incubated at room temperature for 60 min. Time-resolved fluorescence resonance energy transfer (TR-FRET) signals were measured after a final overnight incubation at 4° C. Test compound potency was assessed at 10 serially diluted concentrations. Percentage of inhibition at each concentration was determined to generate an $IC_{50}$ value for each test compound.

For the Bir3 assay, 25.5 nanomolar BIR3 domain, corresponding to amino acids 260-352 of cIAP, was mixed with 41 nM of the peptide AVPIAQKSEK-(ε-biotin)-OH (SEQ ID NO: 24) 1:2 TFA, in the presence of 50 mM Tris-Cl, pH 7.5, 100 mM NaCl, 1 mM dithiothreitol (DTT) and 0.1 mg/mL bovine serum albumin (BSA). Following a 45 min. incubation at 37° C., Europium-Streptavidin and Ailophycocyanin conjugated anti-Histidine antibody were added to a final concentration of 0.6 nM and 6.4 nM, respectively and incubated at room temperature for 60 min. Time-resolved fluorescence resonance energy transfer (TR-FRET) signals were measured after a final overnight incubation at 4° C. Test compound potency was assessed at 10 serially diluted concentrations. Percentage of inhibition at each concentration was determined to generate an $IC_{50}$ value for each test compound.

Cell Viability Assay

SK-OV-3 and HCT-116 cells were obtained from the American Type Culture Collection (ATCC, 10801 University Boulevard Manassas, Va. 20110 USA) and maintained in McCoy's 5A media supplemented with 10% FBS and 2 mmol/L L-glutamine. All media and supplements were purchased from Invitrogen (Life Technologies GmbH, Frankfurter Straße 129B 64293 Darmstadt Germany).

Cell viability was assessed by addition of 3-(4,5-dimethylthiazol-2-yl)-2,5-diphenyl-tetrazolium bromide (MTT) following the manufacturer's protocol (Sigma-Aldrich Chemie GmbH, Eschenstr. 5 82024 Taufkirchen Germany). For single agent activity, SK-OV-3 cells were seeded in 96-well plates (BD Biosciences, Tullastrasse 8-12 69126 Heidelberg Germany) at 2000 cells per well and 24 hours later incubated with indicated concentrations of N-(2-(((S)-3-((2,6-Difluorophenyl)carbamoyl)-2-((S)-2-((S)-2-(methylamino)propanamido)-2-(tetrahydro-2H-pyran-4-yl)acetyl)isoindolin-5-yl)amino)-2-oxoethyl)-6-(4-fluorobenzyl)-3-methyl-1-(2-((2R,5R)-5-methyl-2-(((R)-3-methylmorpholino)methyl)piperazin-1-yl)acetyl)indoline-3-carboxamide trihydrochloride (Example 2). The compound was stored in aliquots as 10 mM stock solution in DMSO at −20° C. For combination, HCT-116 cells were seeded in 96-well plates (BD Biosciences, Tullastrasse 8-12 69126 Heidelberg Germany) at 2000 cells per well and 24 hours later incubated with indicated concentrations of N-(2-(((S)-3-((2,6-Difluorophenyl)carbamoyl)-2-((S)-2-((S)-2-(methylamino)propanamido)-2-(tetrahydro-2H-pyran-4-yl)acetyl)isoindolin-5-yl)amino)-2-oxoethyl)-6-(4-fluorobenzyl)-3-methyl-1-(2-((2R,5R)-5-methyl-2-(((R)-3-methylmorpholino)methyl)piperazin-1-yl)acetyl)indoline-3-carboxamide trihydrochloride alone or in combination with DR5-FAP bispecific antibody X AB (DR5 binder: VH SEQ ID NO.:7, VL SEQ ID NO.: 8, FAP binder: VH SEQ ID NO.:15, VL SEQ ID NO.: 16). After 5 days incubation, cells were treated with MTT for one hour and dyes were extracted with ethanol. The absorbance was measured at 570 nm (Tecan Infinite 200 PRO, Tecan Group Ltd. SeestraB3e 103 8708 Minnedorf Switzerland), and a reference wavelength of 620 nm was used. All assays were performed in duplicate, and data were normalized to control and analyzed using XLfit software.

Percentage of inhibition at each concentration was determined to generate an $IC_{50}$ value for each test compound. These values are listed in the table below.

| Ex | Structure | Name | $IC_{50}$ XIAP BIR2 | $IC_{50}$ XIAP BIR3 | $IC_{50}$ cIAP BIR2 | $IC_{50}$ cIAP BIR3 |
|---|---|---|---|---|---|---|
| 1 | 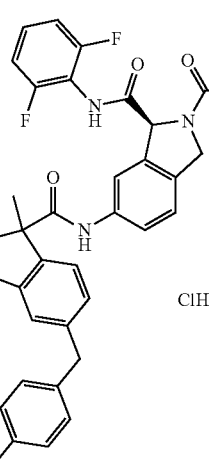 AND Enantiomer | N-((S)-3-((2,6-difluorophenyl)carbamoyl)-2-((S)-2-((S)-2-(methylamino)propanamido)-2-(tetrahydro-2H-pyran-4-yl)acetyl)isoindolin-5-yl)-6-(4-fluorobenzyl)-3-methyl-1-(2-((2R,5R)-5-methyl-2-(((R)-3-methylmorpholino)methyl)piperazin-1-yl)acetyl)indoline-3-carboxamide trihydrochloride | 0.007 | 0.011 | 0.178 | 0.006 |
| 2 | 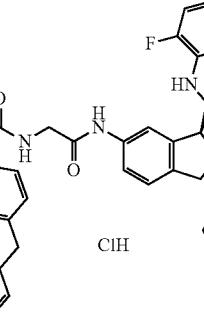 AND Enantiomer | N-(2-(((S)-3-((2,6-difluorophenyl)carbamoyl)-2-((S)-2-((S)-2-(methylamino)propanamido)-2-(tetrahydro-2H-pyran-4-yl)acetyl)isoindolin-5-yl)amino)-2-oxoethyl)-6-(4-fluorobenzyl)-3-methyl-1-(2-((2R,5R)-5-methyl-2-(((R)-3-methylmorpholino)methyl)piperazin-1-yl)acetyl)indoline-3-carboxamide trihydrochloride | 0.006 | 0.013 | 0.0721 | 0.006 |

-continued

| Ex | Structure | Name | IC$_{50}$ XIAP BIR2 | IC$_{50}$ XIAP BIR3 | IC$_{50}$ cIAP BIR2 | IC$_{50}$ cIAP BIR3 |
|---|---|---|---|---|---|---|
| 3 | 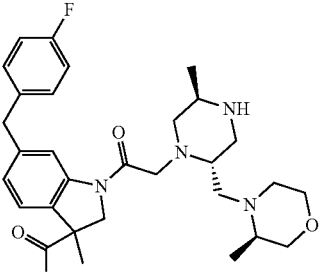 AND Enantiomer ClH | (R,R,R)-N,N'-(ethane-1,2-diyl)bis(6-(4-fluorobenzyl)-3-methyl-1-(2-((2R,5R)-5-methyl-2-(((R)-3-methylmorpholino)methyl)piperazin-1-yl)acetyl)indoline-3-carboxamide)trihydrochloride | >54.2 | 0.003 | 22.7 | 0.010 |
| 4 | 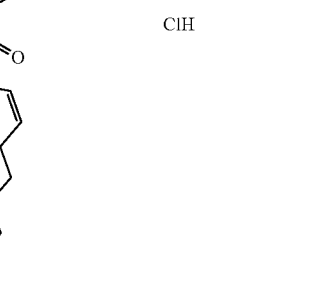 AND Enantiomer ClH | N-(4-(((S)-3-((2,6-difluorophenyl)carbamoyl)-2-((S)-2-((S)-2-(methylamino)propanamido)-2-(tetrahydro-2H-pyran-4-yl)acetyl)isoindolin-5-yl)carbamoyl)phenyl)-6-(4-fluorobenzyl)-3-methyl-1-(2-((2R,5R)-5-methyl-2-(((R)-3-methylmorpholino)methyl)piperazin-1-yl)acetyl)indoline-3-carboxamide trihydrochloride | 0.005 | 0.013 | 0.0347 | 0.004 |

| Ex | Structure | Name | IC$_{50}$ XIAP BIR2 | IC$_{50}$ XIAP BIR3 | IC$_{50}$ cIAP BIR2 | IC$_{50}$ cIAP BIR3 |
|---|---|---|---|---|---|---|
| 5 | 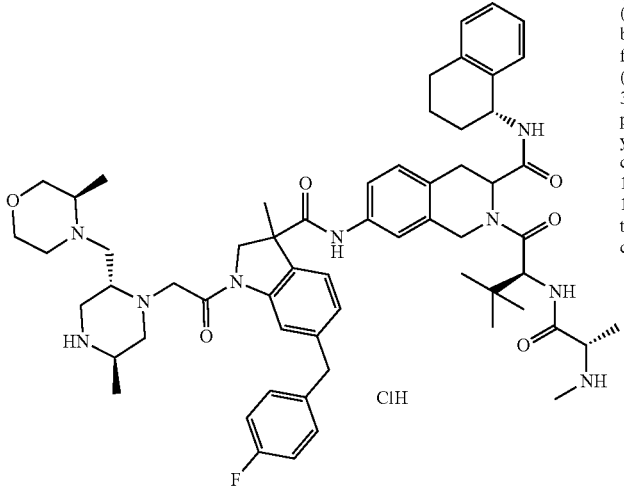 | AND Enantiomer (3S)-2-((S)-3,3-dimethyl-2-((S)-2-(methylamino)propanamido)butanoyl)-7-(6-(4-fluorobenzyl)-3-methyl-1-(2-((2R,5R)-5-methyl-2-(((R)-3-methylmorpholino)methyl)piperazin-1-yl)acetyl)indoline-3-carboxamido)-N-((R)-1,2,3,4-tetrahydronaphthalen-1-yl)-1,2,3,4-tetrahydroisoquinoline-3-carboxamide trihydrochloride | 1.51 | 0.003 | 2.28 | 0.004 |
| 6 | 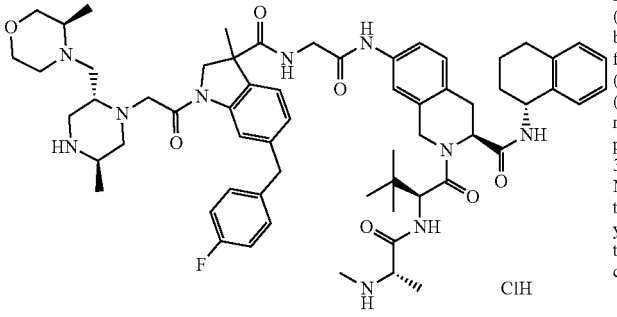 | AND Enantiomer (3S)-2-((S)-3,3-dimethyl-2-((S)-2-(methylamino)propanamido)butanoyl)-7-(2-(6-(4-fluorobenzyl)-3-methyl-1-(2-((2R,5R)-5-methyl-2-(((R)-3-methylmorpholino)methyl)piperazin-1-yl)acetyl)indoline-3-carboxamido)acetamido)-N-((R)-1,2,3,4-tetrahydronaphthalen-1-yl)-1,2,3,4-tetrahydroisoquinoline-3-carboxamide trihydrochloride | 1.64 | 0.008 | 2.33 | 0.004 |
| 7 | 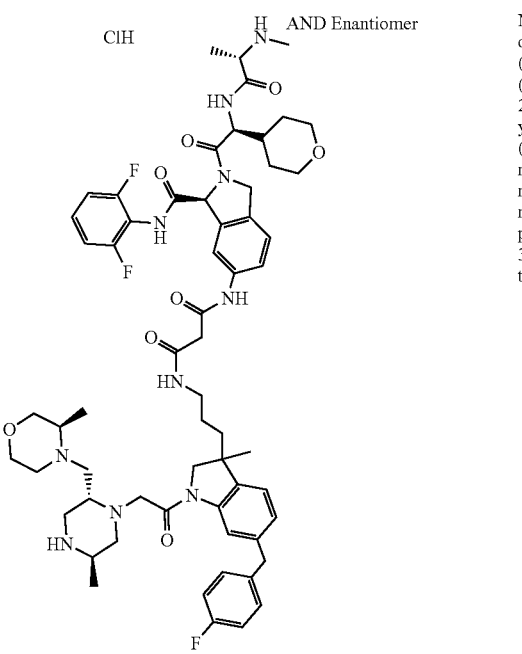 | N1-((S)-3-((2,6-difluorophenyl)carbamoyl)-2-((S)-2-((S)-2-(methylamino)propanamido)-2-(tetrahydro-2H-pyran-4-yl)acetyl)isoindolin-5-yl)-N3-(3-(6-(4-fluorobenzyl)-3-methyl-1-(2-((2R,5R)-5-methyl-2-(((R)-3-methylmorpholino)methyl)piperazin-1-yl)acetyl)indolin-3-yl)propyl)malonamide trihydrochloride | 0.008 | 0.026 | 0.107 | 0.010 |

| Ex | Structure | Name | IC$_{50}$ XIAP BIR2 | IC$_{50}$ XIAP BIR3 | IC$_{50}$ cIAP BIR2 | IC$_{50}$ cIAP BIR3 |
|---|---|---|---|---|---|---|
| 8 | 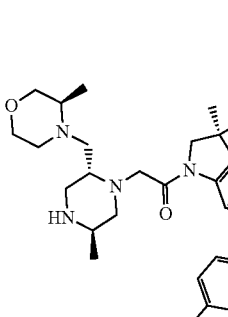 | (3S)-N-[2-[[(3S)-3-[(2,6-difluorophenyl)carbamoyl]-2-[(2S)-2-[[(2S)-2-(methylamino)propanoyl]amino]-2-(oxan-4-yl)acetyl]-1,3-dihydroisoindol-5-yl]amino]-2-oxoethyl]-6-[(4-fluorophenyl)methyl]-3-methyl-1-[2-[(2R,5R)-5-methyl-2-[[(3R)-3-methylmorpholin-4-yl]methyl]piperazin-1-yl]acetyl]-2H-indole-3-carboxamide;trihydrochloride | 0.002 | 0.004 | 0.0348 | 0.002 |
| 9 | 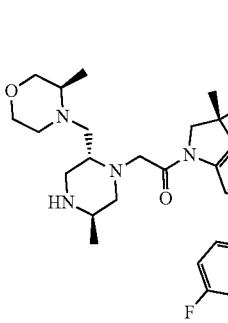 | (3R)-N-[2-[[(3S)-3-[(2,6-difluorophenyl)carbamoyl]-2-[(2S)-2-[[(2S)-2-(methylamino)propanoyl]amino]-2-(oxan-4-yl)acetyl]-1,3-dihydroisoindol-5-yl]amino]-2-oxoethyl]-6-[(4-fluorophenyl)methyl]-3-methyl-1-[2-[(2R,5R)-5-methyl-2-[[(3R)-3-methylmorpholin-4-yl]methyl]piperazin-1-yl]acetyl]-2H-indole-3-carboxamide;trihydrochloride | 0.003 | 0.108 | 0.182 | 0.081 |
| 10 | 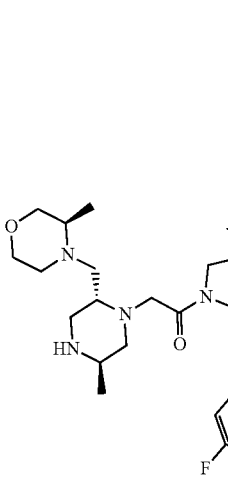 | (3S)-2-[(2S)-3,3-dimethyl-2-[[(2S)-2-(methylamino)propanoyl]amino]butanoyl]-7-[[2-[[(3S)-6-[(4-fluorophenyl)methyl]-3-methyl-1-[2-[(2R,5R)-5-methyl-2-[[(3R)-3-methylmorpholin-4-yl]methyl]piperazin-1-yl]acetyl]-2H-indole-3-carbonyl]amino]acetyl]amino]-N-[(1R)-1,2,3,4-tetrahydronaphthalen-1-yl]-3,4-dihydro-1H-isoquinoline-3-carboxamide;trihydrochloride | 1.26 | 0.002 | 1.62 | 0.002 |

-continued

| Ex | Structure | Name | IC$_{50}$ XIAP BIR2 | IC$_{50}$ XIAP BIR3 | IC$_{50}$ cIAP BIR2 | IC$_{50}$ cIAP BIR3 |
|---|---|---|---|---|---|---|
| 11 | 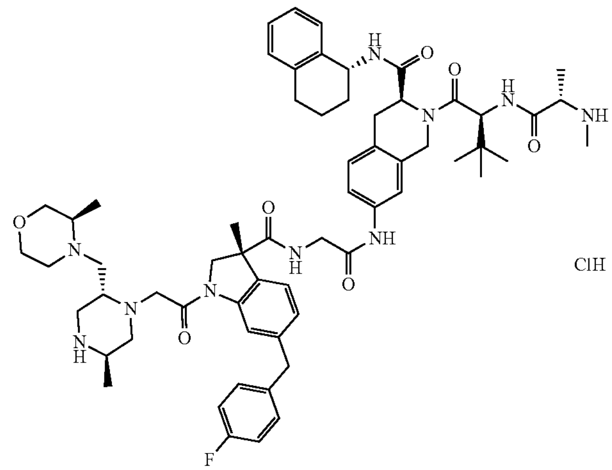 [SMILES: CN[C@@H](C)C(=O)N[C@H](C(=O)N1Cc2cc(NC(=O)CNC(=O)[C@@]3(C)CN(C(=O)CN4C[C@@H](C)NC[C@@H]4CN4CCOC[C@H]4C)c4cc(Cc5ccc(F)cc5)ccc43)ccc2C[C@H]1C(=O)N[C@@H]1CCCc2ccccc21)C(C)(C)C ; Cl] | (3S)-2-[(2S)-3,3-dimethyl-2-[[(2S)-2-(methylamino)propanoyl]amino]butanoyl]-7-[[2-[[(3R)-6-[(4-fluorophenyl)methyl]-3-methyl-1-[2-[((2R,5R)-5-methyl-2-[[(3R)-3-methylmorpholin-4-yl]methyl]piperazin-1-yl]acetyl]-2H-indole-3-carbonyl]amino]acetyl]amino]-N-[(1R)-1,2,3,4-tetrahydronaphthalen-1-yl]-3,4-dihydro-1H-isoquinoline-3-carboxamide;trihydrochloride | 1.38 | 0.018 | 6.99 | 0.007 |
| 12 | 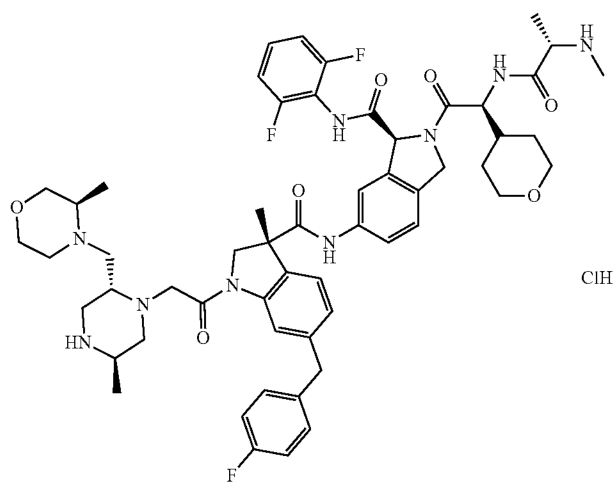 [SMILES: CN[C@@H](C)C(=O)N[C@H](C(=O)N1Cc2ccc(NC(=O)[C@@]3(C)CN(C(=O)CN4C[C@@H](C)NC[C@@H]4CN4CCOC[C@H]4C)c4cc(Cc5ccc(F)cc5)ccc43)cc2[C@H]1C(=O)Nc1c(F)cccc1F)C1CCOCC1 ; Cl] | (R)-N-((S)-3-((2,6-difluorophenyl)carbamoyl)-2-((S)-2-((S)-2-(methylamino)propanamido)-2-(tetrahydro-2H-pyran-4-yl)acetyl)isoindolin-5-yl)-6-(4-fluorobenzyl)-3-methyl-1-(2-((2R,5R)-5-methyl-2-(((R)-3-methylmorpholino)methyl)piperazin-1-yl)acetyl)indoline-3-carboxamide trihydrochloride | 0.003 | 0.017 | 0.105 | 0.16 |
| 13 | 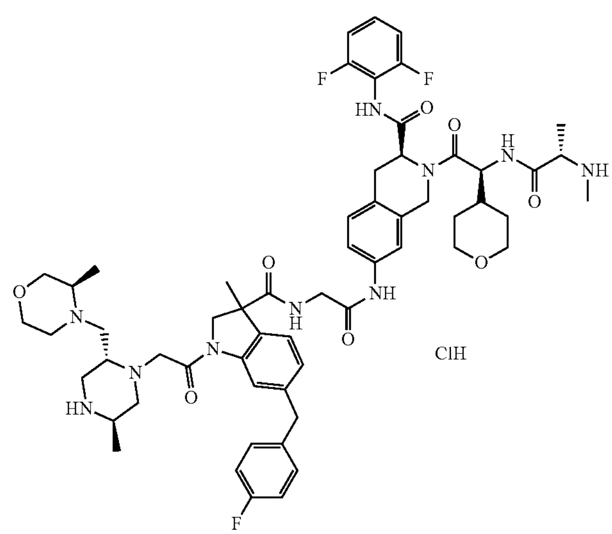 | (3S)-N-(2,6-difluorophenyl)-7-(2-(6-(4-fluorobenzyl)-3-methyl-1-(2-((2R,5R)-5-methyl-2-(((R)-3-methylmorpholino)methyl)piperazin-1-yl)acetyl)indoline-3-carboxamido)acetamido)-2-((S)-2-((S)-2-(methylamino)propanamido)-2-(tetrahydro-2H-pyran-4-yl)acetyl)-1,2,3,4-tetrahydroisoquinoline-3-carboxamide trihydrochloride | 0.048 | 0.029 | 0.97 | 0.010 |

-continued

| Ex | Structure | Name | IC$_{50}$ XIAP BIR2 | IC$_{50}$ XIAP BIR3 | IC$_{50}$ cIAP BIR2 | IC$_{50}$ cIAP BIR3 |
|---|---|---|---|---|---|---|
| 14 | AND Enantiomer ClH | N-(2-(4-fluoro-3-((S)-2-((S)-2-((S)-2-(methylamino)propanamido)-2-(tetrahydro-2H-pyran-4-yl)acetyl)isoindoline-1-carboxamido)benzamido)ethyl)-6-(4-fluorobenzyl)-3-methyl-1-(2-((2R,5R)-5-methyl-2-(((R)-3-methylmorpholino)methyl)piperazin-1-yl)acetyl)indoline-3-carboxamide dihydrochloride | 0.036 | 0.024 | 1.71 | 0.007 |
| 15 | 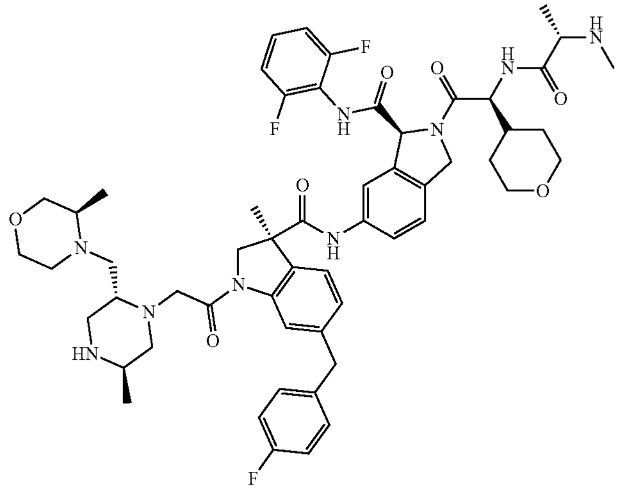 [SMILES: CN[C@@H](C)C(=O)N[C@H](C(=O)N1Cc2ccc(NC(=O)[C@]3(C)CN(C(=O)CN4C[C@@H](C)NC[C@@H]4CN4CCOC[C@H]4C)c4cc(Cc5ccc(F)cc5)ccc43)cc2[C@H]1C(=O)Nc1c(F)cccc1F)C1CCOCC1] | (S)-N-((S)-3-((2,6-difluorophenyl)carbamoyl)-2-((S)-2-((S)-2-(methylamino)propanamido)-2-(tetrahydro-2H-pyran-4-yl)acetyl)isoindolin-5-yl)-6-(4-fluorobenzyl)-3-methyl-1-(2-((2R,5R)-5-methyl-2-(((R)-3-methylmorpholino)methyl)piperazin-1-yl)acetyl)indoline-3-carboxamide | 0.0038 | 0.009 | 0.177 | 0.002 |
| 16 | AND Enantiomer ClH | N-(4-(4-fluoro-3-((S)-2-((S)-2-((S)-2-(methylamino)propanamido)-2-(tetrahydro-2H-pyran-4-yl)acetyl)isoindoline-1-carboxamido)benzamido)phenyl)-6-(4-fluorobenzyl)-3-methyl-1-(2-((2R,5R)-5-methyl-2-(((R)-3-methylmorpholino)methyl)piperazin-1-yl)acetyl)indoline-3-carboxamide trihydrochloride | 0.034 | 0.036 | 0.327 | 0.010 |
| 17 | ClH | (S)-N-(3-(((S)-3-((2,6-difluorophenyl)carbamoyl)-2-((S)-2-((S)-2-(methylamino)propanamido)-2-(tetrahydro-2H-pyran-4-yl)acetyl)isoindolin-5-yl)amino)-3-oxopropyl)-6-(4-fluorobenzyl)-3-methyl-1-(2-((2R,5R)-5-methyl-2-(((R)-3-methylmorpholino)methyl)piperazin-1-yl)acetyl)indoline-3-carboxamide trihydrochloride | 0.006 | 0.007 | 0.203 | 0.002 |

| Ex | Structure | Name | IC$_{50}$ XIAP BIR2 | IC$_{50}$ XIAP BIR3 | IC$_{50}$ cIAP BIR2 | IC$_{50}$ cIAP BIR3 |
|---|---|---|---|---|---|---|
| 18 | 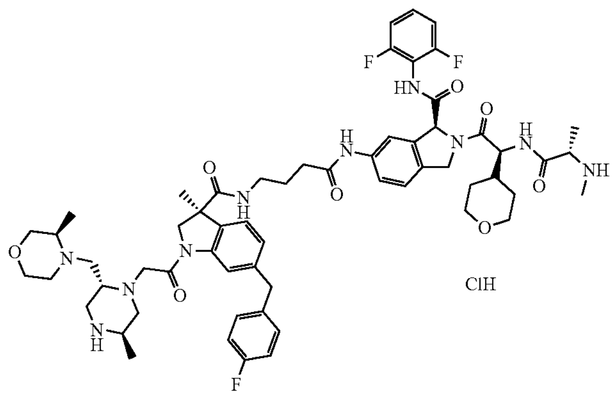 [SMILES: CN[C@@H](C)C(=O)N[C@H](C(=O)N1Cc2ccc(NC(=O)CCCNC(=O)[C@]3(C)CN(C(=O)CN4C[C@@H](C)NC[C@@H]4CN4CCOC[C@H]4C)c4cc(Cc5ccc(F)cc5)ccc43)cc2[C@H]1C(=O)Nc1c(F)cccc1F)C1CCOCC1 ; Cl] | (S)-N-(4-(((S)-3-((2,6-difluorophenyl)carbamoyl)-2-((S)-2-((S)-2-(methylamino)propanamido)-2-(tetrahydro-2H-pyran-4-yl)acetyl)isoindolin-5-yl)amino)-4-oxobutyl)-6-(4-fluorobenzyl)-3-methyl-1-(2-((2R,5R)-5-methyl-2-(((R)-3-methylmorpholino)methyl)piperazin-1-yl)acetyl)indoline-3-carboxamide trihydrochloride | 0.006 | 0.011 | 0.116 | 0.003 |
| 19 | 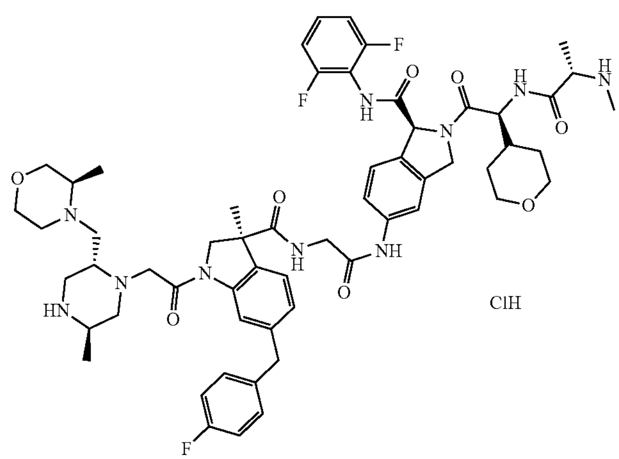 [SMILES: CN[C@@H](C)C(=O)N[C@H](C(=O)N1Cc2cc(NC(=O)CNC(=O)[C@]3(C)CN(C(=O)CN4C[C@@H](C)NC[C@@H]4CN4CCOC[C@H]4C)c4cc(Cc5ccc(F)cc5)ccc43)ccc2[C@H]1C(=O)Nc1c(F)cccc1F)C1CCOCC1 ; Cl] | (S)-N-(2-(((S)-1-((2,6-difluorophenyl)carbamoyl)-2-((S)-2-((S)-2-(methylamino)propanamido)-2-(tetrahydro-2H-pyran-4-yl)acetyl)isoindolin-5-yl)amino)-2-oxoethyl)-6-(4-fluorobenzyl)-3-methyl-1-(2-((2R,5R)-5-methyl-2-(((R)-3-methylmorpholino)methyl)piperazin-1-yl)acetyl)indoline-3-carboxamide trihydrochloride | 0.011 | 0.008 | 0.429 | 0.003 |
| 20 | 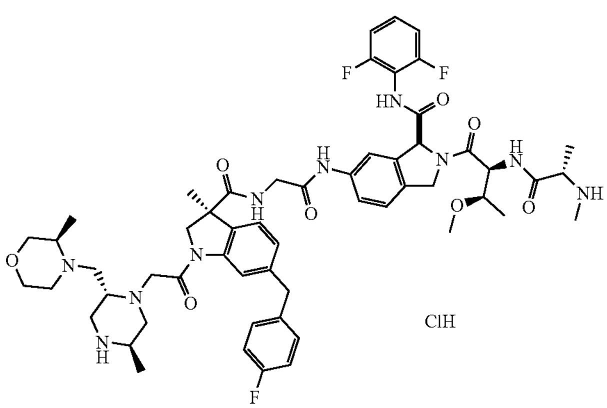 [SMILES: CN[C@@H](C)C(=O)N[C@H](C(=O)N1Cc2ccc(NC(=O)CNC(=O)[C@]3(C)CN(C(=O)CN4C[C@@H](C)NC[C@@H]4CN4CCOC[C@H]4C)c4cc(Cc5ccc(F)cc5)ccc43)cc2[C@H]1C(=O)Nc1c(F)cccc1F)[C@@H](C)OC ; Cl] | (S)-N-(2-(((S)-3-((2,6-difluorophenyl)carbamoyl)-2-((2S,3R)-3-methoxy-2-((S)-2-(methylamino)propanamido)butanoyl)isoindolin-5-yl)amino)-2-oxoethyl)-6-(4-fluorobenzyl)-3-methyl-1-(2-((2R,5R)-5-methyl-2-(((R)-3-methylmorpholino)methyl)piperazin-1-yl)acetyl)indoline-3-carboxamide trihydrochloride | 0.004 | 0.005 | 0.11 | 0.002 |

-continued

| Ex | Structure | Name | IC₅₀ XIAP BIR2 | IC₅₀ XIAP BIR3 | IC₅₀ cIAP BIR2 | IC₅₀ cIAP BIR3 |
|---|---|---|---|---|---|---|
| 21 | 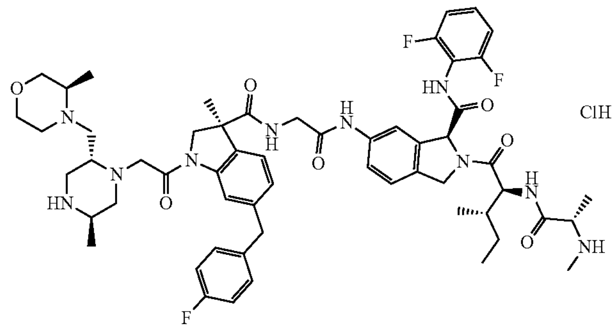 [SMILES: CC[C@H](C)[C@H](NC(=O)[C@H](C)NC)C(=O)N1Cc2ccc(NC(=O)CNC(=O)[C@]3(C)CN(C(=O)CN4C[C@@H](C)NC[C@@H]4CN4CCOC[C@H]4C)c4cc(Cc5ccc(F)cc5)ccc43)cc2[C@H]1C(=O)Nc1c(F)cccc1F ; Cl] | (S)-N-(2-(((S)-3-((2,6-difluorophenyl)carbamoyl)-2-((2S,3S)-3-methyl-2-((S)-2-(methylamino)propanamido)pentanoyl)isoindolin-5-yl)amino)-2-oxoethyl)-6-(4-fluorobenzyl)-3-methyl-1-(2-((2R,5R)-5-methyl-2-(((R)-3-methylmorpholino)methyl)piperazin-1-yl)acetyl)indoline-3-carboxamide trihydrochloride | 0.004 | 0.006 | 0.060 | 0.003 |
| 22 | 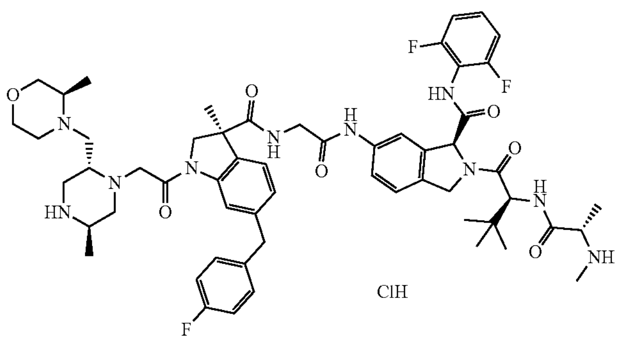 [SMILES: CN[C@@H](C)C(=O)N[C@H](C(=O)N1Cc2ccc(NC(=O)CNC(=O)[C@]3(C)CN(C(=O)CN4C[C@@H](C)NC[C@@H]4CN4CCOC[C@H]4C)c4cc(Cc5ccc(F)cc5)ccc43)cc2[C@H]1C(=O)Nc1c(F)cccc1F)C(C)(C)C ; Cl] | (S)-N-(2-(((S)-3-((2,6-difluorophenyl)carbamoyl)-2-((S)-3,3-dimethyl-2-((S)-2-(methylamino)propanamido)butanoyl)isoindolin-5-yl)amino)-2-oxoethyl)-6-(4-fluorobenzyl)-3-methyl-1-(2-((2R,5R)-5-methyl-2-(((R)-3-methylmorpholino)methyl)piperazin-1-yl)acetyl)indoline-3-carboxamide trihydrochloride | 0.003 | 0.009 | 0.035 | 0.003 |
| A | AND Enantiomer | N-(2-aminoethyl)-6-(4-fluorobenzyl)-3-methyl-1-(2-((2R,5R)-5-methyl-2-(((R)-3-methylmorpholino)methyl)piperazin-1-yl)acetyl)indoline-3-carboxamide dihydrochloride | >54.2 | 0.041 | >54.2 | 0.081 |
| B | 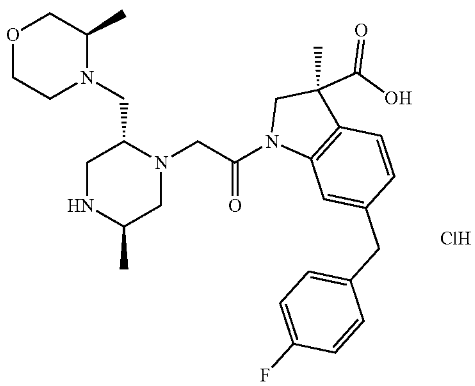 [SMILES: C[C@@H]1CN(CC(=O)N2C[C@@](C)(C(=O)O)c3ccc(Cc4ccc(F)cc4)cc32)[C@@H](CN2CCOC[C@H]2C)CN1 ; Cl] | (S)-6-(4-fluorobenzyl)-3-methyl-1-(2-((2R,5R)-5-methyl-2-(((R)-3-methylmorpholino)methyl)piperazin-1-yl)acetyl)indoline-3-carboxylic acid dihydrochloride | >54.2 | 0.068 | 39.3 | 0.218 |

| Ex | Structure | Name | IC$_{50}$ XIAP BIR2 | IC$_{50}$ XIAP BIR3 | IC$_{50}$ cIAP BIR2 | IC$_{50}$ cIAP BIR3 |
|---|---|---|---|---|---|---|
| C | AND Enantiomer | 1-(6-(4-fluorobenzyl)-3-(hydroxymethyl)-3-methylindolin-1-yl)-2-((2R,5R)-5-methyl-2-(((R)-3-methylmorpholino)methyl)piperazin-1-yl)ethanone dihydrochloride | >54.2 | 0.038 | 29 | 0.103 |
| D | AND Enantiomer | 4-(6-(4-fluorobenzyl)-3-methyl-1-(2-((2R,5R)-5-methyl-2-(((R)-3-methylmorpholino)methyl)piperazin-1-yl)acetyl)indoline-3-carboxamido)benzoic acid dihydrochloride | 42.7 | 0.032 | 47.6 | 0.054 |
| E | AND Enantiomer | 2-(6-(4-fluorobenzyl)-3-methyl-1-(2-((2R,5R)-5-methyl-2-(((R)-3-methylmorpholino)methyl)piperazin-1-yl)acetyl)indoline-3-carboxamido)acetic acid dihydrochloride | 42.7 | 0.056 | >54.2 | 0.1 |

EXAMPLES

Figure 1:
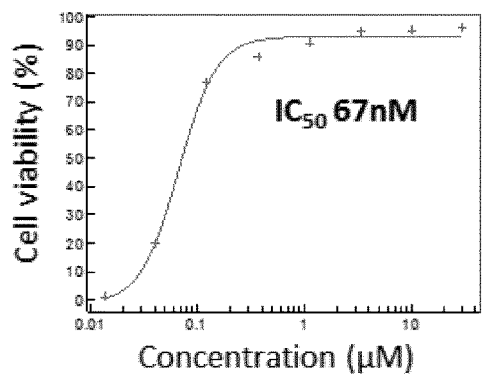
FIG. 1: Single agent activity of N-(2-(((S)-3-((2,6-Difluorophenyl)carbamoyl)-2-((S)-2-((S)-2-(methylamino)propanamido)-2-(tetrahydro-2H-pyran-4-yl)acetyl)isoindolin-5-yl)amino)-2-oxoethyl)-6-(4-fluorobenzyl)-3-methyl-1-(2-((2R,5R)-5-methyl-2-(((R)-3-methylmorpholino)methyl)piperazin-1-yl)acetyl)indoline-3-carboxamide trihydrochloride in the cell viability assay in SK-OV-3 cells
Figure 2:
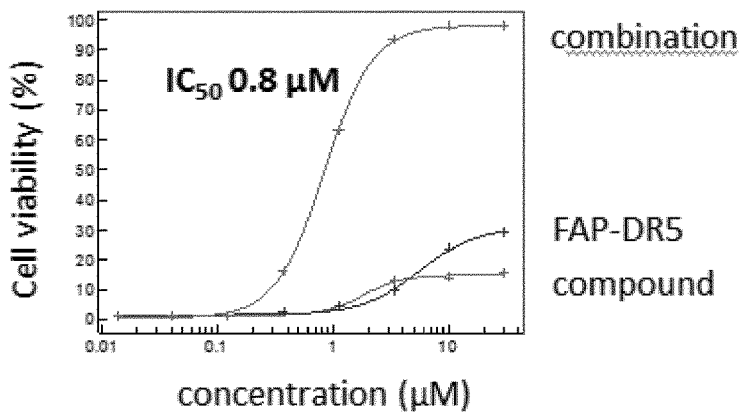
FIG. 2: Activity of N-(2-(((S)-3-((2,6-Difluorophenyl)carbamoyl)-2-((S)-2-((S)-2-(methylamino)propanamido)-2-(tetrahydro-2H-pyran-4-yl)acetyl)isoindolin-5-yl)amino)-2-oxoethyl)-6-(4-fluorobenzyl)-3-methyl-1-(2-((2R,5R)-5-methyl-2-(((R)-3-methylmorpholino)methyl)piperazin-1-yl)acetyl)indoline-3-carboxamide trihydrochloride in the cell viability assay in HCT-116 cells as single agent, and in combination with DR5-FAP bispecific antibody X AB (titrating FAP-DR5 concentration)
Figure 3:
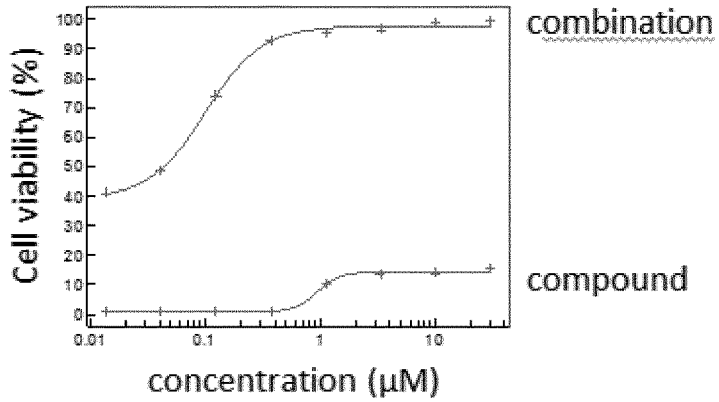
FIG. 3: Activity of N-(2-(((S)-3-((2,6-Difluorophenyl)carbamoyl)-2-((S)-2-((S)-2-(methylamino)propanamido)-2-(tetrahydro-2H-pyran-4-yl)acetyl)isoindolin-5-yl)amino)-2-oxoethyl)-6-(4-fluorobenzyl)-3-methyl-1-(2-((2R,5R)-5-methyl-2-(((R)-3-methylmorpholino)methyl)piperazin-1-yl)acetyl)indoline-3-carboxamide trihydrochloride in the cell viability assay in HCT-116 cells as single agent, and in combination with DR5-FAP bispecific antibody X AB (using a fixed concentration of FAP-DR 5, 1.5 μg/ml))
Figure 4:
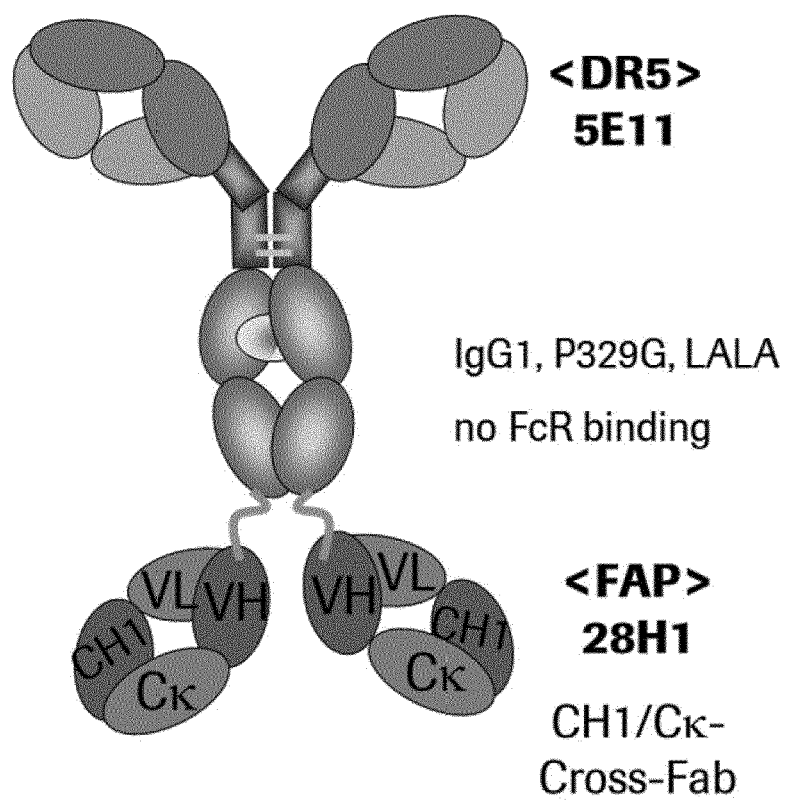
FIG. 4: Schematic representation of the FAP-DR5 bispecific antibody molecule design and mode of action.

The compounds of the present invention may be synthesized according to known techniques. The following examples and references are provided to aid the understanding of the present invention. The examples are not intended, however, to limit the invention, the true scope of which is set forth in the appended claims.

Example 1

N—((S)-3-((2,6-Difluorophenyl)carbamoyl)-2-((S)-2-((S)-2-(methylamino)propanamido)-2-(tetrahydro-2H-pyran-4-yl)acetyl)isoindolin-5-yl)-6-(4-fluorobenzyl)-3-methyl-1-(2-((2R,5R)-5-methyl-2-(((R)-3-methylmorpholino)methyl)piperazin-1-yl)acetyl) indoline-3-carboxamide Trihydrochloride a) 1-tert-Butyl 3-methyl 6-bromo-3-methyl-indoline-1,3-dicarboxylate

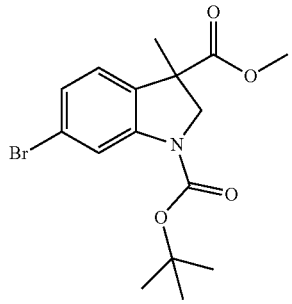 [SMILES: COC(=O)C1(C)CN(C(=O)OC(C)(C)C)c2cc(Br)ccc21]

Boc-anhydride (1.49 g, 1.59 ml, 6.84 mmol, Eq: 1.09) was added to a solution of methyl 6-bromo-3-methylindoline-3-carboxylate (1.696 g, 6.28 mmol, Eq: 1) (described in WO 2012143726 A1) in dichloromethane (30 ml) with DIPEA (933 mg, 1.26 ml, 7.22 mmol, Eq: 1.15) at 0° C. Stirring was continued over weekend while warming slowly to room temperature. Sat. NaHCO₃ solution was added and extracted three times with dichloromethane, dried over magnesium sulfate, filtered and evaporated. The crude material was applied on silica gel and purified by column chromatography using heptane/ethyl acetate (0-50% ethyl acetate) as eluent affording 1-tert-butyl 3-methyl 6-bromo-3-methyl-indoline-1,3-dicarboxylate (1.725 g, 74.2%) as a light yellow oil. MS: m/z (M+H)⁺=357.0 b) tert-Butyl-methyl 6-[(4-fluorophenyl)methyl]-3-methyl-indoline-1,3-dicarboxylate

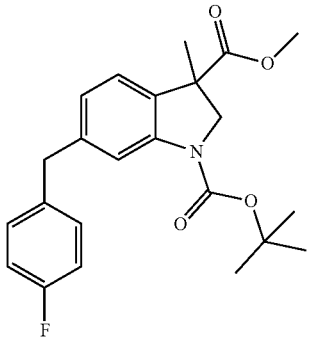 [SMILES: COC(=O)C1(C)CN(C(=O)OC(C)(C)C)c2cc(Cc3ccc(F)cc3)ccc21]

(dppf) PdCl₂.CH₂Cl₂ (56 mg, 68.6 μmol, Eq: 0.01) and a solution of (4-fluorobenzyl)zinc(II) chloride in THF (27.4 ml, 13.7 mmol, Eq: 2) were added to a solution of 1-tert-butyl 3-methyl 6-bromo-3-methylindoline-1,3-dicarboxylate (2.539 g, 6.86 mmol, Eq: 1) in dry THF (13.9 ml). The mixture was stirred in a sealed vial at 90° C. overnight. The crude mixture was applied on silica gel after adding some drops of water and was purified by column chromatography using heptane/ethyl acetate (0-30% ethyl acetate) as eluent affording 1-tert-butyl 3-methyl 6-(4-fluorobenzyl)-3-methylindoline-1,3-dicarboxylate (1.44 g, 52.6%) as a light yellow oil. MS: m/z (M+H)⁺=399.1 c) Methyl 6-[(4-fluorophenyl)methyl]-3-methyl-indoline-3-carboxylate

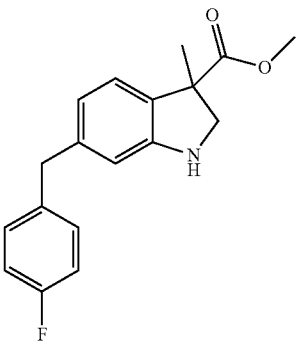

Hydrochloric acid in dioxane (8.63 g, 8.21 ml, 32.9 mmol, Eq: 9.12) was added to 1-tert-butyl 3-methyl 6-(4-fluorobenzyl)-3-methylindoline-1,3-dicarboxylate (1.44 g, 3.6 mmol, Eq: 1) in methanol (10 ml) and stirred at 50° C. for 5 h. The reaction mixture was concentrated in vacuo and the residue partitioned between water and ethyl acetate. The aqueous phase was quenched with sat. aqueous NaHCO₃ and the solid was filtered off. The water phase was extracted three times with ethyl acetate, dried over magnesium sulfate, filtered and evaporated. The crude material was applied on silica gel and was purified by column chromatography using heptane/ethyl acetate (0-50% ethyl acetate) as eluent affording methyl 6-[(4-fluorophenyl)methyl]-3-methyl-indoline-3-carboxylate (1.05 g, 97.3%) as a light brown oil. MS: m/z (M+H)⁺=300.14 d) Methyl 1-[2-[(2S,5R)-4-tert-butoxycarbonyl-5-methyl-2-[[(3R)-3-methylmorpholin-4-yl]methyl]piperazin-1-yl]acetyl]-6-[(4-fluorophenyl)methyl]-3-methyl-indoline-3-carboxylate

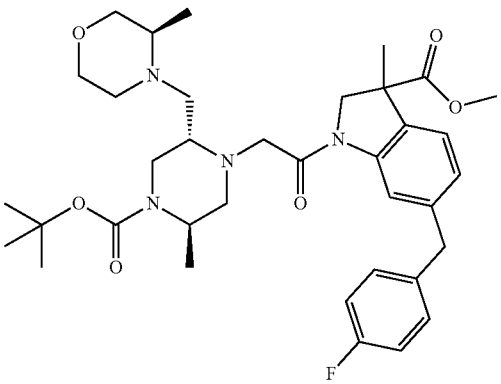 [SMILES: COC(=O)C1(C)CN(C(=O)CN2C[C@@H](C)N(C(=O)OC(C)(C)C)C[C@@H]2CN2CCOC[C@H]2C)c2cc(Cc3ccc(F)cc3)ccc21]

Methyl 6-(4-fluorobenzyl)-3-methylindoline-3-carboxylate (403 mg, 1.35 mmol, Eq: 1) was dissolved in ethyl acetate (4.5 ml) and 2-((2S,5R)-4-(tert-butoxycarbonyl)-5-methyl-2-(((R)-3-methylmorpholino)methyl)piperazin-1-yl) acetic acid (500 mg, 1.35 mmol, Eq: 1) (described in WO 2012143726 A1), N-methylmorpholine (1.36 g, 1.48 ml, 13.5 mmol, Eq: 10) and T3P in EtOAc 50% (2.57 g, 2.4 ml, 4.04 mmol, Eq: 3) were added and stirred overnight at room temperature. The reaction mixture was diluted with ethyl acetate and washed with sat. NaHCO₃, dried over Na₂SO4 and concentrated in vacuo. The crude was applied on silica gel and purified by column chromatography using heptane/ethyl acetate (0-50% ethyl acetate) as eluent affording methyl 1-[2-[(2S,5R)-4-tert-butoxycarbonyl-5-methyl-2-[[(3R)-3-methylmorpholin-4-yl]methyl]piperazin-1-yl]acetyl]-6-[(4-fluorophenyl)methyl]-3-methyl-indoline-3-carboxylate (588 mg, 66.9%) as a white foam. MS: m/z (M+H)⁺=653.37 e) 1-[2-[(2S,5R)-4-tert-Butoxycarbonyl-5-methyl-2-[[(3R)-3-methylmorpholin-4-yl]methyl]piperazin-1-yl]acetyl]-6-[(4-fluorophenyl)methyl]-3-methyl-indoline-3-carboxylic Acid

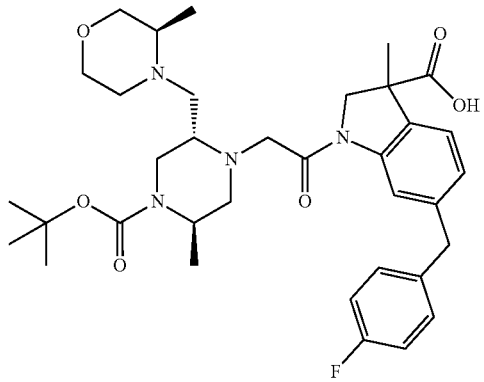 [SMILES: C[C@@H]1COCCN1C[C@H]1CN(C(=O)OC(C)(C)C)[C@H](C)CN1CC(=O)N1CC(C)(C(=O)O)c2ccc(Cc3ccc(F)cc3)cc21]

Methyl 1-(2-((2S,5R)-4-(tert-butoxycarbonyl)-5-methyl-2-(((R)-3-methylmorpholino)methyl)piperazin-1-yl)acetyl)-6-(4-fluorobenzyl)-3-methylindoline-3-carboxylate (2.1 g, 3.22 mmol, Eq: 1) was stirred in ethanol (13 ml) and water (5.2 ml). Lithium hydroxide (231 mg, 9.65 mmol, Eq: 3) was added and stirring was continued for 3 h at 60° C. The solvent was evaporated and the water phase acidified to pH 7 with HCl 1N aq. The mixture was extracted three times with ethyl acetate, dried over magnesium sulfate, filtered and evaporated affording 1-[2-[(2S,5R)-4-tert-butoxycarbonyl-5-methyl-2-[[(3R)-3-methylmorpholin-4-yl]methyl]piperazin-1-yl]acetyl]-6-[(4-fluorophenyl)methyl]-3-methyl-indoline-3-carboxylic acid (2.04 g, 99.3%) as an off-white foam. MS: m/z (M+H)⁺=639.35 f) 3-[[(3S)-2-[(2S)-2-[[(2S)-2-[tert-Butoxycarbonyl(methyl)amino]propanoyl]amino]-2-tetrahydropyran-4-yl-acetyl]-3-[(2,6-difluorophenyl)carbamoyl] isoindolin-5-yl]carbamoyl]-6-[(4-fluorophenyl) methyl]-3-methyl-indolin-1-yl]-2-oxo-ethyl]-2-methyl-5-[[(3R)-3-methylmorpholin-4-yl]methyl] piperazine-1-carboxylate

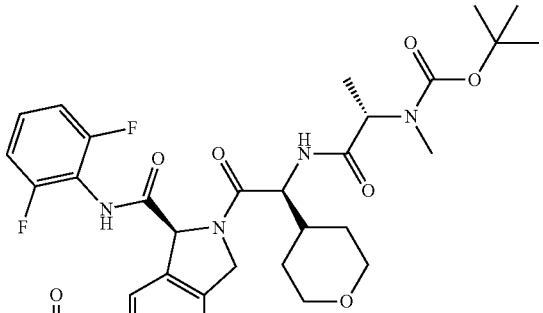

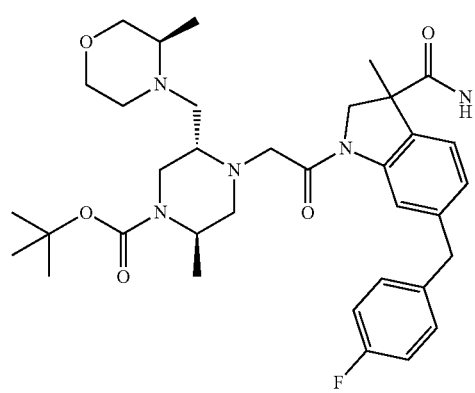

1-(2-((2S,5R)-4-(tert-Butoxycarbonyl)-5-methyl-2-(((R)-3-methylmorpholino)methyl)piperazin-1-yl)acetyl)-6-(4-fluorobenzyl)-3-methylindoline-3-carboxylic acid (100 mg, 157 µmol, Eq: 1) was stirred with tert-butyl ((S)-1-(((S)-2-((S)-6-amino-1-((2,6-difluorophenyl)carbamoyl)isoindolin-2-yl)-2-oxo-1-(tetrahydro-2H-pyran-4-yl)ethyl)amino)-1-oxopropan-2-yl)(methyl)carbamate (96.4 mg, 157 µmol, Eq: 1; Intermediate 2), N-methylmorpholine (158 mg, 172 µl, 1.57 mmol, Eq: 10) and T3P in EtOAc 50% (299 mg, 280 µl, 470 µmol, Eq: 3) in ethyl acetate (600 µl) at room temperature overnight. Sat. NaHCO₃ solution was added and extracted three times with ethyl acetate, dried over magnesium sulfate, filtered and evaporated. The crude material was applied on silica gel and purified by column chromatography using ethyl acetate as eluent affording 3-[[(3S)-2-[(2S)-2-[[(2S)-2-[tert-butoxycarbonyl(methyl)amino]propanoyl]amino]-2-tetrahydropyran-4-yl-acetyl]-3-[(2,6-difluorophenyl)carbamoyl]isoindolin-5-yl]carbamoyl]-6-[(4-fluorophenyl)methyl]-3-methyl-indolin-1-yl]-2-oxo-ethyl]-2-methyl-5-[[(3R)-3-methylmorpholin-4-yl]methyl]piperazine-1-carboxylate (120 mg, 62%) as a white solid. MS: m/z (M+H)⁺=1236.23 g) N-[(3S)-3-[(2,6-Difluorophenyl)carbamoyl]-2-[(2S)-2-[[(2S)-2-(methylamino)propanoyl]amino]-2-tetrahydropyran-4-yl-acetyl]isoindolin-5-yl]-6-[(4-fluorophenyl)methyl]-3-methyl-1-[2-[(2R,5R)-5-methyl-2-[[(3R)-3-methylmorpholin-4-yl]methyl]piperazin-1-yl]acetyl]indoline-3-carboxamide Trihydrochloride

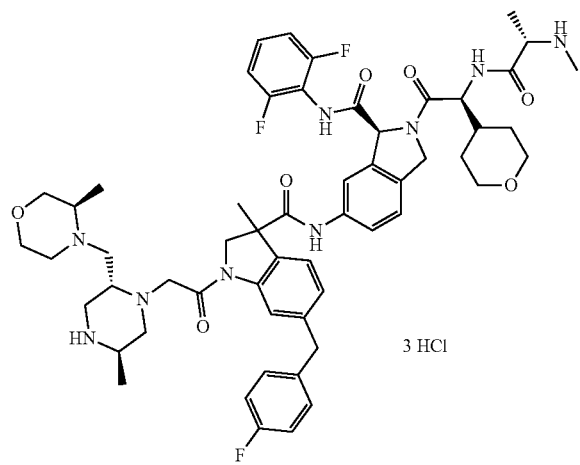 [SMILES: CN[C@@H](C)C(=O)N[C@H](C(=O)N1Cc2ccc(NC(=O)C3(C)CN(C(=O)CN4C[C@@H](C)NC[C@@H]4CN4CCOC[C@H]4C)c4cc(Cc5ccc(F)cc5)ccc43)cc2[C@H]1C(=O)Nc1c(F)cccc1F)C1CCOCC1]

3 HCl (2R,5S)-tert-Butyl 4-(2-(3-(((S)-2-((S)-2-((S)-2-((tert-butoxycarbonyl)(methyl)amino)propanamido)-2-(tetrahydro-2H-pyran-4-yl)acetyl)-3-((2,6-difluorophenyl)carbamoyl)isoindolin-5-yl)carbamoyl)-6-(4-fluorobenzyl)-3-methylindolin-1-yl)-2-oxoethyl)-2-methyl-5-(((R)-3-methylmorpholino)methyl)piperazine-1-carboxylate (110 mg, 89 µmol, Eq: 1) was stirred with HCl in dioxane 4M (2 ml, 8 mmol, Eq: 89.9) in ethyl acetate (1.5 ml) at room temperature overnight. The precipitate was filtered off and washed with ether. The solid was dried under high vacuum affording N-[(3S)-3-[(2,6-difluorophenyl)carbamoyl]-2-[(2S)-2-[[(2S)-2-(methylamino)propanoyl]amino]-2-tetrahydropyran-4-yl-acetyl]isoindolin-5-yl]-6-[(4-fluorophenyl)methyl]-3-methyl-1-[2-[(2R,5R)-5-methyl-2-[[(3R)-3-methylmorpholin-4-yl]methyl]piperazin-1-yl]acetyl]indoline-3-carboxamide trihydrochloride (99.4 mg, 97.5%) as an off-white solid. MS: m/z (M+H)⁺=1036.52

Example 2

N-(2-(((S)-3-((2,6-Difluorophenyl)carbamoyl)-2-((S)-2-((S)-2-(methylamino)propanamido)-2-(tetrahydro-2H-pyran-4-yl)acetyl)isoindolin-5-yl)amino)-2-oxoethyl)-6-(4-fluorobenzyl)-3-methyl-1-(2-((2R,5R)-5-methyl-2-(((R)-3-methylmorpholino)methyl)piperazin-1-yl)acetyl)indoline-3-carboxamide Trihydrochloride a) (2R,5S)-tert-Butyl 4-(2-(6-(4-fluorobenzyl)-3-((2-methoxy-2-oxoethyl)carbamoyl)-3-methylindolin-1-yl)-2-oxoethyl)-2-methyl-5-(((R)-3-methylmorpholino)methyl)piperazine-1-carboxylate

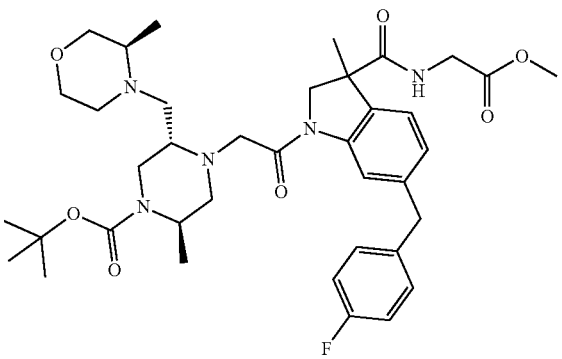 [SMILES: COC(=O)CNC(=O)C1(C)CN(C(=O)CN2C[C@@H](C)N(C(=O)OC(C)(C)C)C[C@@H]2CN2CCOC[C@H]2C)c2cc(Cc3ccc(F)cc3)ccc21]

1-(2-((2S,5R)-4-(tert-Butoxycarbonyl)-5-methyl-2-(((R)-3-methylmorpholino)methyl)piperazin-1-yl)acetyl)-6-(4-fluorobenzyl)-3-methylindoline-3-carboxylic acid (500 mg, 783 µmol, Eq: 1) was stirred with methyl 2-aminoacetate hydrochloride (113 mg), DIPEA (405 mg, 547 µl, 900 µmol, Eq: 1.15) and HATU (387 mg, 1.02 mmol, Eq: 1.3) overnight at room temperature. The reaction mixture was poured into 0.5M HCl aq. and extracted three times with ethyl acetate, washed with brine, dried over magnesium sulfate, filtered and evaporated. The crude material was applied on silica gel and purified by column chromatography using ethyl acetate/methanol (0-5% methanol) as eluent affording (2R,5S)-tert-butyl 4-(2-(6-(4-fluorobenzyl)-3-((2-methoxy-2-oxoethyl)carbamoyl)-3-methylindolin-1-yl)-2-oxoethyl)-2-methyl-5-(((R)-3-methylmorpholino)methyl)piperazine-1-carboxylate (369 mg, 520 µmol, 66.4%) as a light yellow foam. MS: m/z (M+H)⁺=710.39 b) 2-(1-(2-((2S,5R)-4-(tert-Butoxycarbonyl)-5-methyl-2-(((R)-3-methylmorpholino)methyl)piperazin-1-yl)acetyl)-6-(4-fluorobenzyl)-3-methylindoline-3-carboxamido)acetic Acid

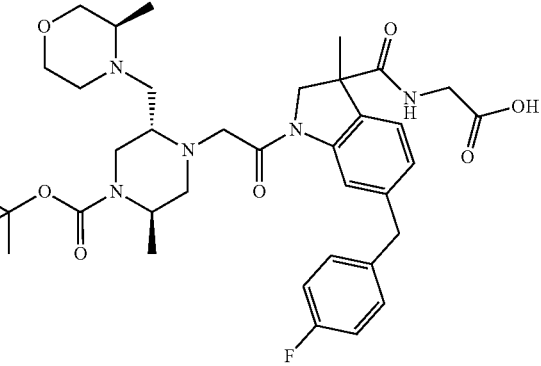

(2R,5S)-tert-Butyl 4-(2-(6-(4-fluorobenzyl)-3-((2-methoxy-2-oxoethyl)carbamoyl)-3-methylindolin-1-yl)-2-oxo ethyl)-2-methyl-5-(((R)-3-methylmorpholino)methyl)piperazine-1-carboxylate (360 mg, 507 μmol, Eq: 1) was stirred in ethanol (2.5 ml) and water (1 ml). Lithium hydroxide (36.4 mg, 1.52 mmol, Eq: 3) was added and stirring was continued for 3 h at 60° C. The solvent was evaporated and the water phase acidified to pH 5-6 with HCl 2N aq. The mixture was extracted three times with ethyl acetate, dried over magnesium sulfate, filtered and evaporated affording 2-(1-(2-((2S,5R)-4-(tert-butoxycarbonyl)-5-methyl-2-(((R)-3-methylmorpholino)methyl)piperazin-1-yl)acetyl)-6-(4-fluorobenzyl)-3-methylindoline-3-carboxamido)acetic acid (306 mg, 440 μmol, 86.7%) as a white solid. MS: m/z (M+H)⁺=696.38 c) tert-Butyl (2R,5S)-4-[2-[3-[[2-[[(3S)-2-[(2S)-2-[[(2S)-2-[tert-butoxycarbonyl(methyl)amino]propanoyl]amino]-2-tetrahydropyran-4-yl-acetyl]-3-[(2,6-difluorophenyl)carbamoyl]isoindolin-5-yl]amino]-2-oxo-ethyl]carbamoyl]-6-[(4-fluorophenyl)methyl]-3-methyl-indolin-1-yl]-2-oxo-ethyl]-2-methyl-5-[[(3R)-3-methylmorpholin-4-yl]methyl]piperazine-1-carboxylate

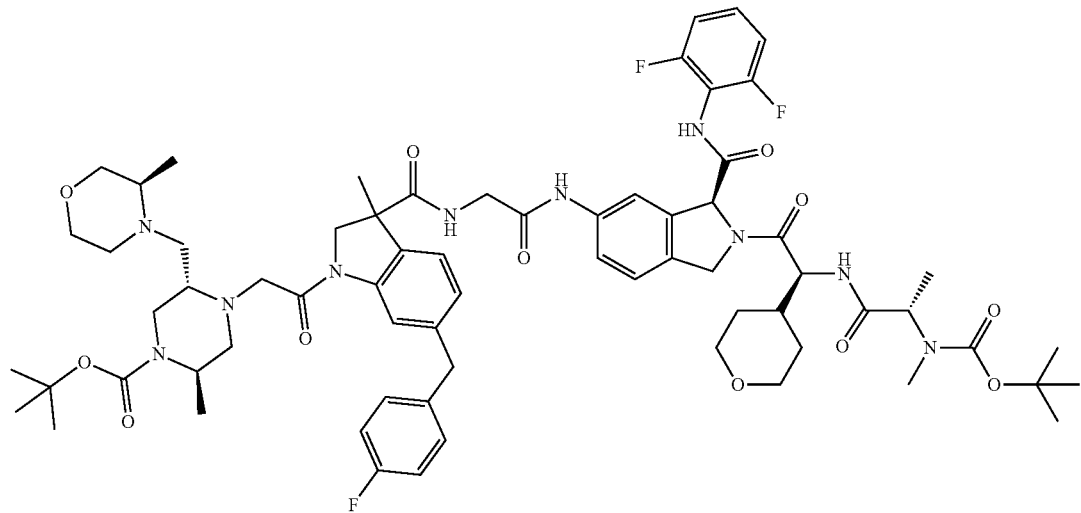

2-(1-(2-((2S,5R)-4-(tert-Butoxycarbonyl)-5-methyl-2-(((R)-3-methylmorpholino)methyl)piperazin-1-yl)acetyl)-6-(4-fluorobenzyl)-3-methylindoline-3-carboxamido)acetic acid (50 mg, 71.9 μmol, Eq: 1) was stirred with tert-butyl ((S)-1-(((S)-2-((S)-6-amino-1-((2,6-difluorophenyl)carbamoyl)isoindolin-2-yl)-2-oxo-1-(tetrahydro-2H-pyran-4-yl)ethyl)amino)-1-oxopropan-2-yl)(methyl)carbamate (44.2 mg, 71.9 μmol, Eq: 1; Intermediate 2), N-methylmorpholine (72.7 mg, 79 μl, 719 μmol, Eq: 10) and T3P in EtOAc 50% (137 mg, 128 μl, 216 μmol, Eq: 3) in ethyl acetate (300 μl) at room temperature overnight. Sat. NaHCO₃ solution was added and extracted three times with ethyl acetate, dried over magnesium sulfate, filtered and evaporated. The crude material was applied on silica gel and purified by column chromatography using ethyl acetate/methanol (0-10% methanol) as eluent affording tert-butyl (2R,5S)-4-[2-[3-[[2-[[(3S)-2-[(2S)-2-[[(2S)-2-[tert-butoxycarbonyl(methyl)amino]propanoyl]amino]-2-tetrahydropyran-4-yl-acetyl]-3-[(2,6-difluorophenyl)carbamoyl]isoindolin-5-yl]amino]-2-oxo-ethyl]carbamoyl]-6-[(4-fluorophenyl)methyl]-3-methyl-indolin-1-yl]-2-oxo-ethyl]-2-methyl-5-[[(3R)-3-methylmorpholin-4-yl]methyl]piperazine-1-carboxylate (48 mg, 51.6%) as a white solid. MS: m/z (M+H)+=1293.65 d) N-[2-[[(3S)-3-[(2,6-Difluorophenyl)carbamoyl]-2-[(2S)-2-[[(2S)-2-(methylamino)propanoyl]amino]-2-tetrahydropyran-4-yl-acetyl]isoindolin-5-yl]amino]-2-oxo-ethyl]-6-[(4-fluorophenyl)methyl]-3-methyl-1-[2-[(2R,5R)-5-methyl-2-[[(3R)-3-methylmorpholin-4-yl]methyl]piperazin-1-yl]acetyl]indoline-3-carboxamide Trihydrochloride

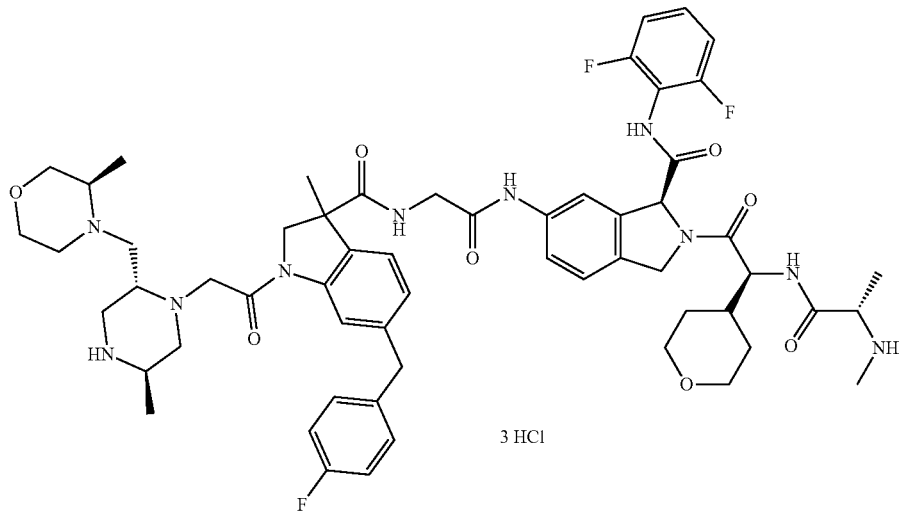 [SMILES: CN[C@@H](C)C(=O)N[C@H](C(=O)N1Cc2ccc(NC(=O)CNC(=O)C3(C)CN(C(=O)CN4C[C@@H](C)NC[C@@H]4CN4CCOC[C@H]4C)c4cc(Cc5ccc(F)cc5)ccc43)cc2[C@H]1C(=O)Nc1c(F)cccc1F)C1CCOCC1]

(2R,5S)-tert-Butyl 4-(2-(3-((2-(((S)-2-((S)-2-((S)-2-((tert-butoxycarbonyl)(methyl)amino)propanamido)-2-(tetrahydro-2H-pyran-4-yl)acetyl)-3-((2,6-difluorophenyl)carbamoyl)isoindolin-5-yl)amino)-2-oxoethyl)carbamoyl)-6-(4-fluorobenzyl)-3-methylindolin-1-yl)-2-oxo ethyl)-2-methyl-5-(((R)-3-methylmorpholino)methyl)piperazine-1-carboxylate was stirred in ethyl acetate (600 μL) with HCl in dioxane 4M (750 μl, 3 mmol, Eq: 92.4) at room temperature overnight. The precipitate was filtered off and washed with diethyl ether. The solid was dried under high vacuum affording N-[2-[[(3S)-3-[(2,6-difluorophenyl)carbamoyl]-2-[(2S)-2-[[(2S)-2-(methylamino)propanoyl]amino]-2-tetrahydropyran-4-yl-acetyl]isoindolin-5-yl]amino]-2-oxo-ethyl]-6-[(4-fluorophenyl)methyl]-3-methyl-1-[2-[(2R,5R)-5-methyl-2-[[(3R)-3-methylmorpholin-4-yl]methyl]piperazin-1-yl]acetyl]indoline-3-carboxamide trihydrochloride (35.5 mg, 90.9%) as a white solid. MS: m/z (M+H)$^+$=1093.54

Example 3 a) (R,R,R)—N,N'-(Ethane-1,2-diyl)bis(6-(4-fluorobenzyl)-3-methyl-1-(2-((2R,5R)-5-methyl-2-(((R)-3-methylmorpholino)methyl)piperazin-1-yl)acetyl)indoline-3-carboxamide) trihydrochloride tert-Butyl (2R,5S)-4-[2-[3-[2-[[1-[2-[(2S,5R)-4-tert-butoxycarbonyl-5-methyl-2-[[(3R)-3-methylmorpholin-4-yl]methyl]piperazin-1-yl]acetyl]-6-[(4-fluorophenyl)methyl]-3-methyl-indoline-3-carbonyl]amino]ethylcarbamoyl]-6-[(4-fluorophenyl)methyl]-3-methyl-indolin-1-yl]-2-oxo-ethyl]-2-methyl-5-[[(3R)-3-methylmorpholin-4-yl]methyl]piperazine-1-carboxylate

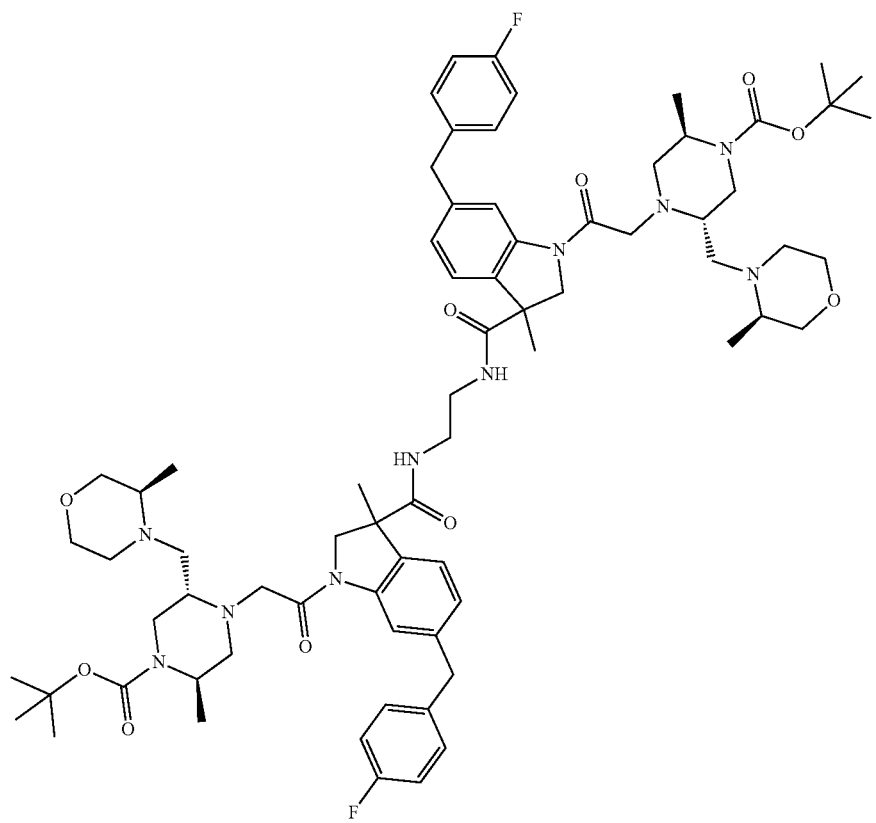 [SMILES: C[C@@H]1COCCN1C[C@H]1CN(C(=O)OC(C)(C)C)[C@H](C)CN1CC(=O)N1CC(C)(C(=O)NCCNC(=O)C2(C)CN(C(=O)CN3C[C@@H](C)N(C(=O)OC(C)(C)C)C[C@@H]3CN3CCOC[C@H]3C)c3cc(Cc4ccc(F)cc4)ccc32)c2ccc(Cc3ccc(F)cc3)cc21]

1-(2-((2S,5R)-4-(tert-Butoxycarbonyl)-5-methyl-2-(((R)-3-methylmorpholino)methyl)piperazin-1-yl)acetyl)-6-(4-fluorobenzyl)-3-methylindoline-3-carboxylic acid (75 mg, 117 μmol, Eq: 2) was stirred with ethane-1,2-diamine (3.53 mg, 3.93 μl, 58.7 μmol, Eq: 1), DIPEA (60.7 mg, 79.9 μl, 470 μmol, Eq: 8) and HATU (58.1 mg, 153 μmol, Eq: 2.6) in DMF (500 μl) at room temperature overnight. The mixture was quenched with 0.5M HCl aq. and extracted three times with ethyl acetate, dried over magnesium sulfate, filtered and evaporated. The crude material was applied on silica gel and purified by column chromatography using ethyl acetate/methanol (0-10% methanol) as eluent affording tert-butyl (2R,5S)-4-[2-[3-[2-[[1-[2-[(2 S,5R)-4-tert-butoxycarbonyl-5-methyl-2-[[(3R)-3-methylmorpholin-4-yl]methyl]piperazin-1-yl]acetyl]-6-[(4-fluorophenyl)methyl]-3-methyl-indoline-3-carbonyl]amino]ethylcarbamoyl]-6-[(4-fluorophenyl)methyl]-3-methyl-indolin-1-yl]-2-oxo-ethyl]-2-methyl-5-[[(3R)-3-methylmorpholin-4-yl]methyl]piperazine-1-carboxylate (56 mg, 73.2%) as a white solid. MS: m/z (M+H)$^+$=1301.75 b) 6-[(4-Fluorophenyl)methyl]-N-[2-[[6-[(4-fluorophenyl)methyl]-3-methyl-1-[2-[(2R,5R)-5-methyl-2-[[(3R)-3-methylmorpholin-4-yl]methyl]piperazin-1-yl]acetyl]indoline-3-carbonyl]amino]ethyl]-3-methyl-1-[2-[(2R,5R)-5-methyl-2-[[(3R)-3-methylmorpholin-4-yl]methyl]piperazin-1-yl]acetyl]indoline-3-carboxamide Trihydrochloride

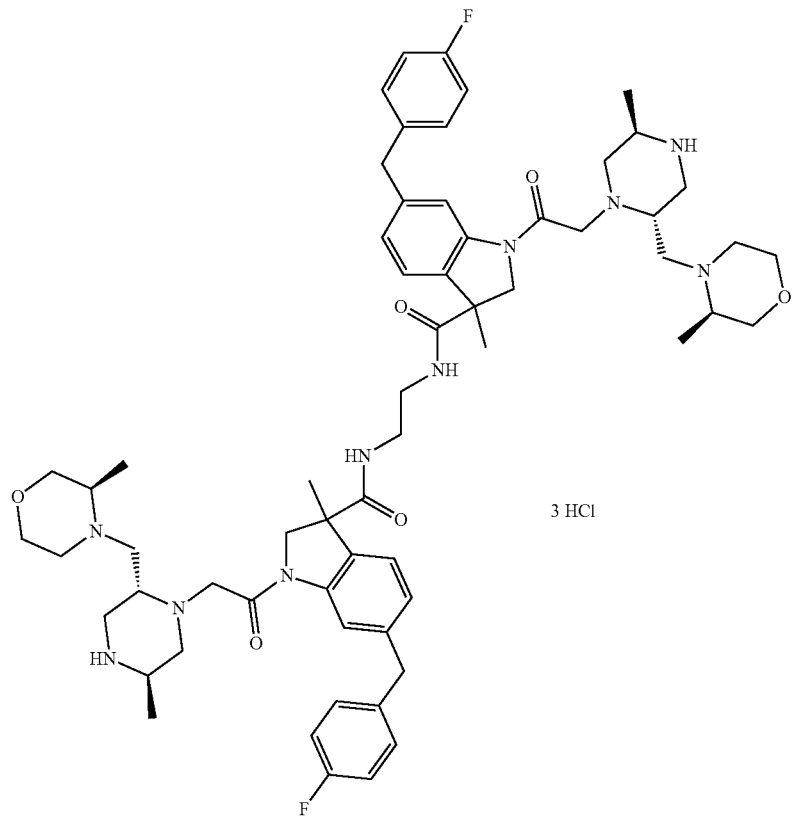 [SMILES: C[C@@H]1CN(CC(=O)N2CC(C)(C(=O)NCCNC(=O)C3(C)CN(C(=O)CN4C[C@@H](C)NC[C@@H]4CN4CCOC[C@H]4C)c4cc(Cc5ccc(F)cc5)ccc43)c3ccc(Cc4ccc(F)cc4)cc32)[C@@H](CN2CCOC[C@H]2C)CN1]

(R,2R,2'R,5S,5'S)-di-tert-Butyl 4,4'-((3,3'-((ethane-1,2-diylbis(azanediyl))bis(carbonyl))bis(6-(4-fluorobenzyl)-3-methylindoline-3,1-diyl))bis(2-oxoethane-2,1-diyl))bis(2-methyl-5-(((R)-3-methylmorpholino)methyl)piperazine-1-carboxylate) (49 mg, 37.6 μmol, Eq: 1) was stirred with HCl in dioxane 4M (850 μl, 3.4 mmol, Eq: 90.3) in ethyl acetate (750 μl) at room temperature overnight. The precipitate was filtered off and washed with diethyl ether. The solid was dried under high vacuum affording (R,R,R)—N,N'-(ethane-1,2-diyl)bis(6-(4-fluorobenzyl)-3-methyl-1-(2-((2R,5R)-5-methyl-2-(((R)-3-methylmorpholino)methyl)piperazin-1-yl)acetyl)indoline-3-carboxamide) trihydrochloride (39.4 mg, 86.4%) as an off-white solid. MS: m/z (M+H)$^+$=1101.65

Example 4

N-(4-(((S)-3-((2,6-Difluorophenyl)carbamoyl)-2-((S)-2-((S)-2-(methylamino)propanamido)-2-(tetrahydro-2H-pyran-4-yl)acetyl)isoindolin-5-yl)carbamoyl)phenyl)-6-(4-fluorobenzyl)-3-methyl-1-(2-((2R,5R)-5-methyl-2-(((R)-3-methylmorpholino)methyl)piperazin-1-yl)acetyl)indoline-3-carboxamide Trihydrochloride a) tert-Butyl (2R,5S)-4-[2-[6-[(4-fluorophenyl)methyl]-3-[(4-methoxycarbonylphenyl)carbamoyl]-3-methyl-indolin-1-yl]-2-oxo-ethyl]-2-methyl-5-[[(3R)-3-methylmorpholin-4-yl]methyl]piperazine-1-carboxylate

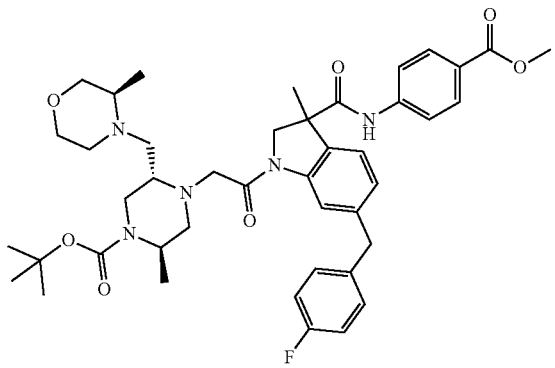 [SMILES: COC(=O)c1ccc(NC(=O)C2(C)CN(C(=O)CN3C[C@@H](C)N(C(=O)OC(C)(C)C)C[C@@H]3CN3CCOC[C@H]3C)c3cc(Cc4ccc(F)cc4)ccc32)cc1]

b) 4-[[1-[2-[(2S,5R)-4-tert-Butoxycarbonyl-5-methyl-2-[[(3R)-3-methylmorpholin-4-yl]methyl]piperazin-1-yl]acetyl]-6-[(4-fluorophenyl)methyl]-3-methyl-indoline-3-carbonyl]amino]benzoic Acid

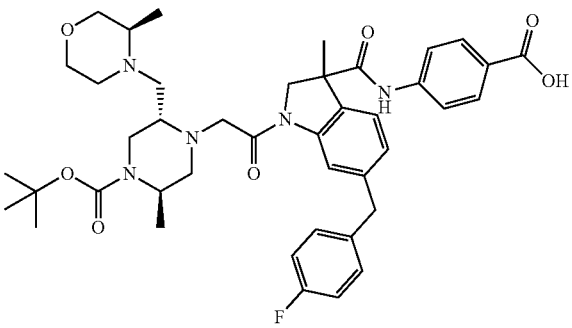 [SMILES: C[C@@H]1COCCN1C[C@H]1CN(C(=O)OC(C)(C)C)[C@H](C)CN1CC(=O)N1CC(C)(C(=O)Nc2ccc(C(=O)O)cc2)c2ccc(Cc3ccc(F)cc3)cc21]

1-(2-((2S,5R)-4-(tert-Butoxycarbonyl)-5-methyl-2-(((R)-3-methylmorpholino)methyl)piperazin-1-yl)acetyl)-6-(4-fluorobenzyl)-3-methylindoline-3-carboxylic acid (300 mg, 470 µmol, Eq: 1) was stirred with methyl 4-aminobenzoate (71 mg, 470 µmol, Eq: 1.0), DIPEA (182 mg, 246 µl, 1.41 mmol, Eq: 3) and HATU (232 mg, 611 µmol, Eq: 1.3) overnight at room temperature. The reaction mixture was poured into 0.5M HCl aq. and extracted three times with ethyl acetate, washed with brine, dried over magnesium sulfate, filtered and evaporated. The crude material was applied on silica gel and was purified by column chromatography using heptane/ethyl acetate (0-100% ethyl acetate) as eluent affording tert-butyl (2R,5S)-4-[2-[6-[(4-fluorophenyl)methyl]-3-[(4-methoxycarbonylphenyl)carbamoyl]-3-methyl-indolin-1-yl]-2-oxo-ethyl]-2-methyl-5-[[(3R)-3-methylmorpholin-4-yl]methyl]piperazine-1-carboxylate (182 mg, 50.2%) as an orange oil. MS: m/z (M+H)$^+$=772.4

(2R,5S)-tert-Butyl 4-(2-(6-(4-fluorobenzyl)-3-((4-(methoxycarbonyl)phenyl)carbamoyl)-3-methylindolin-1-yl)-2-oxoethyl)-2-methyl-5-(((R)-3-methylmorpholino)methyl)piperazine-1-carboxylate (175 mg, 227 µmol, Eq: 1) was stirred in ethanol (1.2 ml) and water (500 µl). Lithium hydroxide (16.3 mg, 680 µmol, Eq: 3) was added and stirring was continued for 3 h at 60° C. The solvent was evaporated and the aqueous layer acidified to pH 6 with HCl 1N aq. The mixture was extracted three times with ethyl acetate, dried over magnesium sulfate, filtered and evaporated affording 4-[[1-[2-[(2S,5R)-4-tert-butoxycarbonyl-5-methyl-2-[[(3R)-3-methylmorpholin-4-yl]methyl]piperazin-1-yl]acetyl]-6-[(4-fluorophenyl)methyl]-3-methyl-indoline-3-carbonyl]amino]benzoic acid (87 mg, 50.6%) as an off-white solid. MS: m/z (M+H)$^+$=758.4 c) tert-Butyl (2R,5S)-4-[2-[3-[[4-[[(3S)-2-[(2S)-2-[[(2S)-2-[tert-butoxycarbonyl(methyl)amino]propanoyl]amino]-2-tetrahydropyran-4-yl-acetyl]-3-[(2,6-difluorophenyl)carbamoyl]isoindolin-5-yl]carbamoyl]phenyl]carbamoyl]-6-[(4-fluorophenyl)methyl]-3-methyl-indolin-1-yl]-2-oxo-ethyl]-2-methyl-5-[[(3R)-3-methylmorpholin-4-yl]methyl]piperazine-1-carboxylate

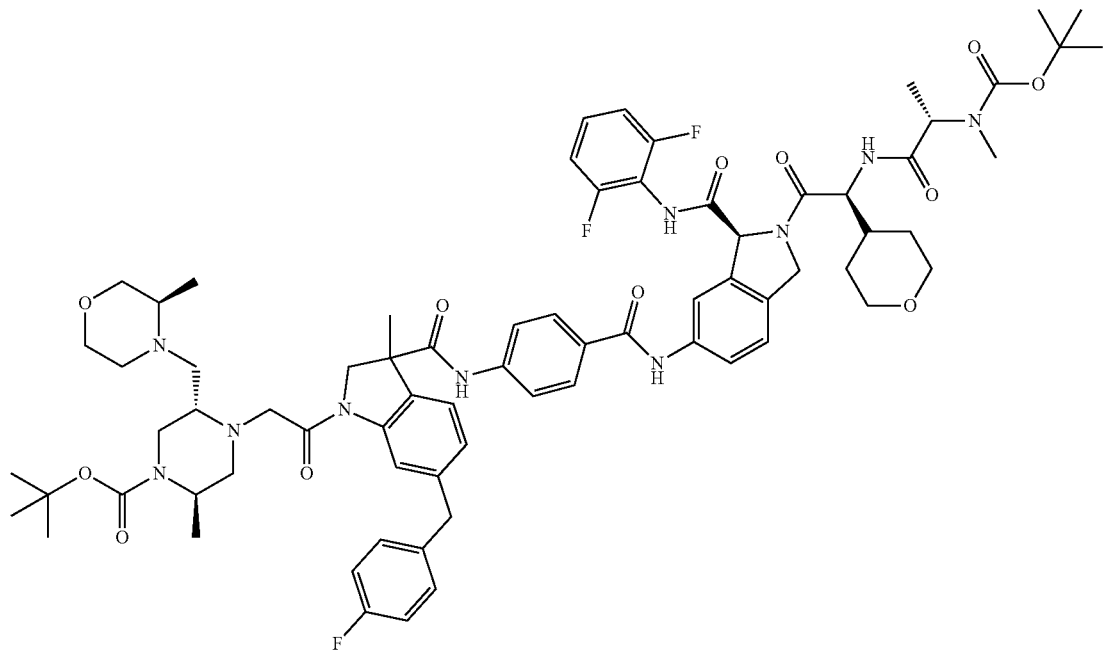 [SMILES: C[C@@H]1COCCN1C[C@H]1CN(C(=O)OC(C)(C)C)[C@H](C)CN1CC(=O)N1CC(C)(C(=O)Nc2ccc(C(=O)Nc3ccc4c(c3)[C@@H](C(=O)Nc3c(F)cccc3F)N(C(=O)[C@@H](NC(=O)[C@H](C)N(C)C(=O)OC(C)(C)C)C3CCOCC3)C4)cc2)c2ccc(Cc3ccc(F)cc3)cc21]

4-(1-(2-((2S,5R)-4-(tert-Butoxycarbonyl)-5-methyl-2-(((R)-3-methylmorpholino)methyl)piperazin-1-yl)acetyl)-6-(4-fluorobenzyl)-3-methylindoline-3-carboxamido)benzoic acid (40 mg, 52.8 µmol, Eq: 1) was stirred with tert-butyl ((S)-1-(((S)-2-((S)-6-amino-1-((2,6-difluorophenyl)carbamoyl)isoindolin-2-yl)-2-oxo-1-(tetrahydro-2H-pyran-4-yl)ethyl)amino)-1-oxopropan-2-yl)(methyl)carbamate (32.5 mg, 52.8 µmol, Eq: 1; Intermediate 2), N-methylmorpholine (53.4 mg, 58 µl, 528 µmol, Eq: 10) and T3P in EtOAc 50% (101 mg, 94.3 µl, 158 µmol, Eq: 3) in ethyl acetate (250 µl) at room temperature overnight. NaHCO$_3$sat. was added and the mixture was extracted three times with ethyl acetate, dried over magnesium sulfate, filtered and evaporated. The crude material was applied on silica gel and was purified by column chromatography using ethyl acetate/methanol (0-5% methanol) as eluent affording tert-butyl (2R,5S)-4-[2-[3-[[4-[[(3S)-2-[(2S)-2-[[(2S)-2-[tert-butoxycarbonyl(methyl)amino]propanoyl]amino]-2-tetrahydropyran-4-yl-acetyl]-3-[(2,6-difluorophenyl)carbamoyl]isoindolin-5-yl]carbamoyl]phenyl]carbamoyl]-6-[(4-fluorophenyl)methyl]-3-methyl-indolin-1-yl]-2-oxo-ethyl]-2-methyl-5-[[(3R)-3-methylmorpholin-4-yl]methyl]piperazine-1-carboxylate (26 mg, 36.3%) as a white solid. MS: m/z (M+H)$^+$=1355.7 d) N-[4-[[(3S)-3-[(2,6-Difluorophenyl)carbamoyl]-2-[(2S)-2-[[(2S)-2-(methylamino)propanoyl]amino]-2-tetrahydropyran-4-yl-acetyl]isoindolin-5-yl]carbamoyl]phenyl]-6-[(4-fluorophenyl)methyl]-3-methyl-1-[2-[(2R,5R)-5-methyl-2-[[(3R)-3-methylmorpholin-4-yl]methyl]piperazin-1-yl]acetyl]indoline-3-carboxamide Trihydrochloride

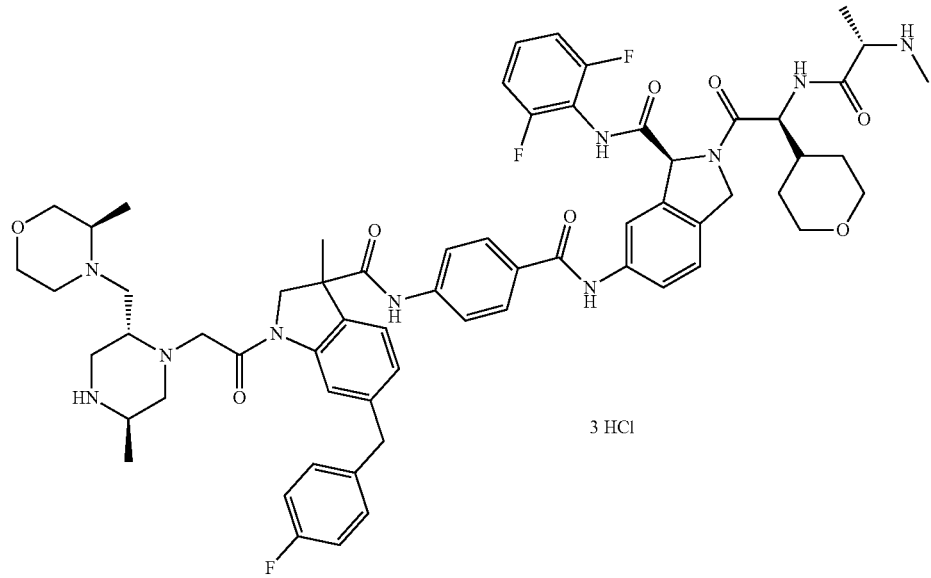 [SMILES: CN[C@@H](C)C(=O)N[C@H](C(=O)N1Cc2ccc(NC(=O)c3ccc(NC(=O)C4(C)CN(C(=O)CN5C[C@@H](C)NC[C@@H]5CN5CCOC[C@H]5C)c5cc(Cc6ccc(F)cc6)ccc54)cc3)cc2[C@H]1C(=O)Nc1c(F)cccc1F)C1CCOCC1]

(2R,5S)-tert-Butyl 4-(2-(3-((4-(((S)-2-((S)-2-((S)-2-((tert-butoxycarbonyl)(methyl)amino)propanamido)-2-(tetrahydro-2H-pyran-4-yl)acetyl)-3-((2,6-difluorophenyl)carbamoyl)isoindolin-5-yl)carbamoyl)phenyl)carbamoyl)-6-(4-fluorobenzyl)-3-methylindolin-1-yl)-2-oxo ethyl)-2-methyl-5-(((R)-3-methylmorpholino)methyl)piperazine-1-carboxylate (22 mg, 16.2 μmol, Eq: 1) was stirred with HCl in dioxane 4M (400 μl, 1.6 mmol, Eq: 98.6) in ethyl acetate (1000 μl) at room temperature overnight. The precipitate was filtered off and washed with diethyl ether. The solid was dried under high vacuum affording N-(4-(((S)-3-((2,6-difluorophenyl)carbamoyl)-2-((S)-2-((S)-2-(methylamino)propanamido)-2-(tetrahydro-2H-pyran-4-yl)acetyl)isoindolin-5-yl)carbamoyl)phenyl)-6-(4-fluorobenzyl)-3-methyl-1-(2-((2R,5R)-5-methyl-2-(((R)-3-methylmorpholino)methyl)piperazin-1-yl)acetyl)indoline-3-carboxamide trihydrochloride (12.1 mg, 59%) as an off-white solid. MS: m/z (M+H)$^+$=1155.6

Example 5

(3S)-2-((S)-3,3-Dimethyl-2-((S)-2-(methylamino)
propanamido)butanoyl)-7-(6-(4-fluorobenzyl)-3-
methyl-1-(2-((2R,5R)-5-methyl-2-(((R)-3-methyl-
morpholino)methyl)piperazin-1-yl)acetyl)indoline-3-
carboxamido)-N—((R)-1,2,3,4-
tetrahydronaphthalen-1-yl)-1,2,3,4-
tetrahydroisoquinoline-3-carboxamide
Trihydrochloride a) tert-Butyl (2R,5S)-4-[2-[3-[[(3S)-2-[(2S)-2-
[[(2S)-2-[tert-butoxycarbonyl(methyl)amino]pro-
panoyl]amino]-3,3-dimethyl-butanoyl]-3-[[(1R)-
tetralin-1-yl]carbamoyl]-3,4-dihydro-1H-
isoquinolin-7-yl]carbamoyl]-6-[(4-fluorophenyl)
methyl]-3-methyl-indolin-1-yl]-2-oxo-ethyl]-2-
methyl-5-[[(3R)-3-methylmorpholin-4-yl]methyl]
piperazine-1-carboxylate

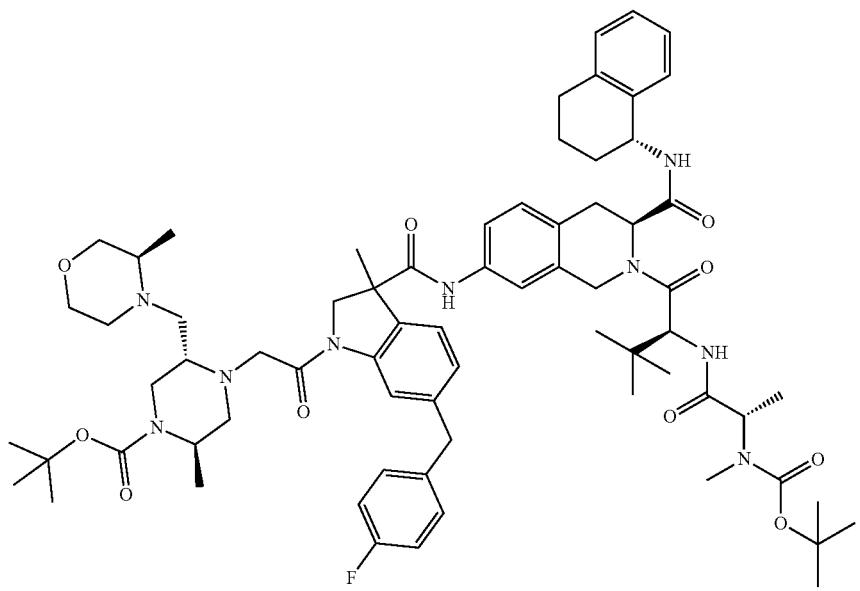 [SMILES: C[C@@H]1COCCN1C[C@H]1CN(C(=O)OC(C)(C)C)[C@H](C)CN1CC(=O)N1CC(C)(C(=O)Nc2ccc3c(c2)CN(C(=O)[C@@H](NC(=O)[C@H](C)N(C)C(=O)OC(C)(C)C)C(C)(C)C)[C@H](C(=O)N[C@@H]2CCCc4ccccc42)C3)c2ccc(Cc3ccc(F)cc3)cc21]

1-(2-((2S,5R)-4-(tert-Butoxycarbonyl)-5-methyl-2-(((R)-3-methylmorpholino)methyl)piperazin-1-yl)acetyl)-6-(4-fluorobenzyl)-3-methylindoline-3-carboxylic acid (40 mg, 62.6 µmol, Eq: 1) was stirred with tert-butyl ((S)-1-(((S)-1-((S)-7-amino-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl)carbamate (38.8 mg, 62.6 µmol, Eq: 1) (described in WO2013/192286 A1), N-methylmorpholine (63.3 mg, 68.8 µl, 626 µmol, Eq: 10) and T3P in EtOAc 50% (120 mg, 112 µl, 188 µmol, Eq: 3) in ethyl acetate (350 µl) at room temperature overnight. NaHCO$_3$sat. was added and extracted three times with ethyl acetate, dried over magnesium sulfate, filtered and evaporated. The crude material was applied on silica gel and purified by column chromatography using ethyl acetate as eluent affording (2R,5S)-tert-butyl 4-(2-(3-(((S)-2-((S)-2-((S)-2-((tert-butoxycarbonyl)(methyl)amino)propanamido)-3,3-dimethylbutanoyl)-3-(((R)-1,2,3,4-tetrahydronaphthalen-1-yl)carbamoyl)-1,2,3,4-tetrahydroisoquinolin-7-yl)carbamoyl)-6-(4-fluorobenzyl)-3-methylindolin-1-yl)-2-oxoethyl)-2-methyl-5-(((R)-3-methylmorpholino)methyl)piperazine-1-carboxylate (44.1 mg, 56.8%) as a white solid. MS: m/z (M+H)$^+$=1240.72 b) (3S)-2-[(2S)-3,3-Dimethyl-2-[[(2S)-2-(methyl-amino)propanoyl]amino]butanoyl]-7-[[6-[(4-fluoro-phenyl)methyl]-3-methyl-1-[2-[(2R,5R)-5-methyl-2-[[(3R)-3-methylmorpholin-4-yl]methyl]piperazin-1-yl]acetyl]indoline-3-carbonyl]amino]-N-[(1R)-tetralin-1-yl]-3,4-dihydro-1H-isoquinoline-3-carboxamide Trihydrochloride

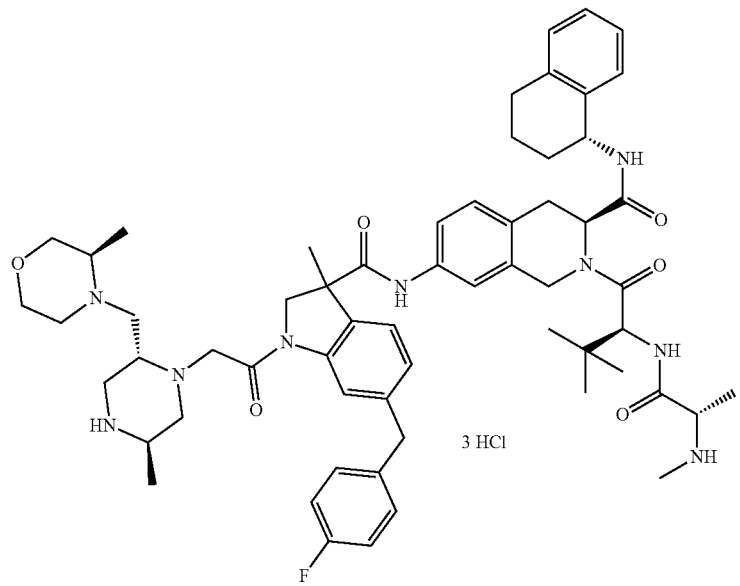 [SMILES: CN[C@@H](C)C(=O)N[C@H](C(=O)N1Cc2cc(NC(=O)C3(C)CN(C(=O)CN4C[C@@H](C)NC[C@@H]4CN4CCOC[C@H]4C)c4cc(Cc5ccc(F)cc5)ccc43)ccc2C[C@H]1C(=O)N[C@@H]1CCCc2ccccc21)C(C)(C)C]

(2R,5S)-tert-Butyl 4-(2-(3-(((S)-2-((S)-2-((S)-2-((tert-bu-toxycarbonyl)(methyl)amino)propanamido)-3,3-dimeth-ylbutanoyl)-3-(((R)-1,2,3,4-tetrahydronaphthalen-1-yl)car-bamoyl)-1,2,3,4-tetrahydroisoquinolin-7-yl)carbamoyl)-6-(4-fluorobenzyl)-3-methylindolin-1-yl)-2-oxoethyl)-2-methyl-5-(((R)-3-methylmorpholino)methyl)piperazine-1-carboxylate (39 mg, 31.4 µmol, Eq: 1) was stirred with HCl in dioxane 4M (700 µl, 2.8 mmol, Eq: 89.1) in ethyl acetate (1 ml) at room temperature overnight. The precipitate was filtered off and washed with diethyl ether. The solid was dried under high vacuum affording (3S)-2-((S)-3,3-dim-ethyl-2-((S)-2-(methylamino)propanamido)butanoyl)-7-(6-(4-fluorobenzyl)-3-methyl-1-(2-((2R,5R)-5-methyl-2-(((R)-3-methylmorpholino)methyl)piperazin-1-yl)acetyl) indoline-3-carboxamido)-N—((R)-1,2,3,4-tetrahydronaphthalen-1-yl)-1,2,3,4-tetrahydroisoquinoline-3-carboxamide trihydrochloride (30 mg, 83%) as an off-white solid. MS: m/z (M+H)$^+$=1040.62

Example 6

(3S)-2-((S)-3,3-Dimethyl-2-((S)-2-(methylamino)propanamido)butanoyl)-7-(2-(6-(4-fluorobenzyl)-3-methyl-1-(2-((2R,5R)-5-methyl-2-(((R)-3-methylmorpholino)methyl)piperazin-1-yl)acetyl)indoline-3-carboxamido)acetamido)-N—((R)-1,2,3,4-tetrahydronaphthalen-1-yl)-1,2,3,4-tetrahydroisoquinoline-3-carboxamide Trihydrochloride a) tert-Butyl (2R,5S)-4-[2-[3-[[2-[[(3S)-2-[(2S)-2-[[(2S)-2-[tert-butoxycarbonyl(methyl)amino]propanoyl]amino]-3,3-dimethyl-butanoyl]-3-[[(1R)-tetralin-1-yl]carbamoyl]-3,4-dihydro-1H-isoquinolin-7-yl]amino]-2-oxo-ethyl]carbamoyl]-6-[(4-fluorophenyl)methyl]-3-methyl-indolin-1-yl]-2-oxo-ethyl]-2-methyl-5-[[(3R)-3-methylmorpholin-4-yl]methyl]piperazine-1-carboxylate

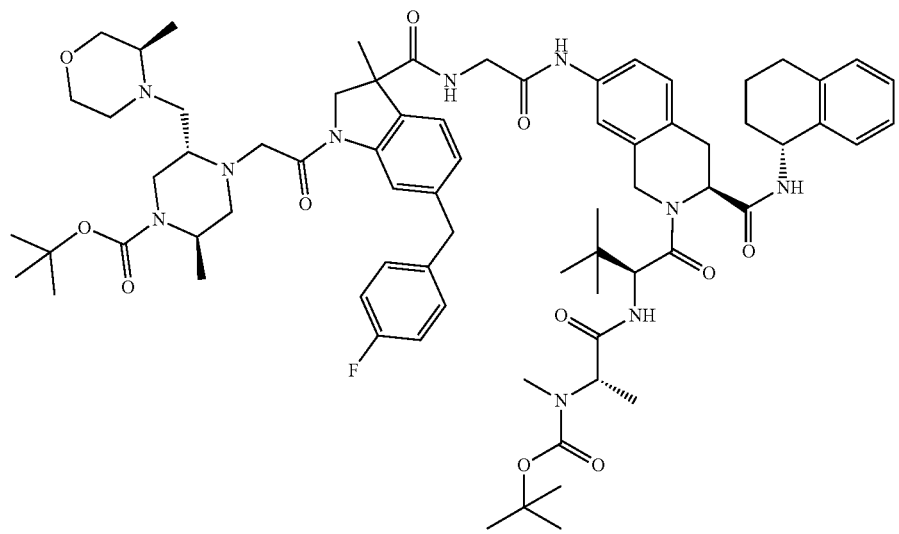 [SMILES: C[C@@H]1COCCN1C[C@H]1CN(C(=O)OC(C)(C)C)[C@H](C)CN1CC(=O)N1CC(C)(C(=O)NCC(=O)Nc2ccc3c(c2)CN(C(=O)[C@@H](NC(=O)[C@H](C)N(C)C(=O)OC(C)(C)C)C(C)(C)C)[C@H](C(=O)N[C@@H]2CCCc4ccccc42)C3)c2ccc(Cc3ccc(F)cc3)cc21]

2-(1-(2-((2S,5R)-4-(tert-Butoxycarbonyl)-5-methyl-2-(((R)-3-methylmorpholino)methyl)piperazin-1-yl)acetyl)-6-(4-fluorobenzyl)-3-methylindoline-3-carboxamido)acetic acid (40 mg, 57.5 µmol, Eq: 1) was stirred with tert-butyl ((S)-1-(((S)-1-((S)-7-amino-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl)carbamate (35.6 mg, 57.5 µmol, Eq: 1), N-methylmorpholine (58.1 mg, 63.2 µl, 575 µmol, Eq: 10) and T3P in EtOAc 50% (110 mg, 103 µl, 172 µmol, Eq: 3) in ethyl acetate (350 µl) at room temperature overnight. Sat. NaHCO3 solution was added and extracted three times with ethyl acetate, dried over magnesium sulfate, filtered and evaporated. The crude material was applied on silica gel and purified by column chromatography using ethyl acetate as eluent affording tert-butyl (2R,5S)-4-[2-[3-[[2-[[(3S)-2-[(2S)-2-[[(2S)-2-[tert-butoxycarbonyl(methyl)amino]propanoyl]amino]-3,3-dimethyl-butanoyl]-3-[[(1R)-tetralin-1-yl]carbamoyl]-3,4-dihydro-1H-isoquinolin-7-yl]amino]-2-oxo-ethyl]carbamoyl]-6-[(4-fluorophenyl)methyl]-3-methyl-indolin-1-yl]-2-oxo-ethyl]-2-methyl-5-[[(3R)-3-methylmorpholin-4-yl]methyl]piperazine-1-carboxylate (40 mg, 53.6%) as an off-white solid. MS: m/z (M+H)$^+$=1297.74 b) (3S)-2-[(2S)-3,3-Dimethyl-2-[[(2S)-2-(methyl-amino)propanoyl]amino]butanoyl]-7-[[2-[[6-[(4-fluorophenyl)methyl]-3-methyl-1-[2-[(2R,5R)-5-methyl-2-[[(3R)-3-methylmorpholin-4-yl]methyl]piperazin-1-yl]acetyl]indoline-3-carbonyl]amino]acetyl]amino]-N-[(1R)-tetralin-1-yl]-3,4-dihydro-1H-isoquinoline-3-carboxamide Trihydrochloride

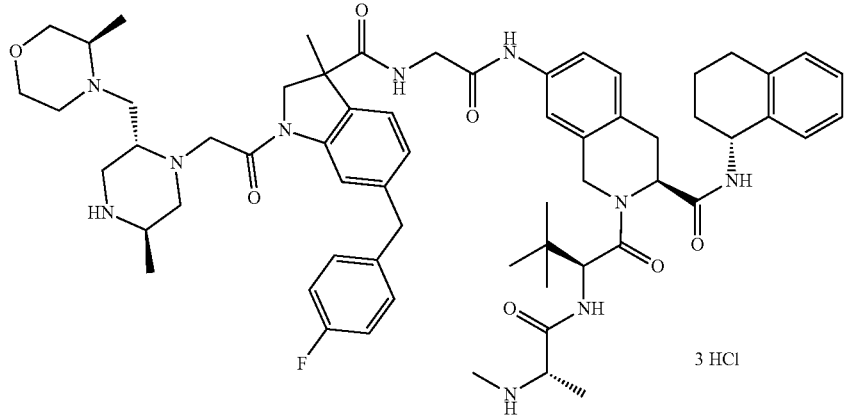 [SMILES: CN[C@@H](C)C(=O)N[C@H](C(=O)N1Cc2cc(NC(=O)CNC(=O)C3(C)CN(C(=O)CN4C[C@@H](C)NC[C@@H]4CN4CCOC[C@H]4C)c4cc(Cc5ccc(F)cc5)ccc43)ccc2C[C@H]1C(=O)N[C@@H]1CCCc2ccccc21)C(C)(C)C]

(2R,5S)-tert-Butyl 4-(2-(3-((2-(((S)-2-((S)-2-((S)-2-((tert-butoxycarbonyl)(methyl)amino)propanamido)-3,3-dimethylbutanoyl)-3-(((R)-1,2,3,4-tetrahydronaphthalen-1-yl)carbamoyl)-1,2,3,4-tetrahydroisoquinolin-7-yl)amino)-2-oxoethyl)carbamoyl)-6-(4-fluorobenzyl)-3-methylindolin-1-yl)-2-oxoethyl)-2-methyl-5-(((R)-3-methylmorpholino)methyl)piperazine-1-carboxylate (36 mg, 27.7 µmol, Eq: 1) was stirred with HCl in dioxane 4M (650 µl, 2.6 mmol, Eq: 93.7) in ethyl acetate (800 µL) at room temperature overnight. The precipitated solid was filtered off and washed with diethyl ether. The solid was dried under high vacuum affording (3S)-2-((S)-3,3-dimethyl-2-((S)-2-(methylamino)propanamido)butanoyl)-7-(2-(6-(4-fluorobenzyl)-3-methyl-1-(2-((2R,5R)-5-methyl-2-(((R)-3-methylmorpholino)methyl)piperazin-1-yl)acetyl)indoline-3-carboxamido)acetamido)-N—((R)-1,2,3,4-tetrahydronaphthalen-1-yl)-1,2,3,4-tetrahydroisoquinoline-3-carboxamide trihydrochloride (24.5 mg, 73.2%) as an off-white solid. MS: m/z (M+H)$^+$=1097.63

Example 7

N1-((S)-3-((2,6-Difluorophenyl)carbamoyl)-2-((S)-2-((S)-2-(methylamino)propanamido)-2-(tetrahydro-2H-pyran-4-yl)acetyl)isoindolin-5-yl)-N3-(3-(6-(4-fluorobenzyl)-3-methyl-1-(2-((2R,5R)-5-methyl-2-(((R)-3-methylmorpholino)methyl)piperazin-1-yl)acetyl)indolin-3-yl)propyl)malonamide Trihydrochloride a) tert-Butyl 3-(2-cyanoethyl)-6-[(4-fluorophenyl)methyl]-3-methyl-indoline-1-carboxylate

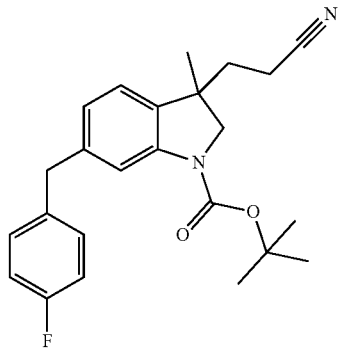 [SMILES: CC(C)(C)OC(=O)N1CC(C)(CCC#N)c2ccc(Cc3ccc(F)cc3)cc21]

(dppf) PdCl$_2$.CH$_2$Cl$_2$ (22.4 mg, 27.4 µmol, Eq: 0.01) and a solution of (4-fluorobenzyl)zinc(II) chloride 0.5M in THF (11 ml, 5.48 mmol, Eq: 2) were added to a light yellow solution of tert-butyl 6-bromo-3-(2-cyanoethyl)-3-methylindoline-1-carboxylate (1000 mg, 2.74 mmol, Eq: 1) (described in WO 2009158011 A1) in THF (10 ml). The sealed tube was closed and the dark brown suspension was heated to 90° C. and stirred for 2 h. The crude mixture was applied on silica gel after adding some drops of water and purified by column chromatography using heptane/ethyl acetate (0-30% ethyl acetate) as eluent affording tert-butyl 3-(2-cyanoethyl)-6-[(4-fluorophenyl)methyl]-3-methyl-indoline-1-carboxylate (1.003 g, 92.9%) as a light yellow solid. MS: m/z (M-BOC+H)$^+$=295.2 b) 3-[6-[(4-Fluorophenyl)methyl]-3-methyl-indolin-3-yl]propanenitrile

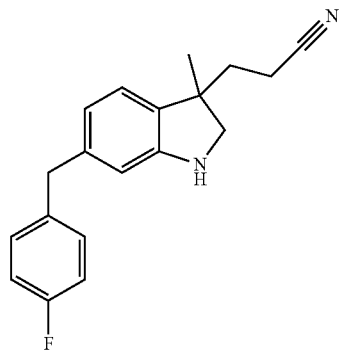 [SMILES: CC1(CCC#N)CNc2cc(Cc3ccc(F)cc3)ccc21]

HCl 4M in dioxane (10.6 ml, 42.6 mmol, Eq: 16) was added to a light yellow suspension of tert-butyl 3-(2-cyanoethyl)-6-(4-fluorobenzyl)-3-methylindoline-1-carboxylate (1.050 g, 2.66 mmol, Eq: 1) in Methanol (10 ml) at room temperature. The yellow solution was stirred at room temperature for 2 h. The solvent was evaporated, the yellow oil was diluted with ethyl acetate and was extracted with sat. aq. NaHCO$_3$. The organic layer was dried over magnesium sulfate, filtered and evaporated affording 3-[6-[(4-fluorophenyl)methyl]-3-methyl-indolin-3-yl]propanenitrile (763 mg, 97.4%) as an orange oil. MS: m/z (M+H)$^+$=295.2 c) tert-Butyl (2R,5S)-4-[2-[3-(2-cyanoethyl)-6-[(4-fluorophenyl)methyl]-3-methyl-indolin-1-yl]-2-oxo-ethyl]-2-methyl-5-[[(3R)-3-methylmorpholin-4-yl]methyl]piperazine-1-carboxylate

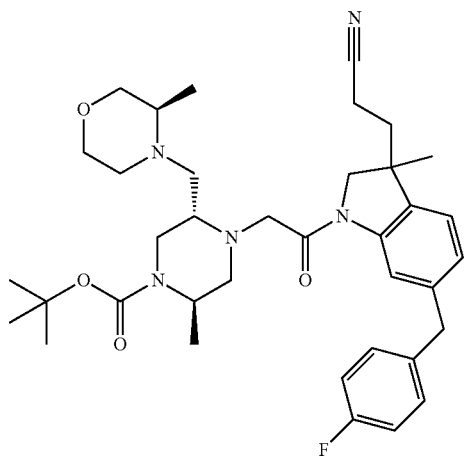 [SMILES: C[C@@H]1COCCN1C[C@H]1CN(C(=O)OC(C)(C)C)[C@H](C)CN1CC(=O)N1CC(C)(CCC#N)c2ccc(Cc3ccc(F)cc3)cc21]

3-(6-(4-Fluorobenzyl)-3-methylindolin-3-yl)propanenitrile (763 mg, 2.59 mmol, Eq: 1) was dissolved in Ethyl acetate (10 ml) and 2-((2S,5R)-4-(tert-butoxycarbonyl)-5-methyl-2-(((R)-3-methylmorpholino)methyl)piperazin-1-yl)acetic acid (963 mg, 2.59 mmol, Eq: 1), T3P in EtOAc 50% (4.95 g, 4.58 ml, 7.78 mmol, Eq: 3) and N-methylmorpholine (2.62 g, 2.85 ml, 25.9 mmol, Eq: 10) were added and the reaction was stirred at room temperature overnight. The reaction mixture was diluted with ethyl acetate and washed with sat. NaHCO₃, dried over Mg₂SO4 and concentrated in vacuo. The crude residue was applied to silica gel and was purified by column chromatography using ethyl acetate/heptane (50-100% ethyl acetate) affording tert-butyl (2R,5S)-4-[2-[3-(2-cyanoethyl)-6-[(4-fluorophenyl)methyl]-3-methyl-indolin-1-yl]-2-oxo-ethyl]-2-methyl-5-[[(3R)-3-methylmorpholin-4-yl]methyl]piperazine-1-carboxylate (983 mg, 58.5%) as a white foam. MS: m/z (M+H)⁺=648.4 d) tert-Butyl (2R,5S)-4-[2-[3-(3-aminopropyl)-6-[(4-fluorophenyl)methyl]-3-methyl-indolin-1-yl]-2-oxo-ethyl]-2-methyl-5-[[(3R)-3-methylmorpholin-4-yl]methyl]piperazine-1-carboxylate

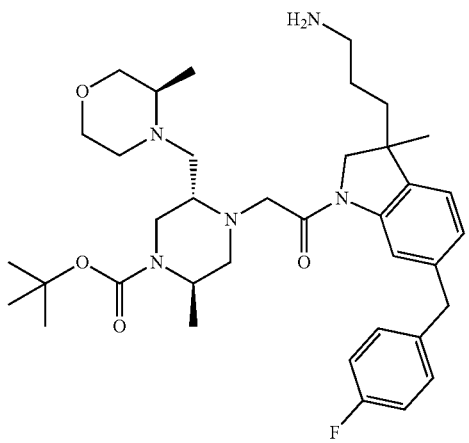 [SMILES: C[C@@H]1COCCN1C[C@H]1CN(C(=O)OC(C)(C)C)[C@H](C)CN1CC(=O)N1CC(C)(CCCN)c2ccc(Cc3ccc(F)cc3)cc21]

(2R,5S)-tert-Butyl 4-(2-(3-(2-cyanoethyl)-6-(4-fluorobenzyl)-3-methylindolin-1-yl)-2-oxoethyl)-2-methyl-5-(((R)-3-methylmorpholino)methyl)piperazine-1-carboxylate (850 mg, 1.31 mmol, Eq: 1) was dissolved in ammonia in MeOH 7N (15.7 g, 20 ml, 140 mmol, Eq: 107) and Raney nickel (1.31 mmol, Eq: 1) was added in catalytic amount with a spatula. The reaction vessel was degassed and purged with hydrogen (3×), the reaction was heated to 50° C. and stirred vigorously under hydrogen atmosphere for 8 h. The reaction was allowed to cool down to room temperature overnight. The reaction mixture was filtered over decalite, washed with methanol and evaporated. The crude residue was applied to silica gel and was purified by column chromatography (basic column) using dichloromethane/methanol (0-5% methanol) as eluent affording tert-butyl (2R,5S)-4-[2-[3-(3-aminopropyl)-6-[(4-fluorophenyl)methyl]-3-methyl-indolin-1-yl]-2-oxo-ethyl]-2-methyl-5-[[(3R)-3-methylmorpholin-4-yl]methyl]piperazine-1-carboxylate (436 mg, 51%) as a white solid. MS: m/z (M+H)⁺=652.4 e) tert-Butyl (2R,5S)-4-[2-[3-[3-[(3-benzyloxy-3-oxo-propanoyl)amino]propyl]-6-[(4-fluorophenyl)methyl]-3-methyl-indolin-1-yl]-2-oxo-ethyl]-2-methyl-5-[[(3R)-3-methylmorpholin-4-yl]methyl]piperazine-1-carboxylate

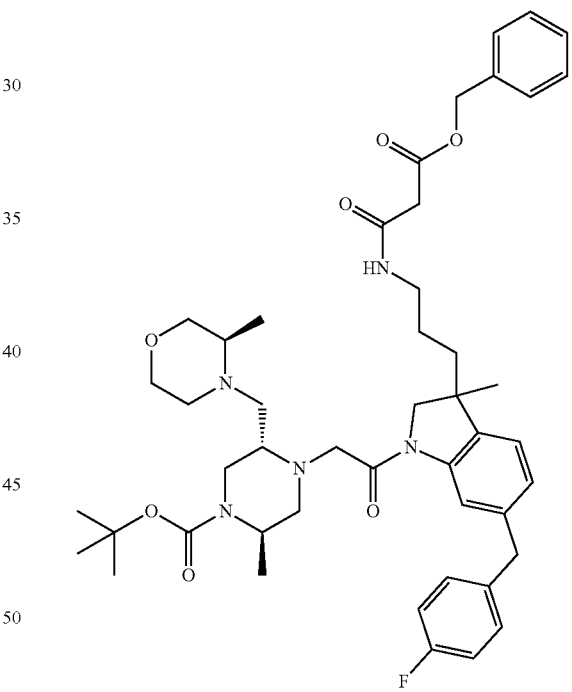

(2R,5S)-tert-Butyl 4-(2-(3-(3-aminopropyl)-6-(4-fluorobenzyl)-3-methylindolin-1-yl)-2-oxoethyl)-2-methyl-5-(((R)-3-methylmorpholino)methyl)piperazine-1-carboxylate (50 mg, 76.7 µmol, Eq: 1), 3-(benzyloxy)-3-oxopropanoic acid (17.2 mg, 84.4 µmol, Eq: 1.1), HATU (32.1 mg, 84.4 µmol, Eq: 1.1) and DIPEA (19.8 mg, 26.8 µl, 153 µmol, Eq: 2) were dissolved in DMF (1 ml) and the light yellow solution was stirred at room temperature overnight. Ethyl acetate was added and the mixture was extracted with water and brine. The crude residue was applied on silica gel and was purified by column chromatography (basic silica) using ethyl acetate/heptane (0-100% ethyl acetate) affording tert-butyl (2R,5S)-4-[2-[3-[3-[(3-benzyloxy-3-oxo-propanoyl)amino]propyl]-6-[(4-fluorophenyl)methyl]-3-methyl-indolin-1-yl]-2-oxo-ethyl]-2-methyl-5-[[(3R)-3- methylmorpholin-4-yl]methyl]piperazine-1-carboxylate (48 mg, 75.6%) as a colorless oil. MS: m/z (M+H)$^+$=828.5 f) 3-[3-[1-[2-[(2S,5R)-4-tert-Butoxycarbonyl-5-methyl-2-[[(3R)-3-methylmorpholin-4-yl]methyl]piperazin-1-yl]acetyl]-6-[(4-fluorophenyl)methyl]-3-methyl-indolin-3-yl]propylamino]-3-oxo-propanoic Acid

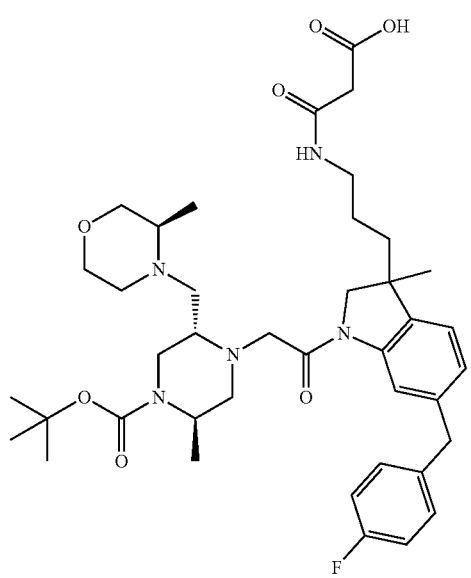 [SMILES: C[C@@H]1COCCN1C[C@H]1CN(C(=O)OC(C)(C)C)[C@H](C)CN1CC(=O)N1CC(C)(CCCNC(=O)CC(=O)O)c2ccc(Cc3ccc(F)cc3)cc21]

Pd—C (14.5 mg, 13.6 µmol, Eq: 0.25) was added to a clear solution of (2R,5S)-tert-butyl 4-(2-(3-(3-(3-(benzyloxy)-3-oxopropanamido)propyl)-6-(4-fluorobenzyl)-3-methylindolin-1-yl)-2-oxoethyl)-2-methyl-5-(((R)-3-methylmorpholino)methyl)piperazine-1-carboxylate (45 mg, 54.3 µmol, Eq: 1) in methanol (0.5 ml) and the reaction was stirred at room temperature under hydrogen atmosphere for 6 h. The reaction mixture was filtered over decalite and was washed with methanol. The filtrate was evaporated affording 3-[3-[1-[2-[(2S,5R)-4-tert-butoxycarbonyl-5-methyl-2-[[(3R)-3-methylmorpholin-4-yl]methyl]piperazin-1-yl]acetyl]-6-[(4-fluorophenyl)methyl]-3-methyl-indolin-3-yl]propylamino]-3-oxo-propanoic acid (33 mg, 82.3%) as a light yellow foam. MS: m/z (M+H)$^+$=738.4 g) tert-Butyl (2R,5S)-4-[2-[3-[3-[[3-[[(3S)-2-[(2S)-2-[[(2S)-2-[tert-butoxycarbonyl(methyl)amino]propanoyl]amino]-2-tetrahydropyran-4-yl-acetyl]-3-[(2,6-difluorophenyl)carbamoyl]isoindolin-5-yl]amino]-3-oxo-propanoyl]amino]propyl]-6-[(4-fluorophenyl)methyl]-3-methyl-indolin-1-yl]-2-oxo-ethyl]-2-methyl-5-[[(3R)-3-methylmorpholin-4-yl]methyl]piperazine-1-carboxylate

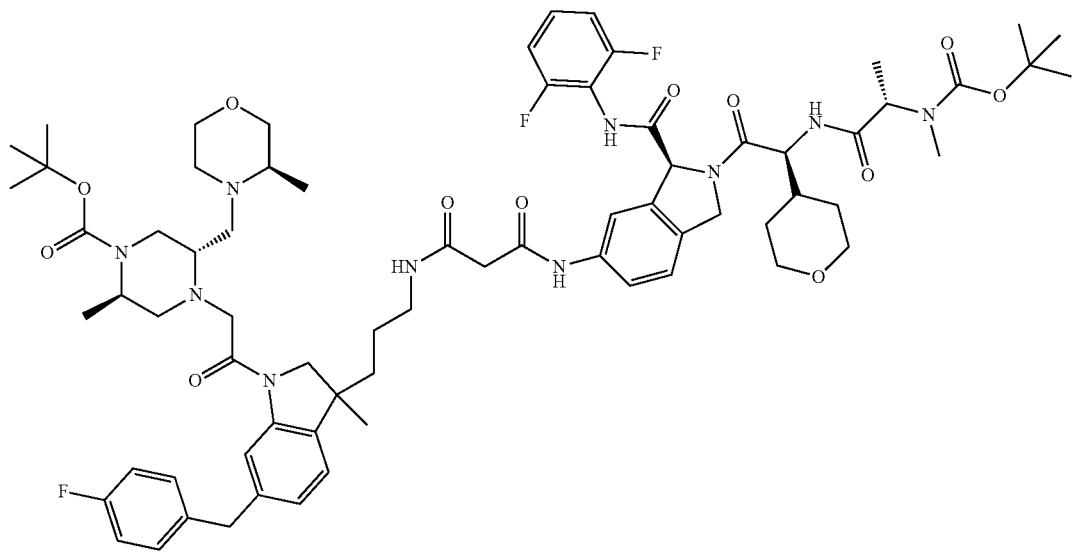 [SMILES: C[C@@H]1COCCN1C[C@H]1CN(C(=O)OC(C)(C)C)[C@H](C)CN1CC(=O)N1CC(C)(CCCNC(=O)CC(=O)Nc2ccc3c(c2)[C@@H](C(=O)Nc2c(F)cccc2F)N(C(=O)[C@@H](NC(=O)[C@H](C)N(C)C(=O)OC(C)(C)C)C2CCOCC2)C3)c2ccc(Cc3ccc(F)cc3)cc21]

3-((3-(1-(2-((2S,5R)-4-(tert-Butoxycarbonyl)-5-methyl-2-(((R)-3-methylmorpholino)methyl)piperazin-1-yl)acetyl)-6-(4-fluorobenzyl)-3-methylindolin-3-yl)propyl)amino)-3-oxopropanoic acid (30 mg, 40.7 µmol, Eq: 1), tert-butyl ((S)-1-(((S)-2-((S)-6-amino-1-((2,6-difluorophenyl)carbamoyl)isoindolin-2-yl)-2-oxo-1-(tetrahydro-2H-pyran-4-yl)ethyl)amino)-1-oxopropan-2-yl)(methyl)carbamate (25 mg, 40.7 µmol, Eq: 1; Intermediate 2), T3P 50% in EtOAc (77.6 mg, 72.6 µl, 122 µmol, Eq: 3) and N-methylmorpholine (41.1 mg, 44.7 µl, 407 µmol, Eq: 10) were combined and dissolved in ethyl acetate (0.3 ml) and the yellow solution was stirred at room temperature overnight. The solvent was evaporated, the crude residue was applied to silica gel and was purified by column chromatography using ethyl acetate/methanol (0-10% methanol) affording tert-butyl (2R,5S)-4-[2-[3-[3-[[3-[[(3S)-2-[(2S)-2-[[(2S)-2-[tert-butoxycarbonyl(methyl)amino]propanoyl]amino]-2-tetrahydropyran-4-yl-acetyl]-3-[(2,6-difluorophenyl)carbamoyl]isoindolin-5-yl]amino]-3-oxo-propanoyl]amino]propyl]-6-[(4-fluorophenyl)methyl]-3-methyl-indolin-1-yl]-2-oxo-ethyl]-2-methyl-5-[[(3R)-3-methylmorpholin-4-yl]methyl]piperazine-1-carboxylate (13 mg, 23.9%) as a yellow solid. MS: m/z (M+H)⁺=1335.7 h) N'-[(3S)-3-[(2,6-Difluorophenyl)carbamoyl]-2-[(2S)-2-[[(2S)-2-(methylamino)propanoyl]amino]-2-tetrahydropyran-4-yl-acetyl]isoindolin-5-yl]-N-[3-[6-[(4-fluorophenyl)methyl]-3-methyl-1-[2-[(2R,5R)-5-methyl-2-[[(3R)-3-methylmorpholin-4-yl]methyl]piperazin-1-yl]acetyl]indolin-3-yl]propyl] propanediamide Trihydrochloride

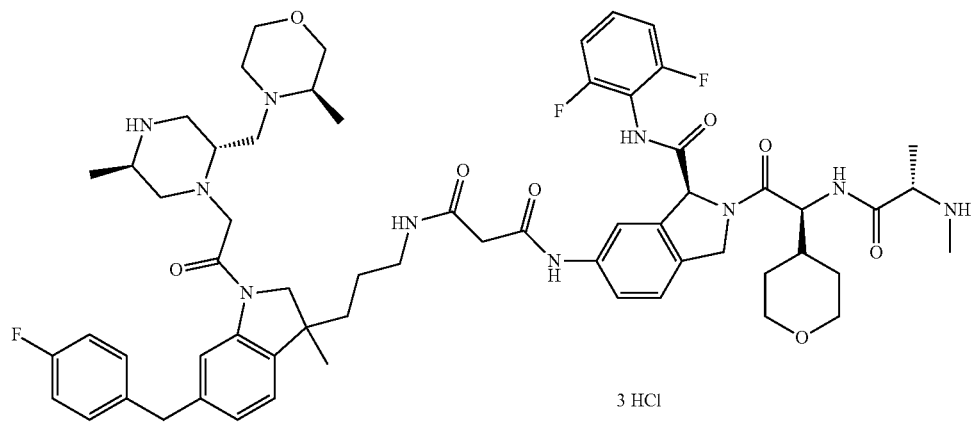 [SMILES: CN[C@@H](C)C(=O)N[C@H](C(=O)N1Cc2ccc(NC(=O)CC(=O)NCCCC3(C)CN(C(=O)CN4C[C@@H](C)NC[C@@H]4CN4CCOC[C@H]4C)c4cc(Cc5ccc(F)cc5)ccc43)cc2[C@H]1C(=O)Nc1c(F)cccc1F)C1CCOCC1]

3 HCl

HCl 4N in dioxane (24.6 mg, 20.5 µl, 674 µmol, Eq: 100) was added to a yellow solution of (2R,5S)-tert-butyl 4-(2-(3-(3-(3-(((S)-2-((S)-2-((S)-2-((tert-butoxycarbonyl)(methyl)amino)propanamido)-2-(tetrahydro-2H-pyran-4-yl)acetyl)-3-((2,6-difluorophenyl)carbamoyl)isoindolin-5-yl)amino)-3-oxopropanamido)propyl)-6-(4-fluorobenzyl)-3-methylindolin-1-yl)-2-oxoethyl)-2-methyl-5-(((R)-3-methylmorpholino)methyl)piperazine-1-carboxylate (9 mg, 6.74 µmol, Eq: 1) in ethyl acetate (0.5 ml) and the reaction was stirred at room temperature overnight. The precipitate was filtered off, washed with diethyl ether and was dried in vacuo affording N1-((S)-3-((2,6-difluorophenyl)carbamoyl)-2-((S)-2-((S)-2-(methylamino)propanamido)-2-(tetrahydro-2H-pyran-4-yl)acetyl)isoindolin-5-yl)-N3-(3-(6-(4-fluorobenzyl)-3-methyl-1-(2-((2R,5R)-5-methyl-2-(((R)-3-methylmorpholino)methyl)piperazin-1-yl)acetyl)indolin-3-yl)propyl)malonamide trihydrochloride (5.6 mg, 66.8%) as a light yellow solid. MS: m/z (M+H)⁺=1135.6

Example 8

(3S)—N-[2-[[(3S)-3-[(2,6-Difluorophenyl)carbamoyl]-2-[(2S)-2-[[(2S)-2-(methylamino)propanoyl]amino]-2-tetrahydropyran-4-yl-acetyl]isoindolin-5-yl]amino]-2-oxo-ethyl]-6-[(4-fluorophenyl)methyl]-3-methyl-1-[2-[(2R,5R)-5-methyl-2-[[(3R)-3-methylmorpholin-4-yl]methyl]piperazin-1-yl]acetyl]indoline-3-carboxamide Trihydrochloride a) tert-Butyl (2R,5S)-4-[2-[(3S)-3-[[2-[[(3S)-2-[(2S)-2-[[(2S)-2-[tert-butoxycarbonyl(methyl)amino]propanoyl]amino]-2-tetrahydropyran-4-yl-acetyl]-3-[(2,6-difluorophenyl)carbamoyl]isoindolin-5-yl]amino]-2-oxo-ethyl]carbamoyl]-6-[(4-fluorophenyl)methyl]-3-methyl-indolin-1-yl]-2-oxo-ethyl]-2-methyl-5-[[(3R)-3-methylmorpholin-4-yl]methyl]piperazine-1-carboxylate

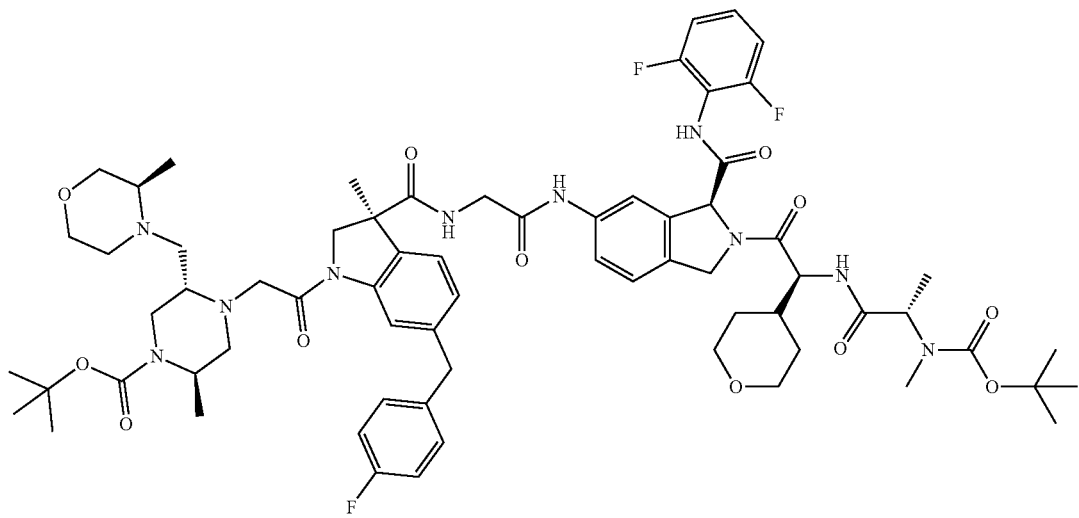 [SMILES: C[C@@H]1COCCN1C[C@H]1CN(C(=O)OC(C)(C)C)[C@H](C)CN1CC(=O)N1C[C@@](C)(C(=O)NCC(=O)Nc2ccc3c(c2)[C@@H](C(=O)Nc2c(F)cccc2F)N(C(=O)[C@@H](NC(=O)[C@H](C)N(C)C(=O)OC(C)(C)C)C2CCOCC2)C3)c2ccc(Cc3ccc(F)cc3)cc21]

2-((S)-1-(2-((2S,5R)-4-(tert-Butoxycarbonyl)-5-methyl-2-(((R)-3-methylmorpholino)methyl)piperazin-1-yl)acetyl)-6-(4-fluorobenzyl)-3-methylindoline-3-carboxamido)acetic acid (140 mg, 201 µmol, Eq: 1) was stirred with tert-butyl ((S)-1-(((S)-2-((S)-6-amino-1-((2,6-difluorophenyl)carbamoyl)isoindolin-2-yl)-2-oxo-1-(tetrahydro-2H-pyran-4-yl)ethyl)amino)-1-oxopropan-2-yl)(methyl)carbamate (124 mg, 201 µmol, Eq: 1; Intermediate 2), N-methylmorpholine (204 mg, 221 µl, 2.01 mmol, Eq: 10) and T3P in EtOAc 50% (384 mg, 359 µl, 604 µmol, Eq: 3) in ethyl acetate (1.1 ml) at room temperature for 3 h. NaHCO$_3$sat. was added and extracted three times with ethyl acetate, dried over magnesium sulfate, filtered and evaporated. The crude material was applied on silica gel and purified by column chromatography using ethyl acetate/methanol (0-10% methanol) as eluent affording tert-butyl (2R,5S)-4-[2-[(3S)-3-[[2-[[(3S)-2-[(2S)-2-[[(2S)-2-[tert-butoxycarbonyl(methyl)amino]propanoyl]amino]-2-tetrahydropyran-4-yl-acetyl]-3-[(2,6-difluorophenyl)carbamoyl]isoindolin-5-yl]amino]-2-oxo-ethyl]carbamoyl]-6-[(4-fluorophenyl)methyl]-3-methyl-indolin-1-yl]-2-oxo-ethyl]-2-methyl-5-[[(3R)-3-methylmorpholin-4-yl]methyl]piperazine-1-carboxylate (195 mg, 74.9%) as a light yellow solid. MS: m/z (M+H)$^+$=1293.7 b) (3S)—N-[2-[[(3S)-3-[(2,6-Difluorophenyl)carbamoyl]-2-[(2S)-2-[[(2S)-2-(methylamino)propanoyl]amino]-2-tetrahydropyran-4-yl-acetyl]isoindolin-5-yl]amino]-2-oxo-ethyl]-6-[(4-fluorophenyl)methyl]-3-methyl-1-[2-[(2R,5R)-5-methyl-2-[[(3R)-3-methylmorpholin-4-yl]methyl]piperazin-1-yl]acetyl]indoline-3-carboxamide Trihydrochloride

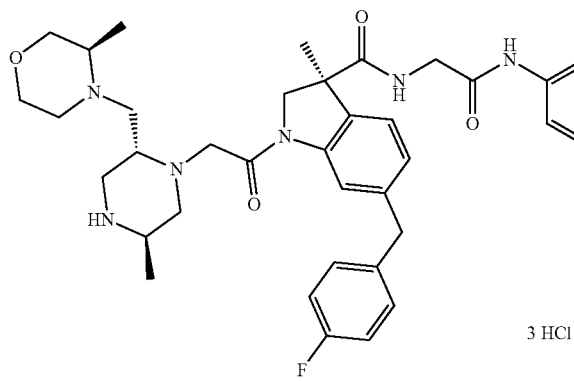

3 HCl (2R,5S)-tert-butyl 4-(2-((S)-3-((2-(((S)-2-((S)-2-((S)-2-((tert-Butoxycarbonyl)(methyl)amino)propanamido)-2-(tetrahydro-2H-pyran-4-yl)acetyl)-3-((2,6-difluorophenyl)carbamoyl)isoindolin-5-yl)amino)-2-oxoethyl)carbamoyl)-6-(4-fluorobenzyl)-3-methylindolin-1-yl)-2-oxoethyl)-2-methyl-5-(((R)-3-methylmorpholino)methyl)piperazine-1-carboxylate (188 mg, 145 µmol, Eq: 1) was stirred in ethyl acetate (3 ml) with HCl in dioxane 4M (3 ml, 12 mmol, Eq: 82.6) at room temperature overnight. The precipitate was filtered off, washed with diethyl ether and dried under high vacuum affording (3S)—N-[2-[[(3S)-3-[(2,6-difluorophenyl)carbamoyl]-2-[(2S)-2-[[(2S)-2-(methylamino)propanoyl]amino]-2-tetrahydropyran-4-yl-acetyl]isoindolin-5-yl]amino]-2-oxo-ethyl]-6-[(4-fluorophenyl)methyl]-3-methyl-1-[2-[(2R,5R)-5-methyl-2-[[(3R)-3-methylmorpholin-4-yl]methyl]piperazin-1-yl]acetyl]indoline-3-carboxamide trihydrochloride (161 mg, 92.1%) as a white solid. MS: m/z (M+H)$^+$=1093.5

Example 9
(3R)—N-[2-[[(3S)-3-[(2,6-Difluorophenyl)carbamoyl]-2-[(2S)-2-[[(2S)-2-(methylamino)propanoyl]amino]-2-tetrahydropyran-4-yl-acetyl]isoindolin-5-yl]amino]-2-oxo-ethyl]-6-[(4-fluorophenyl)methyl]-3-methyl-1-[2-[(2R,5R)-5-methyl-2-[[(3R)-3-methylmorpholin-4-yl]methyl]piperazin-1-yl]acetyl]indoline-3-carboxamide Trihydrochloride a) (R)-1-tert-Butyl 3-methyl 6-(4-fluorobenzyl)-3-methylindoline-1,3-dicarboxylate

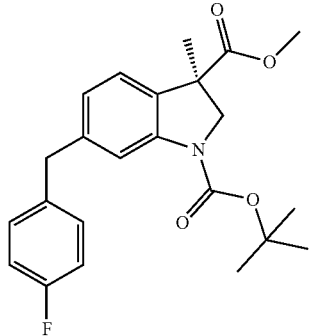 [SMILES: COC(=O)[C@@]1(C)CN(C(=O)OC(C)(C)C)c2cc(Cc3ccc(F)cc3)ccc21]

Chiral separation of racemic tert-butyl-methyl 6-[(4-fluorophenyl)methyl]-3-methyl-indoline-1,3-dicarboxylate (1.21 g, 3.03 mmol, Eq: 1) afforded (R)-1-tert-butyl 3-methyl 6-(4-fluorobenzyl)-3-methylindoline-1,3-dicarboxylate (571 mg, 47.2%) as a colorless oil. MS: m/z M$^+$=399.20 b) Methyl (3R)-6-[(4-fluorophenyl)methyl]-3-methyl-indoline-3-carboxylate

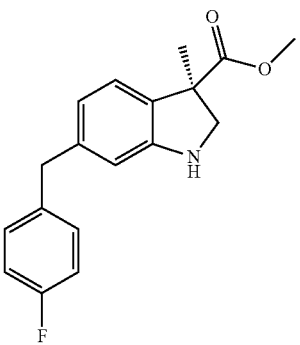 [SMILES: COC(=O)[C@@]1(C)CNc2cc(Cc3ccc(F)cc3)ccc21]

The product was prepared in the same manner as in Example 1c) using (R)-1-tert-butyl 3-methyl 6-(4-fluorobenzyl)-3-methylindoline-1,3-dicarboxylate affording methyl (3R)-6-[(4-fluorophenyl)methyl]-3-methyl-indoline-3-carboxylate (373 mg, 95.4%) as a light yellow solid. MS: m/z (M+H)$^+$=300.14 c) (3R)-1-[2-[(2S,5R)-4-tert-Butoxycarbonyl-5-methyl-2-[[(3R)-3-methylmorpholin-4-yl]methyl]piperazin-1-yl]acetyl]-6-[(4-fluorophenyl)methyl]-3-methyl-indoline-3-carboxylate

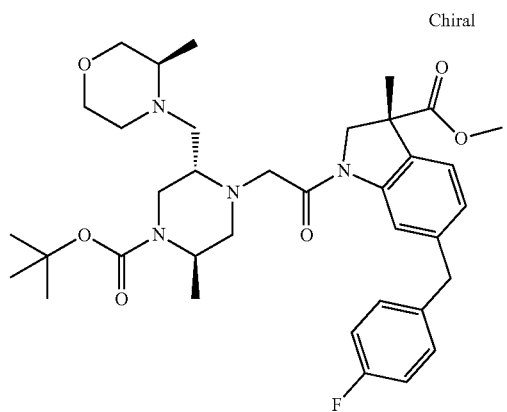 [SMILES: COC(=O)[C@@]1(C)CN(C(=O)CN2C[C@@H](C)N(C(=O)OC(C)(C)C)C[C@@H]2CN2CCOC[C@H]2C)c2cc(Cc3ccc(F)cc3)ccc21]

The product was prepared in the same manner as in Example 1 d) using (R)-methyl 6-(4-fluorobenzyl)-3-methylindoline-3-carboxylate (314 mg, 1.05 mmol, Eq: 1) and 2-((2S,5R)-4-(tert-butoxycarbonyl)-5-methyl-2-(((R)-3-methylmorpholino)methyl)piperazin-1-yl)acetic acid (390 mg, 1.05 mmol, Eq: 1) as starting materials, affording methyl (3R)-1-[2-[(2S,5R)-4-tert-butoxycarbonyl-5-methyl-2-[[(3R)-3-methylmorpholin-4-yl]methyl]piperazin-1-yl]acetyl]-6-[(4-fluorophenyl)methyl]-3-methyl-indoline-3-carboxylate (505 mg, 73.7%) as a light yellow oil. MS: m/z (M+H)$^+$=653.37

(R)-1-(2-((2S,5R)-4-(tert-Butoxycarbonyl)-5-methyl-2-(((R)-3-methylmorpholino)methyl)piperazin-1-yl)acetyl)-6-(4-fluorobenzyl)-3-methylindoline-3-carboxylic Acid

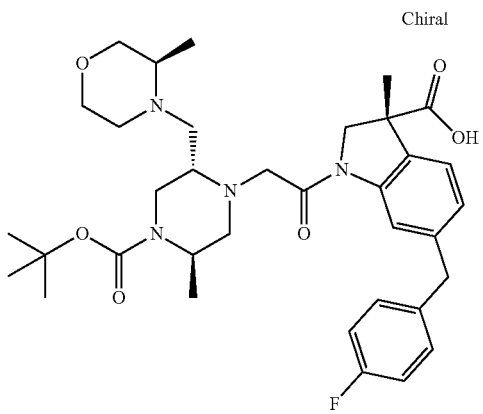 [SMILES: C[C@@H]1COCCN1C[C@H]1CN(C(=O)OC(C)(C)C)[C@H](C)CN1CC(=O)N1C[C@](C)(C(=O)O)c2ccc(Cc3ccc(F)cc3)cc21]

The product was prepared in the same manner as in Example 1e) using (R)-methyl 1-(2-((2S,5R)-4-(tert-butoxycarbonyl)-5-methyl-2-(((R)-3-methylmorpholino)methyl)piperazin-1-yl)acetyl)-6-(4-fluorobenzyl)-3-methylindoline-3-carboxylate (500 mg, 766 µmol, Eq: 1) as starting material, affording (R)-1-(2-((2S,5R)-4-(tert-butoxycarbonyl)-5-methyl-2-(((R)-3-methylmorpholino)methyl)piperazin-1-yl)acetyl)-6-(4-fluorobenzyl)-3-methylindoline-3-carboxylic acid (441 mg, 690 µmol, 90.1%) as an off-white foam. MS: m/z (M+H)$^+$=639.36 d) (2R,5S)-tert-Butyl 4-(2-((R)-6-(4-fluorobenzyl)-3-((2-methoxy-2-oxoethyl)carbamoyl)-3-methylindolin-1-yl)-2-oxoethyl)-2-methyl-5-(((R)-3-methylmorpholino)methyl)piperazine-1-carboxylate

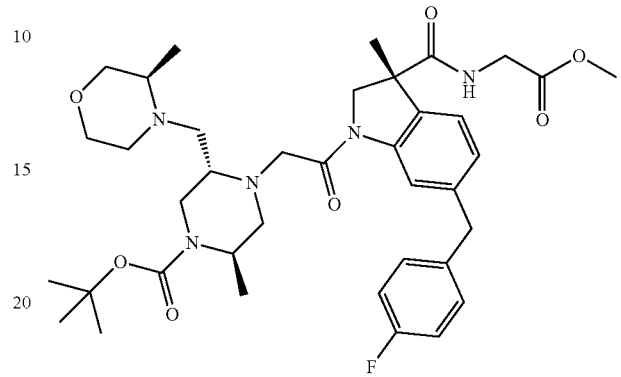

The product was prepared in the same manner as in Example 2a) using (R)-1-(2-((2S,5R)-4-(tert-butoxycarbonyl)-5-methyl-2-(((R)-3-methylmorpholino)methyl)piperazin-1-yl)acetyl)-6-(4-fluorobenzyl)-3-methylindoline-3-carboxylic acid (430 mg, 673 µmol, Eq: 1) as starting material, affording (2R,5S)-tert-butyl 4-(2-((R)-6-(4-fluorobenzyl)-3-((2-methoxy-2-oxoethyl)carbamoyl)-3-methylindolin-1-yl)-2-oxoethyl)-2-methyl-5-(((R)-3-methylmorpholino)methyl)piperazine-1-carboxylate (455 mg, 641 µmol, 95.2%) as a light yellow oil. MS: m/z (M+H)$^+$=710.4 e) 2-[[(3R)-1-[2-[(2S,5R)-4-tert-Butoxycarbonyl-5-methyl-2-[[(3R)-3-methylmorpholin-4-yl]methyl]piperazin-1-yl]acetyl]-6-[(4-fluorophenyl)methyl]-3-methyl-indoline-3-carbonyl]amino]acetic Acid

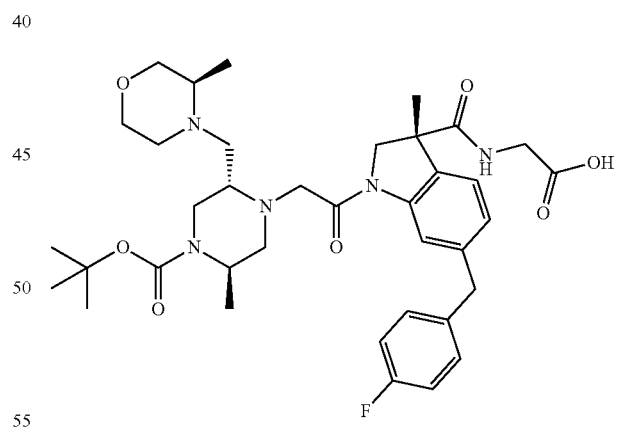

The product was prepared in the same manner as in Example 2b) using (2R,5S)-tert-butyl 4-(2-((R)-6-(4-fluorobenzyl)-3-((2-methoxy-2-oxoethyl)carbamoyl)-3-methylindolin-1-yl)-2-oxoethyl)-2-methyl-5-(((R)-3-methylmorpholino)methyl)piperazine-1-carboxylate (435 mg, 613 µmol, Eq: 1) as starting material, affording 2-[[(3R)-1-[2-[(2S,5R)-4-tert-butoxycarbonyl-5-methyl-2-[[(3R)-3-methylmorpholin-4-yl]methyl]piperazin-1-yl]acetyl]-6-[(4-fluorophenyl)methyl]-3-methyl-indoline-3-carbonyl]amino]acetic acid (283 mg, 66.4%) as a light yellow solid. MS: m/z (M+H)$^+$=696.3793 f) tert-Butyl (2R,5S)-4-[2-[(3R)-3-[[2-[[(3S)-2-[(2S)-2-[[(2S)-2-[tert-butoxycarbonyl(methyl)amino]propanoyl]amino]-2-tetrahydropyran-4-yl-acetyl]-3-[(2,6-difluorophenyl)carbamoyl]isoindolin-5-yl]amino]-2-oxo-ethyl]carbamoyl]-6-[(4-fluorophenyl)methyl]-3-methyl-indolin-1-yl]-2-oxo-ethyl]-2-methyl-5-[[(3R)-3-methylmorpholin-4-yl]methyl]piperazine-1-carboxylate

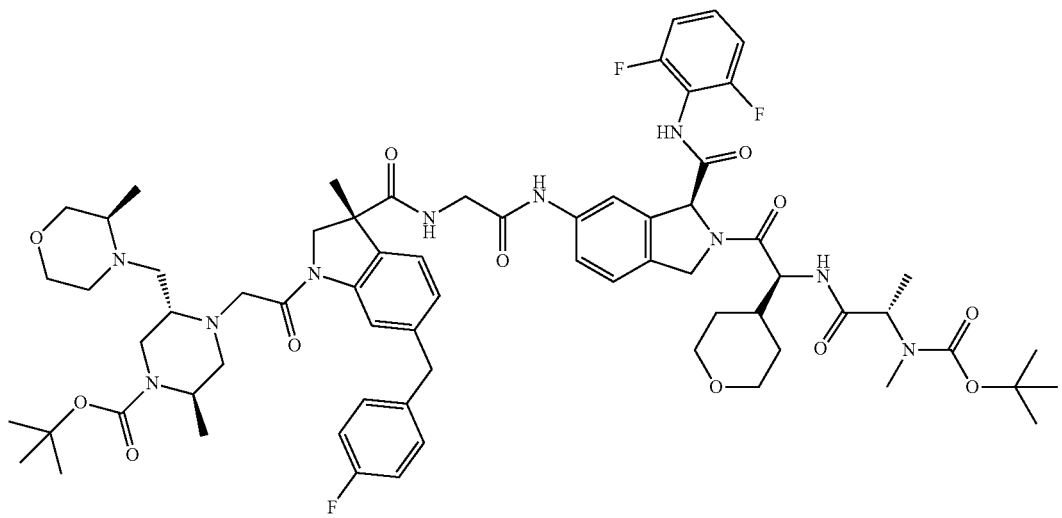 [SMILES: C[C@@H]1COCCN1C[C@H]1CN(C(=O)OC(C)(C)C)[C@H](C)CN1CC(=O)N1C[C@](C)(C(=O)NCC(=O)Nc2ccc3c(c2)[C@@H](C(=O)Nc2c(F)cccc2F)N(C(=O)[C@@H](NC(=O)[C@H](C)N(C)C(=O)OC(C)(C)C)C2CCOCC2)C3)c2ccc(Cc3ccc(F)cc3)cc21]

2-((R)-1-(2-((2S,5R)-4-(tert-Butoxycarbonyl)-5-methyl-2-(((R)-3-methylmorpholino)methyl)piperazin-1-yl)acetyl)-6-(4-fluorobenzyl)-3-methylindoline-3-carboxamido)acetic acid (140 mg, 201 µmol, Eq: 1) was stirred with tert-butyl ((S)-1-(((S)-2-((S)-6-amino-1-((2,6-difluorophenyl)carbamoyl)isoindolin-2-yl)-2-oxo-1-(tetrahydro-2H-pyran-4-yl)ethyl)amino)-1-oxopropan-2-yl)(methyl)carbamate (124 mg, 201 µmol, Eq: 1; Intermediate 2), N-methylmorpholine (204 mg, 221 µl, 2.01 mmol, Eq: 10) and T3P in EtOAc 50% (384 mg, 359 µl, 604 µmol, Eq: 3) in ethyl acetate (1.1 ml) at room temperature overnight. Sat. NaHCO$_3$ solution was added and extracted three times with ethyl acetate, dried over magnesium sulfate, filtered and evaporated. The crude material was applied on silica gel and purified by column chromatography using ethyl acetate/methanol (0-10% methanol) as eluent affording (2R,5S)-tert-butyl 4-(2-((R)-3-((2-(((S)-2-((S)-2-((tert-butoxycarbonyl)(methyl)amino)propanamido)-2-(tetrahydro-2H-pyran-4-yl)acetyl)-3-((2,6-difluorophenyl)carbamoyl)isoindolin-5-yl)amino)-2-oxoethyl)carbamoyl)-6-(4-fluorobenzyl)-3-methylindolin-1-yl)-2-oxo ethyl)-2-methyl-5-(((R)-3-methylmorpholino)methyl)piperazine-1-carboxylate (177 mg, 68%) as a light yellow solid. MS: m/z (M+H)$^+$=1293.66 g) (3R)—N-[2-[[(3S)-3-[(2,6-Difluorophenyl)carbamoyl]-2-[(2S)-2-[[(2S)-2-(methylamino)propanoyl]amino]-2-tetrahydropyran-4-yl-acetyl]isoindolin-5-yl]amino]-2-oxo-ethyl]-6-[(4-fluorophenyl)methyl]-3-methyl-1-[2-[(2R,5R)-5-methyl-2-[[(3R)-3-methylmorpholin-4-yl]methyl]piperazin-1-yl]acetyl]indoline-3-carboxamide Trihydrochloride

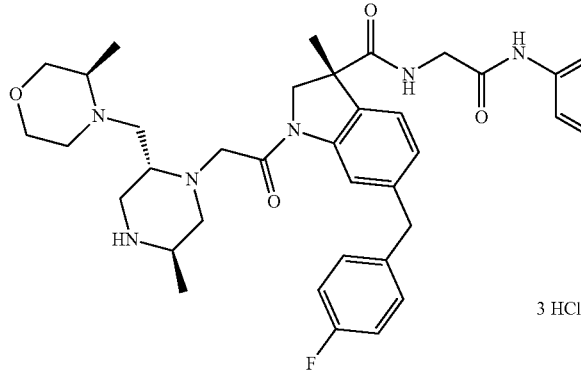
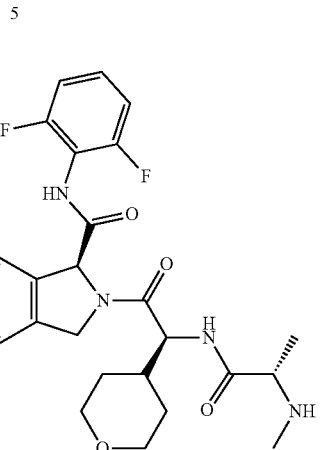

(2R,5S)-tert-Butyl 4-(2-((R)-3-((2-(((S)-2-((S)-2-((S)-2-((tert-butoxycarbonyl)(methyl)amino) propanamido)-2-(tetrahydro-2H-pyran-4-yl)acetyl)-3-((2,6-difluorophenyl)carbamoyl)isoindolin-5-yl)amino)-2-oxoethyl)carbamoyl)-6-(4-fluorobenzyl)-3-methylindolin-1-yl)-2-oxo ethyl)-2-methyl-5-(((R)-3-methylmorpholino)methyl)piperazine-1-carboxylate (178 mg, 138 μmol, Eq: 1) was stirred in ethyl acetate (3 ml) with HCl in dioxane 4M (3 ml, 12 mmol, Eq: 87.2) at room temperature overnight. The precipitate was filtered off and washed with diethyl ether. The solid was dried under high vacuum affording (3R)—N-[2-[[(3S)-3-[(2,6-difluorophenyl)carbamoyl]-2-[(2S)-2-[[(2S)-2-(methylamino)propanoyl]amino]-2-tetrahydropyran-4-yl-acetyl]isoindolin-5-yl]amino]-2-oxo-ethyl]-6-[(4-fluorophenyl)methyl]-3-methyl-1-[2-[(2R,5R)-5-methyl-2-[[(3R)-3-methylmorpholin-4-yl]methyl]piperazin-1-yl]acetyl]indoline-3-carboxamide trihydrochloride (143 mg, 86.4%) as a white solid. MS: m/z (M+H)⁺=1093.55

Example 10
(3S)-2-[(2S)-3,3-Dimethyl-2-[[(2S)-2-(methylamino)propanoyl]amino]butanoyl]-7-[[2-[[(3S)-6-[(4-fluorophenyl)methyl]-3-methyl-1-[2-[(2R,5R)-5-methyl-2-[[(3R)-3-methylmorpholin-4-yl]methyl]piperazin-1-yl]acetyl]indoline-3-carbonyl]amino]acetyl]amino]-N-[(1R)-tetralin-1-yl]-3,4-dihydro-1H-isoquinoline-3-carboxamide Trihydrochloride a) (S)-1-tert-Butyl 3-methyl 6-(4-fluorobenzyl)-3-methylindoline-1,3-dicarboxylate

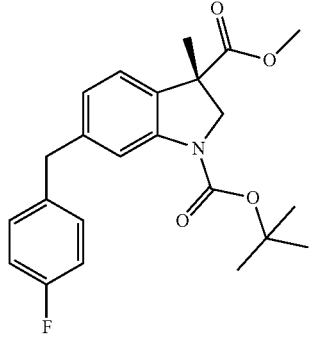 [SMILES: COC(=O)[C@]1(C)CN(C(=O)OC(C)(C)C)c2cc(Cc3ccc(F)cc3)ccc21]

Chiral separation of racemic tert-butyl-methyl 6-[(4-fluorophenyl)methyl]-3-methyl-indoline-1,3-dicarboxylate (1.21 g, 3.03 mmol, Eq: 1) afforded (S)-1-tert-butyl 3-methyl 6-(4-fluorobenzyl)-3-methylindoline-1,3-dicarboxylate (555 mg, 45.9%) as a colorless oil. MS: m/z M+=399.2 b) Methyl (3S)-6-[(4-fluorophenyl)methyl]-3-methyl-indoline-3-carboxylate

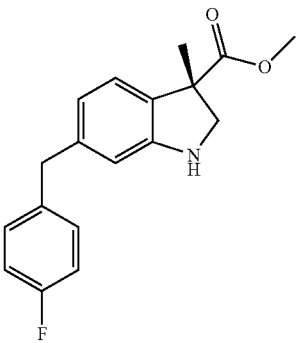 [SMILES: COC(=O)[C@]1(C)CNc2cc(Cc3ccc(F)cc3)ccc21]

The product was prepared in the same manner as in Example 1c) using (S)-1-tert-butyl 3-methyl 6-(4-fluorobenzyl)-3-methylindoline-1,3-dicarboxylate affording methyl (3S)-6-[(4-fluorophenyl)methyl]-3-methyl-indoline-3-carboxylate (365 mg, 95.5%) as a light yellow solid. MS: m/z (M+H)⁺=300.1 c) Methyl (3S)-1-[2-[(2S,5R)-4-tert-butoxycarbonyl-5-methyl-2-[[(3R)-3-methylmorpholin-4-yl]methyl]piperazin-1-yl]acetyl]-6-[(4-fluorophenyl)methyl]-3-methyl-indoline-3-carboxylate

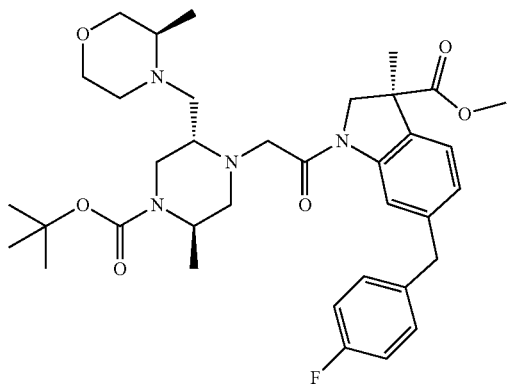 [SMILES: COC(=O)[C@]1(C)CN(C(=O)CN2C[C@@H](C)N(C(=O)OC(C)(C)C)C[C@@H]2CN2CCOC[C@H]2C)c2cc(Cc3ccc(F)cc3)ccc21]

The product was prepared in the same manner as in Example 1d) using (S)-methyl 6-(4-fluorobenzyl)-3-methyl-indoline-3-carboxylate (303 mg, 1.01 mmol, Eq: 1) affording methyl (3S)-1-[2-[(2S,5R)-4-tert-butoxycarbonyl-5-methyl-2-[[(3R)-3-methylmorpholin-4-yl]methyl]piperazin-1-yl]acetyl]-6-[(4-fluorophenyl)methyl]-3-methyl-indoline-3-carboxylate (445 mg, 67.3%) as a light yellow oil. MS: m/z (M+H)$^+$=653.4 d) (3S)-1-[2-[(2S,5R)-4-tert-Butoxycarbonyl-5-methyl-2-[[(3R)-3-methylmorpholin-4-yl]methyl]piperazin-1-yl]acetyl]-6-[(4-fluorophenyl)methyl]-3-methyl-indoline-3-carboxylic Acid

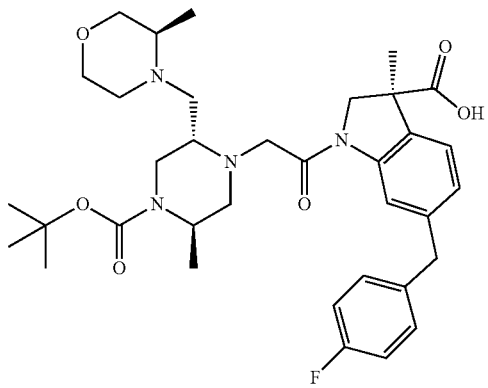 [SMILES: C[C@@H]1COCCN1C[C@H]1CN(C(=O)OC(C)(C)C)[C@H](C)CN1CC(=O)N1C[C@@](C)(C(=O)O)c2ccc(Cc3ccc(F)cc3)cc21]

The product was prepared in the same manner as in Example 1e) using (S)-methyl 1-(2-((2S,5R)-4-(tert-butoxycarbonyl)-5-methyl-2-(((R)-3-methylmorpholino)methyl)piperazin-1-yl)acetyl)-6-(4-fluorobenzyl)-3-methylindoline-3-carboxylate (440 mg, 674 µmol, Eq: 1) affording (S)-1-(2-((2S,5R)-4-(tert-butoxycarbonyl)-5-methyl-2-(((R)-3-methylmorpholino)methyl)piperazin-1-yl)acetyl)-6-(4-fluorobenzyl)-3-methylindoline-3-carboxylic acid (420 mg, 97.6%) as a white foam. MS: m/z (M+H)$^+$=639.4 e) (2R,5S)-tert-Butyl 4-(2-((S)-6-(4-fluorobenzyl)-3-((2-methoxy-2-oxoethyl)carbamoyl)-3-methylindolin-1-yl)-2-oxoethyl)-2-methyl-5-((R)-3-methylmorpholino)methyl)piperazine-1-carboxylate

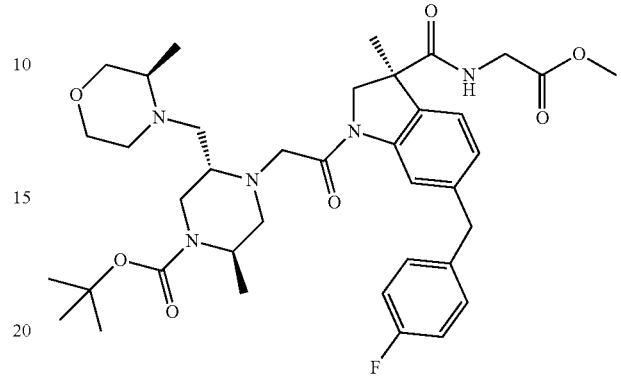

The product was prepared in the same manner as in Example 2a) using (S)-1-(2-((2S,5R)-4-(tert-butoxycarbonyl)-5-methyl-2-(((R)-3-methylmorpholino)methyl)piperazin-1-yl)acetyl)-6-(4-fluorobenzyl)-3-methylindoline-3-carboxylic acid (410 mg, 642 µmol, Eq: 1) affording (2R,5S)-tert-butyl 4-(2-((S)-6-(4-fluorobenzyl)-3-((2-methoxy-2-oxoethyl)carbamoyl)-3-methylindolin-1-yl)-2-oxoethyl)-2-methyl-5-(((R)-3-methylmorpholino)methyl)piperazine-1-carboxylate (508 mg, 111%) as a light yellow oil. MS: m/z (M+H)+=710.4 f) 2-[[(3S)-1-[2-[(2S,5R)-4-tert-Butoxycarbonyl-5-methyl-2-[[(3R)-3-methylmorpholin-4-yl]methyl]piperazin-1-yl]acetyl]-6-[(4-fluorophenyl)methyl]-3-methyl-indoline-3-carbonyl]amino]acetic Acid

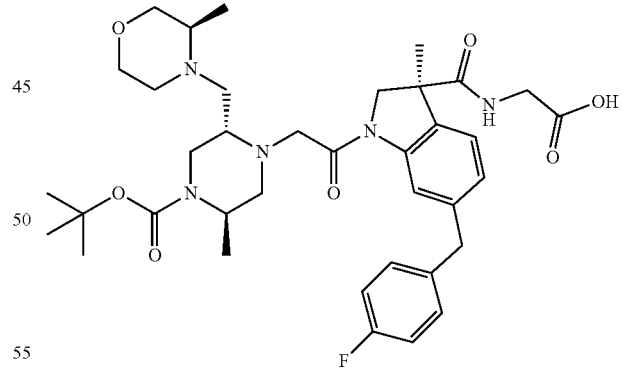

The product was prepared in the same manner as in Example 2b) using (2R,5S)-tert-butyl 4-(2-((S)-6-(4-fluorobenzyl)-3-((2-methoxy-2-oxoethyl)carbamoyl)-3-methylindolin-1-yl)-2-oxoethyl)-2-methyl-5-(((R)-3-methylmorpholino)methyl)piperazine-1-carboxylate (500 mg, 704 µmol, Eq: 1) affording 2-((S)-1-(2-((2S,5R)-4-(tert-butoxycarbonyl)-5-methyl-2-(((R)-3-methylmorpholino)methyl)piperazin-1-yl)acetyl)-6-(4-fluorobenzyl)-3-methylindoline-3-carboxamido)acetic acid (389 mg, 79.4%) as a light yellow solid. MS: m/z (M+H)$^+$=696.4 g) tert-Butyl (2R,5S)-4-[2-[(3S)-3-[[2-[[(3S)-2-[(2S)-2-[[(2S)-2-[tert-butoxycarbonyl(methyl)amino]propanoyl]amino]-3,3-dimethyl-butanoyl]-3-[[(1R)-tetralin-1-yl]carbamoyl]-3,4-dihydro-1H-isoquinolin-7-yl]amino]-2-oxo-ethyl]carbamoyl]-6-[(4-fluorophenyl)methyl]-3-methyl-indolin-1-yl]-2-oxo-ethyl]-2-methyl-5-[[(3R)-3-methylmorpholin-4-yl]methyl]piperazine-1-carboxylate

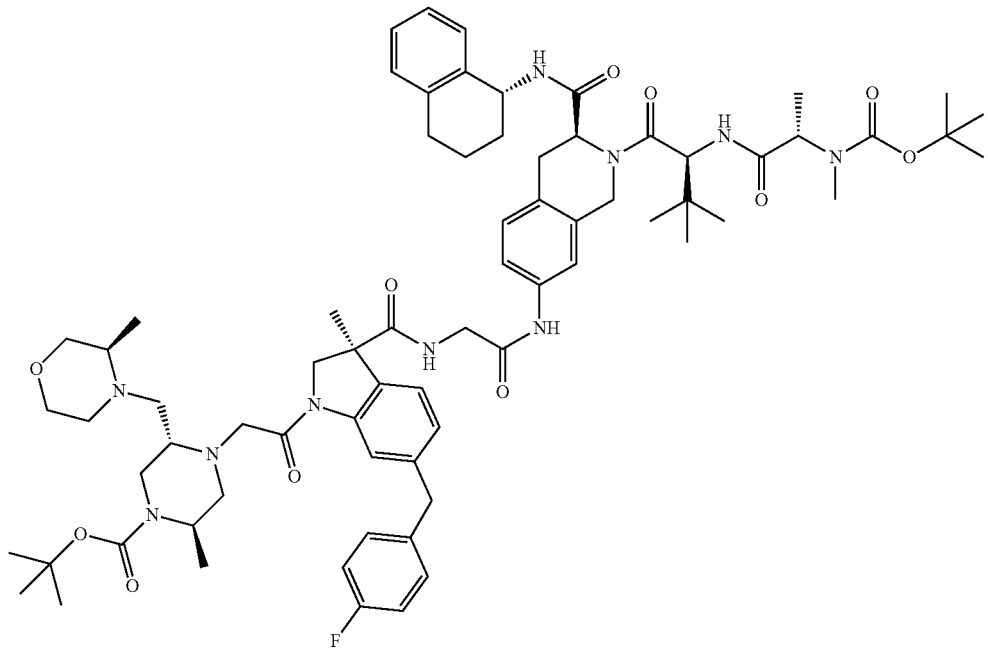 [SMILES: C[C@@H]1COCCN1C[C@H]1CN(C(=O)OC(C)(C)C)[C@H](C)CN1CC(=O)N1C[C@@](C)(C(=O)NCC(=O)Nc2ccc3c(c2)CN(C(=O)[C@@H](NC(=O)[C@H](C)N(C)C(=O)OC(C)(C)C)C(C)(C)C)[C@H](C(=O)N[C@@H]2CCCc4ccccc42)C3)c2ccc(Cc3ccc(F)cc3)cc21]

T3P 50% in EtOAc (137 mg, 128 µl, 216 µmol, Eq: 3) and N-methylmorpholine (72.7 mg, 79 µl, 719 µmol, Eq: 10) were added to a white suspension of 2-((S)-1-(2-((2S,5R)-4-(tert-butoxycarbonyl)-5-methyl-2-(((R)-3-methylmorpholino)methyl)piperazin-1-yl)acetyl)-6-(4-fluorobenzyl)-3-methylindoline-3-carboxamido)acetic acid (50 mg, 71.9 µmol, Eq: 1) and tert-butyl ((S)-1-(((S)-1-((S)-7-amino-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl)carbamate (44.5 mg, 71.9 µmol, Eq: 1) (described in WO2013/192286 A1) in ethyl acetate (1 ml). After stirring 15 min at room temperature everything had dissolved and the light yellow solution was stirred overnight. Aq. sat. NaHCO₃ was added and the mixture was extracted with ethyl acetate. The organic layer was dried over magnesium sulfate, filtered and evaporated. The crude residue was purified by flash chromatography using ethyl acetate/methanol (0-10% methanol) as eluent affording tert-butyl (2R,5S)-4-[2-[(3S)-3-[[2-[[(3S)-2-[(2S)-2-[[(2S)-2-[tert-butoxycarbonyl(methyl)amino]propanoyl]amino]-3,3-dimethyl-butanoyl]-3-[[(1R)-tetralin-1-yl]carbamoyl]-3,4-dihydro-1H-isoquinolin-7-yl]amino]-2-oxo-ethyl]carbamoyl]-6-[(4-fluorophenyl)methyl]-3-methyl-indolin-1-yl]-2-oxo-ethyl]-2-methyl-5-[[(3R)-3-methylmorpholin-4-yl]methyl]piperazine-1-carboxylate (64 mg, 68.6%) as a white solid. MS: m/z (M+H)⁺=1297.7 h) (3S)-2-[(2S)-3,3-Dimethyl-2-[[(2S)-2-(methylamino)propanoyl]amino]butanoyl]-7-[[2-[[(3S)-6-[(4-fluorophenyl)methyl]-3-methyl-1-[2-[(2R,5R)-5-methyl-2-[[(3R)-3-methylmorpholin-4-yl]methyl]piperazin-1-yl]acetyl]indoline-3-carbonyl]amino]acetyl]amino]-N-[(1R)-tetralin-1-yl]-3,4-dihydro-1H-isoquinoline-3-carboxamide Trihydrochloride

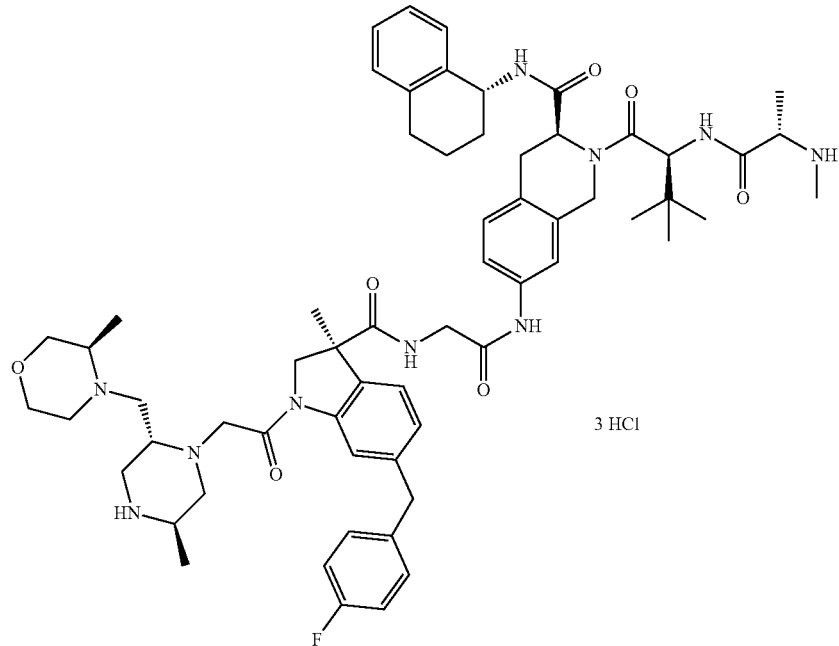 [SMILES: CN[C@@H](C)C(=O)N[C@H](C(=O)N1Cc2cc(NC(=O)CNC(=O)[C@]3(C)CN(C(=O)CN4C[C@@H](C)NC[C@@H]4CN4CCOC[C@H]4C)c4cc(Cc5ccc(F)cc5)ccc43)ccc2C[C@H]1C(=O)N[C@@H]1CCCc2ccccc21)C(C)(C)C]

HCl 4M in dioxane (1.2 g, 1 ml, 4 mmol, Eq: 88) was added to a light yellow solution of (2R,5S)-tert-butyl 4-(2-((S)-3-((2-(((S)-2-((S)-2-((S)-2-((tert-butoxycarbonyl)(methyl)amino)propanamido)-3,3-dimethylbutanoyl)-3-(((R)-1,2,3,4-tetrahydronaphthalen-1-yl)carbamoyl)-1,2,3,4-tetrahydroisoquinolin-7-yl)amino)-2-oxoethyl)carbamoyl)-6-(4-fluorobenzyl)-3-methylindolin-1-yl)-2-oxoethyl)-2-methyl-5-(((R)-3-methylmorpholino)methyl)piperazine-1-carboxylate (59 mg, 45.5 μmol, Eq: 1) in ethyl acetate (0.5 ml) and the reaction was stirred at room temperature for 2 h. The white precipitate was filtered off, washed with diethyl ether and dried in vacuo affording (3S)-2-[(2S)-3,3-dimethyl-2-[[(2S)-2-(methylamino)propanoyl]amino]butanoyl]-7-[[2-[[(3S)-6-[(4-fluorophenyl)methyl]-3-methyl-1-[2-[(2R,5R)-5-methyl-2-[[(3R)-3-methylmorpholin-4-yl]methyl]piperazin-1-yl]acetyl]indoline-3-carbonyl]amino]acetyl]amino]-N-[(1R)-tetralin-1-yl]-3,4-dihydro-1H-isoquinoline-3-carboxamide trihydrochloride (48 mg, 87.5%) as a white solid. MS: m/z (M+H)$^+$=1097.6

Example 11

(3S)-2-[(2S)-3,3-Dimethyl-2-[[(2S)-2-(methylamino)propanoyl]amino]butanoyl]-7-[[2-[[(3R)-6-[(4-fluorophenyl)methyl]-3-methyl-1-[2-[(2R,5R)-5-methyl-2-[[(3R)-3-methylmorpholin-4-yl]methyl]piperazin-1-yl]acetyl]indoline-3-carbonyl]amino]acetyl]amino]-N-[(1R)-1,2,3,4-tetrahydronaphthalen-1-yl]-3,4-dihydro-1H-isoquinoline-3-carboxamide Trihydrochloride a) tert-butyl (2R,5S)-4-[2-[(3R)-3-[[2-[[(3S)-2-[(2S)-2-[[(2S)-2-[tert-butoxycarbonyl(methyl)amino]propanoyl]amino]-3,3-dimethyl-butanoyl]-3-[[(1R)-tetralin-1-yl]carbamoyl]-3,4-dihydro-1H-isoquinolin-7-yl]amino]-2-oxo-ethyl]carbamoyl]-6-[(4-fluorophenyl)methyl]-3-methyl-indolin-1-yl]-2-oxo-ethyl]-2-methyl-5-[[(3R)-3-methylmorpholin-4-yl]methyl]piperazine-1-carboxylate

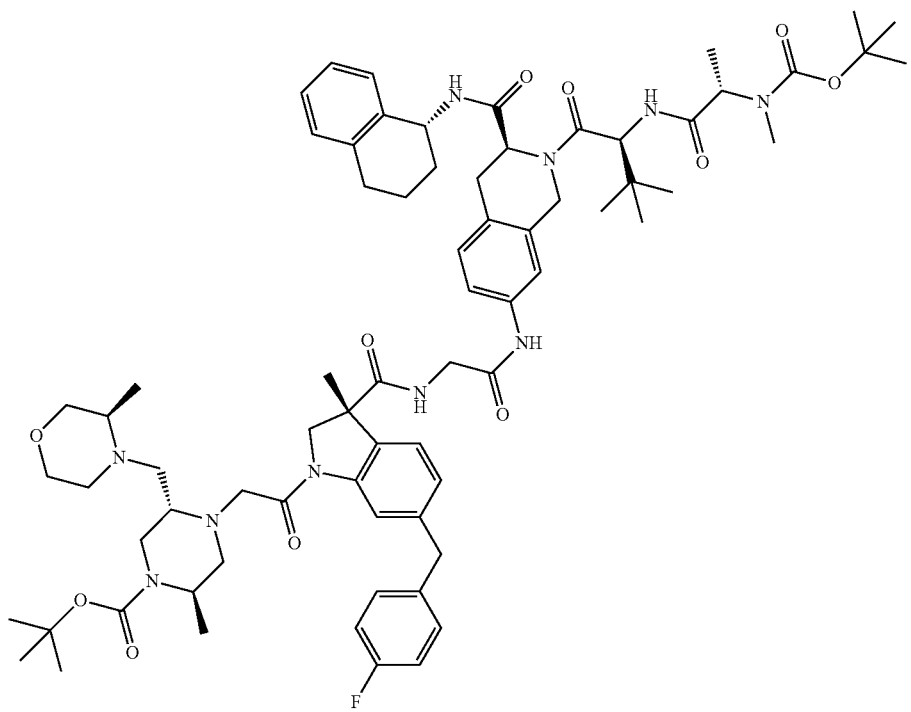 [SMILES: C[C@@H]1COCCN1C[C@H]1CN(C(=O)OC(C)(C)C)[C@H](C)CN1CC(=O)N1C[C@](C)(C(=O)NCC(=O)Nc2ccc3c(c2)CN(C(=O)[C@@H](NC(=O)[C@H](C)N(C)C(=O)OC(C)(C)C)C(C)(C)C)[C@H](C(=O)N[C@@H]2CCCc4ccccc42)C3)c2ccc(Cc3ccc(F)cc3)cc21]

T3P 50% in EtOAc (137 mg, 128 µl, 216 µmol, Eq: 3) and N-methylmorpholine (72.7 mg, 79 µl, 719 µmol, Eq: 10) were added to a white suspension of 2-((R)-1-(2-((2S,5R)-4-(tert-butoxycarbonyl)-5-methyl-2-(((R)-3-methylmorpholino)methyl)piperazin-1-yl)acetyl)-6-(4-fluorobenzyl)-3-methylindoline-3-carboxamido)acetic acid (50 mg, 71.9 µmol, Eq: 1) and tert-butyl ((S)-1-(((S)-1-((S)-7-amino-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl)carbamate (44.5 mg, 71.9 µmol, Eq: 1) in ethyl acetate (1 ml). After stirring 15 min at room temperature everything had dissolved and the light yellow solution was stirred overnight. Aq. sat. NaHCO$_3$ was added and the mixture was extracted with ethyl acetate. The organic layer was dried over magnesium sulfate, filtered and evaporated. The crude residue was purified by flash chromatography using ethyl acetate/methanol (0-10% methanol) as eluent affording tert-butyl (2R,5S)-4-[2-[(3R)-3-[[2-[[(3S)-2-[(2S)-2-[[(2S)-2-[tert-butoxycarbonyl(methyl)amino]propanoyl]amino]-3,3-dimethyl-butanoyl]-3-[[(1R)-tetralin-1-yl]carbamoyl]-3,4-dihydro-1H-isoquinolin-7-yl]amino]-2-oxo-ethyl]carbamoyl]-6-[(4-fluorophenyl)methyl]-3-methyl-indolin-1-yl]-2-oxo-ethyl]-2-methyl-5-[[(3R)-3-methylmorpholin-4-yl]methyl]piperazine-1-carboxylate (54 mg, 57.9%) as a white solid. MS: m/z (M+H)$^+$=1297.7 b) (3S)-2-[(2S)-3,3-Dimethyl-2-[[(2S)-2-(methyl-amino)propanoyl]amino]butanoyl]-7-[[2-[[(3R)-6-[(4-fluorophenyl)methyl]-3-methyl-1-[2-[(2R,5R)-5-methyl-2-[[(3R)-3-methylmorpholin-4-yl]methyl]piperazin-1-yl]acetyl]indoline-3-carbonyl]amino]acetyl]amino]-N-[(1R)-tetralin-1-yl]-3,4-dihydro-1H-isoquinoline-3-carboxamide Trihydrochloride

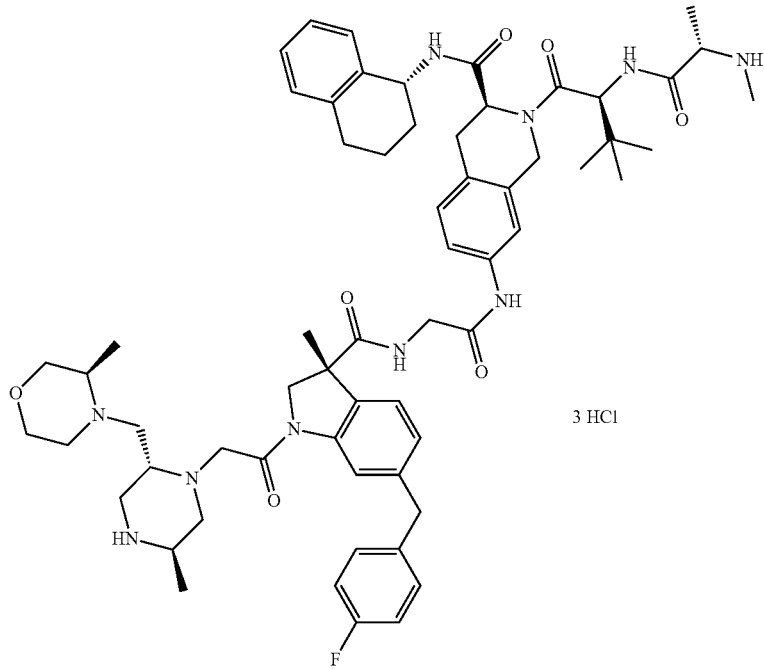 [SMILES: CN[C@@H](C)C(=O)N[C@H](C(=O)N1Cc2cc(NC(=O)CNC(=O)[C@@]3(C)CN(C(=O)CN4C[C@@H](C)NC[C@@H]4CN4CCOC[C@H]4C)c4cc(Cc5ccc(F)cc5)ccc43)ccc2C[C@H]1C(=O)N[C@@H]1CCCc2ccccc21)C(C)(C)C]

3 HCl

HCl 4M in dioxane (963 μl, 3.85 mmol, Eq: 100) was added to a light yellow solution of (2R,5S)-tert-butyl 4-(2-((R)-3-((2-(((S)-2-((S)-2-((S)-2-((tert-butoxycarbonyl)(methyl)amino)propanamido)-3,3-dimethylbutanoyl)-3-(((R)-1,2,3,4-tetrahydronaphthalen-1-yl)carbamoyl)-1,2,3,4-tetrahydroisoquinolin-7-yl)amino)-2-oxoethyl)carbamoyl)-6-(4-fluorobenzyl)-3-methylindolin-1-yl)-2-oxoethyl)-2-methyl-5-(((R)-3-methylmorpholino)methyl)piperazine-1-carboxylate (50 mg, 38.5 μmol, Eq: 1) in ethyl acetate (0.5 ml) and the reaction was stirred at room temperature for 2 h. The white precipitate was filtered off, washed with diethyl ether and dried in vacuo affording (3S)-2-[(2S)-3,3-dimethyl-2-[[(2S)-2-(methylamino)propanoyl]amino]butanoyl]-7-[[2-[[(3R)-6-[(4-fluorophenyl)methyl]-3-methyl-1-[2-[(2R,5R)-5-methyl-2-[[(3R)-3-methylmorpholin-4-yl]methyl]piperazin-1-yl]acetyl]indoline-3-carbonyl]amino]acetyl]amino]-N-[(1R)-1,2,3,4-tetrahydronaphthalen-1-yl]-3,4-dihydro-1H-isoquinoline-3-carboxamide trihydrochloride (40 mg, 86%) as a white solid. MS: m/z (M+H)$^+$=1097.6

Example 12

(R)—N—((S)-3-((2,6-Difluorophenyl)carbamoyl)-2-((S)-2-((S)-2-(methylamino)propanamido)-2-(tetrahydro-2H-pyran-4-yl)acetyl)isoindolin-5-yl)-6-(4-fluorobenzyl)-3-methyl-1-(2-((2R,5R)-5-methyl-2-(((R)-3-methylmorpholino)methyl)piperazin-1-yl)acetyl)indoline-3-carboxamide Trihydrochloride a) tert-Butyl (2R,5S)-4-[2-[(3R)-3-[[(3S)-2-[(2S)-2-[[(2S)-2-[tert-butoxycarbonyl(methyl)amino]propanoyl]amino]-2-tetrahydropyran-4-yl-acetyl]-3-[(2,6-difluorophenyl)carbamoyl]isoindolin-5-yl]carbamoyl]-6-[(4-fluorophenyl)methyl]-3-methyl-indolin-1-yl]-2-oxo-ethyl]-2-methyl-5-[[(3R)-3-methylmorpholin-4-yl]methyl]piperazine-1-carboxylate

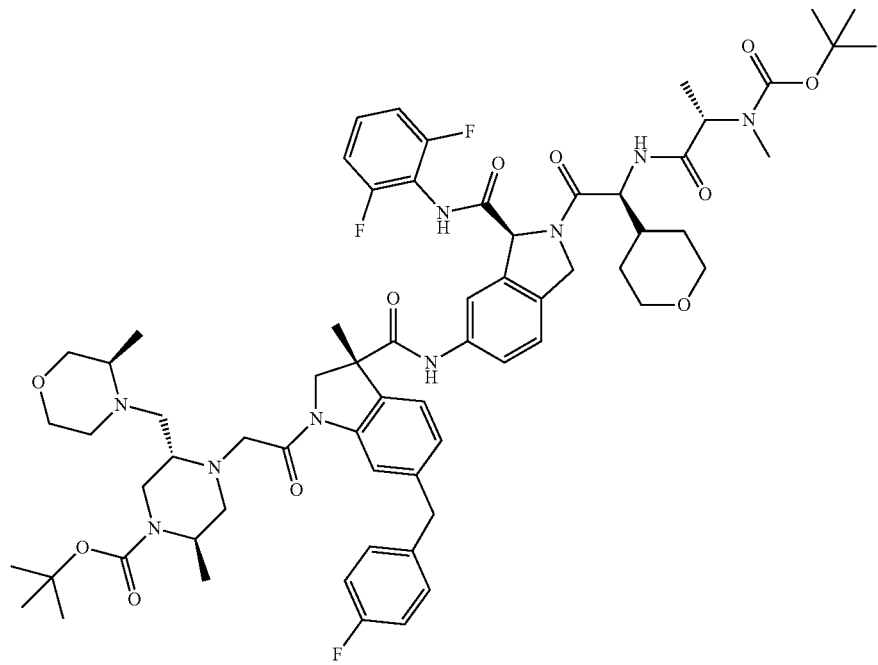 [SMILES: C[C@@H]1COCCN1C[C@H]1CN(C(=O)OC(C)(C)C)[C@H](C)CN1CC(=O)N1C[C@](C)(C(=O)Nc2ccc3c(c2)[C@@H](C(=O)Nc2c(F)cccc2F)N(C(=O)[C@@H](NC(=O)[C@H](C)N(C)C(=O)OC(C)(C)C)C2CCOCC2)C3)c2ccc(Cc3ccc(F)cc3)cc21]

(R)-1-(2-((2S,5R)-4-(tert-Butoxycarbonyl)-5-methyl-2-(((R)-3-methylmorpholino)methyl)piperazin--yl)acetyl)-6-(4-fluorobenzyl)-3-methylindoline-3-carboxylic acid (80 mg, 125 µmol, Eq: 1) was stirred with tert-butyl ((S)-1-(((S)-2-((S)-6-amino-1-((2,6-difluorophenyl)carbamoyl)isoindolin-2-yl)-2-oxo-1-(tetrahydro-2H-pyran-4-yl)ethyl)amino)-1-oxopropan-2-yl)(methyl)carbamate (77.1 mg, 125 µmol, Eq: 1; Intermediate 2), N-methylmorpholine (127 mg, 138 µl, 1.25 mmol, Eq: 10) and T3P in EtOAc 50% (239 mg, 224 µl, 376 µmol, Eq: 3) in ethyl acetate (480 µl) at room temperature over the weekend. Sat. NaHCO₃ solution was added and the mixture was extracted three times with ethyl acetate. The organic layer was dried over magnesium sulfate, filtered and evaporated. The crude material was applied on silica gel and purified by column chromatography using ethyl acetate as eluent affording tert-butyl (2R,5S)-4-[2-[(3R)-3-[[(3S)-2-[(2S)-2-[[(2S)-2-[tert-butoxycarbonyl(methyl)amino]propanoyl]amino]-2-tetrahydropyran-4-yl-acetyl]-3-[(2,6-difluorophenyl)carbamoyl]isoindolin-5-yl]carbamoyl]-6-[(4-fluorophenyl)methyl]-3-methyl-indolin-1-yl]-2-oxo-ethyl]-2-methyl-5-[[(3R)-3-methylmorpholin-4-yl]methyl]piperazine-1-carboxylate (96 mg, 62%) as a white solid. MS: m/z (M+H)⁺=1236.6 b) (3R)—N-[(3S)-3-[(2,6-Difluorophenyl)carbamoyl]-2-[(2S)-2-[[(2S)-2-(methylamino)propanoyl]amino]-2-tetrahydropyran-4-yl-acetyl]isoindolin-5-yl]-6-[(4-fluorophenyl)methyl]-3-methyl-1-[2-[(2R,5R)-5-methyl-2-[[(3R)-3-methylmorpholin-4-yl]methyl]piperazin-1-yl]acetyl]indoline-3-carboxamide Trihydrochloride

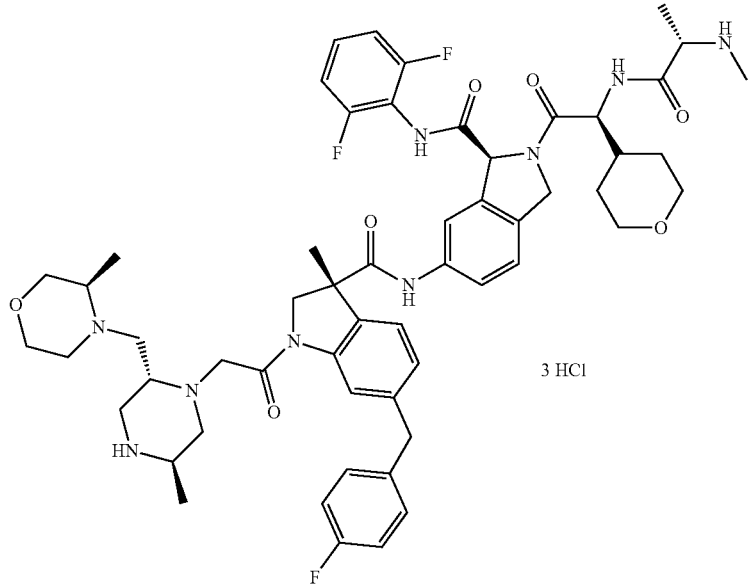 [SMILES: CN[C@@H](C)C(=O)N[C@H](C(=O)N1Cc2ccc(NC(=O)[C@@]3(C)CN(C(=O)CN4C[C@@H](C)NC[C@@H]4CN4CCOC[C@H]4C)c4cc(Cc5ccc(F)cc5)ccc43)cc2[C@H]1C(=O)Nc1c(F)cccc1F)C1CCOCC1]

HCl 4M in dioxane (1.82 ml, 7.28 mmol, Eq: 100) was added to a clear solution of (2R,5S)-tert-butyl 4-(2-((R)-3-(((S)-2-((S)-2-((S)-2-((tert-butoxycarbonyl)(methyl)amino)propanamido)-2-(tetrahydro-2H-pyran-4-yl)acetyl)-3-((2,6-difluorophenyl)carbamoyl)isoindolin-5-yl)carbamoyl)-6-(4-fluorobenzyl)-3-methylindolin-1-yl)-2-oxoethyl)-2-methyl-5-(((R)-3-methylmorpholino)methyl)piperazine-1-carboxylate (90 mg, 72.8 μmol, Eq: 1) in ethyl acetate (1 ml) and the reaction was stirred at room temperature for 2 h. The precipitate was filtered off, washed with diethyl ether and dried affording (R)—N—((S)-3-((2,6-difluorophenyl)carbamoyl)-2-((S)-2-((S)-2-(methylamino)propanamido)-2-(tetrahydro-2H-pyran-4-yl)acetyl)isoindolin-5-yl)-6-(4-fluorobenzyl)-3-methyl-1-(2-((2R,5R)-5-methyl-2-(((R)-3-methylmorpholino)methyl)piperazin-1-yl)acetyl)indoline-3-carboxamide trihydrochloride (78 mg, 93.5%) as an off-white solid. MS: m/z (M+H)$^+$=1036.5

Example 13 a) (3S)—N-(2,6-Difluorophenyl)-7-(2-(6-(4-fluorobenzyl)-3-methyl-1-(2-((2R,5R)-5-methyl-2-(((R)-3-methylmorpholino)methyl)piperazin-1-yl)acetyl)indoline-3-carboxamido)acetamido)-2-((S)-2-((S)-2-(methylamino)propanamido)-2-(tetrahydro-2H-pyran-4-yl)acetyl)-1,2,3,4-tetrahydroisoquinoline-3-carboxamide trihydrochloride tert-Butyl (2R,5S)-4-[2-[3-[[2-[[(3S)-2-[(2S)-2-[[(2S)-2-[tert-butoxycarbonyl(methyl)amino]propanoyl]amino]-2-tetrahydropyran-4-yl-acetyl]-3-[(2,6-difluorophenyl)carbamoyl]-3,4-dihydro-1H-isoquinolin-7-yl]amino]-2-oxo-ethyl]carbamoyl]-6-[(4-fluorophenyl)methyl]-3-methyl-indolin-1-yl]-2-oxo-ethyl]-2-methyl-5-[[(3R)-3-methylmorpholin-4-yl]methyl]piperazine-1-carboxylate

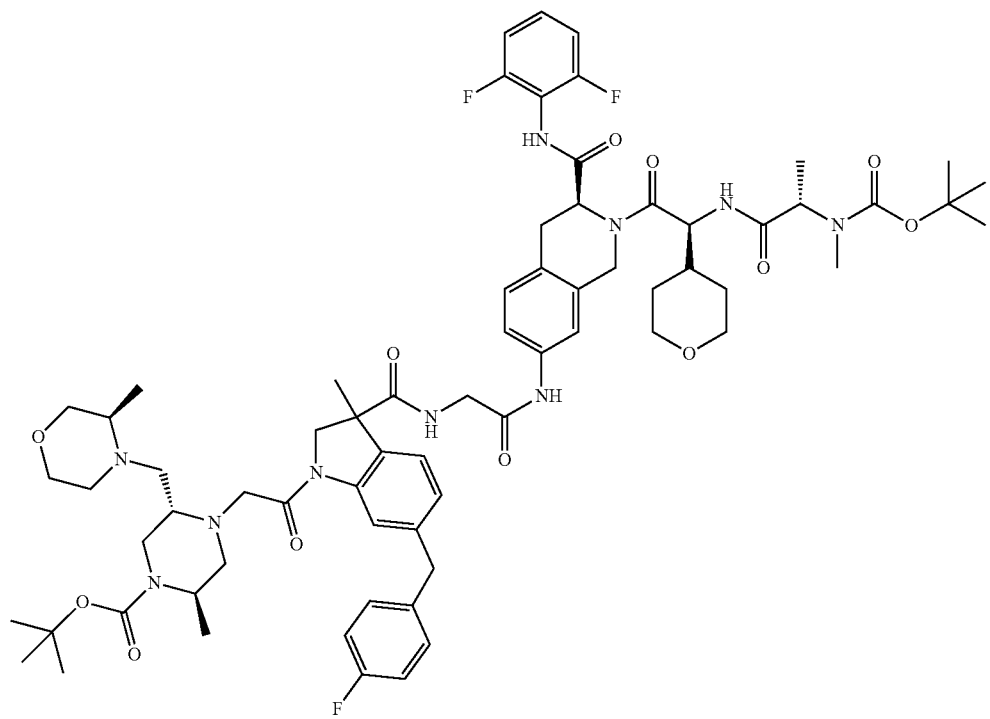 [SMILES: C[C@@H]1COCCN1C[C@H]1CN(C(=O)OC(C)(C)C)[C@H](C)CN1CC(=O)N1CC(C)(C(=O)NCC(=O)Nc2ccc3c(c2)CN(C(=O)[C@@H](NC(=O)[C@H](C)N(C)C(=O)OC(C)(C)C)C2CCOCC2)[C@H](C(=O)Nc2c(F)cccc2F)C3)c2ccc(Cc3ccc(F)cc3)cc21]

N-Methylmorpholine (116 mg, 126 µl, 1.15 mmol, Eq: 10) and T3P 50% in EtOAc (219 mg, 205 µl, 345 µmol, Eq: 3) were added to a white suspension of 2-(1-(2-((2S,5R)-4-(tert-butoxycarbonyl)-5-methyl-2-(((R)-3-methylmorpholino)methyl)piperazin-1-yl)acetyl)-6-(4-fluorobenzyl)-3-methylindoline-3-carboxamido)acetic acid (80 mg, 115 µmol, Eq: 1) and tert-butyl ((S)-1-(((S)-2-((S)-7-amino-3-((2,6-difluorophenyl)carbamoyl)-3,4-dihydroisoquinolin-2(1H)-yl)-2-oxo-1-(tetrahydro-2H-pyran-4-yl)ethyl)amino)-1-oxopropan-2-yl)(methyl)carbamate (72.4 mg, 115 µmol, Eq: 1; Intermediate 3) in ethyl acetate (1.5 ml). After stirring 15 min at room temperature everything had dissolved and the light yellow solution was stirred overnight. Aq. sat. NaHCO$_3$ was added and the mixture was extracted with ethyl acetate. The organic layer was dried over magnesium sulfate, filtered and evaporated. The crude residue was purified by flash chromatography using ethyl acetate/methanol (0-10% methanol) as eluent affording (2R,5S)-tert-butyl 4-(2-(3-((2-(((S)-2-((S)-2-((S)-2-((tert-butoxycarbonyl)(methyl)amino)propanamido)-2-(tetrahydro-2H-pyran-4-yl)acetyl)-3-((2,6-difluorophenyl)carbamoyl)-1,2,3,4-tetrahydroisoquinolin-7-yl)amino)-2-oxoethyl)carbamoyl)-6-(4-fluorobenzyl)-3-methylindolin-1-yl)-2-oxoethyl)-2-methyl-5-(((R)-3-methylmorpholino)methyl)piperazine-1-carboxylate (29 mg, 19.3%) as an off-white solid. MS: m/z (M+H)$^+$=1307.7 b) (3S)—N-(2,6-Difluorophenyl)-7-[[2-[[6-[(4-fluorophenyl)methyl]-3-methyl-1-[2-[(2R,5R)-5-methyl-2-[[(3R)-3-methylmorpholin-4-yl]methyl]piperazin-1-yl]acetyl]indoline-3-carbonyl]amino]acetyl]amino]-2-[(2S)-2-[[(2S)-2-(methylamino)propanoyl]amino]-2-tetrahydropyran-4-yl-acetyl]-3,4-dihydro-1H-isoquinoline-3-carboxamide Trihydrochloride

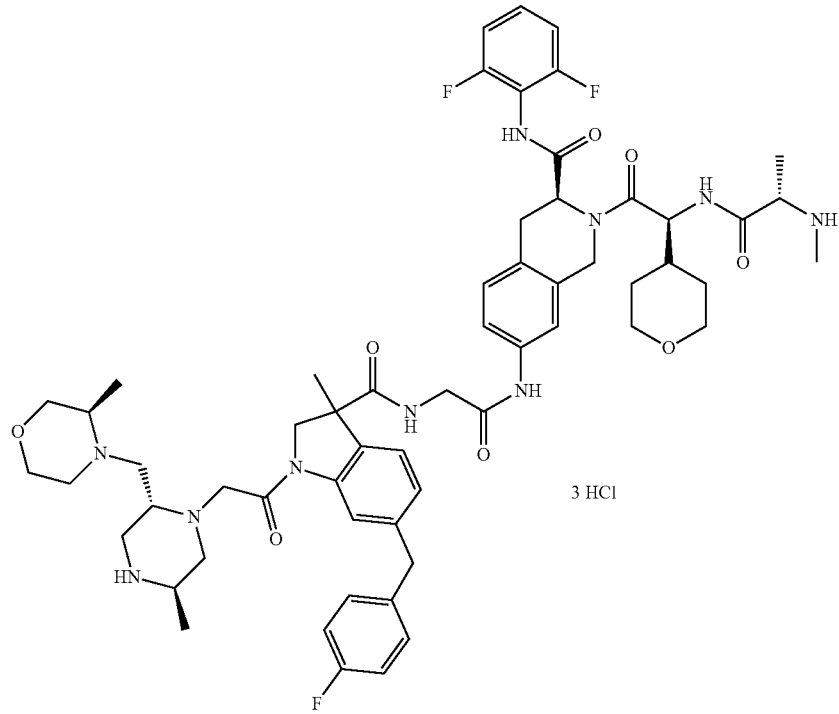 [SMILES: CN[C@@H](C)C(=O)N[C@H](C(=O)N1Cc2cc(NC(=O)CNC(=O)C3(C)CN(C(=O)CN4C[C@@H](C)NC[C@@H]4CN4CCOC[C@H]4C)c4cc(Cc5ccc(F)cc5)ccc43)ccc2C[C@H]1C(=O)Nc1c(F)cccc1F)C1CCOCC1]

(2R,5S)-tert-Butyl 4-(2-(3-((2-(((S)-2-((S)-2-((S)-2-((tert-butoxycarbonyl)(methyl)amino)propanamido)-2-(tetrahydro-2H-pyran-4-yl)acetyl)-3-((2,6-difluorophenyl)carbamoyl)-1,2,3,4-tetrahydroisoquinolin-7-yl)amino)-2-oxoethyl)carbamoyl)-6-(4-fluorobenzyl)-3-methylindolin-1-yl)-2-oxoethyl)-2-methyl-5-(((R)-3-methylmorpholino)methyl)piperazine-1-carboxylate (25 mg, 19.1 µmol, Eq: 1) was stirred with HCl in dioxane 4M (400 µl, 1.6 mmol, Eq: 83.7) in ethyl acetate (600 µL) at room temperature overnight. The precipitated solid was filtered off, washed with diethyl ether and dried under high vacuum affording (3S)—N-(2,6-difluorophenyl)-7-(2-(6-(4-fluorobenzyl)-3-methyl-1-(2-((2R,5R)-5-methyl-2-(((R)-3-methylmorpholino)methyl)piperazin-1-yl)acetyl)indoline-3-carboxamido)acetamido)-2-((S)-2-((S)-2-(methylamino)propanamido)-2-(tetrahydro-2H-pyran-4-yl)acetyl)-1,2,3,4-tetrahydroisoquinoline-3-carboxamide trihydrochloride (14 mg, 60.2%) as a white solid. MS: m/z (M+H)$^+$=1107.6

Example 14

N-(2-(4-Fluoro-3-((S)-2-((S)-2-((S)-2-(methylamino)propanamido)-2-(tetrahydro-2H-pyran-4-yl)acetyl)isoindoline-1-carboxamido)benzamido)ethyl)-6-(4-fluorobenzyl)-3-methyl-1-(2-((2R,5R)-5-methyl-2-(((R)-3-methylmorpholino)methyl)piperazin-1-yl)acetyl)indoline-3-carboxamide Dihydrochloride a) Benzyl 3-[[(1 S)-2-[(2S)-2-[[(2S)-2-[tert-butoxycarbonyl(methyl)amino]propanoyl]amino]-2-tetrahydropyran-4-yl-acetyl]isoindoline-1-carbonyl]amino]-4-fluoro-benzoate

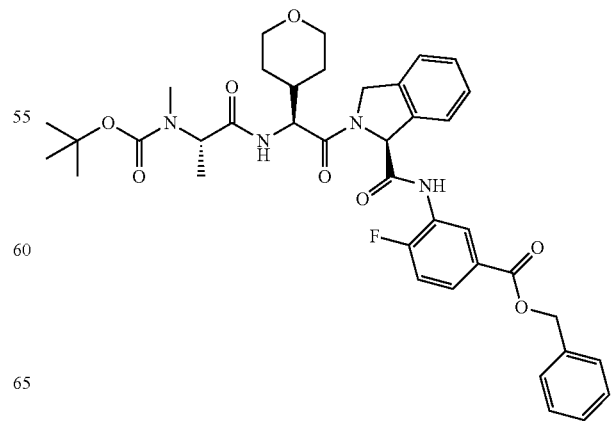

(S)-2-((S)-2-((S)-2-((tert-Butoxycarbonyl)(methyl)amino)propanamido)-2-(tetrahydro-2H-pyran-4-yl)acetyl)isoindoline-1-carboxylic acid (500 mg, 1.02 mmol, Eq: 1; Intermediate 1), benzyl 3-amino-4-fluorobenzoate (276 mg, 1.12 mmol, Eq: 1.1) and T3P 50% in EtOAc (1.3 g, 1.22 ml, 2.04 mmol, Eq: 2) were dissolved in ethyl acetate (3.5 ml). Pyridine (1.75 ml) was added and the yellow solution was stirred at room temperature overnight. The reaction mixture was poured into ethyl acetate and extracted with diluted HCl and brine. The organic layer was dried over magnesium sulfate, filtered and evaporated. The crude material was purified by flash chromatography using ethyl acetate/heptane (0-100% ethyl acetate) as eluent affording benzyl 3-((S)-2-((S)-2-((S)-2-((tert-butoxycarbonyl)(methyl)amino)propanamido)-2-(tetrahydro-2H-pyran-4-yl)acetyl)isoindoline-1-carboxamido)-4-fluorobenzoate (510 mg, 69.7%) as a white foam. MS: m/z (M+H)⁺=717.33 b) 3-[[(1S)-2-[(2S)-2-[[(2S)-2-[tert-Butoxycarbonyl(methyl)amino]propanoyl]amino]-2-tetrahydropyran-4-yl-acetyl]isoindoline-1-carbonyl]amino]-4-fluoro-benzoic Acid

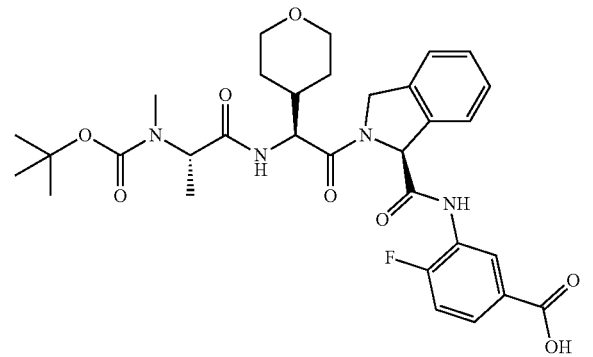 [SMILES: C[C@@H](C(=O)N[C@H](C(=O)N1Cc2ccccc2[C@H]1C(=O)Nc1cc(C(=O)O)ccc1F)C1CCOCC1)N(C)C(=O)OC(C)(C)C]

Pd—C 10% (65 mg, 61.1 µmol, Eq: 0.0973) was added to a clear solution of benzyl 3-((S)-2-((S)-2-((S)-2-((tert-butoxycarbonyl)(methyl)amino)propanamido)-2-(tetrahydro-2H-pyran-4-yl)acetyl)isoindoline-1-carboxamido)-4-fluorobenzoate (450 mg, 628 µmol, Eq: 1) in methanol (15 ml) and the reaction was stirred overnight under hydrogen atmosphere. The reaction mixture was filtered over decalite and concentrated affording 3-((S)-2-((S)-2-((S)-2-((tert-butoxycarbonyl)(methyl)amino)propanamido)-2-(tetrahydro-2H-pyran-4-yl)acetyl)isoindoline-1-carboxamido)-4-fluorobenzoic acid (375 mg, 95.3%) as a white solid. MS: m/z (M+H)⁺=627.28 c) tert-Butyl N-[(1 S)-2-[[(1 S)-2-[(1 S)-1-[[5-[2-(benzyloxycarbonylamino)ethylcarbamoyl]-2-fluoro-phenyl]carbamoyl]isoindolin-2-yl]-2-oxo-1-tetrahydropyran-4-yl-ethyl]amino]-1-methyl-2-oxo-ethyl]-N-methyl-carbamate

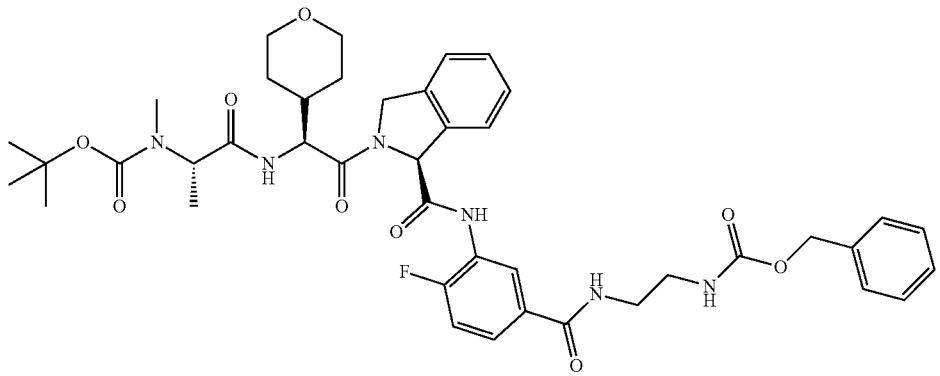 [SMILES: C[C@@H](C(=O)N[C@H](C(=O)N1Cc2ccccc2[C@H]1C(=O)Nc1cc(C(=O)NCCNC(=O)OCc2ccccc2)ccc1F)C1CCOCC1)N(C)C(=O)OC(C)(C)C]

3-((S)-2-((S)-2-((S)-2-((tert-Butoxycarbonyl)(methyl)amino)propanamido)-2-(tetrahydro-2H-pyran-4-yl)acetyl)isoindoline-1-carboxamido)-4-fluorobenzoic acid (120 mg, 191 µmol, Eq: 1) and was stirred with benzyl (2-aminoethyl)carbamate hydrochloride (44.2 mg, 191 µmol, Eq: 1), DIPEA (99 mg, 134 µl, 766 µmol, Eq: 4) and HATU (94.7 mg, 249 µmol, Eq: 1.3) in DMF (1.7 ml) overnight at room temperature. 0.5M HCl was added and extracted three times with ethyl acetate, dried over magnesium sulfate, filtered and evaporated. The crude material was applied on silica gel and purified by column chromatography using ethyl acetate/methanol (0-5% methanol) as eluent affording tert-butyl ((S)-1-(((S)-2-((S)-1-((5-((2-(((benzyloxy)carbonyl)amino)ethyl)carbamoyl)-2-fluorophenyl)carbamoyl)isoindolin-2-yl)-2-oxo-1-(tetrahydro-2H-pyran-4-yl)ethyl)amino)-1-oxopropan-2-yl)(methyl)carbamate (153 mg, 99.5%) as a colorless oil. MS: m/z (M+H)⁺=803.38 d) tert-Butyl N-[(1S)-2-[[(1 S)-2-[(1S)-1-[[5-(2-aminoethylcarbamoyl)-2-fluoro-phenyl]carbamoyl]isoindolin-2-yl]-2-oxo-1-tetrahydropyran-4-yl-ethyl]amino]-1-methyl-2-oxo-ethyl]-N-methyl-carbamate

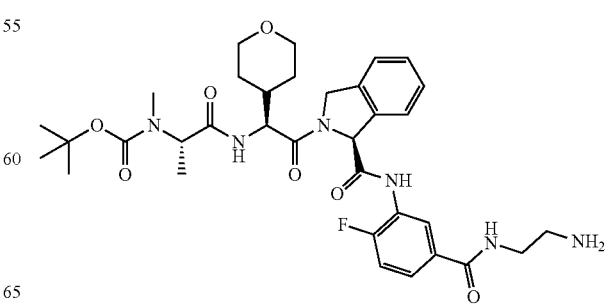

tert-Butyl ((S)-1-(((S)-2-((S)-1-((5-((2-(((benzyloxy)carbonyl)amino)ethyl)carbamoyl)-2-fluorophenyl)carbamoyl)isoindolin-2-yl)-2-oxo-1-(tetrahydro-2H-pyran-4-yl)ethyl)amino)-1-oxopropan-2-yl)(methyl)carbamate (120 mg, 149 µmol, Eq: 1) was stirred with palladium on carbon 10% (16 mg, 15 µmol, Eq: 0.101) in methanol (5 ml) under a hydrogen atmosphere at room temperature overnight. The catalyst was filtered off and the solvent was evaporated affording tert-butyl ((S)-1-(((S)-2-((S)-1-((5-((2-aminoethyl)carbamoyl)-2-fluorophenyl)carbamoyl)isoindolin-2-yl)-2-oxo-1-(tetrahydro-2H-pyran-4-yl)ethyl)amino)-1-oxopropan-2-yl)(methyl)carbamate (90 mg, 90%) as a light yellow oil. MS: m/z (M+H)$^+$=669.34 e) tert-Butyl (2R,5S)-4-[2-[3-[2-[[3-[[(1S)-2-[(2S)-2-[[(2S)-2-[tert-butoxycarbonyl(methyl)amino]propanoyl]amino]-2-tetrahydropyran-4-yl-acetyl]isoindoline-1-carbonyl]amino]-4-fluoro-benzoyl]amino]ethylcarbamoyl]-6-[(4-fluorophenyl)methyl]-3-methyl-indolin-1-yl]-2-oxo-ethyl]-2-methyl-5-[[(3R)-3-methylmorpholin-4-yl]methyl]piperazine-1-carboxylate

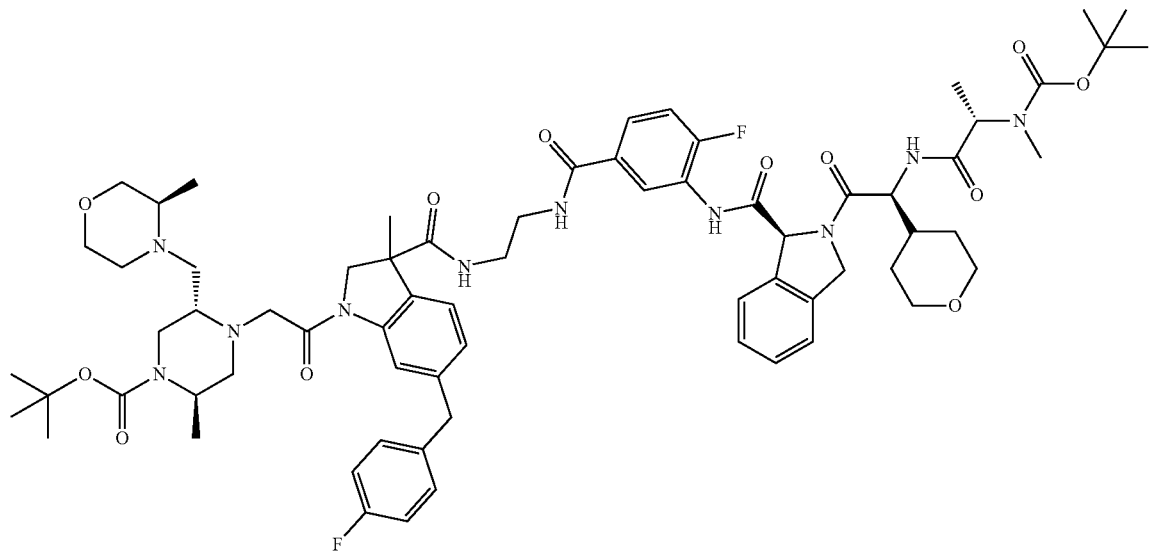 [SMILES: C[C@@H]1COCCN1C[C@H]1CN(C(=O)OC(C)(C)C)[C@H](C)CN1CC(=O)N1CC(C)(C(=O)NCCNC(=O)c2ccc(F)c(NC(=O)[C@@H]3c4ccccc4CN3C(=O)[C@@H](NC(=O)[C@H](C)N(C)C(=O)OC(C)(C)C)C3CCOCC3)c2)c2ccc(Cc3ccc(F)cc3)cc21]

tert-Butyl ((S)-1-(((S)-2-((S)-1-((5-((2-aminoethyl)carbamoyl)-2-fluorophenyl)carbamoyl)isoindolin-2-yl)-2-oxo-1-(tetrahydro-2H-pyran-4-yl)ethyl)amino)-1-oxopropan-2-yl)(methyl)carbamate (85 mg, 127 µmol, Eq: 1) was stirred with 1-(2-((2S,5R)-4-(tert-butoxycarbonyl)-5-methyl-2-(((R)-3-methylmorpholino)methyl)piperazin-1-yl)acetyl)-6-(4-fluorobenzyl)-3-methylindoline-3-carboxylic acid (81.2 mg, 127 µmol, Eq: 1) in presence of DIPEA (65.7 mg, 88.8 µl, 508 µmol, Eq: 4) and HATU (62.8 mg, 165 µmol, Eq: 1.3) in DMF (1 ml) at room temperature overnight. Sat. NaHCO$_3$ sol. aq. was added and extracted three times with ethyl acetate, dried over sodium sulfate, filtered and evaporated. The crude material was applied on silica gel and purified by column chromatography using ethyl acetate/methanol (0-5% methanol) as eluent affording (2R,5S)-tert-butyl 4-(2-(3-((2-(3-((S)-2-((S)-2-((S)-2-((tert-butoxycarbonyl)(methyl)amino)propanamido)-2-(tetrahydro-2H-pyran-4-yl)acetyl)isoindoline-1-carboxamido)-4-fluorobenzamido)ethyl)carbamoyl)-6-(4-fluorobenzyl)-3-methylindolin-1-yl)-2-oxoethyl)-2-methyl-5-(((R)-3-methylmorpholino)methyl)piperazine-1-carboxylate (31 mg, 18.9%) as a white solid. MS: m/z (M+H)$^+$=1289.68 f) N-[2-[[4-Fluoro-3-[[(1 S)-2-[(2S)-2-[[(2S)-2-(methylamino)propanoyl]amino]-2-tetrahydropyran-4-yl-acetyl]isoindoline-1-carbonyl]amino]benzoyl]amino]ethyl]-6-[(4-fluorophenyl)methyl]-3-methyl-1-[2-[(2R,5R)-5-methyl-2-[[(3R)-3-methylmorpholin-4-yl]methyl]piperazin-1-yl]acetyl]indoline-3-carboxamide dihydrochloride

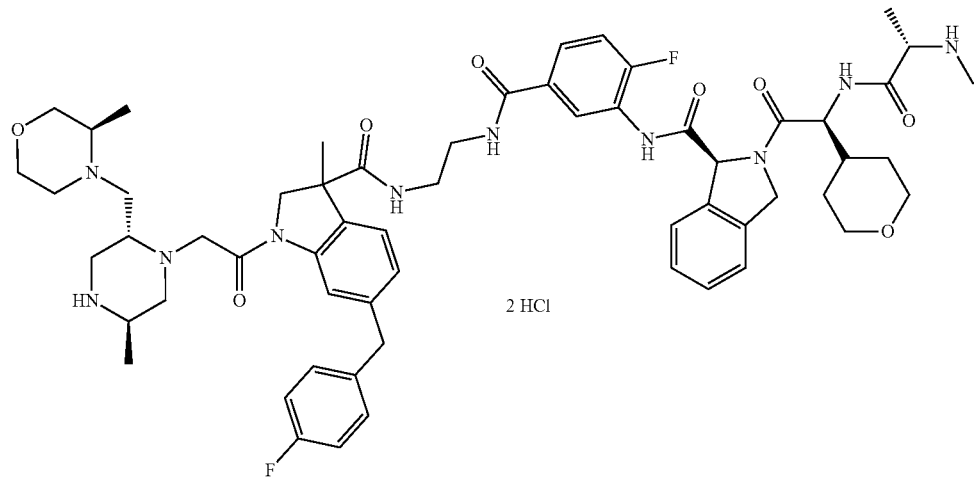 [SMILES: CN[C@@H](C)C(=O)N[C@H](C(=O)N1Cc2ccccc2[C@H]1C(=O)Nc1cc(C(=O)NCCNC(=O)C2(C)CN(C(=O)CN3C[C@@H](C)NC[C@@H]3CN3CCOC[C@H]3C)c3cc(Cc4ccc(F)cc4)ccc32)ccc1F)C1CCOCC1]

(2R,5S)-tert-Butyl 4-(2-(3-((2-(3-((S)-2-((S)-2-((S)-2-((tert-butoxycarbonyl)(methyl)amino) propanamido)-2-(tetrahydro-2H-pyran-4-yl)acetyl)isoindoline-1-carboxamido)-4-fluorobenzamido)ethyl)carbamoyl)-6-(4-fluorobenzyl)-3-methylindolin-1-yl)-2-oxoethyl)-2-methyl-5-(((R)-3-methylmorpholino)methyl)piperazine-1-carboxylate (30 mg, 23.3 µmol, Eq: 1) was stirred in ethyl acetate (500 µL) with HCl in dioxane 4M (500 µl, 2 mmol, Eq: 86) over the weekend at room temperature, the precipitated solid was filtered off and washed with diethyl ether and dried under high vacuum affording N-[2-[[4-fluoro-3-[[(1 S)-2-[(2S)-2-[[(2S)-2-(methylamino)propanoyl]amino]-2-tetrahydropyran-4-yl-acetyl]isoindoline-1-carbonyl]amino]benzoyl]amino]ethyl]-6-[(4-fluorophenyl)methyl]-3-methyl-1-[2-[(2R,5R)-5-methyl-2-[[(3R)-3-methylmorpholin-4-yl]methyl]piperazin-1-yl]acetyl]indoline-3-carboxamide dihydrochloride (23.16 mg, 85.7%) as a white solid. MS: m/z (M+H)$^+$=1089.58

Example 15 a) (S)—N—((S)-3-((2,6-Difluorophenyl)carbamoyl)-2-((S)-2-((S)-2-(methylamino)propanamido)-2-(tetrahydro-2H-pyran-4-yl)acetyl)isoindolin-5-yl)-6-(4-fluorobenzyl)-3-methyl-1-(2-((2R,5R)-5-methyl-2-(((R)-3-methylmorpholino)methyl)piperazin-1-yl)acetyl)indoline-3-carboxamide tert-Butyl (2R,5S)-4-[2-[(3S)-3-[[(3S)-2-[(2S)-2-[[(2S)-2-[tert-butoxycarbonyl(methyl)amino]propanoyl]amino]-2-tetrahydropyran-4-yl-acetyl]-3-[(2,6-difluorophenyl)carbamoyl]isoindolin-5-yl]carbamoyl]-6-[(4-fluorophenyl)methyl]-3-methyl-indolin-1-yl]-2-oxo-ethyl]-2-methyl-5-[[(3R)-3-methylmorpholin-4-yl]methyl]piperazine-1-carboxylate

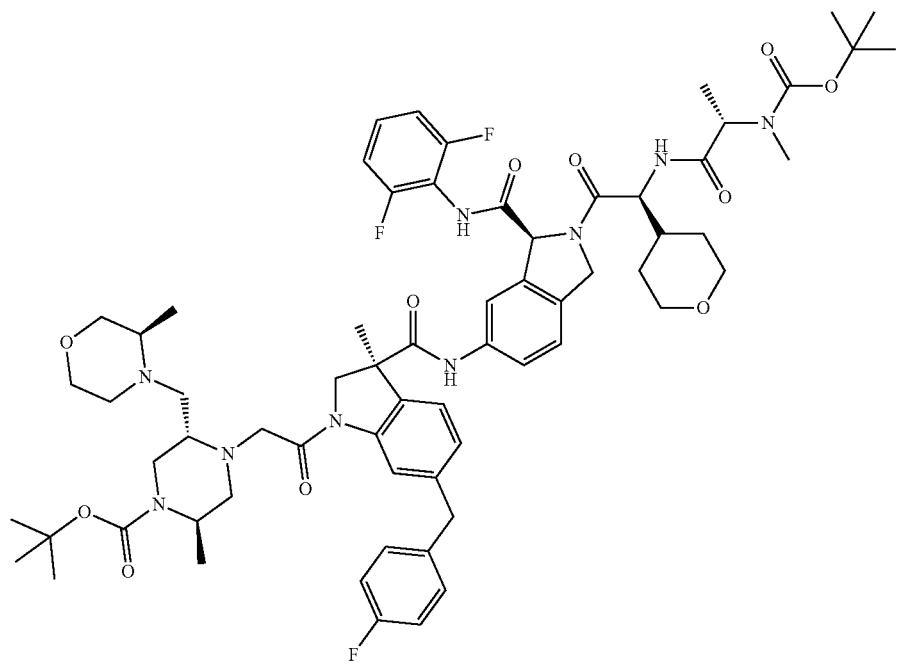 [SMILES: C[C@@H]1COCCN1C[C@H]1CN(C(=O)OC(C)(C)C)[C@H](C)CN1CC(=O)N1C[C@@](C)(C(=O)Nc2ccc3c(c2)[C@@H](C(=O)Nc2c(F)cccc2F)N(C(=O)[C@@H](NC(=O)[C@H](C)N(C)C(=O)OC(C)(C)C)C2CCOCC2)C3)c2ccc(Cc3ccc(F)cc3)cc21]

(S)-1-(2-((2S,5R)-4-(tert-Butoxycarbonyl)-5-methyl-2-(((R)-3-methylmorpholino)methyl)piperazin-1-yl)acetyl)-6-(4-fluorobenzyl)-3-methylindoline-3-carboxylic acid (80 mg, 125 µmol, Eq: 1) was stirred with tert-butyl ((S)-1-(((S)-2-((S)-6-amino-1-((2,6-difluorophenyl)carbamoyl)isoindolin-2-yl)-2-oxo-1-(tetrahydro-2H-pyran-4-yl)ethyl)amino)-1-oxopropan-2-yl)(methyl)carbamate (77.1 mg, 125 µmol, Eq: 1; Intermediate 2), N-methylmorpholine (127 mg, 138 µl, 1.25 mmol, Eq: 10) and T3P in EtOAc 50% (239 mg, 224 µl, 376 µmol, Eq: 3) in ethyl acetate (500 µl) at room temperature over the weekend. Sat. NaHCO₃ solution was added and the mixture was extracted three times with ethyl acetate. The organic layer was dried over magnesium sulfate, filtered and evaporated. The crude material was applied on silica gel and purified by column chromatography using ethyl acetate as eluent to give tert-butyl (2R,5S)-4-[2-[(3S)-3-[[(3S)-2-[(2S)-2-[[(2S)-2-[tert-butoxycarbonyl(methyl)amino]propanoyl]amino]-2-tetrahydropyran-4-yl-acetyl]-3-[(2,6-difluorophenyl)carbamoyl]isoindolin-5-yl]carbamoyl]-6-[(4-fluorophenyl)methyl]-3-methyl-indolin-1-yl]-2-oxo-ethyl]-2-methyl-5-[[(3R)-3-methylmorpholin-4-yl]methyl]piperazine-1-carboxylate (76 mg, 49.1%) as a white solid. MS: m/z (M+H)⁺=1236.6 b) (3S)—N-[(3S)-3-[(2,6-Difluorophenyl)carbamoyl]-2-[(2S)-2-[[(2S)-2-(methylamino)propanoyl]amino]-2-tetrahydropyran-4-yl-acetyl]isoindolin-5-yl]-6-[(4-fluorophenyl)methyl]-3-methyl-1-[2-[(2R,5R)-5-methyl-2-[[(3R)-3-methylmorpholin-4-yl]methyl]piperazin-1-yl]acetyl]indoline-3-carboxamide

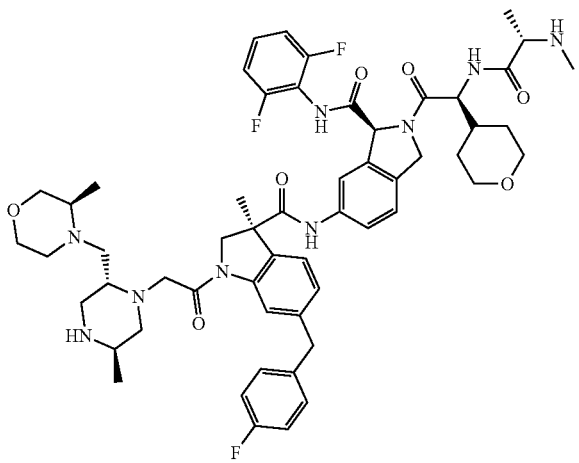 [SMILES: CN[C@@H](C)C(=O)N[C@H](C(=O)N1Cc2ccc(NC(=O)[C@]3(C)CN(C(=O)CN4C[C@@H](C)NC[C@@H]4CN4CCOC[C@H]4C)c4cc(Cc5ccc(F)cc5)ccc43)cc2[C@H]1C(=O)Nc1c(F)cccc1F)C1CCOCC1]

HCl 4M in dioxane (1.37 ml, 5.5 mmol, Eq: 100) was added to a light yellow solution of (2R,5S)-tert-butyl 4-(2-((S)-3-(((S)-2-((S)-2-((S)-2-((tert-butoxycarbonyl)(methyl)amino)propanamido)-2-(tetrahydro-2H-pyran-4-yl)acetyl)-3-((2,6-difluorophenyl)carbamoyl)isoindolin-5-yl)carbamoyl)-6-(4-fluorobenzyl)-3-methylindolin-1-yl)-2-oxoethyl)-2-methyl-5-(((R)-3-methylmorpholino)methyl)piperazine-1-carboxylate (68 mg, 55 μmol, Eq: 1) in ethyl acetate (0.5 ml) and the reaction was stirred at room temperature for 2 h. The precipitate was filtered off, washed with diethyl ether and dried. The material was purified by preparative HPLC affording (S)—N—((S)-3-((2,6-difluorophenyl)carbamoyl)-2-((S)-2-((S)-2-(methylamino)propanamido)-2-(tetrahydro-2H-pyran-4-yl)acetyl)isoindolin-5-yl)-6-(4-fluorobenzyl)-3-methyl-1-(2-((2R,5R)-5-methyl-2-(((R)-3-methylmorpholino)methyl)piperazin-1-yl)acetyl)indoline-3-carboxamide (23 mg, 40.4%) as a light yellow amorphous. MS: m/z (M+H)$^+$=1036.5

Example 16

N-(4-(4-Fluoro-3-((S)-2-((S)-2-((S)-2-(methylamino)propanamido)-2-(tetrahydro-2H-pyran-4-yl)acetyl)isoindoline-1-carboxamido)benzamido)phenyl)-6-(4-fluorobenzyl)-3-methyl-1-(2-((2R,5R)-5-methyl-2-(((R)-3-methylmorpholino)methyl)piperazin-1-yl)acetyl)indoline-3-carboxamide Trihydrochloride a) tert-Butyl N-[(1S)-2-[[(1 S)-2-[(1S)-1-[[5-[[4-(benzyloxycarbonylamino)phenyl]carbamoyl]-2-fluoro-phenyl]carbamoyl]isoindolin-2-yl]-2-oxo-1-tetrahydropyran-4-yl-ethyl]amino]-1-methyl-2-oxo-ethyl]-N-methyl-carbamate

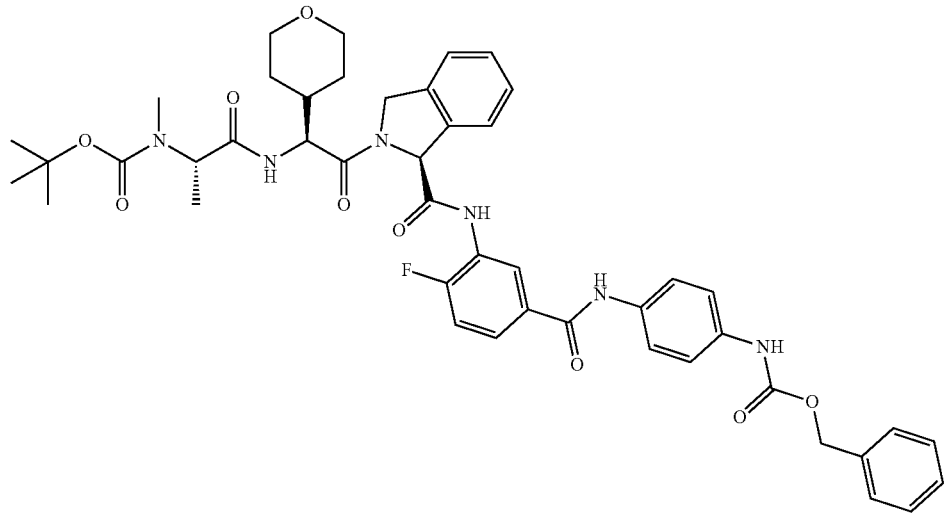 [SMILES: C[C@@H](C(=O)N[C@H](C(=O)N1Cc2ccccc2[C@H]1C(=O)Nc1cc(C(=O)Nc2ccc(NC(=O)OCc3ccccc3)cc2)ccc1F)C1CCOCC1)N(C)C(=O)OC(C)(C)C]

3-((S)-2-((S)-2-((S)-2-((tert-Butoxycarbonyl)(methyl)amino)propanamido)-2-(tetrahydro-2H-pyran-4-yl)acetyl)isoindoline-1-carboxamido)-4-fluorobenzoic acid (120 mg, 191 μmol, Eq: 1) was stirred with benzyl (4-aminophenyl)carbamate (53.4 mg, 220 μmol, Eq: 1.15), N-methylmorpholine (194 mg, 211 μl, 1.91 mmol, Eq: 10) and T3P 50% in EtOAc (366 mg, 342 μl, 574 μmol, Eq: 3) in ethyl acetate (2.5 ml) at room temperature overnight. NaHCO$_3$ sat. aq. was added and extracted three times with ethyl acetate, dried over sodium sulfate, filtered and evaporated. The crude material was applied on silica gel and purified by column chromatography using ethyl acetate/methanol (0-5% methanol) as eluent affording tert-butyl ((S)-1-(((S)-2-((S)-1-((5-((4-(((benzyloxy)carbonyl)amino)phenyl)carbamoyl)-2-fluorophenyl)carbamoyl)isoindolin-2-yl)-2-oxo-1-(tetrahydro-2H-pyran-4-yl)ethyl)amino)-1-oxopropan-2-yl)(methyl)carbamate (103 mg, 63.2%) as a white solid. MS: m/z (M−H)$^-$=849.36 b) tert-Butyl N-[(1S)-2-[[(1 S)-2-[(1S)-1-[[5-[(4-aminophenyl)carbamoyl]-2-fluoro-phenyl]carbamoyl]isoindolin-2-yl]-2-oxo-1-tetrahydropyran-4-yl-ethyl]amino]-1-methyl-2-oxo-ethyl]-N-methyl-carbamate

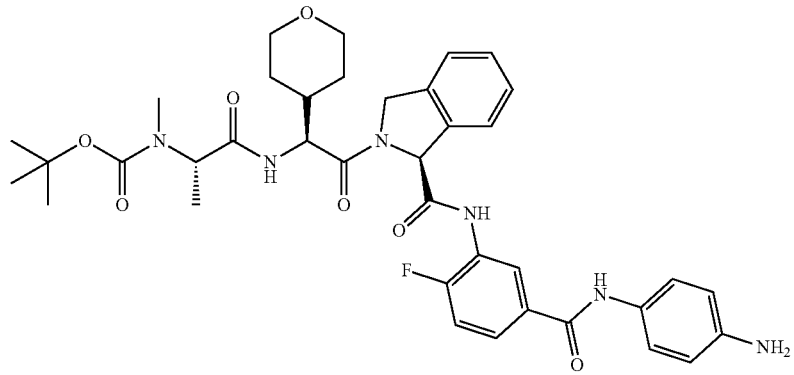 [SMILES: C[C@@H](C(=O)N[C@H](C(=O)N1Cc2ccccc2[C@H]1C(=O)Nc1cc(C(=O)Nc2ccc(N)cc2)ccc1F)C1CCOCC1)N(C)C(=O)OC(C)(C)C]

tert-Butyl ((S)-1-(((S)-2-((S)-1-((5-((4-(((benzyloxy)carbonyl)amino)phenyl)carbamoyl)-2-fluorophenyl)carbamoyl)isoindolin-2-yl)-2-oxo-1-(tetrahydro-2H-pyran-4-yl)ethyl)amino)-1-oxopropan-2-yl)(methyl)carbamate (97 mg, 114 μmol, Eq: 1) was stirred in methanol (2.8 ml) with Pd—C 10% (15 mg, 14.1 μmol, Eq: 0.124) under a hydrogen atmosphere over the weekend at room temperature. The catalyst was filtered off, the solvent was evaporated and dried under high vacuum affording tert-butyl ((S)-1-(((S)-2-((S)-1-((5-((4-aminophenyl)carbamoyl)-2-fluorophenyl)carbamoyl)isoindolin-2-yl)-2-oxo-1-(tetrahydro-2H-pyran-4-yl)ethyl)amino)-1-oxopropan-2-yl)(methyl)carbamate (82 mg, 100%) as a white solid. MS: m/z (M+H)$^+$=717.34 c) tert-Butyl (2R,5S)-4-[2-[3-[[4-[[3-[[(1 S)-2-[(2S)-2-[[(2S)-2-[tert-butoxycarbonyl(methyl)amino]propanoyl]amino]-2-tetrahydropyran-4-yl-acetyl]isoindoline-1-carbonyl]amino]-4-fluoro-benzoyl]amino]phenyl]carbamoyl]-6-[(4-fluorophenyl)methyl]-3-methyl-indolin-1-yl]-2-oxo-ethyl]-2-methyl-5-[[(3R)-3-methylmorpholin-4-yl]methyl]piperazine-1-carboxylate

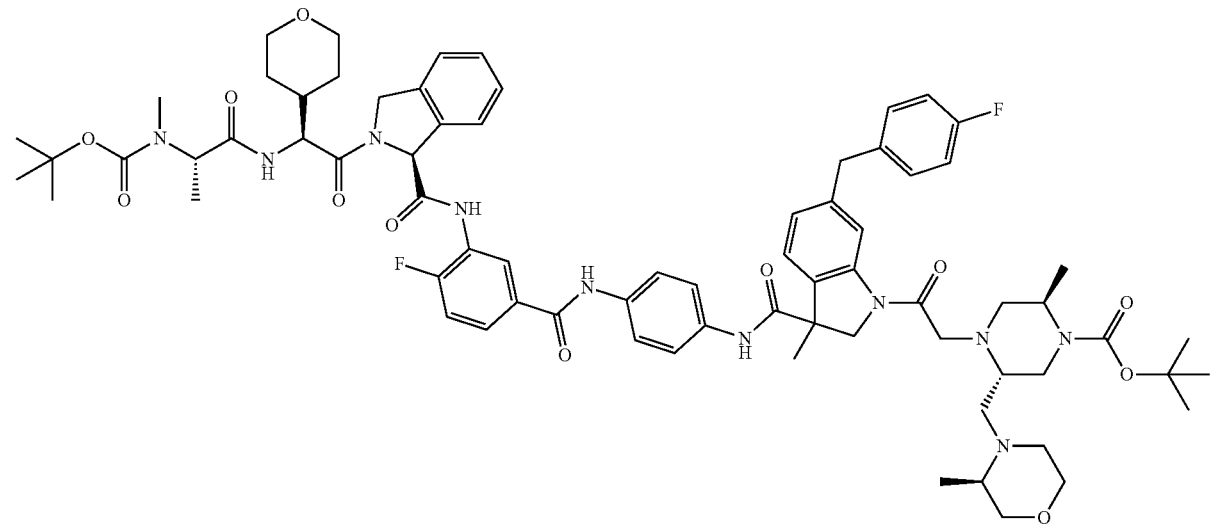 [SMILES: C[C@@H]1COCCN1C[C@H]1CN(C(=O)OC(C)(C)C)[C@H](C)CN1CC(=O)N1CC(C)(C(=O)Nc2ccc(NC(=O)c3ccc(F)c(NC(=O)[C@@H]4c5ccccc5CN4C(=O)[C@@H](NC(=O)[C@H](C)N(C)C(=O)OC(C)(C)C)C4CCOCC4)c3)cc2)c2ccc(Cc3ccc(F)cc3)cc21]

tert-Butyl ((S)-1-(((S)-2-((S)-1-((5-((4-aminophenyl)carbamoyl)-2-fluorophenyl)carbamoyl)isoindolin-2-yl)-2-oxo-1-(tetrahydro-2H-pyran-4-yl)ethyl)amino)-1-oxopropan-2-yl)(methyl)carbamate (78 mg, 109 µmol, Eq: 1) was stirred with 1-(2-((2S,5R)-4-(tert-butoxycarbonyl)-5-methyl-2-(((R)-3-methylmorpholino)methyl)piperazin-1-yl)acetyl)-6-(4-fluorobenzyl)-3-methylindoline-3-carboxylic acid (76.5 mg, 120 µmol, Eq: 1.1), N-methylmorpholine (110 mg, 120 µl, 1.09 mmol, Eq: 10) and T3P 50% in EtOAc (104 mg, 97.2 µl, 326 µmol, Eq: 3) in ethyl acetate (1.5 ml) at room temperature overnight. Sat. NaHCO₃ solution was added and extracted three times with ethyl acetate, dried over sodium sulfate, filtered and evaporated. The crude material was applied on silica gel and purified by column chromatography using ethyl acetate/methanol (0-5% methanol) as eluent affording (2R,5S)-tert-butyl 4-(2-(3-((4-(3-((S)-2-((S)-2-((S)-2-((tert-butoxycarbonyl)(methyl)amino)propanamido)-2-(tetrahydro-2H-pyran-4-yl)acetyl)isoindoline-1-carboxamido)-4-fluorobenzamido)phenyl)carbamoyl)-6-(4-fluorobenzyl)-3-methylindolin-1-yl)-2-oxoethyl)-2-methyl-5-(((R)-3-methylmorpholino)methyl)piperazine-1-carboxylate (75 mg, 51.5%) as an off-white solid. MS: m/z (M+H)⁺=1337.68 d) N-[4-[[4-Fluoro-3-[[(1S)-2-[(2S)-2-[[(2S)-2-(methylamino)propanoyl]amino]-2-tetrahydropyran-4-yl-acetyl]isoindoline-1-carbonyl]amino]benzoyl]amino]phenyl]-6-[(4-fluorophenyl)methyl]-3-methyl-1-[2-[(2R,5R)-5-methyl-2-[[(3R)-3-methylmorpholin-4-yl]methyl]piperazin-1-yl]acetyl]indoline-3-carboxamide Trihydrochloride

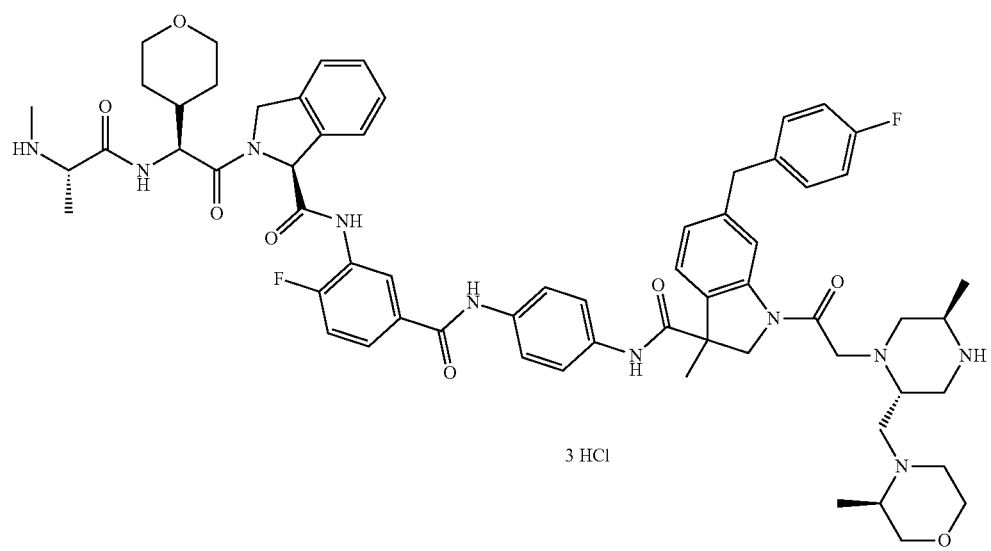 [SMILES: CN[C@@H](C)C(=O)N[C@H](C(=O)N1Cc2ccccc2[C@H]1C(=O)Nc1cc(C(=O)Nc2ccc(NC(=O)C3(C)CN(C(=O)CN4C[C@@H](C)NC[C@@H]4CN4CCOC[C@H]4C)c4cc(Cc5ccc(F)cc5)ccc43)cc2)ccc1F)C1CCOCC1]

3 HCl (2R,5S)-tert-Butyl 4-(2-(3-((4-(3-((S)-2-((S)-2-((S)-2-((tert-butoxycarbonyl)(methyl)amino) propanamido)-2-(tetrahydro-2H-pyran-4-yl)acetyl)isoindoline-1-carboxamido)-4-fluorobenzamido)phenyl)carbamoyl)-6-(4-fluorobenzyl)-3-methylindolin-1-yl)-2-oxoethyl)-2-methyl-5-(((R)-3-methylmorpholino)methyl)piperazine-1-carboxylate (65 mg, 48.6 µmol, Eq: 1) was stirred with HCl in dioxane 4M (1 ml, 4 mmol, Eq: 82.3) in ethyl acetate (1 ml) at room temperature overnight. The precipitated solid was filtered off and washed with diethyl ether. The solid was dried under high vacuum affording N-(4-(4-fluoro-3-((S)-2-((S)-2-((S)-2-(methylamino)propanamido)-2-(tetrahydro-2H-pyran-4-yl)acetyl)isoindoline-1-carboxamido)benzamido)phenyl)-6-(4-fluorobenzyl)-3-methyl-1-(2-((2R,5R)-5-methyl-2-(((R)-3-methylmorpholino)methyl)piperazin-1-yl)acetyl)indoline-3-carboxamide trihydrochloride (56 mg, 92.4%) as a white solid. MS: m/z (M+H)⁺=1137.58

Example 17 a) (S)—N-(3-(((S)-3-((2,6-Difluorophenyl)carbamoyl)-2-((S)-2-((S)-2-(methylamino)propanamido)-2-(tetrahydro-2H-pyran-4-yl)acetyl)isoindolin-5-yl)amino)-3-oxopropyl)-6-(4-fluorobenzyl)-3-methyl-1-(2-((2R,5R)-5-methyl-2-(((R)-3-methylmorpholino)methyl)piperazin-1-yl)acetyl)indoline-3-carboxamide Trihydrochloride tert-Butyl N-[(1 S)-2-[[(1 S)-2-[(1 S)-5-[3-(benzylamino)propanoylamino]-1-[(2,6-difluorophenyl)carbamoyl]isoindolin-2-yl]-2-oxo-1-tetrahydropyran-4-yl-ethyl]amino]-1-methyl-2-oxo-ethyl]-N-methyl-carbamate

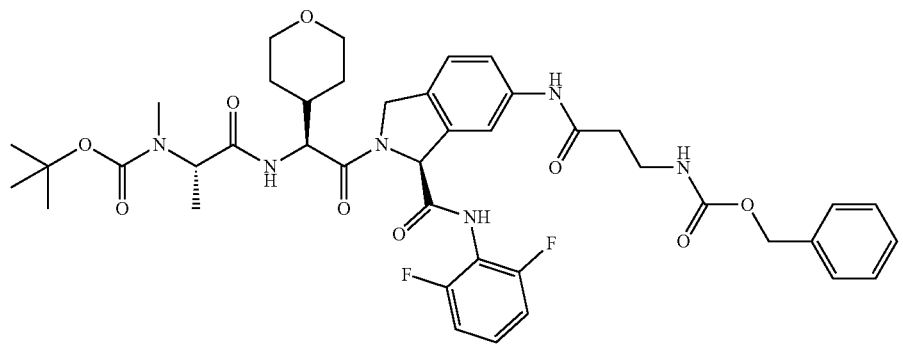 [SMILES: C[C@@H](C(=O)N[C@H](C(=O)N1Cc2ccc(NC(=O)CCNC(=O)OCc3ccccc3)cc2[C@H]1C(=O)Nc1c(F)cccc1F)C1CCOCC1)N(C)C(=O)OC(C)(C)C]

tert-Butyl ((S)-1-(((S)-2-((S)-6-amino-1-((2,6-difluorophenyl)carbamoyl)isoindolin-2-yl)-2-oxo-1-(tetrahydro-2H-pyran-4-yl)ethyl)amino)-1-oxopropan-2-yl)(methyl)carbamate (100 mg, 162 µmol, Eq: 1, Intermediate 2) was stirred with 3-(((benzyloxy)carbonyl)amino)propanoic acid (36.3 mg, 162 µmol, Eq: 1) in presence of T3P in EtOAc 50% (258 mg, 242 µl, 406 µmol, Eq: 2.5) and pyridine (300 µl) in ethyl acetate (600 µl) at room temperature overnight. Sat. NaHCO₃ solution was added and extracted three times with ethyl acetate, dried over magnesium sulfate, filtered and evaporated. The crude material was applied on silica gel and purified by column chromatography using ethyl acetate/methanol (0-5% methanol) as eluent affording tert-butyl ((S)-1-(((S)-2-((S)-6-(3-(((benzyloxy)carbonyl)amino)propanamido)-1-((2,6-difluorophenyl)carbamoyl)isoindolin-2-yl)-2-oxo-1-(tetrahydro-2H-pyran-4-yl)ethyl)amino)-1-oxopropan-2-yl)(methyl)carbamate (118 mg, 88.5%) as a light yellow solid. MS: m/z (M+H)⁺=821.4 b) tert-Butyl N-[(1S)-2-[[(1 S)-2-[(1S)-6-(3-aminopropanoylamino)-1-[(2,6-difluorophenyl)carbamoyl]isoindolin-2-yl]-2-oxo-1-tetrahydropyran-4-yl-ethyl]amino]-1-methyl-2-oxo-ethyl]-N-methyl-carbamate

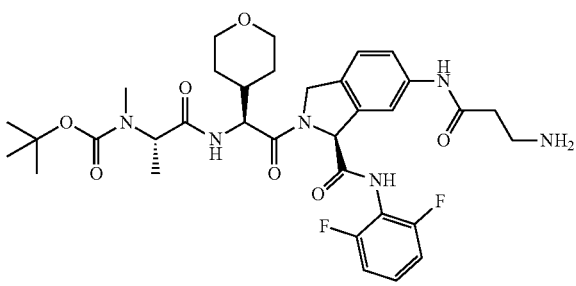 [SMILES: C[C@@H](C(=O)N[C@H](C(=O)N1Cc2ccc(NC(=O)CCN)cc2[C@H]1C(=O)Nc1c(F)cccc1F)C1CCOCC1)N(C)C(=O)OC(C)(C)C]

tert-Butyl ((S)-1-(((S)-2-((S)-1-((2,6-difluorophenyl)carbamoyl)-6-(3-(2-phenylacetamido)propanamido)isoindolin-2-yl)-2-oxo-1-(tetrahydro-2H-pyran-4-yl)ethyl)amino)-1-oxopropan-2-yl)(methyl)carbamate (180 mg, 224 µmol, Eq: 1) was stirred with palladium on carbon 10% (23.8 mg, 22.4 µmol, Eq: 0.1) in methanol (8 ml) under a hydrogen atmosphere at room temperature overnight. The catalyst was filtered off and the solvent was evaporated in vacuo and dried under high vacuum affording tert-butyl ((S)-1-(((S)-2-((S)-6-(3-aminopropanamido)-1-((2,6-difluorophenyl)carbamoyl)isoindolin-2-yl)-2-oxo-1-(tetrahydro-2H-pyran-4-yl)ethyl)amino)-1-oxopropan-2-yl)(methyl)carbamate (93 mg, 60.6%) as a white solid. MS: m/z (M+H)⁺=687.3 c) tert-Butyl (2R,5S)-4-[2-[(3S)-3-[[3-[[(3S)-2-[(2S)-2-[[(2S)-2-[tert-butoxycarbonyl(methyl)amino]propanoyl]amino]-2-tetrahydropyran-4-yl-acetyl]-3-[(2,6-difluorophenyl)carbamoyl]isoindolin-5-yl]amino]-3-oxo-propyl]carbamoyl]-6-[(4-fluorophenyl)methyl]-3-methyl-indolin-1-yl]-2-oxo-ethyl]-2-methyl-5-[[(3R)-3-methylmorpholin-4-yl]methyl]piperazine-1-carboxylate

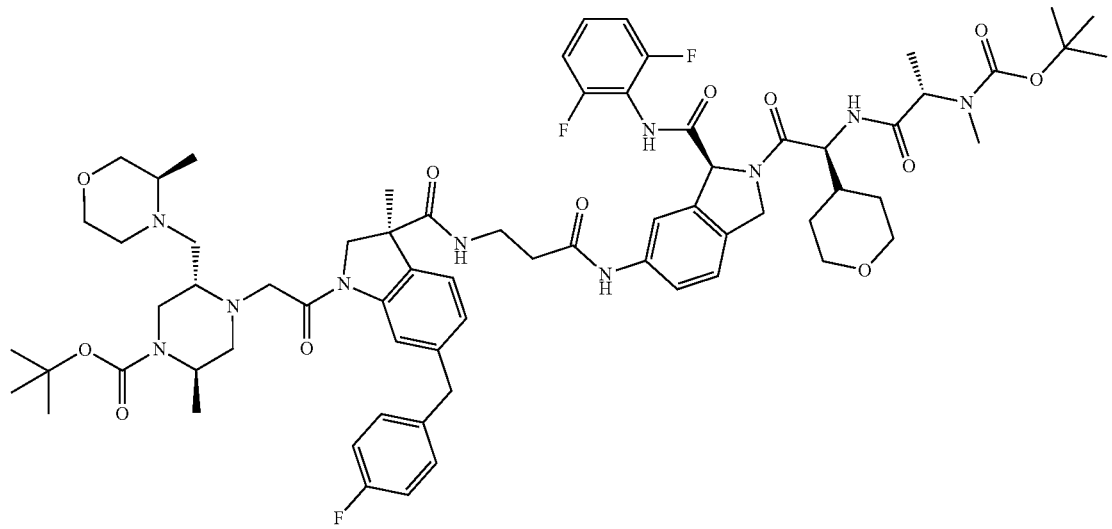 [SMILES: C[C@@H]1COCCN1C[C@H]1CN(C(=O)OC(C)(C)C)[C@H](C)CN1CC(=O)N1C[C@@](C)(C(=O)NCCC(=O)Nc2ccc3c(c2)[C@@H](C(=O)Nc2c(F)cccc2F)N(C(=O)[C@@H](NC(=O)[C@H](C)N(C)C(=O)OC(C)(C)C)C2CCOCC2)C3)c2ccc(Cc3ccc(F)cc3)cc21]

tert-Butyl ((S)-1-(((S)-2-((S)-6-(3-aminopropanamido)-1-((2,6-difluorophenyl)carbamoyl)isoindolin-2-yl)-2-oxo-1-(tetrahydro-2H-pyran-4-yl)ethyl)amino)-1-oxopropan-2-yl)(methyl)carbamate (87 mg, 127 µmol, Eq: 1) was stirred with (S)-1-(2-((2S,5R)-4-(tert-butoxycarbonyl)-5-methyl-2-(((R)-3-methylmorpholino)methyl)piperazin-1-yl)acetyl)-6-(4-fluorobenzyl)-3-methylindoline-3-carboxylic acid (80.9 mg, 127 µmol, Eq: 1), T3P in EtOAc 50% (101 mg, 94.3 µl, 317 µmol, Eq: 2.5) in ethyl acetate (700 µl) and pyridine (350 µl) at room temperature overnight. Sat. NaHCO₃sol. was added and extracted three times with ethyl acetate, dried over sodium sulfate, filtered and evaporated. The crude material was applied on silica gel and purified by column chromatography using ethyl acetate/methanol (0-5% methanol) as eluent affording (2R,5S)-tert-butyl 4-(2-((S)-3-((3-(((S)-2-((S)-2-((tert-butoxycarbonyl)(methyl)amino)propanamido)-2-(tetrahydro-2H-pyran-4-yl)acetyl)-3-((2,6-difluorophenyl)carbamoyl)isoindolin-5-yl)amino)-3-oxopropyl)carbamoyl)-6-(4-fluorobenzyl)-3-methylindolin-1-yl)-2-oxoethyl)-2-methyl-5-(((R)-3-methylmorpholino)methyl)piperazine-1-carboxylate (70 mg, 42.3%) as a white solid. MS: m/z (M+H)⁺=1307.7 d) (3S)—N-[3-[[(3S)-3-[(2,6-Difluorophenyl)car-
bamoyl]-2-[(2S)-2-[[(2S)-2-(methylamino)pro-
panoyl]amino]-2-tetrahydropyran-4-yl-acetyl]isoin-
dolin-5-yl]amino]-3-oxo-propyl]-6-[(4-fluorophenyl)
methyl]-3-methyl-1-[2-[(2R,5R)-5-methyl-2-[[(3R)-
3-methylmorpholin-4-yl]methyl]piperazin-1-yl]
acetyl]indoline-3-carboxamide Trihydrochloride

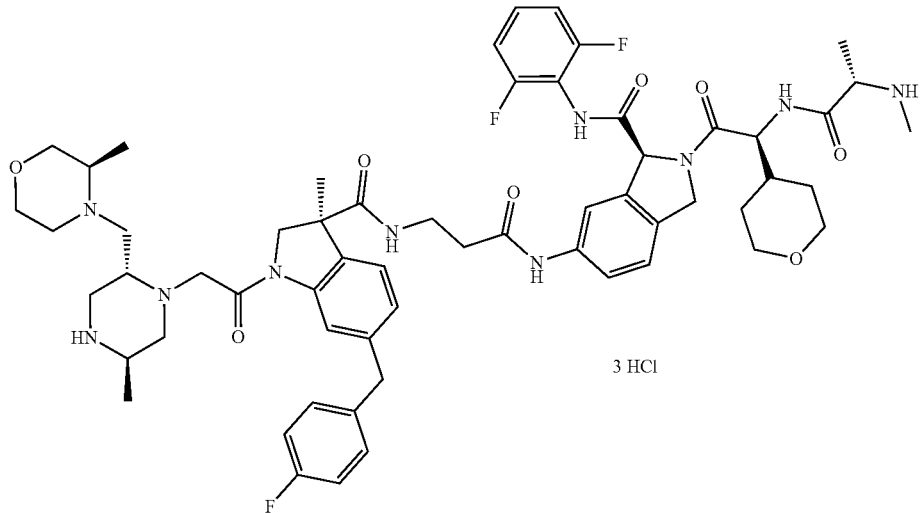 [SMILES: CN[C@@H](C)C(=O)N[C@H](C(=O)N1Cc2ccc(NC(=O)CCNC(=O)[C@]3(C)CN(C(=O)CN4C[C@@H](C)NC[C@@H]4CN4CCOC[C@H]4C)c4cc(Cc5ccc(F)cc5)ccc43)cc2[C@H]1C(=O)Nc1c(F)cccc1F)C1CCOCC1]

3 HCl (2R,5S)-tert-Butyl 4-(2-((S)-3-((3-(((S)-2-((S)-2-((S)-2-((tert-butoxycarbonyl)(methyl)amino) propanamido)-2-(tetrahydro-2H-pyran-4-yl)acetyl)-3-((2,6-difluorophenyl)carbamoyl)isoindolin-5-yl)amino)-3-oxopropyl)carbamoyl)-6-(4-fluorobenzyl)-3-methylindolin-1-yl)-2-oxoethyl)-2-methyl-5-(((R)-3-methylmorpholino)methyl)piperazine-1-carboxylate (64 mg, 48.9 µmol, Eq: 1) was stirred in ethyl acetate (1 ml) with HCl in dioxane 4M (1 ml, 4 mmol, Eq: 81.7) at room temperature overnight. The precipitated solid was filtered off, washed with diethyl ether and dried under high vacuum affording (S)—N-(3-(((S)-3-((2,6-difluorophenyl)carbamoyl)-2-((S)-2-((S)-2-(methylamino)propanamido)-2-(tetrahydro-2H-pyran-4-yl)acetyl)isoindolin-5-yl)amino)-3-oxopropyl)-6-(4-fluorobenzyl)-3-methyl-1-(2-((2R,5R)-5-methyl-2-(((R)-3-methylmorpholino)methyl)piperazin-1-yl)acetyl)indoline-3-carboxamide trihydrochloride (55.5 mg, 45.6 µmol, 93.2% yield) as a white solid. MS: m/z (M+H)$^+$=1107.57

Example 18 a) (S)—N-(4-(((S)-3-((2,6-Difluorophenyl)carbam-
oyl)-2-((S)-2-((S)-2-(methylamino)propanamido)-2-
(tetrahydro-2H-pyran-4-yl)acetyl)isoindolin-5-yl)
amino)-4-oxobutyl)-6-(4-fluorobenzyl)-3-methyl-1-
(2-((2R,5R)-5-methyl-2-(((R)-3-methylmorpholino)
methyl)piperazin-1-yl)acetyl)indoline-3-
carboxamide Trihydrochloride tert-Butyl (2R,5S)-4-
[2-[(3S)-3-[(4-benzyloxy-4-oxo-butyl)carbamoyl]-6-
[(4-fluorophenyl)methyl]-3-methyl-indolin-1-yl]-2-
oxo-ethyl]-2-methyl-5-[[(3R)-3-methylmorpholin-4-
yl]methyl]piperazine-1-carboxylate

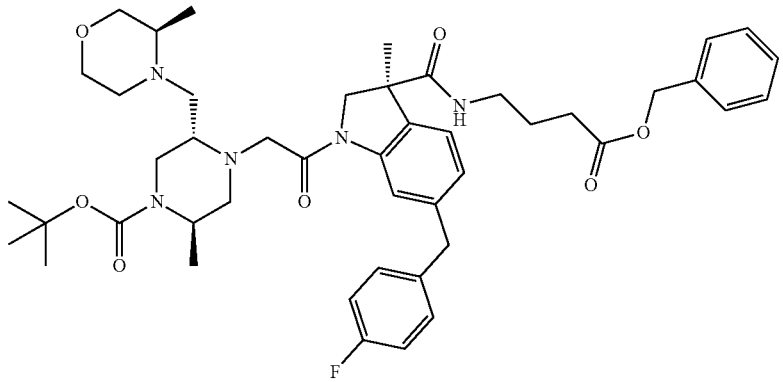 [SMILES: C[C@@H]1COCCN1C[C@H]1CN(C(=O)OC(C)(C)C)[C@H](C)CN1CC(=O)N1C[C@@](C)(C(=O)NCCCC(=O)OCc2ccccc2)c2ccc(Cc3ccc(F)cc3)cc21]

Benzyl 4-aminobutanoate (28.3 mg, 146 μmol, Eq: 1.1) was added to a light yellow suspension of (S)-1-(2-((2S,5R)-4-(tert-butoxycarbonyl)-5-methyl-2-(((R)-3-methylmorpholino)methyl)piperazin-1-yl)acetyl)-6-(4-fluorobenzyl)-3-methylindoline-3-carboxylic acid (85 mg, 133 μmol, Eq: 1) in ethyl acetate (0.85 ml). N-Methylmorpholine (135 mg, 146 μl, 1.33 mmol, Eq: 10) and T3P 50% in EtOAc (254 mg, 238 μl, 399 μmol, Eq: 3) were added and the reaction was stirred at room temperature overnight. The reaction was poured into ethyl acetate and was extracted with water. The organic layer was dried over magnesium sulfate, filtered and evaporated. The crude residue was applied on silica gel and was purified by flash chromatography using ethyl acetate/heptane (80-100% ethyl acetate) as eluent affording tert-butyl (2R,5S)-4-[2-[(3S)-3-[(4-benzyloxy-4-oxo-butyl)carbamoyl]-6-[(4-fluorophenyl)methyl]-3-methyl-indolin-1-yl]-2-oxo-ethyl]-2-methyl-5-[[(3R)-3-methylmorpholin-4-yl]methyl]piperazine-1-carboxylate (67 mg, 61.9%) as a colorless oil. MS: m/z (M+H)$^+$=814.46 b) 4-[[(3S)-1-[2-[(2S,5R)-4-tert-Butoxycarbonyl-5-methyl-2-[[(3R)-3-methylmorpholin-4-yl]methyl]piperazin-1-yl]acetyl]-6-[(4-fluorophenyl)methyl]-3-methyl-indoline-3-carbonyl]amino]butanoic Acid Pd—C (8.5 mg, 7.99 μmol, Eq: 0.1) was added to a clear solution of (2R,5S)-tert-butyl 4-(2-((S)-3-((4-(benzyloxy)-4-oxobutyl)carbamoyl)-6-(4-fluorobenzyl)-3-methylindolin-1-yl)-2-oxoethyl)-2-methyl-5-(((R)-3-methylmorpholino)methyl)piperazine-1-carboxylate (65 mg, 79.9 μmol, Eq: 1) in methanol (0.5 ml) and the reaction was stirred at room temperature under hydrogen atmosphere for 6 h. The catalyst was filtered off, the filtrate was evaporated affording 4-[[(3S)-1-[2-[(2S,5R)-4-tert-butoxycarbonyl-5-methyl-2-[[(3R)-3-methylmorpholin-4-yl]methyl]piperazin-1-yl]acetyl]-6-[(4-fluorophenyl)methyl]-3-methyl-indoline-3-carbonyl]amino]butanoic acid (58 mg, 100%) as a white solid. MS: m/z (M+H)$^+$=724.4

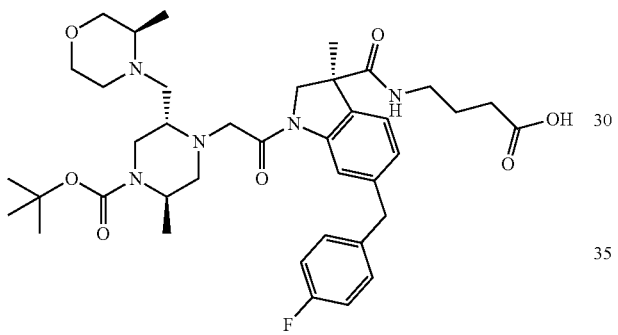

c) tert-Butyl (2R,5S)-4-[2-[(3S)-3-[[4-[[(3S)-2-[(2S)-2-[[(2S)-2-[tert-butoxycarbonyl(methyl)amino]propanoyl]amino]-2-tetrahydropyran-4-yl-acetyl]-3-[(2,6-difluorophenyl)carbamoyl]isoindolin-5-yl]amino]-4-oxo-butyl]carbamoyl]-6-[(4-fluorophenyl)methyl]-3-methyl-indolin-1-yl]-2-oxo-ethyl]-2-methyl-5-[[(3R)-3-methylmorpholin-4-yl]methyl]piperazine-1-carboxylate

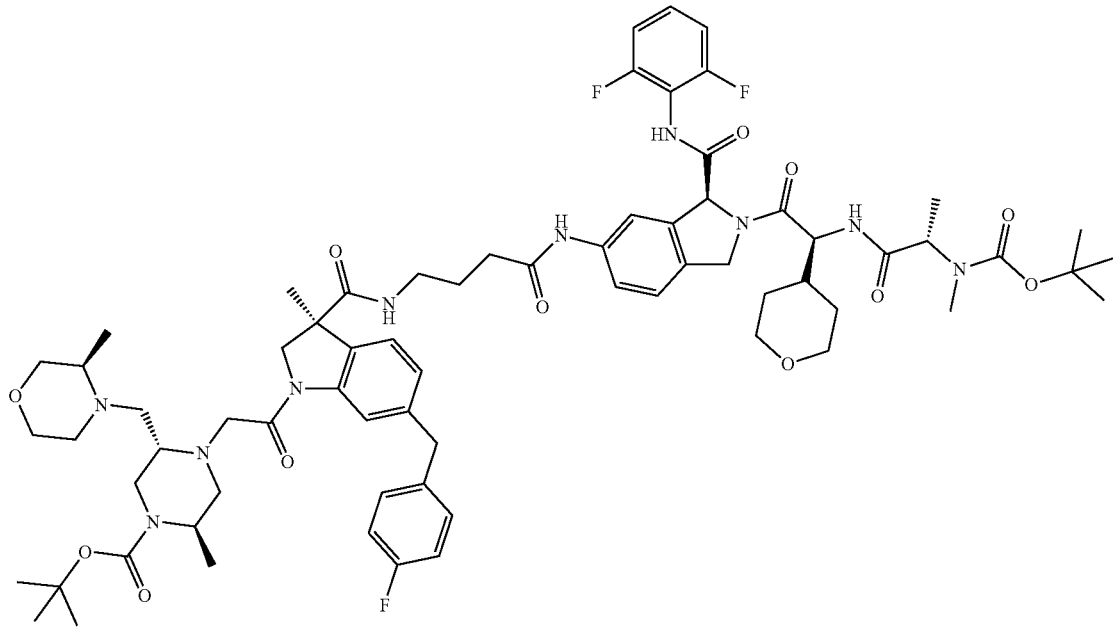 [SMILES: C[C@@H]1COCCN1C[C@H]1CN(C(=O)OC(C)(C)C)[C@H](C)CN1CC(=O)N1C[C@@](C)(C(=O)NCCCC(=O)Nc2ccc3c(c2)[C@@H](C(=O)Nc2c(F)cccc2F)N(C(=O)[C@@H](NC(=O)[C@H](C)N(C)C(=O)OC(C)(C)C)C2CCOCC2)C3)c2ccc(Cc3ccc(F)cc3)cc21]

tert-Butyl ((S)-1-(((S)-2-((S)-6-amino-1-((2,6-difluorophenyl)carbamoyl)isoindolin-2-yl)-2-oxo-1-(tetrahydro-2H-pyran-4-yl)ethyl)amino)-1-oxopropan-2-yl)(methyl)carbamate (46.8 mg, 76 µmol, Eq: 1; Intermediate 2), Pyridine (300 µl) and T3P 50% in EtOAc (145 mg, 136 µl, 228 µmol, Eq: 3) were added to a white suspension of 4-((S)-1-(2-((2S,5R)-4-(tert-butoxycarbonyl)-5-methyl-2-(((R)-3-methylmorpholino)methyl)piperazin-1-yl)acetyl)-6-(4-fluorobenzyl)-3-methylindoline-3-carboxamido)butanoic acid (55 mg, 76 µmol, Eq: 1) in ethyl acetate (0.6 ml) and the now light yellow solution was stirred at room temperature overnight. The reaction was quenched with a few drops of aq. HCl 1N and was extracted with ethyl acetate and water. The organic layer was dried over sodium sulfate, filtered and evaporated. The crude residue was applied on silica gel and was purified by flash chromatography using dichloromethane/methanol (0-20% methanol) as eluent affording tert-butyl (2R,5S)-4-[2-[(3S)-3-[[4-[[(3S)-2-[(2S)-2-[[(2S)-2-[tert-butoxycarbonyl(methyl)amino]propanoyl]amino]-2-tetrahydropyran-4-yl-acetyl]-3-[(2,6-difluorophenyl)carbamoyl]isoindolin-5-yl]amino]-4-oxo-butyl]carbamoyl]-6-[(4-fluorophenyl)methyl]-3-methyl-indolin-1-yl]-2-oxo-ethyl]-2-methyl-5-[[(3R)-3-methylmorpholin-4-yl]methyl]piperazine-1-carboxylate (13 mg, 12.9%) as a white amorphous. MS: m/z (M+H)$^+$=1321.7 d) (3S)—N-[4-[[(3S)-3-[(2,6-Difluorophenyl)carbamoyl]-2-[(2S)-2-[[(2S)-2-(methylamino)propanoyl]amino]-2-tetrahydropyran-4-yl-acetyl]isoindolin-5-yl]amino]-4-oxo-butyl]-6-[(4-fluorophenyl)methyl]-3-methyl-1-[2-[(2R,5R)-5-methyl-2-[[(3R)-3-methylmorpholin-4-yl]methyl]piperazin-1-yl]acetyl]indoline-3-carboxamide Trihydrochloride

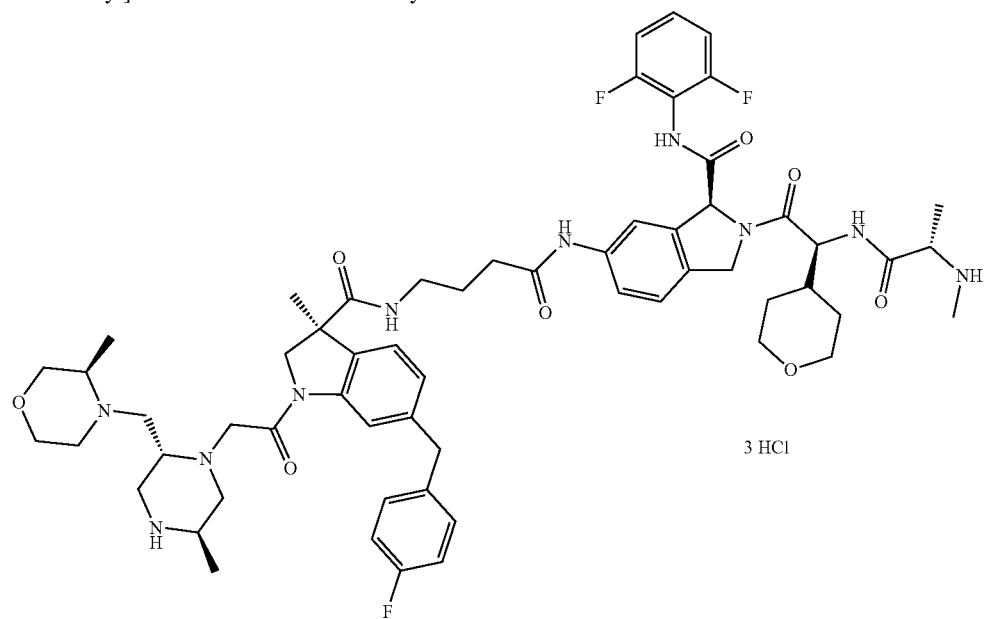

3 HCl

HCl 4M in dioxane (208 µl, 832 µmol, Eq: 100) was added to a light yellow solution of (2R,5S)-tert-butyl 4-(2-((S)-3-((4-(((S)-2-((S)-2-((S)-2-((tert-butoxycarbonyl)(methyl)amino)propanamido)-2-(tetrahydro-2H-pyran-4-yl)acetyl)-3-((2,6-difluorophenyl)carbamoyl)isoindolin-5-yl)amino)-4-oxobutyl)carbamoyl)-6-(4-fluorobenzyl)-3-methylindolin-1-yl)-2-oxoethyl)-2-methyl-5-(((R)-3-methylmorpholino)methyl)piperazine-1-carboxylate (11 mg, 8.32 µmol, Eq: 1) in ethyl acetate (0.2 ml) and the reaction was stirred at room temperature for 2 h. Diethyl ether was added, the white precipitate was filtered, washed with diethyl ether and dried affording (S)—N-(4-(((S)-3-((2,6-difluorophenyl)carbamoyl)-2-((S)-2-((S)-2-(methylamino)propanamido)-2-(tetrahydro-2H-pyran-4-yl)acetyl)isoindolin-5-yl)amino)-4-oxobutyl)-6-(4-fluorobenzyl)-3-methyl-1-(2-((2R,5R)-5-methyl-2-(((R)-3-methylmorpholino)methyl)piperazin-1-yl)acetyl)indoline-3-carboxamide trihydrochloride (9.4 mg, 91.8%) as a white solid. MS: m/z (M+H)+=1121.6

Example 19 a) (S)—N-(2-(((S)-1-((2,6-Difluorophenyl)carbamoyl)-2-((S)-2-((S)-2-(methylamino)propanamido)-2-(tetrahydro-2H-pyran-4-yl)acetyl)isoindolin-5-yl)amino)-2-oxoethyl)-6-(4-fluorobenzyl)-3-methyl-1-(2-((2R,5R)-5-methyl-2-(((R)-3-methylmorpholino)methyl)piperazin-1-yl)acetyl)indoline-3-carboxamide Trihydrochloride tert-Butyl (2R,5S)-4-[2-[(3S)-3-[[2-[[(1S)-2-[(2S)-2-[[(2S)-2-[tert-butoxycarbonyl(methyl)amino]propanoyl]amino]-2-tetrahydropyran-4-yl-acetyl]-1-[(2,6-difluorophenyl)carbamoyl]isoindolin-5-yl]amino]-2-oxo-ethyl]carbamoyl]-6-[(4-fluorophenyl)methyl]-3-methyl-indolin-1-yl]-2-oxo-ethyl]-2-methyl-5-[[(3R)-3-methylmorpholin-4-yl]methyl]piperazine-1-carboxylate

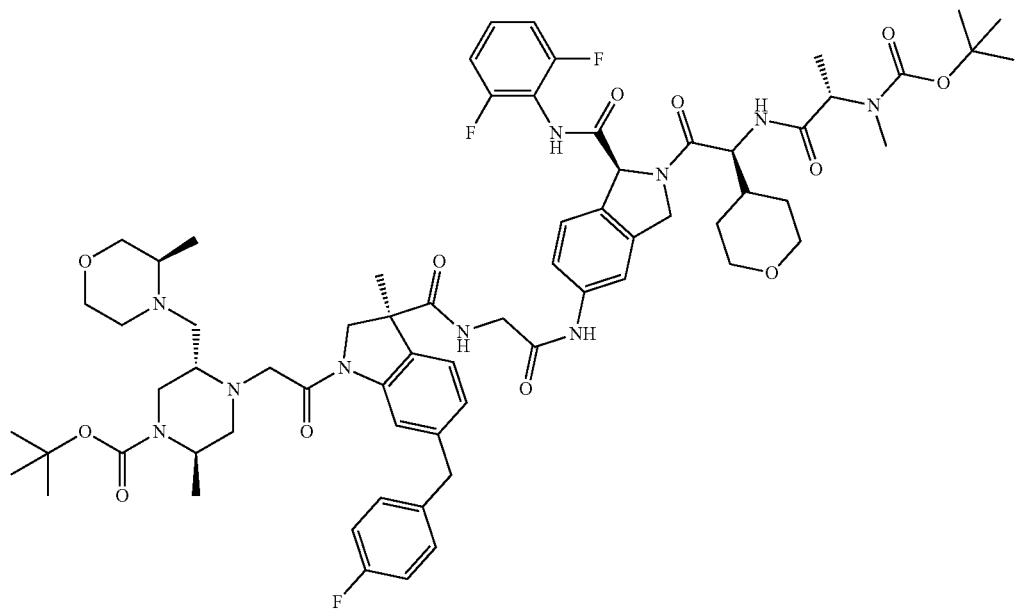 [SMILES: C[C@@H]1COCCN1C[C@H]1CN(C(=O)OC(C)(C)C)[C@H](C)CN1CC(=O)N1C[C@@](C)(C(=O)NCC(=O)Nc2ccc3c(c2)CN(C(=O)[C@@H](NC(=O)[C@H](C)N(C)C(=O)OC(C)(C)C)C2CCOCC2)[C@@H]3C(=O)Nc2c(F)cccc2F)c2ccc(Cc3ccc(F)cc3)cc21]

2-((S)-1-(2-((2S,5R)-4-(tert-Butoxycarbonyl)-5-methyl-2-(((R)-3-methylmorpholino)methyl)piperazin-1-yl)acetyl)-6-(4-fluorobenzyl)-3-methylindoline-3-carboxamido)acetic acid (50 mg, 71.9 µmol, Eq: 1) was stirred with tert-butyl ((S)-1-(((S)-2-((S)-5-amino-1-((2,6-difluorophenyl)carbamoyl)isoindolin-2-yl)-2-oxo-1-(tetrahydro-2H-pyran-4-yl)ethyl)amino)-1-oxopropan-2-yl)(methyl)carbamate (44.2 mg, 71.9 µmol, Eq: 1; Intermediate 4) and T3P in EtOAc 50% (137 mg, 128 µl, 216 µmol, Eq: 3) in ethyl acetate (500 µl) and pyridine (250 µl) at room temperature overnight. Sat. NaHCO$_3$ solution was added and extracted three times with ethyl acetate, dried over magnesium sulfate, filtered and evaporated. The crude material was applied on silica gel and purified by column chromatography using ethyl acetate/methanol (0-10% methanol) as eluent. The isolated product was submitted to prep. HPLC for further purification affording tert-butyl (2R,5S)-4-[2-[(3S)-3-[[2-[[(1 S)-2-[(2S)-2-[[(2S)-2-[tert-butoxycarbonyl(methyl)amino]propanoyl]amino]-2-tetrahydropyran-4-yl-acetyl]-1-[(2,6-difluorophenyl)carbamoyl]isoindolin-5-yl]amino]-2-oxo-ethyl]carbamoyl]-6-[(4-fluorophenyl)methyl]-3-methyl-indolin-1-yl]-2-oxo-ethyl]-2-methyl-5-[[(3R)-3-methylmorpholin-4-yl]methyl]piperazine-1-carboxylate (7 mg, 7.5%) as a colorless amorphous. MS: m/z (M+H)$^+$=1293.8 b) (3S)—N-[2-[[(1S)-1-[(2,6-Difluorophenyl)carbamoyl]-2-[(2S)-2-[[(2S)-2-(methylamino)propanoyl]amino]-2-tetrahydropyran-4-yl-acetyl]isoindolin-5-yl]amino]-2-oxo-ethyl]-6-[(4-fluorophenyl)methyl]-3-methyl-1-[2-[(2R,5R)-5-methyl-2-[[(3R)-3-methylmorpholin-4-yl]methyl]piperazin-1-yl]acetyl]indoline-3-carboxamide trihydrochloride

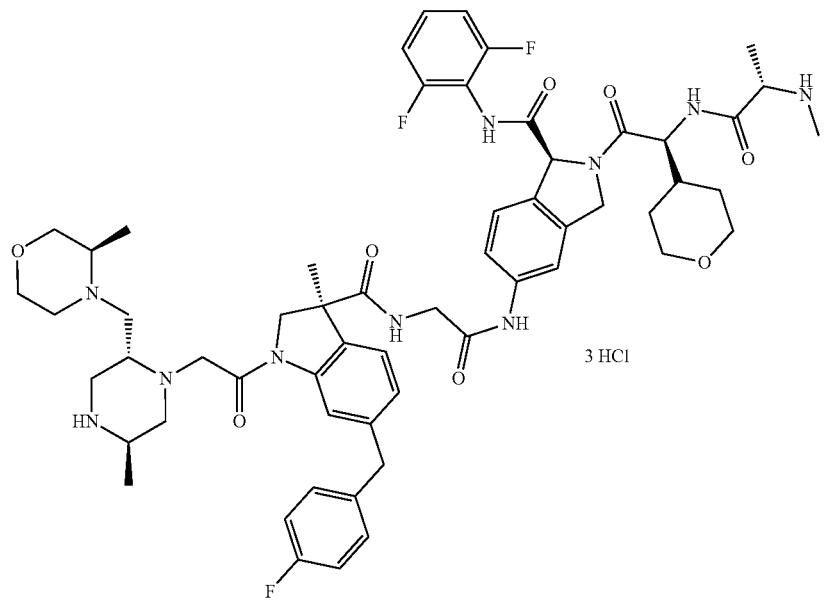 [SMILES: CN[C@@H](C)C(=O)N[C@H](C(=O)N1Cc2cc(NC(=O)CNC(=O)[C@]3(C)CN(C(=O)CN4C[C@@H](C)NC[C@@H]4CN4CCOC[C@H]4C)c4cc(Cc5ccc(F)cc5)ccc43)ccc2[C@H]1C(=O)Nc1c(F)cccc1F)C1CCOCC1]

HCl 4M in dioxane (135 µl, 541 µmol, Eq: 100) was added to a colorless solution of (2R,5S)-tert-butyl 4-(2-((S)-3-((2-(((S)-2-((S)-2-((S)-2-((tert-butoxycarbonyl)(methyl)amino)propanamido)-2-(tetrahydro-2H-pyran-4-yl)acetyl)-1-((2,6-difluorophenyl)carbamoyl)isoindolin-5-yl)amino)-2-oxoethyl)carbamoyl)-6-(4-fluorobenzyl)-3-methylindolin-1-yl)-2-oxo ethyl)-2-methyl-5-(((R)-3-methylmorpholino)methyl)piperazine-1-carboxylate (7 mg, 5.41 µmol, Eq: 1) in ethyl acetate (200 µl) and the reaction was stirred at room temperature overnight. The precipitate was filtered off, washed with diethyl ether and dried in vacuo affording (S)—N-(2-(((S)-1-((2,6-difluorophenyl)carbamoyl)-2-((S)-2-((S)-2-(methylamino)propanamido)-2-(tetrahydro-2H-pyran-4-yl)acetyl)isoindolin-5-yl)amino)-2-oxoethyl)-6-(4-fluorobenzyl)-3-methyl-1-(2-((2R,5R)-5-methyl-2-(((R)-3-methylmorpholino)methyl)piperazin-1-yl)acetyl)indoline-3-carboxamide trihydrochloride (3.7 mg, 56.9%) as a white solid. MS: m/z (M+H)$^+$=1093.54

Example 20

(S)—N-(2-(((S)-3-((2,6-Difluorophenyl)carbamoyl)-2-((2S,3R)-3-methoxy-2-((S)-2-(methylamino)propanamido)butanoyl)isoindolin-5-yl)amino)-2-oxo-ethyl)-6-(4-fluorobenzyl)-3-methyl-1-(2-((2R,5R)-5-methyl-2-(((R)-3-methylmorpholino)methyl)piperazin-1-yl)acetyl)indoline-3-carboxamide trihydrochloride a) tert-Butyl (2R,5S)-4-[2-[(3S)-3-[[2-[[(3S)-2-[(2S,3R)-2-[[(2S)-2-)[tert-butoxycarbonyl(methyl)amino]propanoyl]amino]-3-methoxy-butanoyl]-3-[(2,6-difluorophenyl)carbamoyl]isoindolin-5-yl]amino]-2-oxo-ethyl]carbamoyl]-6-[(4-fluorophenyl)methyl]-3-methyl-indolin-1-yl]-2-oxo-ethyl]-2-methyl-5-[[(3R)-3-methylmorpholin-4-yl]methyl]piperazine-1-carboxylate

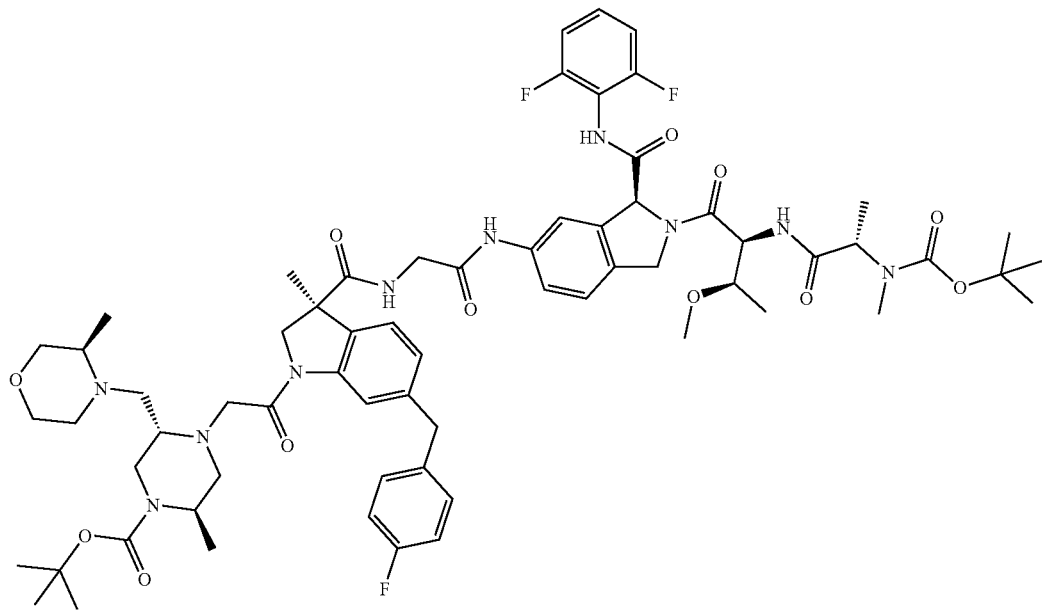 [SMILES: CO[C@H](C)[C@H](NC(=O)[C@H](C)N(C)C(=O)OC(C)(C)C)C(=O)N1Cc2ccc(NC(=O)CNC(=O)[C@]3(C)CN(C(=O)CN4C[C@@H](C)N(C(=O)OC(C)(C)C)C[C@@H]4CN4CCOC[C@H]4C)c4cc(Cc5ccc(F)cc5)ccc43)cc2[C@H]1C(=O)Nc1c(F)cccc1F]

2-((S)-1-(2-((2S,5R)-4-(tert-Butoxycarbonyl)-5-methyl-2-(((R)-3-methylmorpholino)methyl)piperazin-1-yl)acetyl)-6-(4-fluorobenzyl)-3-methylindoline-3-carboxamido)acetic acid (70 mg, 101 μmol, Eq: 1) was stirred with tert-butyl ((S)-1-(((2S,3R)-1-((S)-6-amino-1-((2,6-difluorophenyl)carbamoyl)isoindolin-2-yl)-3-methoxy-1-oxobutan-2-yl)amino)-1-oxopropan-2-yl)(methyl)carbamate (59.3 mg, 101 μmol, Eq: 1; Intermediate 5) and T3P in EtOAc 50% (192 mg, 180 μl, 302 μmol, Eq: 3) in ethyl acetate (700 μl) and pyridine (350 μl) at room temperature overnight. The reaction mixture was extracted with HCl aq. 1N, NaHCO$_3$ sat. and brine. The organic layer was dried over magnesium sulfate, filtered and evaporated. The crude material was applied on silica gel and purified by column chromatography using ethyl acetate/methanol (0-20% methanol) as eluent affording tert-butyl (2R,5S)-4-[2-[(3S)-3-[[2-[[(3S)-2-[(2S,3R)-2-[[(2S)-2-[tert-butoxycarbonyl(methyl)amino]propanoyl]amino]-3-methoxy-butanoyl]-3-[(2,6-difluorophenyl)carbamoyl]isoindolin-5-yl]amino]-2-oxo-ethyl]carbamoyl]-6-[(4-fluorophenyl)methyl]-3-methyl-indolin-1-yl]-2-oxo-ethyl]-2-methyl-5-[[(3R)-3-methylmorpholin-4-yl]methyl]piperazine-1-carboxylate (100 mg, 78.4%) as a white solid. MS: m/z (M+H)$^+$=1267.6 b) (3S)—N-[2-[[(3S)-3-[(2,6-Difluorophenyl)carbamoyl]-2-[(2S,3R)-3-methoxy-2-[[(2S)-2-(methylamino)propanoyl]amino]butanoyl]isoindolin-5-yl]amino]-2-oxo-ethyl]-6-[(4-fluorophenyl)methyl]-3-methyl-1-[2-[(2R,5R)-5-methyl-2-[[(3R)-3-methylmorpholin-4-yl]methyl]piperazin-1-yl]acetyl]indoline-3-carboxamide trihydrochloride

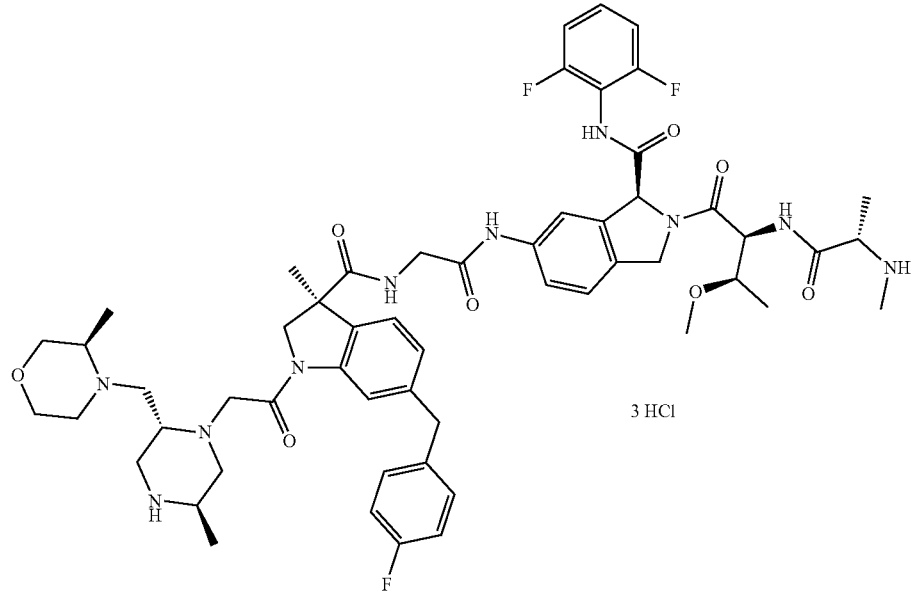 [SMILES: CN[C@@H](C)C(=O)N[C@H](C(=O)N1Cc2ccc(NC(=O)CNC(=O)[C@]3(C)CN(C(=O)CN4C[C@@H](C)NC[C@@H]4CN4CCOC[C@H]4C)c4cc(Cc5ccc(F)cc5)ccc43)cc2[C@H]1C(=O)Nc1c(F)cccc1F)[C@@H](C)OC]

3 HCl

HCl 4M in dioxane (1.87 ml, 7.5 mmol, Eq: 100) was added to a colorless solution of (2R,5S)-tert-butyl 4-(2-((S)-3-((2-(((S)-2-((2S,3R)-2-((S)-2-((tert-butoxycarbonyl)(methyl)amino)propanamido)-3-methoxybutanoyl)-3-((2,6-difluorophenyl)carbamoyl)isoindolin-5-yl)amino)-2-oxoethyl)carbamoyl)-6-(4-fluorobenzyl)-3-methylindolin-1-yl)-2-oxo ethyl)-2-methyl-5-(((R)-3-methylmorpholino)methyl)piperazine-1-carboxylate (95 mg, 75 μmol, Eq: 1) in ethyl acetate (1 ml). The reaction was stirred at room temperature for 45 min. The white precipitate was filtered off, washed with diethyl ether and dried in vacuo affording (S)—N-(2-(((S)-3-((2,6-difluorophenyl)carbamoyl)-2-((2S,3R)-3-methoxy-2-((S)-2-(methylamino)propanamido)butanoyl)isoindolin-5-yl)amino)-2-oxoethyl)-6-(4-fluorobenzyl)-3-methyl-1-(2-((2R,5R)-5-methyl-2-(((R)-3-methylmorpholino)methyl)piperazin-1-yl)acetyl)indoline-3-carboxamide trihydrochloride (76 mg, 86.2%) as a white solid. MS: m/z (M+H)$^+$=1067.5

Example 21 a) (S)—N-(2-(((S)-3-((2,6-Difluorophenyl)carbamoyl)-2-((2S,3S)-3-methyl-2-((S)-2-(methylamino)propanamido)pentanoyl)isoindolin-5-yl)amino)-2-oxoethyl)-6-(4-fluorobenzyl)-3-methyl-1-(2-((2R,5R)-5-methyl-2-(((R)-3-methylmorpholino)methyl)piperazin-1-yl)acetyl)indoline-3-carboxamide trihydrochloride tert-Butyl (2R,5S)-4-[2-[(3S)-3-[[2-[[(3S)-2-[(2 S,3 S)-2-[[(2S)-2-[tert-butoxycarbonyl(methyl)amino]propanoyl]amino]-3-methyl-pentanoyl]-3-[(2,6-difluorophenyl)carbamoyl]isoindolin-5-yl]amino]-2-oxo-ethyl]carbamoyl]-6-[(4-fluorophenyl)methyl]-3-methyl-indolin-1-yl]-2-oxo-ethyl]-2-methyl-5-[[(3R)-3-methylmorpholin-4-yl]methyl]piperazine-1-carboxylate

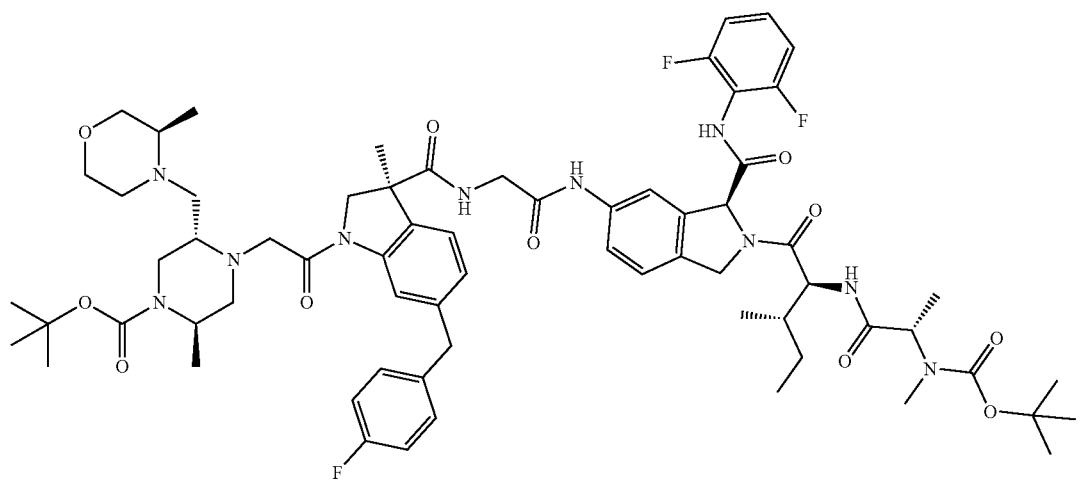 [SMILES: CC[C@H](C)[C@H](NC(=O)[C@H](C)N(C)C(=O)OC(C)(C)C)C(=O)N1Cc2ccc(NC(=O)CNC(=O)[C@]3(C)CN(C(=O)CN4C[C@@H](C)N(C(=O)OC(C)(C)C)C[C@@H]4CN4CCOC[C@H]4C)c4cc(Cc5ccc(F)cc5)ccc43)cc2[C@H]1C(=O)Nc1c(F)cccc1F]

2-((S)-1-(2-((2S,5R)-4-(tert-Butoxycarbonyl)-5-methyl-2-(((R)-3-methylmorpholino)methyl)piperazin-1-yl)acetyl)-6-(4-fluorobenzyl)-3-methylindoline-3-carboxamido)acetic acid (40 mg, 57.5 µmol, Eq: 1) was stirred with tert-butyl ((S)-1-(((2S,3S)-1-((S)-6-amino-1-((2,6-difluorophenyl)carbamoyl)isoindolin-2-yl)-3-methyl-1-oxopentan-2-yl)amino)-1-oxopropan-2-yl)(methyl)carbamate (33.8 mg, 57.5 µmol, Eq: 1; Intermediate 6) and T3P in EtOAc 50% (110 mg, 103 µl, 172 µmol, Eq: 3) in ethyl acetate (0.5 ml) and pyridine (250 µl) at room temperature overnight. The reaction mixture was extracted with aq. NaHCO$_3$ sat. and brine. The organic layer was dried over magnesium sulfate, filtered and evaporated. The crude material was applied on silica gel and was purified by column chromatography using ethyl acetate/methanol (0-20% methanol) as eluent affording tert-butyl (2R,5S)-4-[2-[(3S)-3-[[2-[[(3S)-2-[(2 S,3S)-2-[[(2S)-2-[tert-butoxycarbonyl(methyl)amino]propanoyl]amino]-3-methyl-pentanoyl]-3-[(2,6-difluorophenyl)carbamoyl]isoindolin-5-yl]amino]-2-oxo-ethyl]carbamoyl]-6-[(4-fluorophenyl)methyl]-3-methyl-indolin-1-yl]-2-oxo-ethyl]-2-methyl-5-[[(3R)-3-methylmorpholin-4-yl]methyl]piperazine-1-carboxylate (41 mg, 56.4%) as a yellow amorphous. MS: m/z (M+H)$^+$=1265.7 b) (3S)—N-[2-[[(3S)-3-[(2,6-Difluorophenyl)carbamoyl]-2-[(2S,3S)-3-methyl-2-[[(2S)-2-(methylamino)propanoyl]amino]pentanoyl]isoindolin-5-yl]amino]-2-oxo-ethyl]-6-[(4-fluorophenyl)methyl]-3-methyl-1-[2-[(2R,5R)-5-methyl-2-[[(3R)-3-methylmorpholin-4-yl]methyl]piperazin-1-yl]acetyl]indoline-3-carboxamide Trihydrochloride

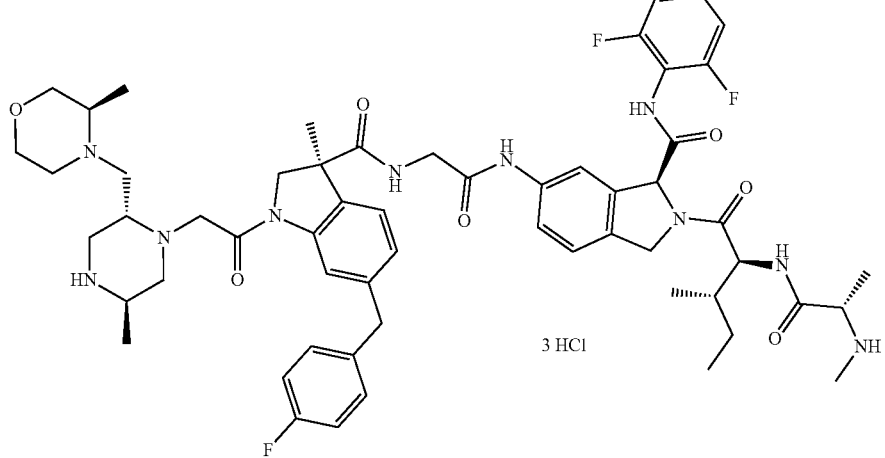

HCl 4M in dioxane (691 μl, 2.77 mmol, Eq: 100) was added to a light yellow solution of (2R,5S)-tert-butyl 4-(2-((S)-3-((2-(((S)-2-((2S,3S)-2-((S)-2-((tert-butoxycarbonyl)(methyl)amino)propanamido)-3-methylpentanoyl)-3-((2,6-difluorophenyl)carbamoyl)isoindolin-5-yl)amino)-2-oxoethyl)carbamoyl)-6-(4-fluorobenzyl)-3-methylindolin-1-yl)-2-oxoethyl)-2-methyl-5-(((R)-3-methylmorpholino)methyl)piperazine-1-carboxylate (35 mg, 27.7 μmol, Eq: 1) in ethyl acetate (0.5 ml) and the reaction was stirred at room temperature for 2 h. The off-white precipitate was filtered off, washed with diethyl ether and dried in vacuo affording (S)—N-(2-(((S)-3-((2,6-difluorophenyl)carbamoyl)-2-((2S,3S)-3-methyl-2-((S)-2-(methylamino)propanamido)pentanoyl)isoindolin-5-yl)amino)-2-oxoethyl)-6-(4-fluorobenzyl)-3-methyl-1-(2-((2R,5R)-5-methyl-2-(((R)-3-methylmorpholino)methyl)piperazin-1-yl)acetyl)indoline-3-carboxamide trihydrochloride (25 mg, 77%) as an off-white solid. MS: m/z (M+H)⁺=1065.55

Example 22 a) (S)—N-(2-(((S)-3-((2,6-Difluorophenyl)carbamoyl)-2-((S)-3,3-dimethyl-2-((S)-2-(methylamino)propanamido)butanoyl)isoindolin-5-yl)amino)-2-oxoethyl)-6-(4-fluorobenzyl)-3-methyl-1-(2-((2R,5R)-5-methyl-2-(((R)-3-methylmorpholino)methyl)piperazin-1-yl)acetyl)indoline-3-carboxamide trihydrochloride tert-Butyl (2R,5S)-4-[2-[(3S)-3-[[2-[[(3S)-2-[(2S)-2-[[(2S)-2-[tert-butoxycarbonyl(methyl)amino]propanoyl]amino]-3,3-dimethyl-butanoyl]-3-[(2,6-difluorophenyl)carbamoyl]isoindolin-5-yl]amino]-2-oxo-ethyl]carbamoyl]-6-[(4-fluorophenyl)methyl]-3-methyl-indolin-1-yl]-2-oxo-ethyl]-2-methyl-5-[[(3R)-3-methylmorpholin-4-yl]methyl]piperazine-1-carboxylate

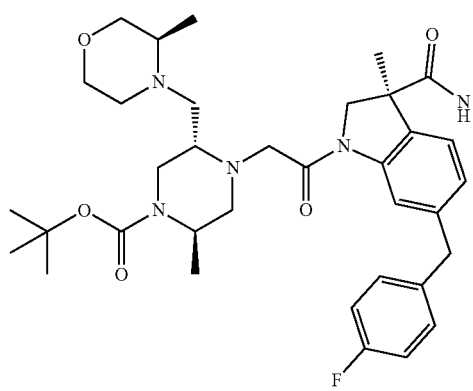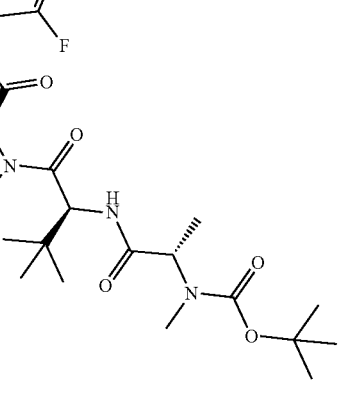

2-((S)-1-(2-((2S,5R)-4-(tert-Butoxycarbonyl)-5-methyl-2-(((R)-3-methylmorpholino)methyl)piperazin-1-yl)acetyl)-6-(4-fluorobenzyl)-3-methylindoline-3-carboxamido)acetic acid (71 mg, 102 µmol, Eq: 1) was stirred with tert-butyl ((S)-1-(((S)-1-((S)-6-amino-1-((2,6-difluorophenyl)carbamoyl)isoindolin-2-yl)-3,3-dimethyl-1-oxobutan-2-yl)amino)-1-oxopropan-2-yl)(methyl)carbamate (60 mg, 102 µmol, Eq: 1; Intermediate 7) and T3P in EtOAc 50% (195 mg, 182 µl, 306 µmol, Eq: 3) in ethyl acetate (800 µl) and pyridine (400 µl) at room temperature overnight. The reaction mixture was extracted with HCl aq. 1N, NaHCO₃ sat. and brine. The organic layer was dried over magnesium sulfate, filtered and evaporated. The crude material was applied on silica gel and purified by column chromatography using ethyl acetate/methanol (0-5% methanol) as eluent affording tert-butyl (2R,5S)-4-[2-[(3S)-3-[[2-[[(3S)-2-[(2S)-2-[[(2S)-2-[tert-butoxycarbonyl(methyl)amino]propanoyl]amino]-3,3-dimethyl-butanoyl]-3-[(2,6-difluorophenyl)carbamoyl]isoindolin-5-yl]amino]-2-oxo-ethyl]carbamoyl]-6-[(4-fluorophenyl)methyl]-3-methyl-indolin-1-yl]-2-oxo-ethyl]-2-methyl-5-[[(3R)-3-methylmorpholin-4-yl]methyl] piperazine-1-carboxylate (86 mg, 66.6%). MS: m/z (M+H)⁺=1265.7 b) (3S)—N-[2-[[(3S)-3-[(2,6-Difluorophenyl)carbamoyl]-2-[(2S)-3,3-dimethyl-2-[[(2S)-2-(methylamino)propanoyl]amino]butanoyl]isoindolin-5-yl]amino]-2-oxo-ethyl]-6-[(4-fluorophenyl)methyl]-3-methyl-1-[2-[(2R,5R)-5-methyl-2-[[(3R)-3-methylmorpholin-4-yl]methyl]piperazin-1-yl]acetyl]indoline-3-carboxamide Trihydrochloride

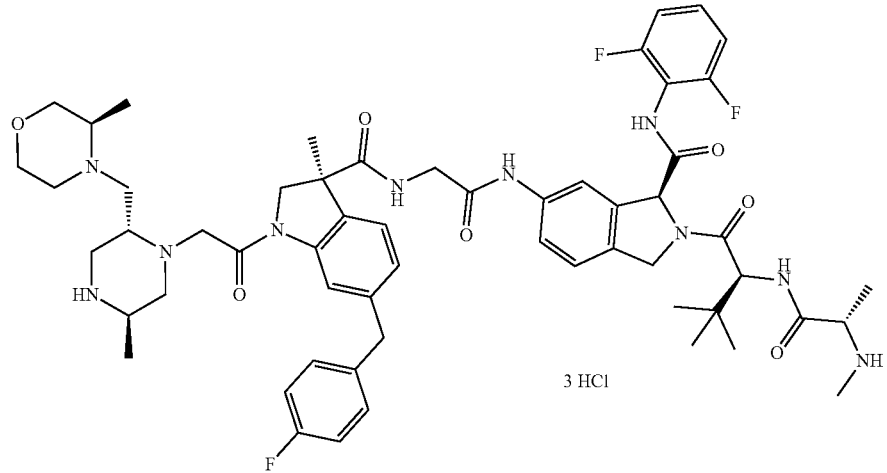 [SMILES: CN[C@@H](C)C(=O)N[C@H](C(=O)N1Cc2ccc(NC(=O)CNC(=O)[C@]3(C)CN(C(=O)CN4C[C@@H](C)NC[C@@H]4CN4CCOC[C@H]4C)c4cc(Cc5ccc(F)cc5)ccc43)cc2[C@H]1C(=O)Nc1c(F)cccc1F)C(C)(C)C]

(2R,5S)-tert-Butyl 4-(2-((S)-3-((2-(((S)-2-((S)-2-((S)-2-((tert-butoxycarbonyl)(methyl)amino)propanamido)-3,3-dimethylbutanoyl)-3-((2,6-difluorophenyl)carbamoyl)isoindolin-5-yl)amino)-2-oxoethyl)carbamoyl)-6-(4-fluorobenzyl)-3-methylindolin-1-yl)-2-oxo ethyl)-2-methyl-5-(((R)-3-methylmorpholino)methyl)piperazine-1-carboxylate (80 mg, 63.2 µmol, Eq: 1) was stirred with HCl in dioxane 4M (1 ml, 4 mmol, Eq: 63.3) in ethyl acetate (1 ml) at room temperature for 2 h. The precipitated solid was filtered off, washed with diethyl ether and dried under high vacuum affording (S)—N-(2-(((S)-3-((2,6-difluorophenyl)carbamoyl)-2-((S)-3,3-dimethyl-2-((S)-2-(methylamino)propanamido)butanoyl)isoindolin-5-yl)amino)-2-oxoethyl)-6-(4-fluorobenzyl)-3-methyl-1-(2-((2R,5R)-5-methyl-2-(((R)-3-methylmorpholino)methyl)piperazin-1-yl)acetyl)indoline-3-carboxamide trihydrochloride (45 mg, 60.6%) as a white solid. MS: m/z (M+H)⁺=1065.55

Monomer A

N-(2-Aminoethyl)-6-(4-fluorobenzyl)-3-methyl-1-(2-((2R,5R)-5-methyl-2-(((R)-3-methylmorpholino)methyl)piperazin-1-yl)acetyl)indoline-3-carboxamide Dihydrochloride a) tert-Butyl (2R,5S)-4-[2-[3-[2-(benzyloxycarbonylamino)ethylcarbamoyl]-6-[(4-fluorophenyl)methyl]-3-methyl-indolin-1-yl]-2-oxo-ethyl]-2-methyl-5-[[(3R)-3-methylmorpholin-4-yl]methyl]piperazine-1-carboxylate

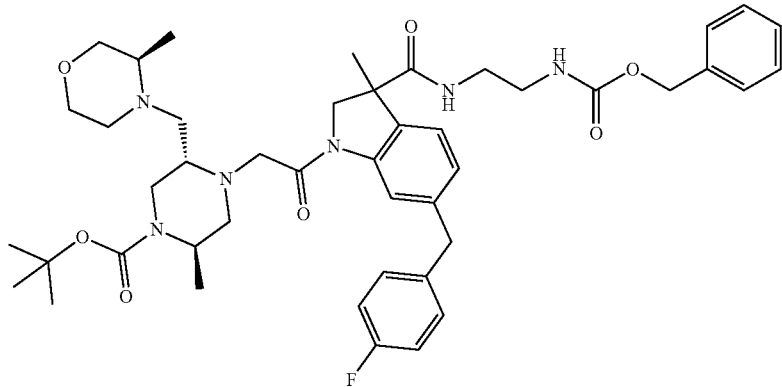 [SMILES: C[C@@H]1COCCN1C[C@H]1CN(C(=O)OC(C)(C)C)[C@H](C)CN1CC(=O)N1CC(C)(C(=O)NCCNC(=O)OCc2ccccc2)c2ccc(Cc3ccc(F)cc3)cc21]

1-(2-((2S,5R)-4-(tert-Butoxycarbonyl)-5-methyl-2-(((R)-3-methylmorpholino)methyl)piperazin-1-yl)acetyl)-6-(4-fluorobenzyl)-3-methylindoline-3-carboxylic acid (300 mg, 470 μmol, Eq: 1) was stirred with DIPEA (243 mg, 328 μl, 1.88 mmol, Eq: 4) and HATU (232 mg, 611 μmol, Eq: 1.3) overnight at room temperature. The reaction mixture was poured into 0.5M HCl aq. and extracted three times with ethyl acetate, washed with brine, dried over magnesium sulfate, filtered and evaporated. The crude material was applied on silica gel and purified by column chromatography using ethyl acetate/methanol (0-5% methanol) as eluent affording tert-butyl (2R,5S)-4-[2-[3-[2-(benzyloxycarbonylamino)ethylcarbamoyl]-6-[(4-fluorophenyl)methyl]-3-methyl-indolin-1-yl]-2-oxo-ethyl]-2-methyl-5-[[(3R)-3-methylmorpholin-4-yl]methyl]piperazine-1-carboxylate (482 mg, 100%) as a light yellow oil. MS: m/z (M+H)$^+$=815.45 b) tert-Butyl (2R,5S)-4-[2-[3-(2-aminoethylcarbamoyl)-6-[(4-fluorophenyl)methyl]-3-methyl-indolin-1-yl]-2-oxo-ethyl]-2-methyl-5-[[(3R)-3-methylmorpholin-4-yl]methyl]piperazine-1-carboxylate

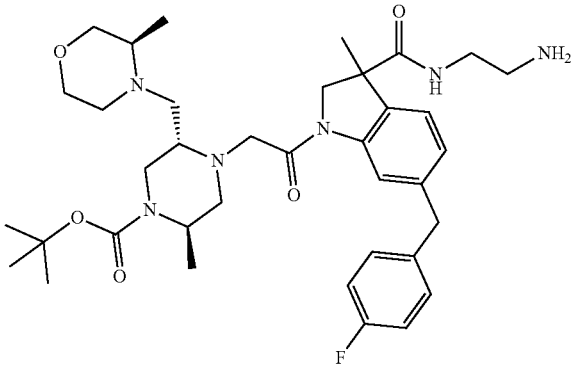 [SMILES: C[C@@H]1COCCN1C[C@H]1CN(C(=O)OC(C)(C)C)[C@H](C)CN1CC(=O)N1CC(C)(C(=O)NCCN)c2ccc(Cc3ccc(F)cc3)cc21]

(2R,5S)-tert-Butyl 4-(2-(3-((2-(((benzyloxy)carbonyl)amino)ethyl)carbamoyl)-6-(4-fluorobenzyl)-3-methylindolin-1-yl)-2-oxoethyl)-2-methyl-5-(((R)-3-methylmorpholino)methyl)piperazine-1-carboxylate (375 mg, 460 μmol, Eq: 1) was stirred in methanol (15 ml) with palladium on carbon 10% (49 mg, 46 μmol, Eq: 0.1) under a hydrogen atmosphere overnight at room temperature. Five drops acetic acid were added and stirring was continued at room temperature under a hydrogen atmosphere for 3 h. The catalyst was filtered off and the solvent was evaporated. Sodium bicarbonate solution was added and the mixture was extracted three times with ethyl acetate, dried over magnesium sulfate, filtered and evaporated affording tert-butyl (2R,5S)-4-[2-[3-(2-aminoethylcarbamoyl)-6-[(4-fluorophenyl)methyl]-3-methyl-indolin-1-yl]-2-oxo-ethyl]-2-methyl-5-[[(3R)-3-methylmorpholin-4-yl]methyl]piperazine-1-carboxylate (281 mg, 89.7%) as a light yellow foam. MS: m/z (M+H)$^+$=681.42 c) N-(2-Aminoethyl)-6-(4-fluorobenzyl)-3-methyl-1-(2-((2R,5R)-5-methyl-2-(((R)-3-methylmorpholino)methyl)piperazin-1-yl)acetyl)indoline-3-carboxamide Dihydrochloride

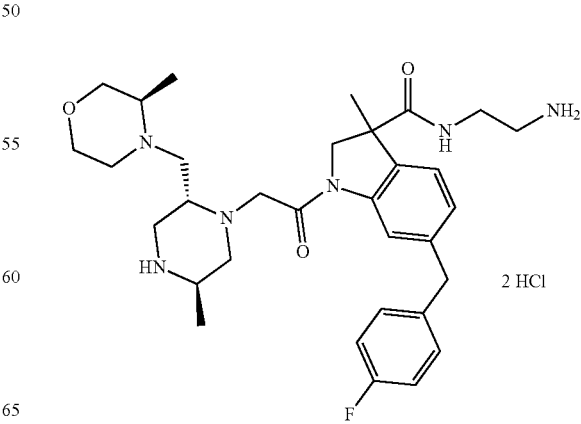

(2R,5S)-tert-Butyl 4-(2-(3-((2-aminoethyl)carbamoyl)-6-(4-fluorobenzyl)-3-methylindolin-1-yl)-2-oxoethyl)-2-methyl-5-(((R)-3-methylmorpholino)methyl)piperazine-1-carboxylate (50 mg, 73.4 µmol, Eq: 1) was stirred with HCl in dioxane 4M (1 ml, 4 mmol, Eq: 54.5) in ethyl acetate (1 ml) at room temperature overnight. The precipitated solid was filtered off and washed with diethyl ether and dried under high vacuum affording N-(2-aminoethyl)-6-(4-fluorobenzyl)-3-methyl-1-(2-((2R,5R)-5-methyl-2-(((R)-3-methylmorpholino)methyl)piperazin-1-yl)acetyl)indoline-3-carboxamide dihydrochloride (35.5 mg, 74%) as a white solid. MS: m/z (M+H)$^+$=581.36

Monomer B (S)-6-(4-Fluorobenzyl)-3-methyl-1-(2-((2R,5R)-5-methyl-2-(((R)-3-methylmorpholino)methyl)piperazin-1-yl)acetyl)indoline-3-carboxylic Acid Dihydrochloride HCl 4M in dioxane (1.96 ml, 7.83 mmol, Eq: 100) was added to a yellow suspension of (S)-1-(2-((2S,5R)-4-(tert-butoxycarbonyl)-5-methyl-2-(((R)-3-methylmorpholino)methyl)piperazin-1-yl)acetyl)-6-(4-fluorobenzyl)-3-methyl-indoline-3-carboxylic acid (50 mg, 78.3 µmol, Eq: 1) in ethyl acetate (0.5 ml) and the reaction was stirred at room temperature for 3 h. The white precipitate was filtered off, washed with diethyl ether and dried in vacuo affording (S)-6-(4-fluorobenzyl)-3-methyl-1-(2-((2R,5R)-5-methyl-2-(((R)-3-methylmorpholino)methyl)piperazin-1-yl)acetyl)indoline-3-carboxylic acid dihydrochloride (30 mg, 62.7%) as an orange solid. MS: m/z (M+H)$^+$=539.3

Monomer C 1-(6-(4-Fluorobenzyl)-3-(hydroxymethyl)-3-methyl-indolin-1-yl)-2-((2R,5R)-5-methyl-2-(((R)-3-methylmorpholino)methyl)piperazin-1-yl)ethanone Dihydrochloride a) tert-Butyl (2R,5S)-4-[2-[6-[(4-fluorophenyl)methyl]-3-(hydroxymethyl)-3-methyl-indolin-1-yl]-2-oxo-ethyl]-2-methyl-5-[[(3R)-3-methylmorpholin-4-yl]methyl]piperazine-1-carboxylate

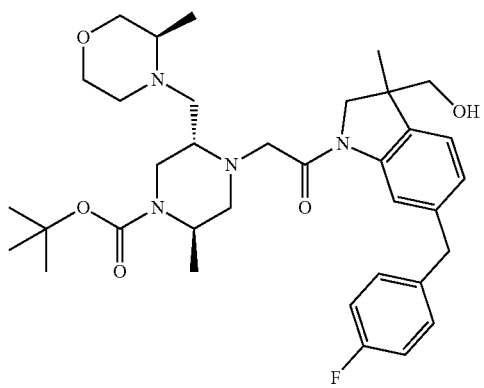 [SMILES: C[C@@H]1COCCN1C[C@H]1CN(C(=O)OC(C)(C)C)[C@H](C)CN1CC(=O)N1CC(C)(CO)c2ccc(Cc3ccc(F)cc3)cc21]

Sodium borohydride (85.8 mg, 2.27 mmol, Eq: 2) was added to a clear solution of methyl 1-(2-((2S,5R)-4-(tert-butoxycarbonyl)-5-methyl-2-(((R)-3-methylmorpholino)methyl)piperazin-1-yl)acetyl)-6-(4-fluorobenzyl)-3-methyl-indoline-3-carboxylate (740 mg, 1.13 mmol, Eq: 1) in THF (5.86 ml) and methanol (5.86 ml) at 0° C. The reaction was stirred at 0° C. for 5 h, was then allowed to warm up to room temperature and was stirred overnight. Aq. sat. sodium carbonate was added and the mixture was extracted with ethyl acetate. The organic layer was dried over magnesium sulfate, filtered and evaporated. The crude residue was applied to silica gel and was purified by flash chromatography using ethyl acetate/heptane (50-100% ethyl acetate) as eluent affording tert-butyl (2R,5S)-4-[2-[6-[(4-fluorophenyl)methyl]-3-(hydroxymethyl)-3-methyl-indolin-1-yl]-2-oxo-ethyl]-2-methyl-5-[[(3R)-3-methylmorpholin-4-yl]methyl]piperazine-1-carboxylate (616 mg, 87%) as a white foam. MS: m/z (M+H)+=625.4 b) 1-[6-[(4-Fluorophenyl)methyl]-3-(hydroxymethyl)-3-methyl-indolin-1-yl]-2-[(2R,5R)-5-methyl-2-[[(3R)-3-methylmorpholin-4-yl]methyl]piperazin-1-yl]ethanone Dihydrochloride

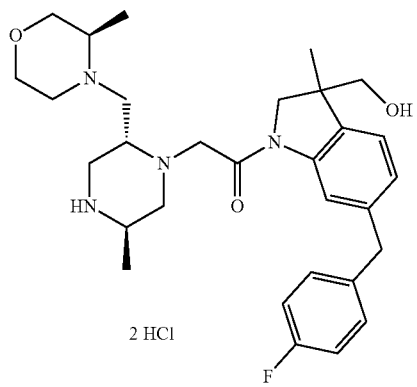 [SMILES: C[C@@H]1CN(CC(=O)N2CC(C)(CO)c3ccc(Cc4ccc(F)cc4)cc32)[C@@H](CN2CCOC[C@H]2C)CN1]

HCl 4M in dioxane (2 ml, 8 mmol, Eq: 100) was added to a clear solution of (2R,5S)-tert-butyl 4-(2-(6-(4-fluorobenzyl)-3-(hydroxymethyl)-3-methylindolin-1-yl)-2-oxo-ethyl)-2-methyl-5-(((R)-3-methylmorpholino)methyl)piperazine-1-carboxylate (50 mg, 80 µmol, Eq: 1) in ethyl acetate (0.5 ml) and the reaction mixture was stirred at room temperature for 3 h. The precipitate was filtered off, washed thoroughly with diethyl ether (very hygroscopic) and dried in vacuo affording 1-(6-(4-fluorobenzyl)-3-(hydroxymethyl)-3-methylindolin-1-yl)-2-((2R,5R)-5-methyl-2-(((R)-3-methylmorpholino)methyl)piperazin-1-yl)ethanone dihydrochloride (43 mg, 89.9%) as an orange solid. MS: m/z (M+H)$^+$=525.3

Monomer D 4-(6-(4-Fluorobenzyl)-3-methyl-1-(2-((2R,5R)-5-methyl-2-(((R)-3-methylmorpholino)methyl)piperazin-1-yl)acetyl)indoline-3-carboxamido)benzoic Acid Dihydrochloride 4-(1-(2-((2S,5R)-4-(tert-Butoxycarbonyl)-5-methyl-2-(((R)-3-methylmorpholino)methyl)piperazin-1-yl)acetyl)-6-(4-fluorobenzyl)-3-methylindoline-3-carboxamido)benzoic acid (28 mg, 36.9 µmol, Eq: 1) was stirred with HCl in dioxane 4M (0.75 ml, 3 mmol, Eq: 81.2) in ethyl acetate (0.75 ml) at room temperature overnight. The precipitated solid was filtered off, washed with diethyl ether and dried under high vacuum affording 4-(6-(4-fluorobenzyl)-3- methyl-1-(2-((2R,5R)-5-methyl-2-(((R)-3-methylmorpholino)methyl)piperazin-1-yl)acetyl)indoline-3-carboxamido)benzoic acid dihydrochloride (20 mg, 74.1%) as a white solid. MS: m/z (M+H)$^+$=658.3

Monomer E 2-(6-(4-Fluorobenzyl)-3-methyl-1-(2-((2R,5R)-5-methyl-2-(((R)-3-methylmorpholino)methyl)piperazin-1-yl)acetyl)indoline-3-carboxamido)acetic Acid Dihydrochloride 2-(1-(2-((2S,5R)-4-(tert-Butoxycarbonyl)-5-methyl-2-(((R)-3-methylmorpholino)methyl)piperazin-1-yl)acetyl)-6-(4-fluorobenzyl)-3-methylindoline-3-carboxamido)acetic acid (50 mg, 71.9 µmol, Eq: 1) was stirred with HCl in dioxane 4M (1 ml, 4 mmol, Eq: 55.7) in ethyl ether (1 ml) at room temperature overnight. The precipitated solid was filtered off, washed with diethyl ether and dried under high vacuum affording 2-(6-(4-fluorobenzyl)-3-methyl-1-(2-((2R,5R)-5-methyl-2-(((R)-3-methylmorpholino)methyl)piperazin-1-yl)acetyl)indoline-3-carboxamido)acetic acid dihydrochloride (39 mg, 81.2%) as a white solid. MS: m/z (M+H)$^+$=596.3

Intermediate 1

(S)-2-((S)-2-((S)-2-((tert-Butoxycarbonyl)(methyl)amino)propanamido)-2-(tetrahydro-2H-pyran-4-yl)acetyl)isoindoline-1-carboxylic Acid

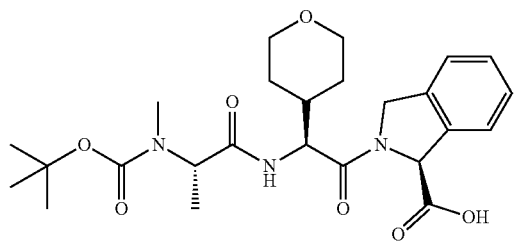 [SMILES: C[C@@H](C(=O)N[C@H](C(=O)N1Cc2ccccc2[C@H]1C(=O)O)C1CCOCC1)N(C)C(=O)OC(C)(C)C]

a) (S)-1-Benzyl 2-tert-butyl isoindoline-1,2-dicarboxylate

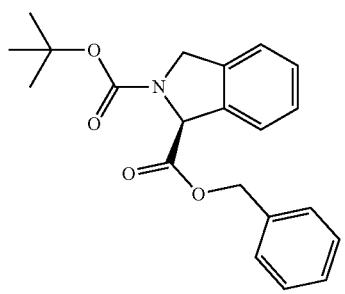 [SMILES: CC(C)(C)OC(=O)N1Cc2ccccc2[C@H]1C(=O)OCc1ccccc1]

In a 25 mL round-bottomed flask, (1S)-2-tert-butoxycarbonylisoindoline-1-carboxylic acid (CAS 1093651-93-4; 220 mg, 836 µmol, Eq: 1) and potassium bicarbonate (167 mg, 1.67 mmol, Eq: 2) were combined with DMF (3 ml). Benzyl bromide (214 mg, 149 µl, 1.25 mmol, Eq: 1.5) was added. The reaction mixture was stirred for 2 h at room temperature to form a light brown suspension. The reaction mixture was poured into ethyl acetate and extracted with diluted aqueous hydrochloric acid and brine. The organic layer was dried over Na$_2$SO$_4$ and concentrated in vacuo. The crude material was purified by flash chromatography (silica gel, 12 g, 0% to 40% EtOAc in heptane): 194 mg colorless oil, MS: m/z (M-C$_6$H$_5$CH$_2$OCO)$^+$=218.1 b) (S)-Benzyl isoindoline-1-carboxylate 2,2,2-trifluoroacetate

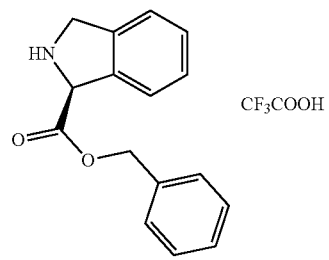 [SMILES: O=C(OCc1ccccc1)[C@H]1NCc2ccccc21 ; "CF3COOH"]

In a 50 mL round-bottomed flask, (S)-1-benzyl 2-tert-butyl isoindoline-1,2-dicarboxylate (190 mg, 538 µmol, Eq: 1) was combined with dichloromethane (6 ml). Trifluoroacetic acid (3 ml) was added. The mixture was stirred 2 h at room temperature whereupon a light yellow solution was formed. The reaction mixture was concentrated in vacuo to give 235 mg of a yellow oil. MS: m/z (M+H)$^+$=254.2 c) (S)-Benzyl 2-((S)-2-((tert-butoxycarbonyl)amino)-2-(tetrahydro-2H-pyran-4-yl)acetyl)isoindoline-1-carboxylate

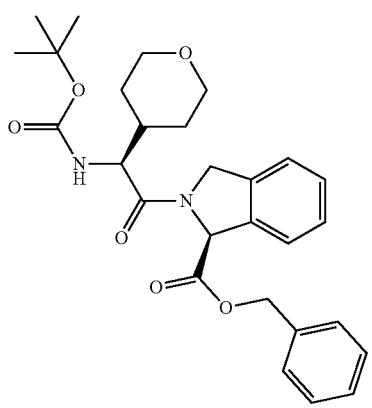 [SMILES: CC(C)(C)OC(=O)N[C@H](C(=O)N1Cc2ccccc2[C@H]1C(=O)OCc1ccccc1)C1CCOCC1]

In a 25 mL round-bottomed flask, (S)-benzyl isoindoline-1-carboxylate 2,2,2-trifluoroacetate (230 mg, 526 µmol, Eq: 1), (S)-2-(tert-butoxycarbonylamino)-2-(tetrahydro-2H-pyran-4-yl)acetic acid (150 mg, 579 µmol, Eq: 1.1) and DIPEA (340 mg, 459 µl, 2.63 mmol, Eq: 5) were combined with DMF (5 ml), then HATU (260 mg, 684 µmol, Eq: 1.3) was added. The mixture was stirred for 3 h at room temperature. The reaction mixture was poured into ethyl acetate and extracted with diluted HCl and brine. The organic layer was dried over Na2SO4 and concentrated in vacuo. The crude material was purified by flash chromatography (silica d) (S)-Benzyl 2-((S)-2-amino-2-(tetrahydro-2H-pyran-4-yl)acetyl)isoindoline-1-carboxylate 2,2,2-trifluoroacetate

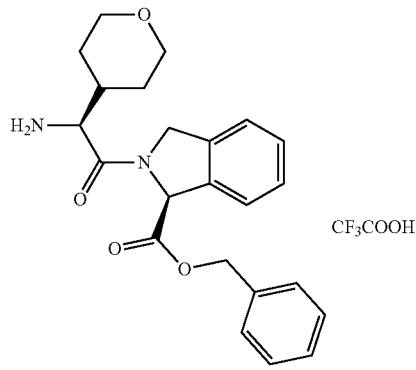

CF₃COOH

In a 50 mL round-bottomed flask, (S)-benzyl 2-((S)-2-((tert-butoxycarbonyl)amino)-2-(tetrahydro-2H-pyran-4-yl)acetyl)isoindoline-1-carboxylate (185 mg, 374 µmol, Eq: 1) was combined with dichloromethane (6 ml) to give a colorless solution. Trifluoroacetic acid (3 ml) was added. The mixture was stirred 1 h at room temperature, then concentrated in vacuo: 283 mg colorless oil. MS: m/z (M+H)⁺=395.3 e) (S)-Benzyl 2-((S)-2-((S)-2-((tert-butoxycarbonyl)(methyl)amino)propanamido)-2-(tetrahydro-2H-pyran-4-yl)acetyl)isoindoline-1-carboxylate

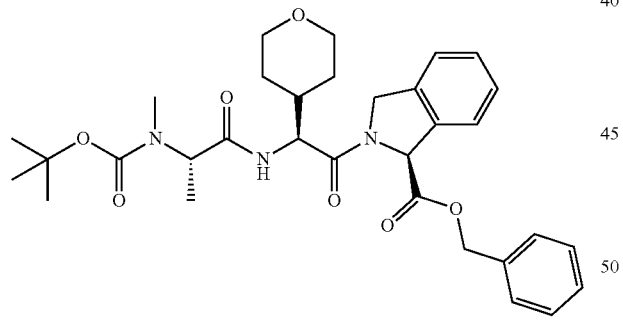

In a 25 mL round-bottomed flask, (S)-benzyl 2-((S)-2-amino-2-(tetrahydro-2H-pyran-4-yl)acetyl)isoindoline-1-carboxylate 2,2,2-trifluoroacetate (280 mg, 369 µmol, Eq: 1.00) and Boc-N-methyl-L-alanine (82.5 mg, 406 µmol, Eq: 1.1) were combined with DMF (4 ml) to give a yellow solution. DIPEA (286 mg, 387 µl, 2.21 mmol, Eq: 6) and HATU (168 mg, 443 µmol, Eq: 1.2) were added. The reaction mixture was stirred at room temperature overnight. The reaction mixture was poured into ethyl acetate and extracted with diluted HCl, brine. The organic layer was dried over Na2SO4 and concentrated in vacuo. The crude material was purified by flash chromatography (silica gel, 12 g, 0% to 100% Ethyl acetate in heptane): 166 mg white solid. MS: m/z (M+H)⁺=580.4 f) (S)-2-((S)-2-((S)-2-((tert-Butoxycarbonyl)(methyl)amino)propanamido)-2-(tetrahydro-2H-pyran-4-yl)acetyl)isoindoline-1-carboxylic Acid

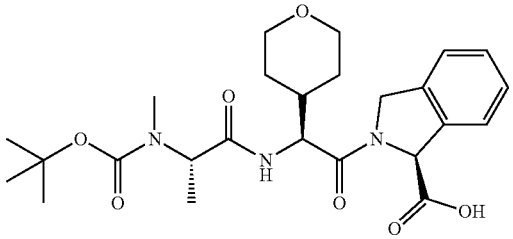 [SMILES: C[C@@H](C(=O)N[C@H](C(=O)N1Cc2ccccc2[C@H]1C(=O)O)C1CCOCC1)N(C)C(=O)OC(C)(C)C]

In a 50 mL round-bottomed flask, (S)-benzyl 2-((S)-2-((S)-2-((tert-butoxycarbonyl)(methyl)amino) propanamido)-2-(tetrahydro-2H-pyran-4-yl)acetyl)isoindoline-1-carboxylate (160 mg, 276 µmol, Eq: 1) was dissolved in methanol (10 ml). Argon was bubbled into the reaction mixture for 5 min. Palladium on charcoal (Pd—C 10%, 29.4 mg, 27.6 µmol, Eq: 0.1) was added. Hydrogen gas was bubbled in for 5 min. The reaction mixture was stirred for 2 h under hydrogen atmosphere. The reaction mixture was filtered through celite and concentrated in vacuo to give 164 mg of a yellow oil. MS: m/z (M+H)⁺=490.255

Intermediate 2 tert-Butyl ((S)-1-(((S)-2-((S)-6-amino-1-((2,6-difluorophenyl)carbamoyl)isoindolin-2-yl)-2-oxo-1-(tetrahydro-2H-pyran-4-yl)ethyl)amino)-1-oxopropan-2-yl)(methyl)carbamate

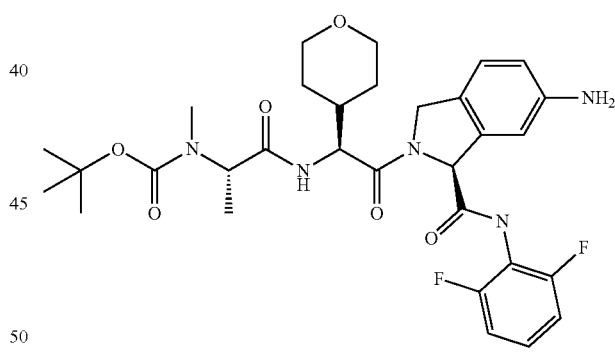

a) (S)-6-Nitroisoindoline-1-carboxylic Acid

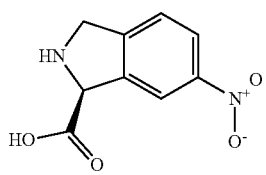

(S)-Isoindoline-1-carboxylic acid hydrochloride (2 g, 10 mmol, Eq: 1) was added to concentrated H₂SO₄ (9.83 g, 5.34 ml, 100 mmol, Eq: 10) and the mixture was stirred to afford a brown solution. The reaction mixture was cooled to −15° C. (ice/NaCl bath) and then 65% aqueous nitric acid (1.94 g, 1.39 ml, 20 mmol, Eq: 2) was added. The reaction mixture was stirred for 2 h while allowing it to warm slowly from −15° C. to room temperature, resulting in a light yellow solution. LC-MS showed the reaction was complete. The reaction mixture was poured onto ice and 17 ml 25% aqueous ammonia was added dropwise at 0° C. to afford a brown solution (pH 8). The reaction mixture was concentrated in vacuo to afford 15.5 g of a dark grey solid. MS: m/z (M+H)$^+$=209.1 b) (S)-2-(tert-Butoxycarbonyl)-6-nitroisoindoline-1-carboxylic Acid

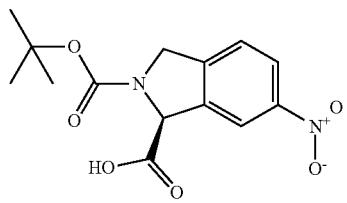

To a solution of (S)-6-nitroisoindoline-1-carboxylic acid (15.5 g, 9.9 mmol, Eq: 1) and sodium bicarbonate (3.33 g, 39.6 mmol, Eq: 4) in THF (80 ml) and water (80 ml) was added Boc-anhydride (4.32 g, 4.6 ml, 19.8 mmol, Eq: 2). The reaction mixture was stirred at RT overnight. Saturated aq. Na$_2$CO$_3$ solution was then added and the mixture was extracted twice with EtOAc. 2 N aq. HCl was added dropwise to the aqueous layer (pH 1) and the aqueous layer was extracted with EtOAc. The organic layer was dried over Na$_2$SO$_4$ and concentrated in vacuo to afford 2.15 g of a brown foam which was used in the next step without further purification.

c) (S)-tert-Butyl 1-((2,6-difluorophenyl)carbamoyl)-6-nitroisoindoline-2-carboxylate

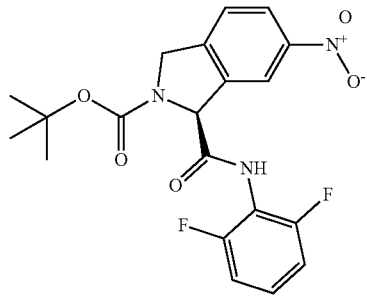

To a stirred solution of (S)-2-(tert-butoxycarbonyl)-6-nitroisoindoline-1-carboxylic acid (2.15 g, 6.97 mmol, Eq: 1) in EtOAc (10 ml) were added sequentially 2,6-difluoroaniline (1.08 g, 846 µl, 8.37 mmol, Eq: 1.2), pyridine (5 ml) and a 50% solution of T3P in EtOAc (8.88 g, 8.3 ml, 13.9 mmol, Eq: 2). The reaction mixture was stirred at room temperature for 1 h to afford a yellow solution. LC-MS showed the reaction was complete. The reaction mixture was poured into EtOAc and extracted sequentially with 1 N aq. HCl and with saturated brine. The organic layer was separated, dried over Na$_2$SO$_4$, and concentrated in vacuo. The crude material was purified by flash chromatography (silica gel, 80 g, 0% to 100% EtOAc in heptane) to afford 2.16 g of a light brown solid. MS: m/z (M+H-C$_4$H$_8$)$^+$=364.1 d) (S)—N-(2,6-Difluorophenyl)-6-nitroisoindoline-1-carboxamide

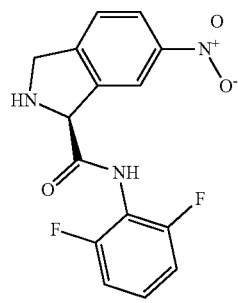

To a solution of (S)-tert-butyl 1-((2,6-difluorophenyl) carbamoyl)-6-nitroisoindoline-2-carboxylate (2.1 g, 5.01 mmol, Eq: 1) in CH$_2$Cl$_2$ (20 ml) was added TFA (14.8 g, 10 ml, 130 mmol, Eq: 26). The reaction mixture was stirred at RT for 2 h. The reaction mixture was then concentrated in vacuo, and the residue was dissolved in EtOAc and extracted sequentially with saturated aq. NaHCO$_3$ and with saturated brine. The organic layer was dried over Na$_2$SO$_4$ and concentrated in vacuo to afford 1.41 g of a brown solid which was used in the next step without further purification. MS: m/z (M+H)+=320.1 e) tert-Butyl ((S)-2-((S)-1-((2,6-difluorophenyl)carbamoyl)-6-nitroisoindolin-2-yl)-2-oxo-1-(tetrahydro-2H-pyran-4-yl)ethyl)carbamate

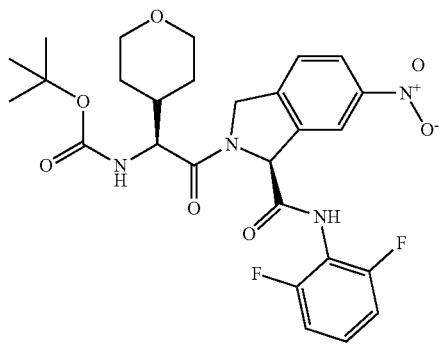

To a solution of (S)—N-(2,6-difluorophenyl)-6-nitroisoindoline-1-carboxamide (1.4 g, 4.39 mmol, Eq: 1), (S)-2-(tert-butoxycarbonylamino)-2-(tetrahydro-2H-pyran-4-yl)acetic acid (1.19 g, 4.6 mmol, Eq: 1.05) and DIPEA (1.13 g, 1.53 ml, 8.77 mmol, Eq: 2) in DMF (10 ml) was added HATU (2.17 g, 5.7 mmol, Eq: 1.3). The reaction mixture was stirred at RT overnight. The reaction mixture was then poured into EtOAc and extracted sequentially with 0.5 N aq. HCl and with saturated brine. The organic layer was separated, dried over Na$_2$SO$_4$, and concentrated in vacuo. The crude material was purified by flash chromatography (silica gel, 80 g, heptane/CH₂Cl₂/MeOH) to afford 2.27 g of a yellow foam. MS: m/z (M+H)⁺=561.2 f) (S)-2-((S)-2-Amino-2-(tetrahydro-2H-pyran-4-yl)acetyl)-N-(2,6-difluorophenyl)-6-nitroisoindoline-1-carboxamide

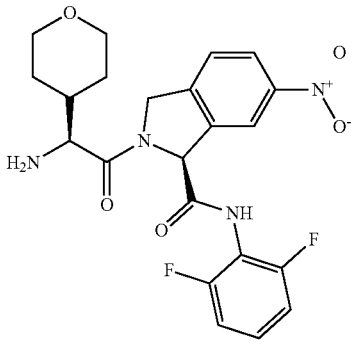

To a solution of tert-butyl ((S)-2-((S)-1-((2,6-difluorophenyl)carbamoyl)-6-nitroisoindolin-2-yl)-2-oxo-1-(tetrahydro-2H-pyran-4-yl)ethyl)carbamate (2.27 g, 4.05 mmol, Eq: 1) in CH₂Cl₂ (12 ml) was added TFA (9.24 g, 6.24 ml, 81 mmol, Eq: 20) and the reaction mixture was stirred at RT for 2 h. The reaction mixture was concentrated in vacuo, and the residue was dissolved in EtOAc and extracted sequentially with aq. NaHCO₃ and with saturated brine. The organic layer was separated, dried over Na₂SO₄, and concentrated in vacuo to afford 1.68 g of a dark yellow solid. MS: m/z (M+H)⁺=461.2 g) tert-Butyl ((S)-1-(((S)-2-((S)-1-((2,6-difluorophenyl)carbamoyl)-6-nitroisoindolin-2-yl)-2-oxo-1-(tetrahydro-2H-pyran-4-yl)ethyl)amino)-1-oxopropan-2-yl)(methyl)carbamate

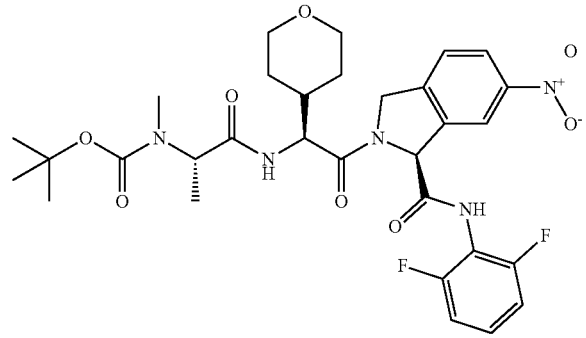

To a solution of (S)-2-((S)-2-amino-2-(tetrahydro-2H-pyran-4-yl)acetyl)-N-(2,6-difluorophenyl)-6-nitroisoindoline-1-carboxamide (1.68 g, 3.65 mmol, Eq: 1), BOC-MEALA-OH (816 mg, 4.01 mmol, Eq: 1.1) and DIPEA (1.41 g, 1.91 ml, 10.9 mmol, Eq: 3) in DMF (8 ml) was added HATU (1.8 g, 4.74 mmol, Eq: 1.3). The reaction mixture was stirred at RT for 4 h. LC-MS, TLC showed the reaction was complete. The reaction mixture was poured into EtOAc and extracted sequentially with 0.5 N aq. HCl and with saturated brine. The organic layer was separated, dried over Na₂SO₄ and concentrated in vacuo. The crude material was purified by flash chromatography (silica gel, 80 g, heptane/CH₂Cl₂/MeOH) to afford 2.0 g of an off-white foam. MS: m/z (M−H)⁻=644.4 h) tert-butyl ((S)-1-(((S)-2-((S)-6-amino-1-((2,6-difluorophenyl)carbamoyl)isoindolin-2-yl)-2-oxo-1-(tetrahydro-2H-pyran-4-yl)ethyl)amino)-1-oxopropan-2-yl)(methyl)carbamate

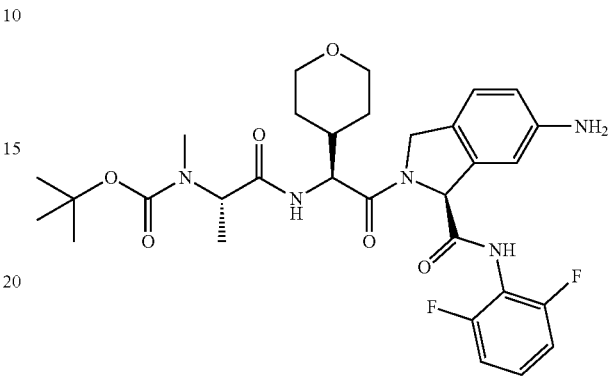

A solution of tert-butyl ((S)-1-(((S)-2-((S)-1-((2,6-difluorophenyl)carbamoyl)-6-nitroisoindolin-2-yl)-2-oxo-1-(tetrahydro-2H-pyran-4-yl)ethyl)amino)-1-oxopropan-2-yl)(methyl)carbamate (2 g, 3.1 mmol, Eq: 1) on methanol (5 ml) was purged with argon for 10 min. 10% Pd—C (330 mg, 310 µmol, Eq: 0.1) was added. The reaction mixture was purged with H₂ for 10 min, then stirred under a balloon of H₂ for 1 h. TLC showed the reaction was complete. The reaction mixture was filtered through celite. 9 g silica gel was added to the filtrate and the mixture was concentrated in vacuo. The crude material was purified by flash chromatography (silica gel, 80 g, 0% to 10% MeOH in CH₂Cl₂) to afford 1.57 g of a white solid. MS: m/z (M+H)⁺=616.3

Intermediate 3 tert-Butyl ((S)-1-(((S)-2-((S)-7-amino-3-((2,6-difluorophenyl)carbamoyl)-3,4-dihydroisoquinolin-2(1H)-yl)-2-oxo-1-(tetrahydro-2H-pyran-4-yl)ethyl)amino)-1-oxopropan-2-yl)(methyl)carbamate

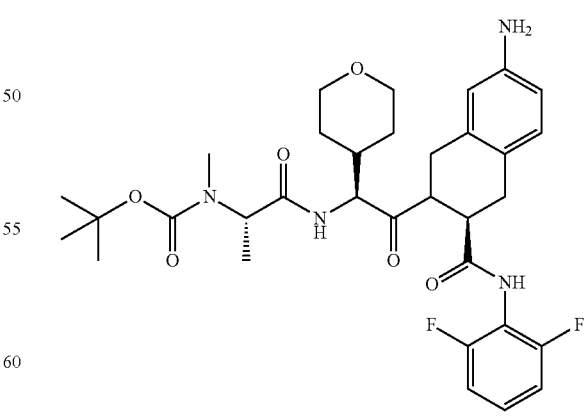

The title compound was prepared in analogy to Intermediate 2 starting from (S)-1,2,3,4-tetrahydroisoquinoline-3-carboxylic acid instead of (S)-isoindoline-1-carboxylic acid hydrochloride. Yellow solid. MS: m/z (M+H)⁺=630.3

Intermediate 4 tert-Butyl ((S)-1-(((S)-2-((S)-5-amino-1-((2,6-difluorophenyl)carbamoyl)isoindolin-2-yl)-2-oxo-1-(tetrahydro-2H-pyran-4-yl)ethyl)amino)-1-oxopropan-2-yl)(methyl)carbamate

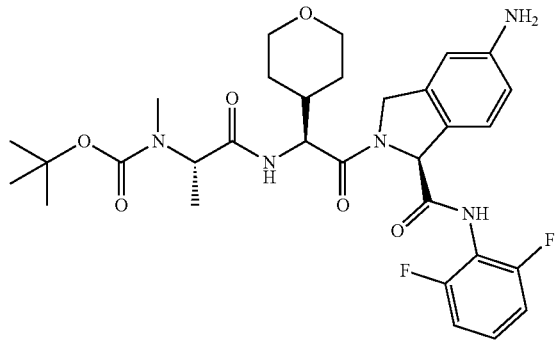 [SMILES: C[C@@H](C(=O)N[C@H](C(=O)N1Cc2cc(N)ccc2[C@H]1C(=O)Nc1c(F)cccc1F)C1CCOCC1)N(C)C(=O)OC(C)(C)C]

a) tert-Butyl ((2S)-1-(((1S)-2-(5-amino-1-((2,6-difluorophenyl)carbamoyl)isoindolin-2-yl)-2-oxo-1-(tetrahydro-2H-pyran-4-yl)ethyl)amino)-1-oxopropan-2-yl)(methyl)carbamate

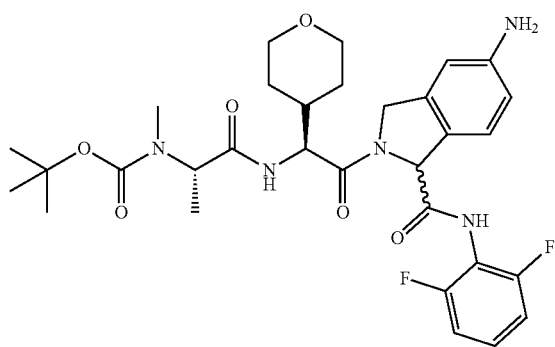 [SMILES: C[C@@H](C(=O)N[C@H](C(=O)N1Cc2cc(N)ccc2C1C(=O)Nc1c(F)cccc1F)C1CCOCC1)N(C)C(=O)OC(C)(C)C]

The title compound was prepared in analogy to Intermediate 2 steps (b)-(h) starting from 5-nitroisoindoline-1-carboxylic acid hydrochloride instead of (S)-6-nitroisoindoline-1-carboxylic acid. Brown solid. MS: m/z (M+H)$^+$=614.5 b) tert-Butyl ((S)-1-(((S)-2-((S)-5-amino-1-((2,6-difluorophenyl)carbamoyl)isoindolin-2-yl)-2-oxo-1-(tetrahydro-2H-pyran-4-yl)ethyl)amino)-1-oxopropan-2-yl)(methyl)carbamate

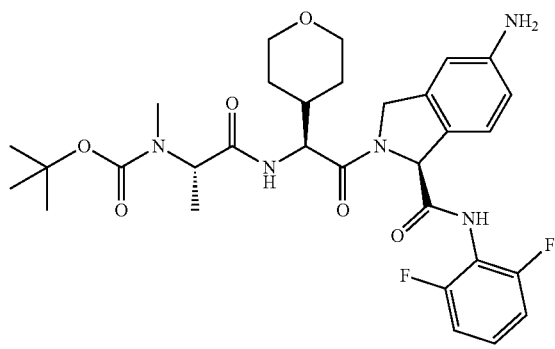 [SMILES: C[C@@H](C(=O)N[C@H](C(=O)N1Cc2cc(N)ccc2[C@H]1C(=O)Nc1c(F)cccc1F)C1CCOCC1)N(C)C(=O)OC(C)(C)C]

tert-Butyl ((2S)-1-(((1 S)-2-(5-amino-1-((2,6-difluorophenyl)carbamoyl)isoindolin-2-yl)-2-oxo-1-(tetrahydro-2H-pyran-4-yl)ethyl)amino)-1-oxopropan-2-yl)(methyl)carbamate was separated by chiral HPLC (column: Reprosil Chiral-NR; eluant: gradient of NH$_4$OAc/EtOH/heptane) to yield:

(+)-epimer, retention time=11 min, tert-butyl ((S)-1-(((S)-2-((R)-5-amino-1-((2,6-difluorophenyl)carbamoyl)isoindolin-2-yl)-2-oxo-1-(tetrahydro-2H-pyran-4-yl)ethyl)amino)-1-oxopropan-2-yl)(methyl)carbamate. Yellow solid. MS: m/z (M–H)$^-$=614.5

(–)-epimer, retention time=21 min, tert-butyl ((S)-1-(((S)-2-((S)-5-amino-1-((2,6-difluorophenyl)carbamoyl)isoindolin-2-yl)-2-oxo-1-(tetrahydro-2H-pyran-4-yl)ethyl)amino)-1-oxopropan-2-yl)(methyl)carbamate. Off-white solid. MS: m/z (M–H)$^-$=614.5

Intermediate 5 tert-Butyl ((S)-1-(((2S,3R)-1-((S)-6-amino-1-((2,6-difluorophenyl)carbamoyl)isoindolin-2-yl)-3-methoxy-1-oxobutan-2-yl)amino)-1-oxopropan-2-yl)(methyl)carbamate

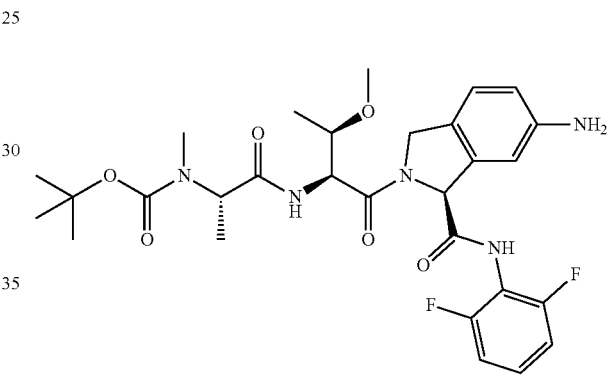

The title compound was prepared in analogy to Intermediate 2 using N-Boc-O-methyl-L-threonine instead of (S)-2-(tert-butoxycarbonylamino)-2-(tetrahydro-2H-pyran-4-yl)acetic acid. White solid. MS: m/z (M+H)$^+$=590.27

Intermediate 6 tert-Butyl ((S)-1-(((2S,3S)-1-((S)-6-amino-1-((2,6-difluorophenyl)carbamoyl)isoindolin-2-yl)-3-methyl-1-oxopentan-2-yl)amino)-1-oxopropan-2-yl)(methyl)carbamate

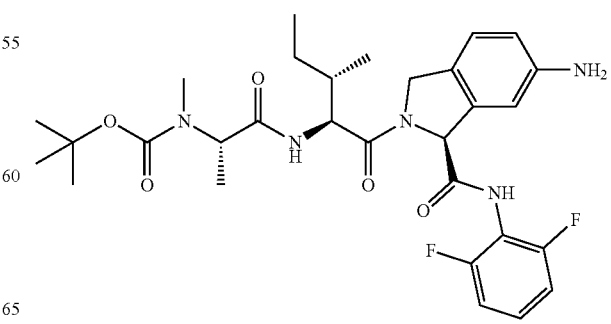

The title compound was prepared in analogy to Intermediate 2 using Boc-L-isoleucine instead of (S)-2-(tert-butoxycarbonylamino)-2-(tetrahydro-2H-pyran-4-yl)acetic acid. Light yellow solid. MS: m/z (M+H)$^+$=588.3

Intermediate 7 tert-Butyl N-[(1 S)-2-[[(1 S)-1-[(1 S)-6-amino-1-[(2,6-difluorophenyl)carbamoyl]isoindoline-2-carbonyl]-2,2-dimethyl-propyl]amino]-1-methyl-2-oxo-ethyl]-N-methyl-carbamate

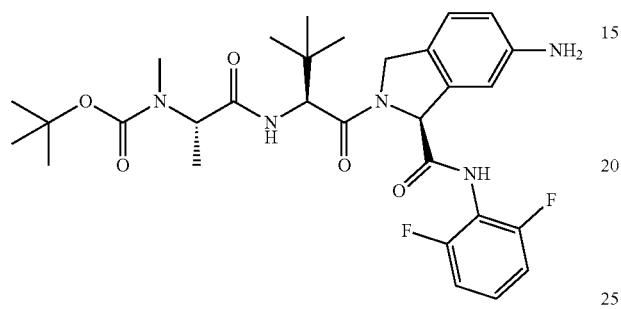

The title compound was prepared in analogy to Intermediate 2 using Boc-L-tert-leucine instead of (S)-2-(tert-butoxycarbonylamino)-2-(tetrahydro-2H-pyran-4-yl)acetic acid. Light yellow oil. MS: m/z (M+H)$^+$=588.3.

The invention claimed is:

1. A compound of Formula I

wherein

A is selected from the group consisting of

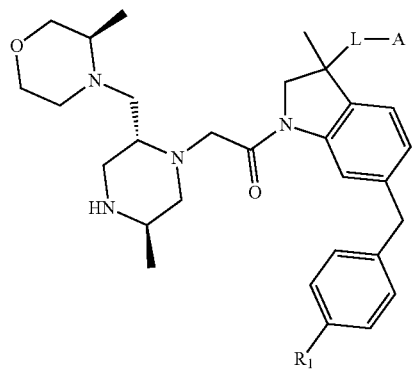
A-1

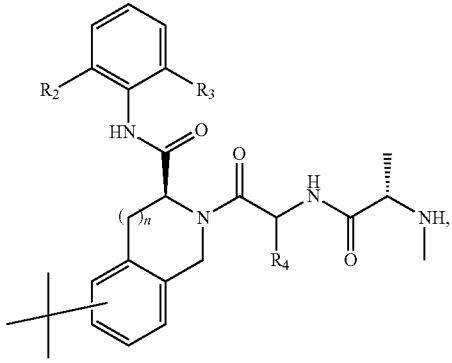
A-2

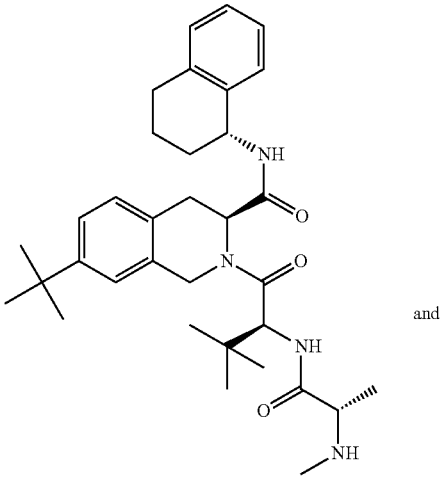
A-3

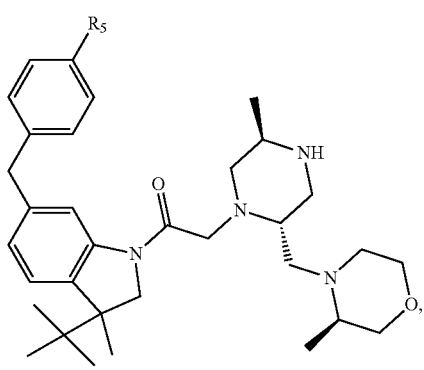
A-4 n = 0 or 1,

R$_1$ is selected from the group consisting of H, halogen or C$_{1-6}$-alkyl,

R$_2$ is selected from the group consisting of H, halogen or C$_{1-6}$-alkyl,

R$_3$ is selected from the group consisting of H, halogen or C$_{1-6}$-alkyl,

R$_4$ is selected from the group consisting of C$_{1-6}$-alkyl, C$_{1-6}$-alkoxy-C$_{1-6}$-alkyl or C$_{3-6}$-heterocycloalkyl, R$_5$ is selected from the group consisting of H, halogen or C$_{1-6}$-alkyl, R$_6$ is selected from the group consisting of H, halogen or C$_{1-6}$-alkyl, L is selected from the group consisting of

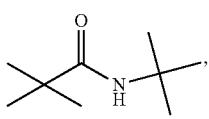
L-1

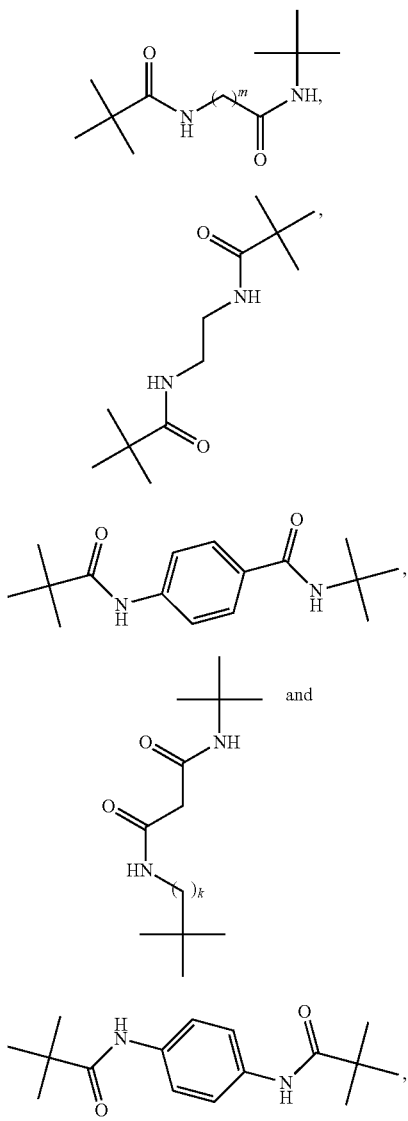

m = 1, 2 or 3,
k = 1, 2 or 3, or a pharmaceutically acceptable salt thereof.

2. The compound according to claim 1, wherein $R_1$ is F.

3. The compound according to claim 1, wherein A is A-1 and $R_2$ and $R_3$ are F and $R_4$ is selected from the group consisting of

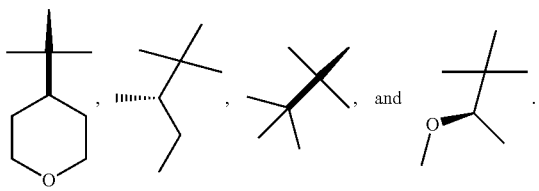

4. The compound according to claim 1, wherein A is A-2 and $R_5$ is F or wherein A is A-4 and $R_6$ is F.

5. The compound according to claim 1, wherein L is L-1, L-2, or L-3.

6. The compound according to claim 1, wherein L is L-4 or L-6.

7. The compound according to claim 1, wherein L is L-5 and k is 3.

8. The compound according claim 1, selected from the group consisting of:

N—((S)-3-((2,6-di fluorophenyl)carbamoyl)-2-((S)-2-((S)-2-(methylamino)propanamido)-2-(tetrahydro-2H-pyran-4-yl)acetyl)isoindolin-5-yl)-6-(4-fluorobenzyl)-3-methyl-1-(2-(2R,5R)-5-methyl-2-(((R)-3-methylmorpholino)methy)piperazin-1-yl)acetyl) indoline-3-carboxamide trihydrochloride, (3R)—N-[2-[[(3S)-3-[(2,6-difluorophenyl)carbamoyl]-2-[(2S)-2-[(2S)-2-(methylamino)propanoyl]amino]-2-(oxan-4-yl)acetyl]-1,3-dihydroisoindol-5-yl]amino]-2-oxoethyl]-6-[(4-fluorophenyl)methyl]-3-methy-1-[2-(2R,5R)-5-methyl-2-[[(3R)-3-methylmorpholin-4-yl]methyl]piperazin-1-yl]acetyl]-2H-indole-3-carboxamide trihydrochloride, (3S)—N-[2-[[(3S)-3-[(2,6-difluorophenyl)carbamoyl]-2-[(2S)-2-[[(S)-2-(methylamino)propanoyl]amino]-2-(oxan-4-yl)acetyl]-1,3-dihydroisoindol-5-yl]amino]-2-oxoethyl]-6-[(4-fluorophenyl)methyl]-3-methyl-1-[2-[(2R,5R)-5-methyl-2-[[(3R)-3-methylmorpholin-4-yl]methyl]piperazin-1-yl]acetyl]-2-indole-3-carboxamide trihydrochloride, (3S)-2-[(2S)-3,3-dimethyl-2-[[(2S)-2-(methylamino)propanoyl]amino]butanoyl]-7-[[2-[[(3S)-6-[(4-fluorophenyl)methyl]-3-methyl-1-[2-[(2R,5R)-5-methyl-2-[[(3R)-3-methylmorpholin-4-yl]methyl]piperazin-1-yl]acetyl]-2H-indole-3-carbonyl]amino]acetyl]amino]-N-[(1R)-1,2,3,4-tetrahydronaphthalen-1-yl]-3,4-dihydro-1H-isoquinoline-3-carboxamide trihydrochloride, (3S)-2-[(2S)-3,3-dimethyl-2-[[(2S)-2-(methylamino)propanoyl]amino]butanoyl]-7-[[2-[[(3R)-6-[(4-fluorophenyl)methyl]-3-methyl-1-[2-[(2R,5R)-5-methyl-2-[[(3R)-3-methylmorpholin-4-yl]methyl]piperazin-1-yl]acetyl]-2H-indole-3-carbonyl]amino]acetyl]amino]-N-[(1R)-1,2,3,4-tetrahydronaphthalen-1-yl]-3,4-dihydro-1H-isoquinoline-3-carboxamide trihydrochloride, (3S)-2-((S)-3,3-dimethyl-2-((S)-2-(methylamino)propanamido)butanoyl)-7-(6-(4-fluorobenzyl)-3-methyl-1-(2-((2R,5R)-5-methyl-2-(((R)-3-methylmorpholino)methyl)piperazin-1-yl)acetyl)indoline-3-carboxamido)-N—((R)-1,2,3,4-tetrahydronaphthalen-1-yl)-1,2,3,4-tetrahydroisoquinoline-3-carboxamide trihydrochloride, (3S)-2-((S)-3,3-dimethyl-2-((S)-2-(methylamino)propanamido)butanoyl)-7-(2-(6-(4-fluorobenzyl)-3-methyl-1-(2-((2R,5R)-5-methyl-2-(((R)-3-methylmorpholino)methyl)piperazin-1-yl)acetyl)indoline-3-carboxamido)acetamido-N—((R)-1,2,3,4-tetrahydronaphthalen-1-yl)-1,2,3,4-tetrahydroisoquinoline-3-carboxamide trihydrochloride, (3S)—N-(2,6-difluorophenyl)-7-(2-(6-(4-fluorobenzyl)-3-methyl-1-(2-((2R,5R)-5-methyl-2-(((R)-3-methylmorpholino)methyl)piperazin-1-yl)acetyl)indoline-3-carboxamido)acetamido)-2-((S)-2-((S)-2-(methylamino)propanamido)-2-(tetrahydro-2H-pyran-4-yl)acetyl)-1,2,3,4-tetrahydroisoquinoline-3-carboxamide trihydrochloride, (R)—N—((S)-3-((2,6-difluorophenyl)carbamoyl)-2-((S)-2-((S)-2-(methylamino)propanamido)-2-(tetrahydro-2H-pyran-4-yl)acetyl)isoindolin-5-yl)-6-(4-fluorobenzyl)-3-methyl-1-(2(2R,5R)-5-methyl-2-(((R)-3- methylmorpholino)methyl)piperazin-1-yl)acetyl)
indoline-3-carboxamide trihydrochloride,
(R,R,R)—N,N'-(ethane-1,2-diyl)bis(6-(4-fluorobenzyl)-
3-methyl-1-(2-((2R,5R)-5-methyl-2-(((R)-3-methyl-
morpholino)methyl)piperazin-1-yl)acetyl)indoline-3-
carboxamide) trihydrochloride,
(S)—N—((S)-3-((2,6-difluorophenyl)carbamoyl)-2-((S)-
2-((S)-2-(methylamino)propanamido)-2-(tetrahydro-
2H-pyran-4-yl)acetyl)isoindolin-5-yl)-6-(4-fluoroben-
zyl)-3-methyl-1-(2-((2R,5R)-5-methyl-2-(((R)-3-
methylmorpholino)methyl)piperazin-1-yl)acetyl)
indoline-3-carboxamide,
(S)—N-(2-(((S)-1-((2,6-difluorophenyl)carbamoyl-2-
((S)-2-((S)-2-(methylamino)propanamido)-2-(tetra-
hydro-2H-pyran-4-yl)acetyl)isoindolin-5-yl)amino)-2-
oxoethyl)-6-(4-fluorobenzyl)-3-methyl-1-(2-((2R,5R)-
5-methyl-2-(((R)-3-methylmorpholino)methyl)
piperazin-1-yl)acetyl)indoline-3-carboxamide
trihydrochloride,
(S)—N-(2-((S)-3-((2,6-difluorophenyl)carbamoyl)-2-
((2S,3R)-3-methoxy-2-((S)-2-(methylamino)propana-
mido)butanoyl)isoindolin-5-yl)amino)-2-oxoethyl)-6-
(4-fluorobenzyl)-3-methyl-1-(2-((2R,5R)-5-methyl-2-
(((R)-3-methylmorpholino)methyl)piperazin-1-yl)
acetyl)indoline-3-carboxamide trihydrochloride,
(S)—N-(2-(((S)-3-((2,6-difluorophenyl)carbamoyl)-2-
((2S,3 S)-3-methyl-2-((S)-2-(methylamino)propana-
mido)pentanoyl)isoindolin-5-yl)amino)-2-oxoethyl)-6-
(4-fluorobenzyl)-3-methyl-1-(2-((2R,5R)-5-methyl-2-
(((R)-3-methylmorpholino)methy)piperazin-1-yl)
acetyl)indoline-3-carboxamide trihydrochloride,
(S)—N-(2-(((S)-3-((2,6-difluorophenyl)carbamoyl)-2-
((S)-3,3-dimethyl-2-((S)-2-(methylamino)propana-
mido)butanoyl)isoindolin-5-yl)amino)-2-oxoethyl)-6-
(4-fluorobenzyl)-3-methyl-1-(2-((2R,5R)-5-methyl-2-
(((R)-3-methylmorpholino)methyl)piperazin-1-yl)
acetyl)indoline-3-carboxamide trihydrochloride,
(S)—N-(3-(((S)-3-((2,6-difluorophenyl)carbamoyl)-2-
((S)-2-((S)-2-(methylamino)propanamido)-2-(tetra-
hydro-2H-pyran-4-yl)acetyl)isoindolin-5-yl)amino)-3-
oxopropyl)-6-(4-fluorobenzyl)-3-methyl-1-(2-((2R,
5R)-5-methyl-2-(((R)-3-methylmorpholino)methyl)
piperazin-1-yl)acetyl)indoline-3-carboxamide
trihydrochloride,
(S)—N-(4-(((S)-3-((2,6-difluorophenyl)carbamoyl)-2-
((S)-2-((S)-2-(methylamino)propanamido)-2-(tetra-
hydro-2H-pyran-4-yl)acetyl)isoindolin-5-yl)amino-4-
oxobutyl)-6-(4-fluorobenzyl)-3-methyl-1-(2-((2R,5R)-
5-methyl-2-(((R)-3-methylmorpholino)methyl)
piperazin-1-yl)acetyl)indoline-3-carboxamide
trihydrochloride,
N-(2-(((S)-3-((2,6-difluorophenyl)carbamoyl)-2-((S)-2-
((S)-2-(methylamino)propanamido)-2-(tetrahydro-2H-
pyran-4-yl)acetyl)isoindolin-5-yl)amino)-2-oxoethyl)-
6-(4-fluorobenzyl)-3-methyl-1-(2-((2R,5R)-5-methyl-
2-(((R)-3-methylmorpholino)methyl)piperazin-1-yl)
acetyl)indoline-3-carboxamide trihydrochloride,
N-(2-(4-fluoro-3-((S)-2-((S)-2-((S)-2-(methylamino)pro-
panamido)-2-(tetrahydro-2H-pyran-4-yl)acetyl)isoin-
doline-1-carboxamido)benzamido)ethyl)-6-(4-fluo-
robenzyl)-3-methyl-1-(2-((2R,5R)-5-methyl-2-((((R)-
3-methylmorpholino)methyl)piperazin-1-yl)acetyl)
indoline-3-carboxamide dihydrochloride,
N-(4-(((S)-3-((2,6-difluorophenyl)carbamoyl)-2-((S)-2-
((S)-2-(methylamino)propanamido)-2-(tetrahydro-2H-
pyran-4-yl)acetyl)isoindolin-5-yl)carbamoyl)phenyl)-
6-(4-fluorobenzyl)-3-methyl-1-(2-((2R,5R)-5-methyl-
2-(((R)-3-methylmorpholino)methyl)piperazin-1-yl)
acetyl)indoline-3-carboxamide trihydrochloride,
N4-(4-(4-fluoro-3-((S)-2-((S)-2-(methylamino)propana-
mido)-2-(tetrahydro-2H-pyran-4-yl)acetyl)isoindoline-
1-carboxamido)benzamido)phenyl)-6-(4-fluoroben-
zyl)-3-methyl-1-(2-((2R,5R)-5-methyl-2-(((R)-3-
methylmorpholino)methyl)piperazin-1-yl)acetyl)
indoline-3-carboxamide trihydrochloride, and
N1-((S)-3-((2,6-difluorophenyl)carbamoyl)-2-((S)-2-
((S)-2-(methylamino)propanamido)-2-(tetrahydro-2H-
pyran-4-yl)acetyl)isoindolin-5-yl)-N3-(3-(6-(4-fluo-
robenzyl)-3-methyl-1-(2-((2R,5R)-5-methyl-2-(((R)-3-
methylmorpholino)methyl)piperazin-1-yl)acetyl)
indolin-3-yl)propyl)malonamide trihydrochloride.

9. A method for treating cancer, comprising the step of administering a therapeutically effective amount of a compound according to claim 1, or a pharmaceutically acceptable salt thereof, to a patient in need thereof.

10. Monomers of Formula I-a of dimeric compounds of Formula I:

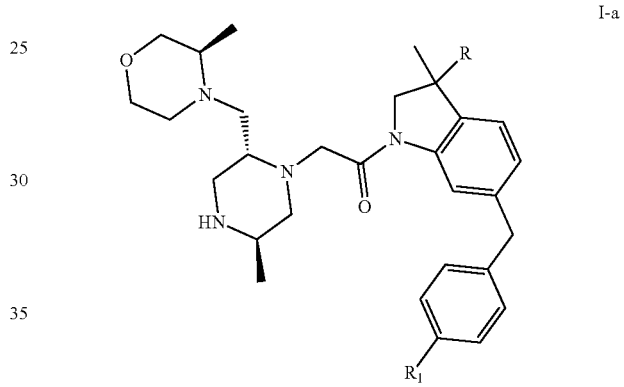

I-a wherein
$R_1$ is selected from the group consisting of H, halogen or $C_{1-6}$-alkyl, and
R is selected from the group consisting of

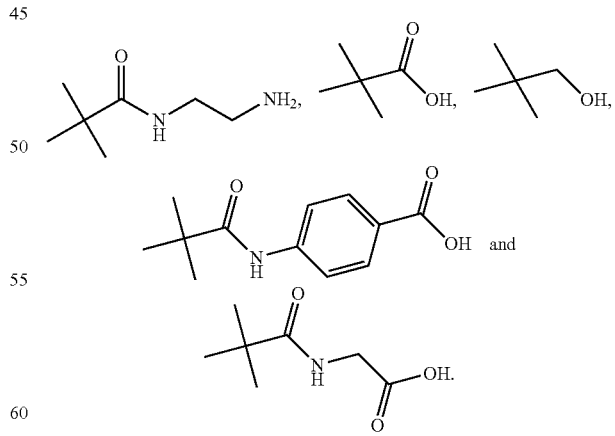

11. A method of treating cancer with a combination therapy, comprising the step of administering to a patient in need thereof a compound of Formula I according to claim 1 which acts as an inhibitor of SMAC protein binding to Inhibitor of Apoptosis Proteins (IAPs), and/or an inhibitor of activated caspase protein binding to IAPs, in combination, simultaneously or sequentially, with a bispecific antibody, wherein the bispecific antibody comprises at least one antigen binding site specific for DR5 comprising a variable heavy chain comprising an amino acid sequence of SEQ ID NO.:7 and a variable light chain comprising an amino acid sequence of SEQ ID NO.:8; and at least one antigen binding site specific for FAP comprising a heavy chain variable region comprising an amino acid sequence of SEQ ID NO.:15 and a light chain variable region comprising an amino acid sequence of SEQ ID NO.:16.

12. A pharmaceutical combination, comprising a compound of Formula I according to claim 1 which act as an inhibitor of SMAC protein binding to Inhibitor of Apoptosis Proteins (IAPs), and/or an inhibitor of activated caspase protein binding to IAPs, and a bispecific antibody that binds to Death Receptor 5 (DR5) and Fibroblast Activation Protein (FAP), wherein the bispecific antibody comprises at least one antigen binding site specific for DR5 comprising a variable heavy chain comprising an amino acid sequence of SEQ ID NO.:7 and a variable light chain comprising an amino acid sequence of SEQ ID NO.:8; and at least one antigen binding site specific for FAP comprising a heavy chain variable region comprising an amino acid sequence of SEQ ID NO.:15 and a light chain variable region comprising an amino acid sequence of SEQ ID NO.:16.

* * * * *

UNITED STATES PATENT AND TRADEMARK OFFICE
CERTIFICATE OF CORRECTION

PATENT NO.        : 10,398,702 B2
APPLICATION NO.   : 16/095262
DATED             : September 3, 2019
INVENTOR(S)       : Alexander Flohr et al.

Page 1 of 1

It is certified that error appears in the above-identified patent and that said Letters Patent is hereby corrected as shown below:

In the Claims

At Column 210, Line 5, "to" should be added prior to "claim 1."

At Column 210, Lines 11 and 16, "methy" should be replaced with "methyl."

At Column 210, Line 22, "[(2S)-2-[[(S)-2" should be replaced with "[(2S)-2-[[(2S)-2."

At Column 210, Line 26, "acetyl]-2-indole-3" should be replaced with "acetyl]-2H-indole-3."

At Column 211, Line 13, "carbamoyl-2-" should be replaced with "carbamoyl)-2-."

At Column 211, Line 30, "methy" should be replaced with "methyl."

At Column 211, Line 47, "amino-4-" should be replaced with "amino)-4-."

At Column 212, Line 3, "N4-(4-(4-fluoro-3-" should be replaced with "N-(4-(4-fluoro-3-."

Signed and Sealed this
Twenty-sixth Day of November, 2019

Andrei Iancu
*Director of the United States Patent and Trademark Office*